US008716004B2

(12) United States Patent
Wang

(10) Patent No.: US 8,716,004 B2
(45) Date of Patent: May 6, 2014

(54) GENE INACTIVATED MUTANTS WITH ALTERED PROTEIN PRODUCTION

(75) Inventor: Huaming Wang, Fremont, CA (US)

(73) Assignee: Danisco US Inc., Palo alto, CA (US)

( * ) Notice: Subject to any disclaimer, the term of this patent is extended or adjusted under 35 U.S.C. 154(b) by 475 days.

(21) Appl. No.: 12/639,956

(22) Filed: Dec. 16, 2009

(65) Prior Publication Data

US 2011/0070612 A1    Mar. 24, 2011

Related U.S. Application Data

(63) Continuation of application No. 11/401,696, filed on Apr. 11, 2006, now Pat. No. 7,691,621.

(60) Provisional application No. 60/670,415, filed on Apr. 12, 2005.

(51) Int. Cl.
 *C12N 1/00* (2006.01)
 *C12N 1/15* (2006.01)
 *C07H 21/02* (2006.01)

(52) U.S. Cl.
 USPC ............... 435/254.1; 435/254.11; 536/23.1

(58) Field of Classification Search
 None
 See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,760,025 | A | 7/1988 | Estell et al. |
| 4,965,188 | A | 10/1990 | Mullis et al. |
| 5,840,570 | A | 11/1998 | Berka et al. |
| 5,846,802 | A | 12/1998 | Buxton et al. |
| 5,874,276 | A | 2/1999 | Fowler et al. |
| 6,022,725 | A | 2/2000 | Fowler et al. |
| 6,268,328 | B1 | 7/2001 | Mitchinson et al. |
| 6,509,171 | B1 | 1/2003 | Berka et al. |
| 7,279,564 | B2 | 10/2007 | De Nobel et al. |
| 7,323,327 | B2 | 1/2008 | Edens et al. |

FOREIGN PATENT DOCUMENTS

| | | |
|---|---|---|
| EP | 0 137 280 A1 | 4/1985 |
| EP | 0 215 594 | 3/1987 |
| EP | 0 244 234 | 4/1987 |
| WO | WO97/22705 | 6/1997 |
| WO | WO 99/02705 | 1/1999 |
| WO | WO 02/068623 A2 | 9/2002 |
| WO | WO 2004/067709 | 8/2004 |

OTHER PUBLICATIONS

Altschul, S.F. et al. "Local alignment statistics." *Methods Enzymol* 266: 460-80, 1996.
Altschul, S.F. et al. "Basic local alignment search tool." *J. Mol. Biol* 215(3): 403-410, 1990.
Bartkeviciute et al. "Disruptioin of the MNN 10 gene enhances prtein secretin in *Kluveromyces lactis* and *Saccharomyces cerevisiae*" FEMS Yest Research, v.4 (2004) pp. 883-840.
Berka, R.M. et al. "Molecular cloning and deletion of the gene encoding aspergillopepsin A from *Aspergillus awamori*." *Gene* 86(2): 153-162, Feb. 14, 1990.
Billings, P.C. et al. "A growth-regulated protease activity that is inhibited by the anticarcinogenic Bowman-Birk protease inhibitor." *Proc. Natl. Acad. Sci. U.S.A* 89(7): 3120-4, Apr. 1, 1992.
Birk, Y. "The Bowman-Birk inhibitor. Trypsin- and chymotrypsin-inhibitor from soybeans." *Int. J. Pept. Protein Res* 25(2): 113-31, Feb. 1985.
Blundell, T. et al. "The high resolution structure of endothiapepsin." In *Aspartic Proteinases and their Inhibitors*, edited by V. Kostka, pp. 151-161. Berlin: Walter de Gruyter, 1985.
Boel, E. et al. "Glucoamylases G1 and G2 from *Aspergillus niger* are synthesized from two different but closely related mRNAs." *The EMBO Journal* 3(5): 1097-1102, May 1984.
Bonifacino, J.S. et al. "Ubiquitin and the control of protein fate in the secretory and endocytic pathways." *Annu Rev Cell Dev Biol* 14: 19-57, 1998.
Campbell, E.I. et al. "Improved transformation efficiency of *Aspergillus niger* using the homologous niaD gene for nitrate reductase." *Current Genetics* 16(1): 53-56, Jul. 1, 1989.
Cao, Q.N. et al. "Penicillopepsin-JT2, a recombinant enzyme from *Penicillium janthinellum* and the contribution of a hydrogen bond in subsite S3 to k(cat)." *Protein Sci* 9(5): 991-1001, May 1, 2000.
Cullen, D. et al. "Controlled Expression and Secretion of Bovine Chymosin in *Aspergillus nidulans*." *Bio/Technology* 5(4): 369-376, Apr. 1987.
Dean, N. et al. "Molecular and phenotypic analysis of the *S. cerevisiae* MNN10 gene identifies a family of related glycosyltransferases." *Glycobiology* 6(1): 73-81, Jan. 1996.
Devereux, P. et al. "A comprehensive set of sequence analysis programs for the VAX." *Nucl. Acids Res* 12: 387-395, 1984.
Feng, D.F. et al. "Progressive sequence alignment as a prerequisite to correct phylogenetic trees." *J. Mol. Evol* 25(4): 351-360, 1987.
Finkelstein, D.B. "Transformation." In *Biotechnology of Filamentous Fungi: Technology and Products*, edited by D.B. Finkelstein et al., pp. 113-156. Boston, MA: Butterworth-Heinemann, 1992.
Frederick, G.D. et al. "Cloning and characterisation of pepC, a gene encoding a serine protease from *Aspergillus niger*." *Gene* 125(1): 57-64, Mar. 15, 1993.
Gwynne, D.I. et al. "Genetically Engineered Secretion of Active Human Interferon and a Bacterial Endoglucanase from *Aspergillus nidulans*." *Bio/Technology* 5(7): 713-719, Jul. 1987.
Harkki, A. et al. "Genetic engineering of *Trichoderma* to produce strains with novel cellulase profiles." *Enzyme Microb. Technol* 13(3): 227-33, Mar. 1991.

(Continued)

*Primary Examiner* — Michele K Joike

(74) *Attorney, Agent, or Firm* — Danisco US Inc.

(57) ABSTRACT

A recombinant filamentous fungal cell (e.g. *Aspergillus*) having one or more inactivated chromosomal genes is provided. The chromosomal genes in some embodiments correspond to derA, derB, htmA, mnn9, mnn10, ochA, dpp4, dpp5, pepAa, pepAb, pepAc, pepAd, pepF and combinations thereof. The recombinant fungal cells may include further inactivated chromosomal genes which correspond to pepA, pepB, pepC and pepD. The recombinant filamentous fungal cells may include a heterologous nucleic acid encoding a protein of interest. Also provided are methods of producing a protein of interest in said recombinant filamentous fungal cell.

18 Claims, 66 Drawing Sheets

(56) References Cited

OTHER PUBLICATIONS

Harkki, A. et al. "A Novel Fungal Expression System: Secretion of Active Calf Chymosin from the Filamentous Fungus *Trichoderma reesei*." *Bio/Technology* 7(6): 596-603, Jun. 1989.

Higgins, D.G. et al. "Fast and sensitive multiple sequence alignments on a microcomputer." *CABIOS* 5:2, 151-153, 1989.

Hiller, M.M. et al. "ER Degradation of a Misfolded Luminal Protein by the Cytosolic Ubiquitin-Proteasome Pathway." *Science* 273(5282): 1725-1728, Sep. 20, 1996.

Van Den Hombergh, J.P. et al. "Cloning, characterization and expression of pepF, a gene encoding a serine carboxypeptidase from *Aspergillus niger*." *Gene* 151(1-2): 73-9, Dec. 30, 1994.

Van Den Hondel, C. et al. "Heterologous gene expression in Filamentous Fungi." In *More Gene Manipulations in Fungi*, edited by J.W. Bennett et al., pp. 396-428. San Diego, CA: Academic Press, 1991.

Inoue, H. et al. "High efficiency transformation of *Escherichia coli* with plasmids." *Gene* 96(1): 23-8, Nov. 30, 1990.

Jakob, C.A. et al. "Htm1p, a mannosidase-like protein, is involved in glycoprotein degradation in yeast." *EMBO Reports* 2(5): 423-430, May 15, 2001.

James, M.N.G. et al. "X-ray diffraction studies on penicillopepsin and its complexes: the hydrolytic mechanism." In *Aspartic Proteinases and their Inhibitors*, edited by V. Kostka, pp. 163-177. Berlin: Walter de Gruyter, 1985.

Jarai, G. et al. "Cloning and characterization of the pepD gene of *Aspergillus niger* which codes for a subtilisin-like protease." *Gene* 139(1): 51-57, Feb. 11, 1994.

Karlin, S. et al. "Applications and statistics for multiple high-scoring segments in molecular sequences." *Proc. Natl. Acad. Sci. USA* 90(12): 5873-7, Jun. 15, 1993.

Kennedy, A.R. "The Bowman-Birk inhibitor from soybeans as an anticarcinogenic agent." *Am J Clin Nutr* 68(6): 1406S-1412, Dec. 1, 1998.

Knop et al. "Der1, a novel protein specifically required for endoplasmic reticulum degradation in yeast" The EMBO J., V. 15, N4, pp. 763 1996.

Kramer, W. et al. "The gapped duplex DNA approach to oligonucleotide-directed mutation construction." *Nucl. Acids Res.* 12(24): 9441-9456, Dec. 21, 1984.

Kück, U. et al. "The 5'-sequence of the isopenicillin N-synthetase gene (pcbC) from *Cephalosporium acremonium* directs the expression of the prokaryotic hygromycin B phosphotransferase gene (hph) in *Aspergillus niger*." *Applied Microbiology and Biotechnology* 31(4): 358-365, 1989.

Maddox, D.E. "Elevated serum levels in human pregnancy of a molecule immunochemically similar to eosinophil granule major basic protein." *J. Exp. Med.* 158(4): 1211-1226, 1983.

Morinaga, Y. et al. "Improvement of Oligonucleotide-Directed Site-Specific Mutagenesis Using Double-Stranded Plasmid DNA." *Bio/Technology* 2(7): 636-639, Jul. 1984.

Nakayama, K. et al. "OCH1 encodes a novel membrane bound mannosyltransferase: outer chain elongation of asparagine-linked oligosaccharides." *EMBO J.* 11(7): 2511-2519, Jul. 1992.

Needleman, S.B. et al. "A general method applicable to the search for similarities in the amino acid sequence of two proteins." *J. Mol. Biol* 48(3): 443-53, Mar. 1970.

Nevalainen, K.M.H. et al. "The Molecular Biology of *Trichoderma* and its Application to the Expression of Both Homologous and Heterologous Genes." In *Molecular Industrial Mycology*, edited by S.A. Leong et al., pp. 129-148. New York: Marcel Dekker, 1991.

Nunberg, J.H. et al. "Molecular cloning and characterization of the glucoamylase gene of *Aspergillus awamori*." *Mol. Cell. Biol.* 4(11): 2306-2315, Nov. 1, 1984.

Oka et al. "Molecular characterization of protein O-mannosyltransferase and its invlobement in cell-wall synthesis in *Aspergillus nidulns*", Microbiology, V. 150, pp. 1973-1982, 2004.

Pearson, W.R. et al. "Improved Tools for Biological Sequence Comparison." *Proc. Natl. Acad. Sci. USA* 85(8): 2444-2448, Apr. 15, 1988.

Smith, T.F. et al. "Comparison of biosequences." *Adv. Appl. Math* 2: 482-489, 1981.

Stepanov, V.A. "Fungal aspartyl proteinases." In *Aspartic Proteinases and their Inhibitors*, edited by V. Kostka, pp. 27-40. Berlin: Walter de Gruyter, 1985.

Timberlake, W.E. "Cloning and Analysis of Fungal Genes." In *More Gene Manipulations in Fungi*, edited by J.W. Bennett et al., pp. 70-76. San Diego, CA: Academic Press, 1991.

Upshall, A. et al. "Secretion of Active Human Tissue Plasminogen Activator from the Filamentous Fungus *Aspergillus nidulans*," *Bio/Technology* 5(12): 1301-1304, Dec. 1987.

Van Den Hombergh et al. "*Aspergillus* as a host for heterologous protein production: the problem of proteases," Tibtect, Jul. 1997, V. 15 pp. 256-263.

Van Den Hombergh et al. "Disruption of three acid proteases in *Aspergillus niger* Effects on protease spectrum, intracellular proteolysis, and degradationor target proteins", eur.J. Biochem, pp. 605-613 (1997).

Ward, M. et al. "Use of *Aspergillus* overproducing mutants, cured for intergrated plasmid, to overproduce heterologous proteins." *Applied Microbiology and Biotechnology* 39(6): 738-743, 1993.

Yip, C.L. et al. "Cloning and analysis of the *Saccharomyces cerevisiae* MNN9 and MNN1 genes required for complex glycosylation of secreted proteins." *Proc. Natl. Acad. Sci. U.S.A* 91(7): 2723-7, Mar. 29, 1994.

Zhu, H. et al. "Isolation of genomic DNAs from fungi using benzyl chloride." *Acta Mycologica Sinica* 13(1): 34-40, 1994. Abstract.

Zhu, H. et al. "Isolation of genomic DNAs from plants, fungi and bacteria using benzyl chloride." *Nucl. Acids Res.* 21(22): 5279-5280, Nov. 11, 1993.

Zukowski, M.M. "Production of commercially valuable products." In *Biology of Bacilli: Applications to Industry*, edited by R.H. Doi et al., pp. 311-337. Stoneham, MA: Butterworth-Heinemann, 1992.

Van Den Hombergh, Johannes, P. T. W., et al., "Disruption of Three Acid Proteases in *Aspergillus niger* Effects on Protease Spectrum, Intracellular Proteolysis, and Degradation of Target Proteins," *European Journal of Biochemistry*, 247(2):605-613 (1997).

Doumas, A. et al., "Characterization of the Prolyl Dipeptidyl Peptidase Gene (*dppIV*) from the Koji Mold *Aspergillus oryzae*." *Applied and Environmental Microbiology* 64(12): 4809-4815, 1998.

Moralejo, F.J., et al., "Silencing of the Aspergillopepsin B (*pepB*) gene of *Aspergillus awamori* by antisense RNA expression or protease removal by gene disruption results in a large increase in thaumatin production." *Applied and Environmental Microbiology* 68(7): 3550-3559, 2002.

Schaap, P.J., "*Aspergillus niger* dapB gene for dipeptidyl aminopeptidase type IV, exons 1-3." Database EM_FUN Accession No. AJ278532 dated Jun. 6, 2001.

Official Communication for European Patent Application No. EP10188484.9 dated Jul. 17, 2012.

Official Communication for European Patent Application No. EP10188484.9 dated Oct. 23, 2012.

Supplemental European Search Report for European Patent Application No. EP10188484.9 dated Jul. 5, 2011.

European Search Report for European Patent Application No. EP10188484.9 dated Nov. 10, 2011.

Partial European Search Report for European Patent Application No. EP09005625.0 dated Sep. 18, 2009.

European Search Report for European Patent Application No. EP09005625.0 dated Dec. 7, 2009.

Official Communication for European Patent Application No. EP09005625.0 dated Sep. 26, 2012.

Partial European Search Report for European Patent Application No. 10188499.7 dated Jul. 18, 2011.

European Search Report for European Patent Application No. 10188499.7 dated Nov. 15, 2011.

Official Communication for European Patent Application No. 10188499.7 dated Jul. 25, 2012.

Partial European Search Report for European Patent Application No. 10188507.7 dated Jul. 4, 2011.

(56) References Cited

OTHER PUBLICATIONS

European Search Report for European Patent Application No. 10188507.7 dated Nov. 15, 2011.

Official Communication for European Patent Application No. 10188507.7 dated Sep. 26, 2012.

International Search Report and the Written Opinion of the International Searching Authority for International Application No. PCT/US2006/013355 dated Jan. 10, 2007.

FIG. 1A

CCCCGGGCGAGTCAATGACGCTTTAGGTTTAAATGGTGTGAGGTGGTGCGCCAACTCGT

CGTCTCCTGGCGGCCTGAGGCTTTGAATAAATTGAGCTCTGGGCGCGATCGACTGGCAC

AGTCGAGAAATAAGCTGCAAGGCGAAAACCGCGGAGGAGCGTTTGTCAGGGATGAGATT

GCATGCGAGAGAGGGACCCATCCGGGAGGCCGAACGGACTATGAAGTGATGGAATCCCC

AGCCATCCGAATTCTTGTCCGGACGCGTGCGAGGCGCGTCTTTGCGGCGTCGAAGCGCG

CGGGAGCGACACGTGACATATGCGCCGGGGAGTGACAGGTGACACCTGAGGCCAAAAGG

CCAGCTGGAGCTCGGCGATTACGGCGGAACTAAACTGGCAGTTATTTAGTGGTGATTCG

GCATCATCCCCTTATCGATCATACTCGCCCGTCTTCTCGAGTCCTTAAACGCCAAAA

GACGACTGTCTGCATCCTCTCTATTTCGCTTACCGCTTCGTCGCATCGTACCCGCCACC

CGAGCAACCTCCCCCCTAAGTTAATCCCAACGTTCGCAACTCTACTACCCATCAATTAT

GGCCGCCATCTGGGGTAACGGCGGGCAGGCTGGCCAGTTCCCGCTGGAGCAATGGTTCT

ATGAAATGCCCCCTGTAACTCGATGGTGGACAGCAGCCACAGTTGCCACTTCAGTCTTG

GTCCAATGTCACGTCCTCACCCCATTCCAGCTGTTTTATAGCTTCCGCGCAGTCTATGT

TAAGTCTCAGGTACGTCGCAGCTAGTACTTCCGTCCACTGTATAGGGTAGACGAATCAC

GCGGCTAACCATCGCATAGTATTGGCGTCTGTTCACAACCTTCCTATACTTCGGACCAC

TCAATCTCGACTTACTATTTCATGTGTTCTTCTTGCAGCGATACTCGCGCCTCTTGGAG

GAATCATCGGGGCGATCGCCGGCCCACTTCTCGTGGCTTCTGTTCTACGCCATGGCCTC

TCTCCTCGTCCTCTCGCCATTTCTCTCCCTTCCATTCCTGGGCACGGCTCTCTCTTCCA

GTCTGGTCTACATCTGGAGTCGTCGCAACCCGGAAACTCGCCTCAGCTTCCTAGGAATG

CTGGTCTTCACCGCCCCTATCTCCCCTGGGTTCTGATGGCATTCAGCCTGGTCGTCCA

TGGCATCGTGCCCAAGGATGAAATCTGCGGCGTTGTCGTCGGCCACGTCTGGTACTTCT

TCAACGATGTTTACCCTTCGCTTCACGGTGGTCACCGTCCTTTCGATCCTCCTATGTGG

TGGGTGCGTCTGTTTGAGTCAGGGCCCGGGGAACGAGGCACCGACGCTGCCAACGTCAA

CGGGGAATTCGCCGCTGCTGCTGCACCCGAAGTTCGGTGAGCTATTTGTGCACCCCACT

GGGGCATTTACTGCATGGCGATGCAAAGAATCGTCCGCGTAATCGCTCTGGAAACGTCA

GCATATATGTGTGTACTGCCAACTACTCGCGCCGACACGCGCGAAGCATGAGAAGTTAA

TACTGTCAGGATATAAGCAAGGATCACGGCGGCAGACTTGATGGGATTTCTTATCGTGT

GGCTTGTCTTGTCCAGGGAGAGTCATTTGATCTGCCCCACGCCGCCGTGGCTGATTGC

FIG. 1B

GCTCTGGCCTCCTATTAGAAATGCCGCAAGGACAAGACCGTCAGAGTCCCCGAGTATCA
ATATGCGAGAGGCAGAGCAATCAACTTATTTCGCCAACCAGTGGAAGGAGTTGGGATCA
CTTGTGGGGAAGATGTGCAAGAAAGGAAGAGAGGAGTATCATCAAGGCAATAGCGGGCG
CTCTGTCTGCGGGGGTTAGTAACAGGTGTGTCTGTAAGAGAGACAGACTATCATGGCGA
TCAATCAGCTAGTAGTTCAATGAAAATACCCAAGTCATGTTTTTAGCTGATAATTTACA
TTTTGCGAGAGGGGAGGAGGGGGGCCGTGAACGCATGGACGCATGAGGCTGCTCTCCCA
TATGCAGTAGGAATATCGTAGCATCCCAATTACCTGAACGGGCGGCCCACGTGTCGATC
CAGGGTGCAAGCTCGAAGTTTGGGGTAAATTCTCCGCAATGTCTATCCCAATGTCGCTT
TCTACTTTCTTCTTTCCCACTTTTAATCAATGCCATACAGACTTGTATCCAGGATTTGC
CCCTAGTTCAGTATCGTATGGTTTGATCCAATCGATCGATCTGGACTTCCTCTCTTTCC
CCGCGTTACATAGCACCACCGGTATAGTTACCATGTAGAACAACCATGACAATACTTCT
CTGCCTGAGCGTTGATCAACCAGTCAGAGACAGACGCTTTGGCCGATCAAAGACAAGAT
AGTCTTAATTCTCTCACCATGAAGACTAGCTATCTACACA

FIG. 2

MAAIWGNGGQAGQFPLEQWFYEMPPVTRWWTAATVATSVLVQCHVLTPFQLFYSFRAVY

VKSQYWRLFTTFLYFGPLNLDLLFHVFFLQRYSRLLEESSGRSPAHFSWLLFYAMASLL

VLSPFLSLPFLGTALSSSLVYIWSRRNPETRLSFLGMLVFTAPYLPWVLMAFSLVVHGI

VPKDEICGVVVGHVWYFFNDVYPSLHGGHRPFDPPMWWVRLFESGPGERGTDAANVNGE

FAAAAAPEVR

FIG. 3A

```
GGCTCAGCACAATGGGCTCCACTACGGCGGAAATACAACCTCTTCACGTATCACCACTC
GCCAAATCCAGCGACAGAGATGAAAACAGAGAAGCTACCGCTTAACCAGATGGATTTGT
CTAATAAGCAGCAAATGCAGCTGGTCCAATCATCTCAGAGTGGCCAAGAAACGGGCGAA
TATCACCAATTCGCCTACGTGGACGAGCCTTTCTTGTCGTGGGATTTTGGTCTACGCTC
GGCTGACAAACAGCTGATCGGCTCTGTGAATCGCAACTTTGCCGGGTTTGCCCGGGAAA
TCTTCACGGATACGGGTGTCTATGCTCTGCGAATGGACTCTGCTTCTCCAGCGAAGAG
TTCCTCGACAAGAACCGTGCGGCTACTGGGATGACATTCGACCAGCGTGCCGTGATGCT
GGCAACCGCTGTGAGCATTGACTTTGACTACTTTAGTCGCCATAGCAACTCGGGTGGAT
TTGGTTTCATGCCTCTCTGGATCCCTGGATTTGGTGGTGAGGCAGCTGCTGGGGGTGCT
GCCGGGGGCGCAGCAGCCGGTGAAGCAGGTGCCGTGGGGAAGCGGCCGCGGGAACTCT
TGGTCGGGCTGGGGCAGCCGGTGGAATGGCTGATGGCGCTGCAGCAGGTGCAGCAGGTG
CGGGCGCAATGGCTGGCTACGAAGCCATGTCCCGTGGGATGGGAGGCAGCCAGCCTGCT
CCCGATCAGCAAGCGGCACCTGTAGACCAACAGCCACCGACGCCAGGTCAAACGGGTCC
GTATGGAGATGTCTGGGGGGAAGAGTCCGAGAACCCATGGGGAAAGGAGCCTGAGAACA
CATGGGGCCAGGAAGAGGATCCGTGGGCAGATGAAGCCGACGAGGGCGAGGGAGGCGAT
GATTTCGATTGGTTTTAAGCGGCTGATAACTACAAACAGGCAGTAAGATCAGGATGGTT
GACATTGTGAGACGGTCAGACATATACTATCCCCCATTCATGCAGGGATAACGACGAC
AGAGCTCATGTAATCGGGGCACTGAGAATCACCGTAACGGCTTCAATGACATGGCCTG
CGGCATACTCGACATGATCTGACCGAGTAGACATCGACGTCATTCATACTCGGCCCTGC
TTGAAGTGCAAAGCGGTTTATGCAGCTGACTGACGATGATTAGCCCGATGTACCATAAC
GACAATAAAATCTCCAAATAACTGTATAATATCACGCGAAAAATGAAACAATGCTAGCC
AGAAATAAACTCAAGATCATTCTCCTTTCATACTGATGAAAGCGGCGATAAGCATCATT
GCAGCCTCAGGCACCCAACACATCCCACCGGCTCAACCATCGATGAATGGAACCTCAAT
CACTCAATCATTCATTGGCTTTCAGAGTGGCAAACCTTGATTTCTCCTCCAATTCAATT
CCAACCCACTCATCTTCCCCAGTAAACCGACCTCTAAAAAGTTTTTCTTAGTCCTATCT
CCTCAACGCCACCCCAGGTACATAACCACCACCCCTATTAAGTACCCCGGTGTCCTCA
CCCTCTCCGGTCCGATCTCCGCACTCTCCTCTCCCCTCTTTATCTAATCGCCAGATAGA
CAGCCAGACCGCCACCACCACCAGCACCAAAAACCCACTACCTGCTTCCCTCCCACGAC
```

FIG. 3B

GCCGGAGAAATTAAGCCAATAATTAAAACCAATACTTCAATAGAGAAAGAAAGGCAGTG
ATCAATCAAAATGTCCTCCGTCGCCCAGAAACGCCTCTTTCACGATACAAAAACCTCTC
CACCAACCCCCCGAGGGCATCACCGCCGGCCCCGTCACCGAAGATGACATGTTCCACT
GGGAAGCACTAATCCAGGGGCCTGAAGGTACGCCCTTCGAGGGCGGCGTGTTCGCGGCC
GAGTTGAAGTTCCCTAAAGATTATCCGCTTAGTCCGCCTACAATGAAGTTTGTGGGTGG
TGGGGTTTGGCATCCTAATGGTAAATAACTCCTTCTTTTCCCCTTCTTTCTCTGTCTGG
ATTTTTCTTTGTCTTCAAGTCTTTTCTGGTGATGCTTGGTTGAGCTTATGCTAACGTGT
TTTGGACATACGTATAGTATACCCCAACGGAACCGTGTGCATTTCCATCCTCCACCCCC
CCGGTGACGACCCCAACCATTACGAACATGCTTCGGAGCGGTGGTCTCCTATCCAGAGC
GTGGAGAAGATTCTCATCTCCGTTATGAGTATGTTGGCGGAGCCGAATGATGAGTCTCC
GGCGAACGTGGAGGCTGCGAAGATGTGGAGGGAGCGGAGGGGGAGTATGAGCGGAAGG
TGAGGGATGAGGTTAGGAAGGGATTGGGGCTGTGAAACCCTCTCTTCTTTAATTTGAGT
TGAATGGTGAAGGGGAGGGGCTTGGTCATATATAAGTGACCGGTTGGTGCGCTGGTTGC
TCACTGTCTGTCTATACTCTGTGTCGTGGAGGAAAATGTGGCATAGCTTGGATGGATGC
ATTGGTTGCTTGGGTTGGCGTTGTGGTGCGTTCGTTCTTTCTCTTTCTTTCATCTTTAT
ATATATTCTATTTGATGCCCACTTCTAGGGGTAGATGCATGGCCAGGAATGCATAGATG
CTTTGTTCAGTATATATCGGTATCTTTCGTCGTGATAATGGTACGAAGTCATGAATACT
CGAATTCGCCCTATAGTA

FIG. 4

MSSVAQKRLFXIQKXFXTNPPEGITAGPVTEDDMFHWEALIQGPEGTPFEGGVF

AAELKFPKDYPLSPPTMKFVGGGVWHPNVYPNGTVCISILHPPGDDPNHYEHAS

ERWSPIQSVEKILISVMSMLAEPNDESPANVEAAKMWRERRGEYERKVRDEVRK

GLGL

FIG. 5A

```
GATATAATAGTGAACTGCTTGTCGCACTCTCTCCGTGCTGAACCGAATCACCCTCCCCT
AACCGGCTGGCCTGGTGCTCGCCCTGTTCCTTCGCTTTTTCTACGCGTTCGTTTCAAAG
CCCAATTTTCTTCTATCTACTCTATCCCGAGACGGATTTACCAATCCTCTTGCTATCTA
ATTGCCTTTGGGTCGCCATCGCCCGTGTCCTGTGACTCCGCGATCGGGATTCCTGCGTC
TGATGCTGCTCTCCCCTGGGCCCCCCTCCTACACCCCAGGCTCGATCTTCATTATGAAT
GTATAGCGTCCGAAATCATAACGAATTTCCCAGTTCGGCCACAGATATCCGCCTTCGCC
AGCAATTATCCGCTTTGCGTCGTAAAGGTCCTCATTCCAGGCGGTTTGCATCCGGTTCT
GCGTTCCCGCGACGCTTATTTGTGTGTTGTTCAACGAATGCGGAAGTGGGCAGTACATA
TCGACGCAAAACATATCATATTCGCGATTGGAGTTACCGCTGTCGACGCCTATAATATT
AATCAGTGATCTCTGCGAAACACTTGAAAGTCGCGCCCTACGTCTGTCCAGATGTCATT
GTACGATTGCTAGTTTGAATTGACATGGAATCGGTTCAGCTGTCTCATTCGGGATCGAC
AACACATTCCAGCTCGATCCCCGGCATGTTCTCGCCCGATCGCTCTTCGCATGTCAATA
CCAGTGGGTCAATCGCAGATGACCAGCCTCGACGAGCTCCCAATCGGGAGGAGCGATTC
ACATCATGGGTAGCCGACCATCGTCTCGACCTGGAACAGCGAATCCTTGGTGACCGCGC
TGAGCGTCGCGAATCGCGTCTACCTGGTCGACCAGCGCCATCGCATAGTTCTCTTAGAG
ACGCTGCTGCATCTCAATATGCGCCAAGAGGGCCGTATGTCCCAATTGAGTTGCAGTCC
GCAGCAGCAGGAAGCTCCGGCGAAGCGCGGTCGCATGCGCGCTCAGAACGAGAATCGCA
TTCAGCACACTCCCCGCCTGACCCTGAAGACCTCCGATGCAGGCAATCGCAATCGTTCG
TATCACGGCTGAAGGAGAAGAGGCTACGGAGGCGACTGATTACGCTGGTTATATCTGCA
TGTTTTCTCATCCTCGTTATCGCCATTTACCTCGCATTCGCTGCTTCCCGTACGACATT
GGGCCGAGAGCTCCAAATACTTCTCATCTTCATGATCTTAATTCTTGGCATTGTTTTCT
GTCATTCTCTCACGCGCTTCTTGATGGCACTATTACGACGGCCTGACTCTGATGTCGCT
ACGAATCGCATACCCAGTAGGGCAGGGCCAGCCGGCTATGCGCAACCAGCGCGTCCCAT
CCACGTTATTCTAGCTGGAGATGAGGACGTTGGAGCCGCGAGTCCGAATGCCGTGCGCG
AAAAGGTCACGGCGCCTCCTCCGGCATACGGTCTTTGGCGAGAAAGTGTGGTAAGTACA
TGATTACAGGAATGGCGTTATTTCCTTGATGGTGACCAGTCCCGCTAACTTTGTGCAGA
GGATTAACCCCGACTTGTTGTACTGGCAGCGCATCGAAAATAACAATGCGCACGTACCC
AAGGGTGTTTGGCAGGCATGGGAGCAATAAATCGCGGATCCACGGCCGCCTAGCTACA
```

FIG. 5B

CCTCTGACAACGGCGTCGACTATGTGATAGAAGCGCAACCCCGATCATTCACCCAATGG
CGGATTCCTGAAGAATCAGGGCATCAGCCATGACCCATACATATCTCTCTCTCTTTTCT
CGACATACTGAAGCTGGATTCACCGACACAATGACATCCACAATCGTCTCGTTATCCGC
AAAATCATTTATATAGCGGTACTGTGATCACCTTCATCTGTATTTCTTTTGCTCGAGAT
ATCCCCTGTGACTTGGCTTCTTTCCCTTTTTTTTCACCCTTTTGCGGCATTCTCATCAC
CAATCATGTGATGTTTCTTTGTTTTCTTTTGTACCTGAAAATTCTTGGATGAAGCGGGA
GTTACATTGGCATACACACTGATCTTCCTGGCGAGCATTTGTTTGAGCGCTATTTCATT
AAGCTTGGTTTTCTAACTTACTGCAAAGTACATCTTAACCCTTCTAAATGTTAAAGTAT
CTGGGAAACGAGGCCTACCGTAAGCAAGCCGATTCGTCAAAAATCCTGTATTAATAATA
TAAACATCCCCTAAAATTGAATTAAGGGATCCTGTAGTCCGAAGGGAAGGGGGAGTGGA
GGGAGAATGTAAACGGCATATCTGGCCGCAAATTGGTTCGCCGCGGATTGAATACGACC
TCACGTGCGGCGCCGCTGCCACCACCAACTTCCCCTCAAGCCTCCCCCCTCAGGAACCC
TTCTCTGGAGGCAGTTCAGTTCGCCGGTCTGCGGGTTTTCACATTGAACAGTTCATCA
ACGCGCTCCCATGCCATTGATAACTGTTTCGCTACTGCGGTAATGCGCTCGGGATGTTG
GCACTCGCAGATGTCCGCCCTCCGTTCAGCATGGATCATGACCTGGGTCTTGCTGCTGT
CGCTGTGGCTCGCCATGGCCCAGGGCATGCGGACCGGTCAGGTTAACGAACTCAGGTAA
ATCTCACCAGTCATTACCTGATTCCCGGTTTCGCTGGTATAGGGGCCGATCGACTGACA
CCCTCGATATTTAGGAAGGAGACAGAGCATATGTTCTACCACGGATTCGAAAACTATCT
CGAACACGCCTTTCCTGAAGACGAACTCCGTCCTTTAACATGCCGTCCGCTGGTTCGCG
ACCGAGAGAATCCCGCGCATGCAGAGCTCAACGATGTCCTGGGTAATTATTCATTGACT
CTGATCGACAGTCTGTCCTCCCTGGCAATACTTTCGTCGAGTCCCGACCAGGGCCAGAA
GGCTTGGGATTACTTCCAGAATGGAGTGAAGGATTTTGTTACACTGTACGGCGATGGAT
CCGATGGCCCCGCGGGCCAGGGTCAGAGGGGACGAGGATTCGATATGGATAGTAAAGTG
CAAGTGTTCGAGACGGTGATTCGAGGGTTAGGTAGGCATCGGATCTTGTGCATGGGGAG
TATGCATCTCGATTAATGGTTTTCTCTAGGTGGCCTACTCAGCGCTCATCTTTTTGCTG
TGGGCGATCTTCCTATCACCGGATACAATCCGCCGGAGACCGAAGCCAACTTCGCCAGA
GCCTGGGATAAGCACTCCTTCCCTGAAGGCAGTCGCGGCATCGAGTGGAAGGACGGATT
CGTCTACGATGGCCAACTTCTACGGCTTGCTGTCGATCTTGCAAATCGAATTTTACCCG

FIG. 5C

CGTTCTATACGGACACTGGACTCCCTTACCCTCGAGTGAACTTGAAGTACGGGGTGCAA
CGGCAGCCGTACTACGCAAACTCACCGTTTAATGCAGCCCCTACGTGTGATAAAGCCAA
TCCTGAACAGTGCCAAAAGCCTCGCCGCTCCTCGACCTTTGAGACTACGGAAACCTGCA
GCGCTGGCGCTGGCAGTCTAGTCCTCGAGTTTACAGTTTTGAGCAGACTTACAGGCGAT
GGACGATATGAGGAGCTTGCCAAGCGAGCATTCTGGGCCGTTTGGGCAAGGAGGAGTGA
TATTGGACTGATTGGGTCCGGTATTGATGCCGAGTCAGGTAGATGGGTTCATTCCTATA
CCGGGGTGAGTCAAATCAAGCACGTGCATTTGAATATGGCTAACACTACCACGTCCCAG
ATCGGCGCAGGAATTGATAGCTTTTTCGAGTATGCTTTCAAGTCCTACGTACTACTCTC
GTCAGGGGAACGGCCCCCGGCCAATACTAGCAGCCCGTGGCATGCCCTGGACGACTATT
TCCTACCACTTTCAGAATACGAGCACTCCGCCGATGCCTTTCTGAAGGTCTGGGAGAAG
TCTCATGCCTCAATAAAACGTCACCTATACCGCGGAGAGGGCCATCAGCACCCGCATCT
GATCCAGGGAGACATCTTCACCGGAGCGACTCGTGCTTTTGGATCGACAGTCTTAGCG
CCTTCTACCCCGGACTTCTTACTTTAGCGGGAGAAGTGGATGAAGCCATTGGCATCCAT
CTTCTGACGACGGCAGTCTGGACTCGATTTTCCGGTCTTCCTGAGCGATGGAATGTTGC
CACCGGGGACATTGAACAGGGCCTTTCCTGGTATGGTGGCCGCCCTGAGTTCGTGGAAT
CTACTTACTACCTCTACCGAGCGACAAAGGACCCCTGGTATCTGCATGTCGGAGAGATG
GTACTGCGGGATTTGAAACGGCGATGCTGGACCAAGTGCGGTTGGGCTGGTATTCAGGA
CGTTCGGAATGGCGAGCTCAATGACCGCATGGAGAGCTTCTTCCTGGGTGAAACTGCCA
AGTACATGTTTCTGCTGTACGATTTTGATCATCCCCTCAATAAGCTAGACCAGCCGTTC
GTCTTCTCCACCGAGGGCCACCCTCTAATTATCCCCAAGAACAGCACGGCACAGCGCGC
TGAGCGCAAGCAGGTACCAGTCGTTGTGGAGAGCGAGGGTTTGACATGCCCAACAGCAC
CTCAGCCTCCAACGCTGGGGGTTTCATCCACTGCGGCACGGTCCGATCTGTTCCACGCC
GCGAACCTGGCACGCCTACACCTCATGCCGAGTAGAGGTCTAGCGGAAGGCCCTCTTCT
GGATTACGCTCGGGACCACCCGAGCGTATCAGTGTCGGACTTGTCGTCGCCCACCAACT
ACACATTCTTCCCATGGACATTGCCTCCAGAGCTTGTGCCATTTAACGCAACCAGCGCG
CCGATGACAATCCGTCCTACGCTCGACATTTCTTTCCCCGCGCTTCCCGGTATGGTCGT
GGGGCCTGGATCACTGGAACGAGTGCGGGATGGCATCTTTATCAAAGCCATCGGGGGCC
TACGACTAAGTATGGTTCAGGATGTCCCTGTGCAAGGGGAATCCGGGAGCGCAGAGAGT

FIG. 5D

```
GATGAATTCCGGGTCCAGGTTATCAACAACGTGCCACTGGGCAAAGACGAGAAGGTATA
TCTTCTACGGGAAATCACATTTGATGTCCTCGACCCCACCGACCCGAATTTCACGCGGG
TTCGCGACACCGCCATGATTGACATCGTCATTGACGTTATCCCAGAGATTATCCGTCGA
CGAAATGATTCAGATGATAGTCATGAACCAGCTGCGCCTCGACGTGCCAACGGAGCCAT
CGTCCATGGCTCCAGCTCCGTCGACAGTAAAGTCGGCAGCGTAGATGCGTCGACCTCCA
GCATGAAGACTGTGCTCTCCTCGCTAGTCAACACTCTATCTACACTCCTTCGGGATGAA
GTACAGGGCCAGACCAGCCTGCCGCAGAAGAAAGCCACCTCGTTACGTCTCCTGCTCCC
GGCCGCCATCTCCACGGGGCTCGGCTCGGCCCCGCTCCCCGACGTGGAAGACGCCACGA
CAGTCTCCATCACGGGCGACCCTTCCAAGCAACGCCTCACATGGAACAGCATCTACTTC
GCGGACGAGCTCTGCGACAACCGCATCCTACGAGAAGTTGCACAGAACCACCAGGTCCT
CGTAATCAAGCGAGGCGGATGCAACTTTTCGCAGAAGCTGCGCAACATTGCCGCGTATC
CGCCTTCTCGGTACGCCCTGAAACTAGTCATCGTGGTCTCCTACGACGATGAAGTAGTC
GAGGAGGAGCAGCGCGAGGAATCAGACACCACCACGACCCCGGGGCTAGCTGCGGTCCG
CGCGGAACCTTATCTGGTGCGGCCCCATCTGGACGAGACGCAAATGACAGCCGCGGGCG
TCCCGCGGCGCCAGCTGCTCAGCGTAGTCATGGTAGGCGGAGGGCAAGAAACATACGAG
CTACTGCGACAAGCCACGGGGGTGGGCATTAAACGGCGATATTCGGTGCGATCGCAGGG
AGTTCCCATCAACAATCTGTATATTTTGTGAGAAGGATATGAGTGACCCTTAGCACATG
CCCCATTGCAACGAGTTTACCTATATGATATAGCATCATAGCATAGCTTTTTCATCCTA
GTCATAACATATTAGTAGCATTCCCAGTACACGTCACTCCTCCCGCCTCCCTCCACCTT
GGGAATACTGACATACCAAACACTATGCCCATGACATACGTACATACATACATACATAC
ATACCATGAATGACATGATGACATACCAAAAACACCCTGATCTTCATTTTCAACCCTCG
CCACCTCCGGACGGGAAACCCCGATCGATCGGCAATCGTTCGGTGGCCCTCCCCCTGCC
ACAACCGAGATCCGGCGTCACGTCAAATGTCGCCATTAAGATTAATGGTTAAGCAAAGT
ATTGGCTGTGGCTGCCACGGGGAACCAGCTGACTCAGCTGCTCAGCCTTCAGATGTTCC
GAATGTTTGAAAGGCTTGAAGGCTTGAAGAAGTGGCGGTGGGGCAGGTTTACTTGCCGA
TTGGTTCAATCCCCCGTGGAGCAACGGATAAGAAAACCCCTGCCGATAGAACGAAAAGC
AAAATGTAAGGCGGGATGGCAAATGAAAGCGAGGAGGTTTAAGGTTTACGTGGTTTGGA
```

FIG. 5E

ATGTGTCCCTGATTTGGGGGGGGGTGTGTGGCAGTGGGCTGTGGGAAGGGTTATAAATA

CCTGCTTCCTTTTCTCTTTTCTTTTTAAGGGTAGAGAGAGAGGGATCTCTAGATCTGAA

TCAATAACGAGGATTTACTTGTCTATTTGATTATACATATACATATTTGGACTGGTTCT

GGTACTATATATCCGGACACTCATTGAGTCCTAGTATTTACTCATTCACTTCTTTCCTC

GAGTATATATCTATTATAACAGTCCTATCCCTCTCAACTACTACTATTACTACACAACC

CACTACGAACCAAAATCAAAATGCATCTCCACACAGACCTCGACGTCGACACCACCCCC

TCCACCCTCATCAACATCACCACGGCCACCTCCGCAGCCAAACCCACCACAACCGCCAC

AACCACCCTCACCGAACTCACCTCCACAACCCCGTCCC

FIG. 6

RTQVNLTSHYLIPGFAGIGADRLTPSIFRKETEHMFYHGFENYLEHAFPEDELRPLTCR
PLVRDRENPAHAELNDVLGNYSLTLIDSLSSLAILSSSPDQGQKAWDYFQNGRGRGFDM
DSKVQVFETVIRGLGGLLSAHLFAVGDLPITGYNPPETEANFARAWDKHSFPEGSRGIE
WKDGFVYDGQLLRLAVDLANRILPAFYTDTGLPYPRVNLKYGVQRQPYYANSPFNAAPT
CDKANPEQCQKPRRSSTFETTETCSAGAGSLVLEFTVLSRLTGDGRYEELAKRAFWAVW
ARRSDIGLIGSGIDAESGRWVHSYTGVSQIKHVHLNMANTTTSQIGAGIDSFFEYAFKS
YVLLSSGERPPANTSSPWHALDDYFLPLSEYEHSADAFLKVWEKSHASIKRHLYRGEGH
QHPHLIQGDIFTGATRAFWIDSLSAFYPGLLTLAGEVDEAIGIHLLTTAVWTRFSGLPE
RWNVATGDIEQGLSWYGGRPEFVESTYYLYRATKDPWYLHVGEMVLRDLKRRCWTKCGW
AGIQDVRNGELNDRMESFFLGETAKYMFLLYDFDHPLNKLDQPFVFSTEGHPLIIPKNS
TAQRAERKQVPVVVESEGLTCPTAPQPPTLGVSSTAARSDLFHAANLARLHLMPSRGLA
EGPLLDYARDHPSVSVSDLSSPTNYTFFPWTLPPELVPFNATSAPMTIRPTLDISFPAL
PGMVVGPGSLERVRDGIFIKAIGGLRLSMVQDVPVQGESGSAESDEFRVQVINNVPLGK
DEKVYLLREITFDVLDPTDPNFTRVRDTAMIDIVIDVIPEIIRRRNDSDDSHEPAAPRR
ANGAIVHGSSSVDSKVGSVDASTSSMKTVLSSLVNTLSTLLRDEVQGQTSLPQKKATSL
RLLLPAAISTGLGSAPLPDVEDATTVSITGDPSKQRLTWNSIYFADELCDNRILREVAQ
NHQVLVIKRGGCNFSQKLRNIAAYPPSRYALKLVIVVSYDDEVVEEEQREESDTTTTPG
LAAVRAEPYLVRPHLDETQMTAAGVPRRQLLSVVMVGGGQETYELLRQATGVGIKRRYS
VRSQGVPINNLYIL

FIG. 7A

ATCCGGAGTACCAGAGCAACATTCTTCCGGGATTATGGCCAAGGCCGATACACCAAAGA
ACAGCCCGCCAAAGTCACAAAGCTCTAAGCATGACTATAAAGGCTTTGTAGCGGGAGTC
TTCTCAGGAATCGCCAAACTTAGTGGTATGTTCTGGCCCGCGGTGCGCATAGTCTGCGT
GCTTTTTTGGGAGTAACCATCGCTAACAGATTCCGATGCATAGTTGGCCATCCGTACGT
GACTGCGCACCTTCTTCCTCTTCCCCGCCACTTATACTGCCTCTCAATGGACAACTCCA
TATAATCTCACAAATTGACCATGGGTGATTCTCGCGCAGATTCGACACAATCAAGGTAC
GCTTACAGACGAGCCATGATGGGCATTTCCGGGGCCCATTGGACTGTCTGCTACAAACG
GTCCGCAAAGAGGGTGTTAGTGGGTTGTATAAGGGAGCCACTCCGCCGCTGGTCGGTTG
GATGGTCATGGACTCTGTGTGAGTAACTTTGCCCGGCGGCTGGAAAACGCCAAAAAGAG
AAAAGAGAGAGAGAGAGAGAGAGAGACGGAAGGACTGATCAGTCAAACACAGCATGC
TGGGTTCCTTAACCTTATATCGCCGGCTATTACTGGAAAGCGTGTTTTCGAAACCAGAG
ATTCGCGCAAGCATGCCGTTCATTGGCAAGCAGACGGATCTTCACACGCTCCCTAGCTT
CGGTCATGGCATTGCGGGCATCATGGCTGGAACGACTGTCAGTTTCATTGCCGCACCGG
TGGAGCACGTCAAGGCGCGTCTTCAGATTCAGTACTCTGCAGATAAATCCAAGCGCCTG
TATAGTGGACCTATAGATTGCGTTCGCAAGATGGTAAGAAATACGGGTCTCCTAAAACG
TCCGACCTTGTTGGCTGACCTATATACATAGCTTCGCACACGGCATTGCCGGGTTAT
ATCGTGGACTCTGCGCGACCATGGTATTTCGGTCGTTCTTTTTCTTCTGGTGGGGTTCC
TACGACGTCCTTACTCGGTTGATGAAGGAGAAGACCAGCCTGTCTGCTCCTGCCATCAA
CTTCTGGGCCGGGGGGATTTCCGCGCAAGTTTTCTGGATCACGTCGTATCCGTCCGATG
TGGTGAAGCAGCGCCTCATGACGGACCCGATGGGAGGCGCCCTGGGCGACGGGCAGCGC
AGGTTCCAGTGGTGGAAGGATGCTGCAGTGGCGGTCTATCGGGAACGAGGGTGGAGGGG
GTATTGGCGAGGGTTTGTGCCATGCTTCTTACGAGCATTCCCGGCGAATGCCATGGCTT
TGGTTGCATTTGAGGGTGTGATGCGGTGGCTGCCGTGAGATCGTGGTTCGCCGCCGAGG
CAGAAGGCGACGATGAAGCTACAGAAGCACAACACACGGATCTCGCTAGACCCGAACGA
TTAAAATGAACGGGACTCCAATAGATCCTGAAAAGAAGGCTATGTAATGTGATAGACGA
TAGAAATAGAATTGAATTCTCCAGCCAACCCATCCAACGGGCCCGATCGTGGGGCGCGT
CTCACAGCAGGGATTCATCAATCTGGCCGGGTGCAACGGCCGCATGCGGCGATGCCTCG
CCCAATGCAGCCACTGCTGCACCTTCCACTACCTTGTGCAATCCATGGAACAAATCCTT

FIG. 7B

```
CGGATTCTTGTCTACGAAGAAATCAAGTTTGACTGACCCAAATCGGTGAGAGGAGACGG
CAGGATGTTGTGGTAGACAGAAGAGACAGAGAGTGAGAGAGACAAGTGTGTGCAGGAGG
TGAATCGGGAGACAGAGAGAGGGTTCGGGCTCCGCGTGTACTTTTTCCGGCCTGCTTCA
ACCTTGCCATAGTTCGTTCCATCCCGTCATCTCCAATCTATCTTCTTCCCTCACTTCCT
CCTCATCTCCTTGTCCGTCTTGAACTTCTTCGGCTCCCTCTCCTTTCCCTCCGCAGTCT
CTTCCGCTATGTCCGGGGACCGGGATCATCCGCCTTCTGATTGCTGGCTAAAGAGCTCT
CTCGCCTTCTCGCCGGGCCAGATCGATTCCGCCGCCGCCTTATCCAATCGCGCAGTCCA
ACCACAACCATCACCTTGACTGCGAACCTCCCCCCTTCTCCCTCAATCAGCAAACGGCT
ACGATGGCCGTCGCACGCTCGATGCGTCGCACAAGCCCCATTACGGTCTTCCTGGCTGC
TCTGCTAGCTTTCGGATTCCTTTGCTTTCTGCTCTCCCCTTCCTCGTCCGCCGCCGCCC
GCCGCTCCTCCTGTCACCGATTCCTCCTCGCAGCTACGACGAGAAGATGCCGCCGAACA
TCCCCTTTCTCCTCCGACGAAACCCTTCCTCAAATCTCAAGCCGTCCGCGAAGATGGCC
TGAAAGCACCCCCGCCAGTGATGCACTACAATCTGAACGAGCTCAGCAGCACCAGCGAA
TCCATTAAGAAAGGGGAACGGGTGCTGATTCTGACCCCATTGGCCCGCTTCTACCAAGA
ATTCTGGGACAATGTAGTGAAACTGAGCTATCCACATGAGCTCATCTCGATTGGATTCA
TCGTCCCTAACACCAAGGACGGCCATGCCGCGGTCACCGCGCTGGAGCAGGCAATCAGC
GAGACTCAGTCTGGTCCGATTGACAGCCGCTTTCGCCAGCATCAGCATCCTTCGCCAGG
ACTTCGACCCGCCCATTCAATCGCAGGACGAGAAAGAGCGCCACAAAATGTCCAACCAG
AAAGCACGTCGTGAGTCCATGAGTCGCGCCCGCAAACAGCCTCCTCTTCACCACCCTCG
GTCCTAGCACCTCCTGGGTACTCTGGCTCGACTCCGACATTGTCGAGACCCCAGCGACC
CTTATTCAAGATCTGACTGCCCACAACCGACCTGTGATTGTCCCGAACTGCTTCCAGCG
CTACTATAACAAGGATGCCAAGAAGATGGATGTCCGCCCTTATGACTTCAACTCGTGGA
TCGACAGTTCGACCGCCGAACAGCTTGCGGAGACAATGGGGCCGGACGAGATCTCCTCG
AGGGAAAAGCTGGACTGCCCACCCTCCGGCACCCCGGAGGCCCACAAGGCCAAATTCCG
GGGGCGCCCCGTCCTAGCCGCGAAATCGAACTCGACGGCGTCGGTGGNACAGCACTCC
TTGTCAAAGCGGATGTGCATCGTGACGGCGCCATGTTCCCCGCCTTCCCGTTCTATCAC
CTCGTCGAGACGGAGGGTTTCGCCAAGATGGCGAAGCGTCTGGGATATTCCGTCTACGG
```

FIG. 7C

CTTGCCTGATTACTTTGTACGTTCCCCTACAATTTCCCATCCGATTGAACCCACTAACG
CCATGGCCACAGGTGTATCACTATAACGAGTGATGCGATAGATTTCAATTACGAGATGA
GTTCACATGAAGCGAACATCCGACAATAGACCGGAACGGAGAATGTTTTTTTTTTTTT
TTTCTTGCTTTGCTTTATTTTGCTTTGATTAGACTATCCTAGTTGGCGATTTCCACGTC
CACTACAAGATTCAGACTTCACTTTATCCATCTACATCTACTTGGGGCGTTATTATTTT
ACGTCCGCGCGCTGGGCGCTTAGTGGTTCTGGTGTTCGGGCTGAGTAGCTGTCTTACAA
CTACTACTACTATATATAGTTAGGATTTATGTCCATTTGCTATACACTGCACTCGCCTG
TTCAATGCGCAAACAGTCAATAAGCCGAGGAAGCGTAGGTTTCGTCCGTGCAATATGGA
CGAGATTACTCCTTAGTGGTAATATGGCACTAGTACCTCGAAACTTCGGTATTGAAATT
GTCTATTCTGTGGCGAAGTCCACACCATTATTTACTACTAAGATACTGATTCTATATCC
ATAAGCCGTCTCTCCGTTTTTCAATGTGCTTCCTTCTCATAATCGTCAGTCGAGCTATC
GCGTTGGGCTTGTTGTCTAATCCCAAGAAATGCTACGATGACCGTTAGCGATGGAGATA
ATCACGATGTGTCGTACCAAGGAAGGAGGGATAGAAACATACACAAGCATAATCCCCGC
CCCCAACCATAACGGCCAAGAACTGCACGATTGTCTTCTTGATCTCCACGCGCTTATCC
TTGCCCGTTTCCAATAACTCCGGGATAACGGAAACTGTTCCTACGTAGAGGAATGTCCC
TGCCGTGAAGGGTAGGAGCATATCGCCCCAGGTGAGGCTTGTTCCGAGGAGGCCGGTTG
GCAGGCTATTAGTGGATGTGGAGGTGGCAGCAGTGGAGCCATTCCGCCCAACTCTTGG
ACGGCGATTCCGATGAAAGTGCCGAGGAAGGCGCCAATGGCTGTGACGAATTGCGCGCC
CATAGCTTTGCGCTTTGAGAAGCCGGATTGGATGAGGAGTGCGAAGTCGCCAACCTCGT
GGGGGATTTCGTGGAAGAAGACGGCGACAGTGGTGGTTGCGCCGATGGTGGGGAGGCG
TAGAAGGACGAGGACATGGCGAGGCCGTCGGTAATGTTGTGAGTGAAGTCGGCAATCAG
GTTGAGGTAGCCGCCCAATTTGACGCTGAGGTTGATATCCTTCTCGTCGTCCTTGTCGG
CGGGTTGGGGAGCGGTGTTGCTGCTTGCGGGCTTGCGCTGTTTGAGATCGGTGGAGGGT
TGCGGGGAGGCGCCGGTTGTTGTGCCTGTGGGTTTGTGGTCGTCGTTGGCGCTGTCAGT
GTGAGCGTGGGCGTGGGAGTGGTCGTGTCCAGCTCCTCCGGTGGCGATACGTAGGGTTT
TGTCCATTGCGACGAAGGTGAAGAAGCCCACCATGATTCCCAGGCCCAGGAGGAGGTTG
CGGTTTGGCTCAACCATCACGAAGCGAACATGGTCTGGGGAGTCTTCGCCGAGAAAGAT

FIG. 7D

CTCGGGGAGCAAGTGGAAGATGGTATCGCCTAGGAGGCCGCCTACTGCGAACGCGACCA

TGACGGACAGGGAGGAGGGATCGATGTTTGGAGGGCATAGGCCAGGAGGA

FIG. 8

LSDSFAFCSPLPRPPPPAAPPVTDSSSQLRREDAAEHPLSPPTKPFLKSQAVREDGLKA
PPPVMHYNLNELSSTSESIKKGERVLILTPLARFYQEFWDNVVKLSYPHELISIGFIVP
NTKDGHAAVTALEQAISETQSGPIDSRFRQHQHPSPGLRPAHSIAGRERAPQNVQPEST
SLLFTTLGPSTSWVLWLDSDIVETPATLIQDLTAHNRPVIVPNCFQRYYNKDAKKMDVR
PYDFNSWIDSSTAEQLAETMGPDEISSREKLDCPPSGTPEAHKAKFRGRPRPSREIELD
GVGGTALLVKADVHRDGAMFPAFPFYHLVETEGFAKMAKRLGYSVYGLPDYFVRSPTIS
HPIEPTNAMATGVSL

FIG. 9A

CGAAATGCTGATATGTTCGGCTTTTGGCGACTGGTGATCCAGTTTTTATTCAACGACAT

GTCATGCTATTCCTCTTCCGTCGTTTCGAGCTGGTGACTCCTGAACCGAAGAGTAATTT

TACTTTAATTTCTAGCTCTCTTTTAATTTTCTGGGTCGATAGCGATCTGTTACTTCACT

AACGTATCTCCTACACCTCCGCTCCAAAACCTCGTCCTTTTTTTCCATCCTGCTGCGCT

CCTGTTCCCCAAGTTGCGGGCGCCCGTTTCAAAGAAGACATCTCCCATTGACCTCCTC

CACAGCGGCCCTCTGCCGAGCACGAACTCCCCAATCACGCCCGCCTGTGGCTGCTCCGC

GGGCCGTTGTGCTCGCCCGCCATTGCCCTTCCTGCCGGCATCCCTGTCGGTTCCGACTC

CCCGCTCATGTCCTTGTCGCGATCGCCCTCTCCCACCCCGCGGGAGCAGGATGGTCTA

GTCCTGGACTCACTTCGCCCAGTGGCTCTACCACGCCTCACAATGGCTTCCTGTCGCCA

AATCCCATAGGCGCCAGCGGCATCTCCTGGGCCGCCGCCAAAGCGAAGAGCGACGAGGT

ACGAGGCTACCCGTCCTTTTCGACGAAGAACAGCGGATTCTTCTCGCGCTCAAGACGCC

AGCTCTCCGCCACTTTGCCGCGCTTTCGTCTGGGCTCGGGTCTCCGAATGGTTATGTC

GATAAGGATGAGTTTGGCCGGGGCGGCCTCTCTCCCAGCTACGGGCTGGCGCTTGGG

GTTTGGCAGGTCGGTTCTGCGGCGCAGACGATCGCGCTTGCTCGTGGCGCTGATCTTTC

TTTTGCTGGGCTATATGTTTTTTGGGGCGTGTAAGTGAATCGCATACCAATGGGAAGAA

AGCCTGCAGGTAGCTGACCTTGTTACAGCTCTTCTCCAGAAGTATCGGCGCTCTCCGCT

AGGCGGTGGGCGCAAATTCGTGATCATACTGGAATCCAACATAGAAGGCGGCGTGATGG

AGTGGAAGGGAGCGCGCGAATGGGCGATCGAGCGCAACAGCATATGGAACAAGAAGAAT

TATGTGGAACGATGGGGCTACGAGTTGGAAACCGTCAACATGTTGGCGAAGAAGCGGTA

TTCACACGAATGGCGCGAGAGCTGGGAGAAGGTGGACCTTATCCGGGAGACGATGCGAA

AGCATCCCGATGCTGAATGGTATGCTTGCCGTATTTGATTCCGTGAGCGTCACTGACAT

CTTGTGCAGGTTTTGGTGGCTGGACCTTAGCACTTGGATCATGGAATACTCCTACTCGT

TACAGGACCATATATTCGACCGCTTGGATGAAATCATTTACCGGGACATCAATGTCTAT

AACCCATTGAACATCAGCCACCCGCCGGACGACGCTTATCTGGACGAGGTGTCTCGTTC

GCCAAACGGAGACGGGGACCCATCATCGGTACATATGCTATTGTCGCAGGACTGTGGGG

GCTTCAACCTCGGCTCTTTCTTCATCCGGCGCTCCCTCTGGGCCGACCGCCTGCTGGAC

GCGTGGTGGGACCCAGTCATGTACGAACAGAAACATATGGAGTGGGAGCATAAAGAGCA

GGATGCGATGGAATACCTCTATGCGACGCAGCCGTGGGTTCGCAGCCACGTTGGCTTCC

FIG. 9B

```
TCCCTCAACGCTATATCAACTCGTATCCCCAGGGGGCATGTGGGGACGAGAATGACCCG
AATGTCCACTACCAGGAAGATGAAAGAGACTTCCTGGTCAACATGGCTGGGTGTCAGTA
TGGACGCGACTGCTGGGGCGAGATGTACCAGTACCGTGAAATCAGCAAGCAGCTGAACC
TGACATGGTGGGAGCGGATGAAGGACAAGTTGAACGGCCTTTACGAGAAGCTTTTCCCG
GGCGAGGAACAGCAAGTTGAATGAAAAGTCCGTTGCTGGGATACGGCATGTTGCTTCA
CTTTGATGTTTACTGCAGATGATGATTGGTCTGAGACATGACCATGTAAAATGCGGACT
AATAACGACCTGGCTGACGGCGTATGGGATGGATTCTACGTGTTTGGCTGATTTGCTAT
TTTTGGCGAGGCGTTTGGTGTTAGCGGTAGCTATCTAGACTTCAAGTAGCTCATCTACT
ACCTCTTTATCTGTGCTCTGCAATAATCAAAAGACTTACGAACTAAGTATTATACAATT
GTAGTTGCACAACTAACCACTCATAACCCGCTTAGTAATTATCCACAGCCCCACGTGAC
ACAATGAACTTAGCACACCCGACCGCCCACACCCCCAACCAATCAAACCACCGCAATT
GCATCTGCTACTCTCGCGACCTCCGGAATTGAACTTGATACACTGACTGACCTCTCTAC
GTACGTACTCTCCCTCCGGTCCCTCCTCCAACCTACACACCGAACCTCCTCCCCCCGAA
GGCAACAACCAAGGGAACACCGAAAATGCCGACCCCCGAATCCGCCTCCTTCCTGGCCA
AGAAGCCCACCGTGCCGCCGACCTACGACGGCGTCGACTTCGAAGACAACGTCGCTGTC
CACAACGCCCGCGACGCCATTATCCGTGAACAATGGGTCCGCAGTATGATGTCTCGTCT
GGTCGGGGAGGAATTGGGAAAGTGTTATGCGCGTGAGGGCGTTAATCATTTGGAGAAGT
GTGGGGTTTTGAGGGGTGAGTTTATACCTGTTCTTTCTTTCTTTCTATCCCGGGAGCCC
TTTTGGGGATGGTGTGGGCTAGCGAAGATAGAGTGAGAATTATGGCTAATATGTGTCTC
TCTTTTCGGTGTGTAGAGAAGTACTTCGAGTTGCTGGGCGAGCGCAAGATCAAGGGTTA
CTTGTTCCAGGAGAAGAACTACTTTGCTGGGGAGGGAAACAAGTCTGCTTAGATTTTGC
TCGGTGGATTGAATCGAAATTGGGTTTGCAGGGTTTCTGTGTTATGTTATGTGATATAC
AATATATGCATTGTGGTTTCTTTTCCTACTTCTTTTTCTTTTTCTTCTGGGTTTGGTTT
GTGGGGAGTTAGAGGGTGTGGATGCTGGTTTTGACCAGTCCCGGGCTGTGATTGTATGA
TATGCTTCGAGATGGGGTGGATTTGGCTCTGCCGTGGTTTATATACTGGGTTGTGAGGT
GCGAGTGAGGGGTCGAGTGTCTGTATTGATACTGCGTATGTGGAGTAAGCATTATGGGA
TGGTAATATGCTTGTGCTCAGTGATACATGTATAGGAAGAAGCTCGAAGCTCGAAGCTC
```

FIG. 9C

GAAGCTCGAAGCTGAGATCAATAATAGGCACTGTCGCTCCGCTCCGGTACTGTCCCCGG
CGTATACACACGCGCCACACTGGCTGCCTCCTCGTCACTGTCCTCGACATCACTTCCCG
GTCCAAAGTCGTCCTCCACCGGCGGCGCACGCATGCGCACCAGCTGCTCCTCATCCAGC
GAGGGAATCTTGTATGGTGCTGGCGCCGAATGGATATCTCGACCGGAGGGCAAGTTGGC
AAGCAAGGTCCGTAGAGGGTGGGATCAGCTGGGTATTGATCTGTGTTCGTCAGCAACAT
CATCCTAAACCAATGACGTGAACATCACCAACCGTATCATTCATCCGCACCCACTTCGT
CTCCAACATCTCAATCACTCGACTCTCCTCCTCCCGACCTGCATTATCCCCGGTCCTA
GCTCGCCCTTCTCCGTCCGATCCCGACTGCCCGCATCTTTCTCCATTCGTCTCTCCTCC
CGCCGCTCCATCCAACCCTGCTTCAATCTCGACAGTCCGGTCCGACTCTTAGTATTCGT
CTCCTTTGTTTCCGCTGCAGCTGTTCCAGCTCCCGGACCCCCAATGCCCCCTTCGCTG
CTCTCAGCCATGCAATGCCCTCCCCGATCTTCCCAGACAATTCCGCATCCACCCCGAAG
AACCGGCAGGCTCTCGCCCGCGCAACCCGTCCCAGTACCCGCGTATACCCTAGCAGATC
ATCATCAATTCCCATCCGCCCCTCTGAGCGGACAGATCCCAGCCCCGCAGCAGCTTGTT
CCGCATACTCCGCAGCCCGGATACATAATCTAGCGAAGAGGTGCGCCCGGACCTTGGGG
ATCTCCGGCGCGCGGACCATCCAGTCCTTGTCATTGGGATTGCGCGCTTGAATACAGGC
CGCGACGTAGGAATCGTCCTTCAAGACAGCGAGGAGAGTTGCTTCTGCGAGGGCGAGAC
AGGACAGGGCCGCTTGCGTGGCGGGGTCGAGGTCCGGGAGGGTAGATGTTCCATTTTTG
TTATTGCAGATGGAATGGGCTGCAGTTGCGAAAGACGGCGAGGAAGCGAGGAGCGAGTG
TACGGCGCTGGCTTGGAGGAGGTGTTTGGTGGCTGTTTGGATGGCGGCGGTGCGCTGTT
CCGGAGTCGGGGTCGCGGATGCGTAAAGTGTGCGGGTGACGCCAATGCGGGCGAGCGAG
TTGAGCACGTAGCTGAGGGTGGAGAGGACAAAGGCTATCTCGAAGTCGAGGCCCTGTCC
TGGATGCGGGTGGTGGTGGGCCGCTGTTGAGGAGAGCGTG

FIG. 10

MSLSRSPSPHPAGAGWSSPGLTSPSGSTTPHNGFLSPNPIGASGISWAAAKAKSDEVRG

YPSFSTKNSGFFSRSRRQLSATLPRFRLGSGSPNGYVDKDEFGRGRPLSPATGWRLGFG

RSVLRRRRSRLLVALIFLLLGYMFFGASDLVTALLQKYRRSPLGGGRKFVIILESNIEG

GVMEWKGAREWAIERNSIWNKKNYVERWGYELETVNMLAKKRYSHEWRESWEKVDLIRE

TMRKHPDAEWFWWLDLSTWIMEYSYSLQDHIFDRLDEIIYRDINVYNPLNISHPPDDAY

LDEVSRSPNGDGDPSSVHMLLSQDCGGFNLGSFFIRRSLWADRLLDAWWDPVMYEQKHM

EWEHKEQDAMEYLYATQPWVRSHVGFLPQRYINSYPQGACGDENDPNVHYQEDERDFLV

NMAGCQYGRDCWGEMYQYREISKQLNLTWWERMKDKLNGLYEKLFPGEEQQVE

FIG. 11A

CTATATGCTGCTTACACTGATCTGCTTTTGATCGTCGGCGGAGCTTAGCGGCAGAGACG
GCTGCGGTTCTACATAACACAGCTGTCTGCCAGCTCATTGCGCCTGTGTGACAATCCAC
CTAATTAGCGATCTTCTCATATTCCCACAGAGATGCTCACCTTCCGGAAGTCGCTACTC
GCGGCTGCGCTTCTGATTACCTTTATCGTCTACCTCCGATCGTCGCATACCGCCTCTTC
CCTTCCGTCTCCGGATACCTCCTCCGCCGGACACCTCTACAACCAGGATTACGATGGTC
ATGCAGACAATGAGCGAAAAGGTGGAACTAGAGACACCGTACAACAGCTGCCGCTGACC
CCGCCACCGAGCGCCCCCTTGCGCGATCGCTTGCGCTACCACTTTCCGTACGATCTGGA
AGCCAAGTTCCCGGCGTTCATCTGGCAGACGTGGAAATATGCGCCGTCATCGATGTTCT
TCAGCGAAAGCCTGCGTGATCCGGAGTCCAGCTGGTCCGAGTTACATCCCGGATTCGTC
CACGAGGTCGTTCCCGATGATACCCAACGCCATCTGATCAAATACCTGTACGGCGCTGT
TCCTGATGTGTTCGAGGCTTACGATGCTATGCCGTTGCCCGTCTTGAAGGCCGACTTCT
TCCGATACTTGATCTTGCTCGCGCGGGGTGGAATCTACAGCGATATCGATACCACGGCG
TTGAAGCCGGCGTCTGACTGGCTGCCAGCCGAGTTGGATCTGGCCACAGTTGGAGCGGT
GGTGGGCATTGAGGCGGATCCTGACCGCCCCGACTGGCATGACTGGTATGCGCGCAGAA
TCCAGTTCTGCCAATGGACCATCCAAGCCAAACCCGGACACCCCATCATGCGCGATATT
GTCTCCTACATTACGGAGGAGACATTGCGGATGAAGAAGGCGGGTATTCTAAAGACTGG
CAAGATGGACAAGACCGTCATGGAGTACACTGGGCCAGGCGCTTGGACGGATGCGGTTT
TCCGGTATTTCAACGATCCAGAGTACTTCAACATTGAACCCGGCTCGACGTTGAACATC
ACCTATGAGGACTTTACGGGTCAGGAGGGATATAAGAAGGTCGGAGATGTGGTGGTCTT
GCCCATCACCAGCTTCAGCCCGGGAGTGCACCAAATGGGTGCCGGAGATGTTGATGATC
CCATGGCATTCGTGAAGCATCACTTTGAAGGTATGCCGCCTCAATTCCTCCTATTGCTT
GACTCAAAGCTAACACGCCAACCAGGAACTTGGAAGGATGACTCCTCTCTATAAGCCGT
CATTATAAATCGCTTTACATTACACCTTACACTACGATACGTGCGCGTGGTTGAATCCC
ACTGCTTCGTCGACAGGACTTGCACAACGCACGTCCTTAGACAGCTGGATATGACCATA
TAGCATAAGTGGCATATCATCAGATCCTTGCACCTTGTCGGTCGGACACGAGCAGGGGC
CCTTCATGGCCACCTACACAACAACCTCGCAGCATCCACCCAACATTTTCCGTCCTCAA
ACTCAATCTAATGCCCCTTGCTCACCCAAGCTAGCCATGTCCCGTATACGAAAATGCTG
GCTCTCCGGCAGAGTGAGCTATTGCTTTGTGCTCATGACTCACGGCTCTCAGCTTAGCT

FIG. 11B

```
TTCCATCCATGACAAGCATGTCCGAGCTGTAGCTCGATCGCTAGCATGCTTGTCAAATG
GGCCCCCGTCTGTTTCTTCTCTGTGTCCATATAACCTACATATGTTTTAGTGTCTTGC
TCCAAAATCTTTAGAATTTGATACCCGCAGGCTGGGAACACGAATGAGAACAGCGATGC
ACTTTGATCTCTTGACATATGTTTTACCTAATCTAGAGTTACATTGCATTCCGGAATGT
GCCTTTGCGCATACTTTAATAGAAACTCGTAATTTGCGCTCTTCCTTTCCTTCATAGGT
CGAATGAAACGGTAATGCTTTAATTGTCTACAAGAACGACAACATCTTGCTGTCTTGAA
GCATTATGACTCTACTTCATAGCGGAAATCACTTCGTATCCGCTCTACCAACCGCAGAC
AATCGCGTCTCTTCTCAGCCGTGACCAACATCCAGGCAATAAAATGGACCTCGCTCGAC
TTTGGTCCGACCAATCTGTCCCCTTTCTTCTTGATTGTCGCGTACAGCGGCACATGTGG
CTCCAATTCAGGGTACTGATGGAGCAGCTCCGCTGTGGCATCTTCGGTCTTCATGATCC
CGGCAACATCTTCTTGGAGGACGAGCACCGAGAGATTATAGCGAGGTCCATTTAAGAAT
GGATGGCACAAAGCCCTGTATCGAAGCTCGTCATTGACTGCGAAGAGCATCTGCTGGGC
GAAATAATCCACTCCGTAGACCAAGTTGACGCCAACAGTCTCCAGATACCCTGCTGGGC
GGGCGTTTATCTCGAGGAGGTACACACGCACACTCTTCTTCCCATCATTGGTCTTACCT
TGTCGAGGATACAAATCCTCAACCCCGTTCTCCCTGTCTTTTCGGAACTCATGACTCGA
ATACTGTAAACGTGCTTCACAATGAAAGGTACCCGTTAGAAATCCTTGACGAAGAATAC
TCTGGTGCAGCGCGTTCCGGATGGCCTTCAGCTCATGCGGTGGAAGCGCAGAGGGATA
TGGACCATAGTCTCCACGAAGTTATGGCTTTGTTGTGCGTCTAGGGTCCCCAGGGCTTG
GAAAGTCGTCACTAATCTCGCAAAAGATGACTTCACCATTTAGCAGGACGAAGTTCGCG
TCGACTTCCGGTCCATCGATGTATGGCTCAATAACGGCGTCACTTCGCTTCTGTGGACC
AAGTGCATGGCAGTCACAGGCTTTTTCGACTGCTTGAAATAGCTCGTCTTCCGTGGACA
CTTTGGTGACAGCTTGACTTCCCCACCCTAAGCACGGCTTGACGATGAGGGGATATGAC
ACTTCGGTGGACCGAAGAACCTTATCTAACTCGTCCGTCCCGAAGACCCGAAATGCCCC
GTGCGTGTCTGGTTCCATTAGTCGAGTTTGATACTTATCTCCGGCGAGGATATAGGCTG
AAGATGGTGAGGTAGGGTATCCGAGGATCTCACACGCTCGAGCCACCCCGATCATGCGG
CTATCGCTCACTGTCATCAAGCCATCAATGGGCTTATCGTAGCTGCGGACGGCCGTGAT
```

FIG. 11C

```
GATCCTATCGACGAATCCCTCATCCACGTCAATATTTGCGGCGACAAATCCTTCTCGGA
GATGGGCGTACGGGCCGTTGTCATTCTGCAGCCAATGCCCCGGCTTGTCAATGATCACC
AGAGAGATCCCTAGGGCTGCTGCCGCCTCGTACATGCGTCGACTCGTATCCGCGTCTTT
GCGACCTTCTACCCATGCAAGGCGTTTTGGCACAATTGATGTAGGGACTACCCATGGAT
ATGAAATCCGGTTACAGAGCGCCTCTTCGACGCTCTGGAGGGTGTCGTGAAGATCAGAG
CCAGAGCCAGTGTCGAGAAGGACCGCACCGACAGACATCGACAGAAGTGTGCTCAGATC
ATGCGCTGTTCCATCTATCTGGACTTGAGCGGTCGTGACTTGTTGTAGTGGACGCGAAA
GAGCTACCACCTTGGCAATGTGCTTCACCCCATCTAAGCGCTGCTCTAAGAAATCGGAT
CGAGCGAGATAGCCGTCTACCCTGGATAGGATAAACTTCATGATAACCGGGCTCTTATT
ATCAGCCCCTTTGTTGCGTTCAAAAATAGTCGTGGTAATGAAACTTGTGATTTCTGGGG
TCAGATACCAAGGGGTGCAGGACTCCTTGTCATTATCATTTTGGTAACCGTCGAAGCAT
ACTGCTGATGCAGCATCTTTGTTGTTATAGGTCTTTGTAACTATGGTATTCGTAGGGTA
GAGTGTGAGATTGACAGATTCATGTTTCTGGCCAACAAAGCCCTTGACTGGGATCGCCT
TGTTCCATTCACATGTAAAATGGTCTGATATGCAAATCCATGATTAGATAATGATCAGT
GAAGCAAGAAATGGCTTGTTGGTGGTGGTGTACCAATCTGATCCTGGGTAGTGAGAGCT
AGGAAGCAACTGTAGGCCATTGTGGGCGCTGGCAAGACAGAGTCTCGATGAAATTGGGT
TTGGGGGGGGGGAAAGATGAGTTAGTAGATGAGAGCCTTTCAGCCTGGAGTTTTAATA
CCCGAGTAGCAGGAACACCTTCACCTGTGTCATACTCTTTCCTTGACCAAGCGAGGCAG
TTTCAGTATTGGGAGAAGCTCCAGGCTCGGATTCGGCGTACCGTACTGACTGGCTACGT
AGTCAGTCACTACTTACTCCGCAGTCCGGGGTTTACTCCGATGCCGTCCACCAGTGAGC
CCTTATTCGTGCAAATTATGTGGGTACCTGGAATTATAGGCCACTTTAGCCCTTATCCG
CATATGATACTTCTTGGGTTAATTCTCAAACAGAAGTGTCATTTGCTGTTGACACTCAC
TCCAAGGCAAGATACTATTGAGTACTTGCATTGGTTCGATGATTACAATTGCTAGATCT
GCACCGCGTGTCCAGTCACTGGCCTCACTGTTCCTGATTTAAGGACTTCAAGTCAAAT
TCACATCACCCAATTGCCCTTCCCGGTTAGGCATTCATCTCTGGCACATGTGCATTAAT
GTAGGTCAGCCTTTTTGAAATGCGTGACAAAGTGGAGTATGATCTTTTCGGCCAGCAAC
CTGCACAGCTCGGTGTCCCAAGATTAGCGGCCATTGGAAATTATTTTAGTAAGTCCAGT
```

FIG. 11D

```
ACTTGTCATTCTTGGGGTCGGTCCCTTTTGGGTAAGAAGTAGTACAAATTAGCTACCAC
TGTTTCATTAGGAGCCTCCACCGGTTTTCTACCGTCACCAAGTCAGAACCGGAATTAAC
CATTTGGACCAGGATGGACCATCTTAAAACTTGATTCCCAGAATCTGTATTTATTGCCT
TCAACAAACCAGAAGGTCCCAAAAATTGTTCTTTTGGATTGCATTGACAAATAAGCATT
CTTATCAAAGCATCTCCTTGCACGGGCCCACAGGCGGGTATTTTGCCAATATTTTCTTC
GGACAAGTCCTCACGGATAGCTTCGATGAGATCAGCGTCACAACTTTCAAACACCTTTA
CTAACCGTTCTGTTACTGGAACAGGCAAGCTATGCATAATACATATTTCGATCAGAGGC
ATTAAGCCACTGTAGTGTCTTTTAATCGAGTCTTGATCACGAGCAGATGAATTCCGGGC
ACTCTGAAAGACTTCCTCCGATAGATCGACTGCTCTAGTATATCGAACAATGTGGCTCG
CAGCTTTATACTGAACTGTTGGCAGAATGAAAGGCTTATGACAATTTAAATAGTCACAG
TTGTTCCTTTCAAACCTCCAGATCGCTCTCCAAACGTCGTTGAAGTCTATTTCGGCAGG
CCACTTATGGAGGAGCCACTGTAGCCCGGAAAGGCTGGTTGCGGCAGCAGCAACCATGA
CTCTTTCAGTAAGTGGCAGTGCCTGGAAGCCATACCTTTCAATTAACCAAGGTAATGCA
GACAGTTTTTGATAAGTGGCAAGCATAACCACTTTCTCAGTTAGGAAAGGAGGCACATC
GGGTCCAAGTGCGTGGAGAAGAAGTTGAAAAGCGTCCAAGGTGTACGAGGCTGCCAACA
GAACTTTCTCAGTTATTGGTACTTGTGGGCCACAATGAGCGAGAATCCGTCTTATATTG
TTGGTCGGTCTTTCTGCTCCTGCCACGGCTATCATGAATTCTTCCGAGATTGGAATATC
CTCTATTCGCTCATCGAGCAGAATGCACAGTGCTTTCTCGTGGGATGCTGCTGCTGCTC
GGATGGCGGCTTTCTCTGTGATGCATACACACGGTGCTGTCCGCAGCAGGAGTTCCAAA
GCTGGATGATTGTGCGCAAATCTTTCCACAATTCCTTGGTCAACTTCGAAGAGCTTTCT
GTCCAAAAGGAGTTGGATTATTTCTGTAGCACTCTGATGATTACCGTACTTTTCTAATG
TTATTAGCATCTTCGAGACCGGTAATTGTCCATGCGGTTGTTTCATTAGAAGCGCTAGC
ATCGATGAATCGCAACTGCATGCTTCAACAAACATATTATCGCTCACTTTGGCCATTGG
TCGTACGCGGAAAATTGCCTTCACAGTGTTAGTTGTGAAGCGTCTTACAGCATGCGACA
TGACTTTTTCCGTGAGAGGAAGGGCCTCTATTTGAGACCTTGCTTCAAGATCTAATAGA
AAACAGATCAAGGCTTCACTCCTTGAATTGAGCAATATGTCTTCGGTTATTGAGATCCT
CAAGCCTCCGTTGTTCATGAGTATCTCAAAGATATCTTTACCTTGTGGGTTAGAGGCTG
```

FIG. 11E

CTTGGCATAGAATTGCATGAGTGACGGTGAATCCAGCTTGCTGCCTGTGTAAAAGCATG

TTGAGAATCTCAGCTGCATATATCCATTTGTTCACGATCTTCAGCATGACTTTTTCGCT

TATTGAAAAATCCGGACCACAGTCATCTAGTAGGAGTTCAAGCATTTCGAGACAATGGG

GTGCGTTCGTATTACACACTGCCGTACAGAGTACATCCTCGCTAACCTGTGCCCGATTC

TGTCGTCGACGAAGAATTTGACGCAAGACATCGACATGGAGTCCATTATTAGCCGCTCC

TACGAACACTTTTCAGCCAGCAAGAAATCGTCATTCATGTACTTAGATCTCGATCTA

FIG. 12

MLTFRKSLLAAALLITFIVYLRSSHTASSLPSPDTSSAGHLYNQDYDGHADNERKGGTR
DTVQQLPLTPPPSAPLRDRLRYHFPYDLEAKFPAFIWQTWKYAPSSMFFSESLRDPESS
WSELHPGFVHEVVPDDTQRHLIKYLYGAVPDVFEAYDAMPLPVLKADFFRYLILLARGG
IYSDIDTTALKPASDWLPAELDLATVGAVVGIEADPDRPDWHDWYARRIQFCQWTIQAK
PGHPIMRDIVSYITEETLRMKKAGILKTGKMDKTVMEYTGPGAWTDAVFRYFNDPEYFN
IEPGSTLNITYEDFTGQEGYKKVGDVVVLPITSFSPGVHQMGAGDVDDPMAFVKHHFEG
MPPQFLLLLDSKLTRQPGTWKDDSSL

FIG. 13A

GTCGACGCCACCGGCCGACTCCGAGAGCAGGTGGTCTTGGGTGACGGCTGAGGGAAGGG
GGTTTTATTAACTTAACTCATGTTGTACGCGGTGCATGTACCTAGAACTATGGCAGGTG
GGAAGGCCGGGCGGGCGGTGGGAAAAGGCCTTCACACCGAGATGGTTATGAGCCGTCTT
ATATATCATCAACTACCCTCAATACCTACAATGAATCATTCGACCACATTTGACGATGG
TAGTAGTAGTAGTAGTAGTAGTAGTAGTATAGATGTTCTGTAGAAGTATGTATAAGCCT
CAAGCCTAATGTCCATCCCCATTGGTTGCATTTCCAACCAGTAATAATAAGATTTTAGT
AGTATGCTGCAGAACATCCCGAAAAGGCCGTCAATAGAAGCCCGGCTTGAATAACACAG
TGGATGCCTCAGGCGACAAACACCCCGTAGATCTGCTGCGCCTCCCGTTTCACTTGCT
GATCTCCTCCAACTCTCCGGCCGTCGTGTCGGAAACTCAACCTTGACAATCCCTCTTCT
GCTTTGATTCTCGAGTCCATGACTGCATTCGTTCTTTAAGAGCACGAACCGGTGCACAA
ACTGTTCACTACCTTTCGCACTCCTCTTCGACCCCATCACCGCCGATCCCCGAGCCGA
CGATAACGATCCCTCGGCTCTTATCTACCGGAGCTGCCAGTGACTCCCTTCCACCGCTA
CCCTCGTGATCATATGTGACACGGAGACACTCTCCAGCCTTGCCTCCTTTAGGATCCTC
TCCCAGAATGGGGAAATACCCAAGAGGGTGACAACAACGAATTCCTCCCATGAGCAGTC
CACGGCCGTCCACGTCCTCAACATCCTCCGATTCGGGTCTCTCCGTCGATACCACCGCC
TACCCCGAAGAATCCAAGTACACTTCAACCGCCCCCGGCGCCGGTGGACTGTCCGATGA
GAATAGATACCGAGATGTAGAAGAGGGAGAAGCAGGGGCAGACGAGCCGTTCCTCCCTT
CGGCAAAGAAGCAAGCTGCCTCCGGAAGCCGCACGTCTCGTCTGATTTGGGGCCTGGTG
ATACTCTGCGTCGCCGGTTGGCTTTGGGGCCTGGTGTTGTTTGTGACTCAAAATCGCTC
GGCCCAGCAGTCAGTTTCCGAAGCGCTGCAATCGCACGAGTCGGGTGCGATCTCCGGGA
GTTCGAGTTCTGGAAAACCGGTTACGCTGGAGCAGGTGCTTACGGGACAGTGGCTTCCT
CGGTCCCATGCTGTTTCTTGGATTGCAGGACCTAATGGCGAGGATGGTCTTTTGGTGGA
GCAAGGAGAGGATCAGGGCAAGGGATATTTGCGGGTCGACGACATTCGGAGTCGCAAAG
GCGATGCGACTAGCCAGGAAAGCAGGGTGCTGATGGAAAAGGCAATTGTGCAAGTGGAT
GGACGGACGATCTTCCCGGTCTCAACATGGCCGAGCCCAAACTTGAACAAGGTGCTGCT
TTTGTCCGAGCGCGAGAAGAACTGGAGACACTCTTTCACTGGGAAATATTGGATCTTCG
ATGTGGCTACCCAAACCGCACAGCCGCTTGACCCAAGTAACCCTGATGGACGCGTGCAG
CTCGCAATCTGGTCGCCAACCTCAGACATGGTTGCCTTCGTGAGGGACAACAACTTGTA

FIG. 13B

CTTGCGTAGATTGTCCTCGAAGGAGGTGGTTCCTATTACAAAAGACGGCGGTGCGGATC

TTTTCTACGGCATTCCCGATTGGGTCTATGAGGAAGAGGTCTTTTCGGGCAATAGTGTA

ACATGGTGGTCTGGAGACGGGAAATACGTGGCTTTCCTGCGAACCAACGAGACGGCTGT

CCCTGAATTTCCCGTCCAGTACTACCTGTCACGGCCATCTGGCAAGCGACCTCCCCGG

GGCTGGAGGATTACCCAGAAGTCAGGGAGATCAAGTACCCCAAGGCTGGCGCTCCCAAC

CCCGTTGTCAGTCTGCAGTTCTACGACGTTGAGAAACAAGAAGTCTTCTCGATCGAAGC

ACCGGATGATTTCGAGGATGACGATCGCATCGTCATTGAGATCGTGTGGGGCACCGAAG

GGAAGATCCTTGTGCGCGCAACCAACCGAGAAAGCGATGTCCTGAAGGTGTTCTTGTTC

GACACGAAAGCCAGAACCAGCAAACTTGTACGTACTGAGAATGTCGCTGATATCGACGG

TGGCTGGGTAGAGCCTACGCAGTACACATGGTTCATCCCAGCAGATCCCAGCAATGGCC

GCCCTCATGATGGATATCTCGATACTGTGATCCACGAGGGTTACGAGCACCTGGGTTAC

TTCACGCCCCTGGACAACTCAGAACCCATTCTCCTCACCCAGGGTGAGTGGGAAGTAGT

GGACGCGCCAACCGCCGTGGACTTGCGCAAAGGCATCGTGTACTTCATCTCTACAAAGG

AATCCCCCACTGAGCGACACCTCTACCAGGTGAATCTAGACGGATCCAACCTCAAGCCT

CTAACAGACACCTCCAAGCCCGGCTACTACGACGTATCCTTCTCCCACGGAACCGGCTA

CGCCCTGCTCAGCTACCGAGGTCCTTCCATTCCATGGCAAGCGATCGTCAACACCGAGA

CCGACGAGCTGAAGTACGAGGAGACCATCGAAGACAACGCCGGTCTGGCACGTATGGTT

GACTCATACGCCCTTCCCACTGAGATCTACCAGAACGTGACGATCGACGGCTTCACCCT

ACAAGTCGTCGAGCGCCGTCCCCCACACTTCAACCCAGCCAAGAAGTACCCGGTCCTCT

TCTACCTCTACAACGGCCCACGCTCCCAAACCGTCGACCGCAAATTCAGCATCGACTTC

CAATCCTACGTCGCCTCCAGCCTCGGCTACATCGTCGTGACCGTCGACGGCCGCGGCAC

CGGTTTCTCTGGCCGCAAAACCCGCTGCATCGTCCGCGGCAACCTAGGCTACTACGAAG

CCTACGACCAAATCACCACGGCGAACCTCTGGGGCGAGAAGCCTTACGTCGATGAAACC

CGCATGTCCATCTGGGGCTGGAGTTACGGCGGATTCATGACACTTAAGACATTGGAACA

AGATGCCGGGCAGACCTTCCAGTACGGCATGGCCGTAGCCCCTGTGACTGACTGGCGAC

ATTATGGTAGGCCCCTCCTTAACCCTCTCCTCTTATAAACTCACACTAAAACTAATAAT

AAATAGACTCGATCTACACCGAACGCTACATGCACACCCCAGCCCACAACCCCAACGGC

FIG. 13C

TACGACAACACCTCCATAACCGACATGACCGCTCTCCAACAAACCGTGCGATTCCTCGT

CATCCACGGCGCCTCGGACGACAACGTCCACATTCAAAACACGCTCGTCCTCGTGGATA

AACTGGACCTGGCGGGCGTGCAGAACTACGATTTGCATTTCTATCCAGATTCAGATCAT

AGTATCAACTTTCACAATGCGCATAGGATGGTTTATGAGCGTGAGCCCCCTTCCCTTC

CCCAATCCCGTGGATGTCAAGTACGGGTGGTATTGAGACATGTACTGATGATATTGATA

ATAGGACTATCGAGCTGGCTCGTCAACGCTTTCAACGATGAATGGCATCGCATAGCGGA

TCCGGTCCCGGATGACTCAATGTGGGAGAAGGTGAAGAGGTCGTTGCCGATGTTGGTGA

ATTGAATTGAATTGATTTGTTTGATACTAGTGCATACATATATATCATGGTTTCGGGGT

CATATCTAGTTCCTACATACTACATAGCATGATACGTATGTATGGACATGTCAAAGGCG

TTTTCTATTCACTATAGGTACTCATCTATCACGGAAAAGGGAAGTACTTTAATCGCATT

AAAGCATTACAGTAGTAGTAGTATTTTTCATATCACCATGCAACTGAAACAACAATCAA

CAAAACATCCCAACATCTCTATGCTATGCAAGTTTCAGCTCAAAACCAACATCAACATC

AACACCAACATCTGTACAATGAAGGCATATAGCAAG

FIG. 14

MGKYQEDDNNEFLPMSSPRPSTSSTSSDSGLSVDTTAYPEESKYTSTAPGAGGLSDENR

YRDVEEGEAGADEPFLPSAKKQAASGSRTSRLIWGLVILCVAGWLWGLVLFVTQNRSAQ

QSVSEALQSHESGAISGSSSSGKPVTLEQVLTGQWLPRSHAVSWIAGPNGEDGLLVEQG

EDQGKGYLRVDDIRSRKGDATSQESRVLMEKAIVQVDGRTIFPVSTWPSPNLNKVLLLS

EREKNWRHSFTGKYWIFDVATQTAQPLDPSNPDGRVQLAIWSPTSDMVAFVRDNNLYLR

RLSSKEVVPITKDGGADLFYGIPDWVYEEEVFSGNSVTWWSGDGKYVAFLRTNETAVPE

FPVQYYLSRPSGKRPPPGLEDYPEVREIKYPKAGAPNPVVSLQFYDVEKQEVFSIEAPD

DFEDDDRIVIEIVWGTEGKILVRATNRESDVLKVFLFDTKARTSKLVRTENVADIDGGW

VEPTQYTWFIPADPSNGRPHDGYLDTVIHEGYEHLGYFTPLDNSEPILLTQGEWEVVDA

PTAVDLRKGIVYFISTKESPTERHLYQVNLDGSNLKPLTDTSKPGYYDVSFSHGTGYAL

LSYRGPSIPWQAIVNTETDELKYEETIEDNAGLARMVDSYALPTEIYQNVTIDGFTLQV

VERRPPHFNPAKKYPVLFYLYNGPRSQTVDRKFSIDFQSYVASSLGYIVVTVDGRGTGF

SGRKTRCIVRGNLGYYEAYDQITTAKLWGEKPYVDETRMSIWGWSYGGFMTLKTLEQDA

GQTFQYGMAVAPVTDWRHYDSIYTERYMHTPAHNPNGYDNTSITDMTALQQTVRFLVIH

GASDDNVHIQNTLVLVDKLDLAGVQNYDLHFYPDSDHSINFHNAHRMVYERLSSWLVNA

FNDEWHRIADPVPDDSMWEKVKRSLPMLVN

FIG 15A

ATGGGAGCTCTTCAGTGGCTGTCCATCACGGCTGCTGCGGCCTCCGCAGTGTCAGCCTT
GACCCCGGAGTAAGTATCTCCAATCATCTCGAATTGACCCATATCGTGCATAGCTAACC
AGCTTACCTGCATAGGCAGATGATCGGTGCCCCACGGAGAACCGAAGTTATACCAAACC
CCTCCGGTGTATGCCCATTGCCAGGTCCAGCCTTACAAAGAAGCGTCGTCTGCTGACAC
GAGAAGGACACCGGTCTATTCTCGACCTCCCAATGGTCGTTTGACACTCATTCTGAGAG
CACCTGGTGGAGCTTGATCGACCTCGAATCGGGCGAGACCACCACTCTCACCGATGATA
GCGATATCGAGGAGATCATCTGGCTGGGTTCCGACAGTTCCACGCTCCTCTACATCAAC
AGCACCAACGCGCAGGTTCCCGGTGGTGTGGAGCTGTGGATTGCAGACTCTTCTGACTT
TGCTAATGCGTTGGTTCAGACCTTTAACCATGCCTCTGCAGACTAGTGCTAATCCTACC
TGCTGCAGTTACAAGGCAGCCTCTCTCTCCGCCGGTTTCCTCGGCATCAAATCAACCGT
GACAGATTCCGGCGACGTGCATTTCATCCTTCGTGGAAAGTCCTATCCCAACGGAACGG
CATACAATGATCAGCTCGCAGAGACCTATCCCAGTACAGCCCGCATCTACGACAGCATC
TTTGTGCGGCACTGGGACACTTACCTGACCACCGCCTCCCACGCTGTATTCTCCGGTAC
TCTGCAAAGCTCGACCAGCGACGACGGCAATGTTCAATATACCTCTTCAGGGGGATTGA
CGAACCTGGTTAACCCAGTCAAGGGTGCCGAAAGCCCATTCCCTCCTTTTGGAGGCAAC
GACGACTATGACCTCTCGCCTGACGGCAAATGGGTTACCTTCAAGAGCAAAGCGCCAGA
GCTGCCTCTTGCTAACAACACGGCTGCCTATGTCTATCTCGTCCCACACGACGGCTCTG
CGACTGCCTTTGCTGTCAACGGCCCTGATAGTCCTGCAACCCCGGAGGGAGTTGAAGGA
GAATCCAATAATCCCGTGTTCTCCCCTGATAGCGACAAAATAGCGTACTTCCAAATGGC
AACTAATACATACGAGTCGGACCGCAACGTGCTATACGTATACTCCATCGCCGATGACA
CTATCACCCCCCTTGCAAAGGACTGGGACCGATCCCCTAGCTCCGTGACATGGGTCGAT
GGAGACAACCTCGTCGTGGCAAGCCAAGATCTAGGACGAACCAGACTTTTCGCCATCCC
AGGCGATGCAGGGACGACTTCAAGCCCACGAACTTCACCGACGGCGGGTCCGTGTCGGC
TCAATACGTCCTATCCAACTCTACCCTCCTTGTCACGTCCAGCGCCTTCTGGACAAGCT
GGAGCGTCTACACCGCCAGCCCTGACGAGGGCGTGATCAACACACTGGCCTCAGCCAAC
GAGATCGACCCCGAGCTTAGCGGCCTTAGTTCCTCCGACTTTGAAGAGTTCTACTTTGA
CGGCAACTGGACTACCGTAAGTCTATCCCTCCTTCCCTCCACCACCACATCACAAACAT
ACTAAACTCACCGCAGCTCCAAGGATGGATCACCTACCCCCAAGACTTCGACTCATCCA

FIG. 15B

```
AGAAATACCCCCTCGCCTTCCTCATTCACGGCGGCCCCGAAGACGCCTGGGCGGATGAG
TGGAACCTGAAATGGCACTCCAAGGTCTTCGCCGACCAGGGATACGTCGTCGTCCAGCC
AAACCCCACAGGAAGCACCGGGTTCGGCCAGCAGCTCACAGACGCTATCCAACTTAACT
GGAGTACGCCATTCCCTATCCCCAAACTCCCCTCTTAAACATACAGCTAACAAATGAAA
TAACAGCCGGCGCCGCCTACGACGACCTAACCAAAGCCTGGCAATACGTGCACGATACC
TACGACTTCATCGACACAGACAACGGCGTCGCCGCGGGTCCCAGCTTCGGCGCGTTCAT
GATCACCTGGATCCAGGGCGATGACTTTGGACGCAAGTTCAAGGCGCTGGTTAGCCATG
ATGGTCCGTTCATTGGCGATGCGTGGGTCGAGACGGATGAGTTATGGTTTGTTGAGCAT
GAGGTGAGTGGACCAAACCAAACCCCCTTTTCTTCCCTTACACCATTAGCCCTATACA
AATATGATGATTCTGACCGTGTATAGTTCAACGGCACCTTCTGGCAAGCGCGCGACGCA
TTCCACAACACGGACCCATCCGGCCCCAGCCGCGTCCTCGCATACAGCACCCCCCAGCT
CGTCATCCACAGTGACAAGGATTATCGCATACCTGTGGCGAATGGGATTGGACTGTTTA
ATACGCTGCAGGAGAGGGGCGTGCCCAGTCGGTTTTTGAATTTCCCGGATGAGGATCAT
TGGTATGTTCATACCCTTTTCTTCCCCCTTTTTTCTCCCATGATTATGGGTGTTGTGGA
TGCTGATGTAGCTATGTGTGTGTTTAGGGTCACCGGGCAAGAAAACAGCCTCGTCTGGT
ATCAGCAGGTGCTGGGATGGATCAATCGGTATTCTGGGGTGGGAGGGTCGAATCCTGAT
GCGATTGCTTTGGAGGATACGGTGAATCCGGTGGTGGATTTGAATCCTTGA
```

FIG. 16

MGALQWLSITAAAASAVSALTPEQMIGAPRRTEVIPNPSGDTGLFSTSQWSFDTHSEST
WWSLIDLESGETTTLTDDSDIEEIIWLGSDSSTLLYINSTNAQVPGGVELWIADSSDFA
NAYKAASLSAGFLGIKSTVTDSGDVHFILRGKSYPNGTAYNDQLAETYPSTARIYDSIF
VRHWDTYLTTASHAVFSGTLQSSTSDDGNVQYTSSGGLTNLVNPVKGAESPFPPFGGND
DYDLSPDGKWVTFKSKAPELPLANNTAAYVYLVPHDGSATAFAVNGPDSPATPEGVEGE
SNNPVFSPDSDKIAYFQMATNTYESDRNVLYVYSIADDTITPLAKDWDRSPSSVTWVDG
DNLVVASQDLGRTRLFAIPGDAGXDFKPTNFTDGGSVSAQYVLSNSTLLVTSSAFWTSW
SVYTASPDEGVINTLASANEIDPELSGLSSSDFEEFYFDGNWTTLQGWITYPQDFDSSK
KYPLAFLIHGGPEDAWADEWNLKWHSKVFADQGYVVVQPNPTGSTGFGQQLTDAIQLNW
TGAAYDDLTKAWQYVHDTYDFIDTDNGVAAGPSFGAFMITWIQGDDFGRKFKALVSHDG
PFIGDAWVETDELWFVEHEFNGTFWQARDAFHNTDPSGPSRVLAYSTPQLVIHSDKDYR
IPVANGIGLFNTLQERGVPSRFLNFPDEDHWVTGQENSLVWYQQVLGWINRYSGVGGSN
PDAIALEDTVNPVVDLNP

FIG. 17A

```
CTATGGACACTTTCTTCTCTTCCCTCCCCTCCCATCCCCGCCGGTGTCAGGCAAATGAA
GATGGGTTTCCCCTGGGTTTCTCCCGTGAGTCCAGGCTAACTGGGCCTGGATCATCCAG
GATTGGTTGATGATTCCACCGCTGGGCTTTTGGGACCAGACTGGTCCAGCTAGTTGGAA
CAATGCCACCCCTCCAGCCTCCGTGCTGGGTGGATCGATGTAGAGTGCGAAAGTCTTGG
TGTCTGGGGCGAATCAACTATAGTAGGCCTGCTAAAAGTCGCTCGACGGTGAATAATGC
CTCGCCGAACTTTTTCCTGTTCGACTTGCTGCCCTTTTATAGACTGCACTTCTTTCCCC
TTTTTGTTTACATTTCTCTTCTAGTTTGTTAACCTTAGTGTTCTTTCATTTCTCGTTCC
CGCTGTCACTTTCTTTCTCATCTGCCGGGCTTTGTTGGGCTGAGCGCTACTTCTTTCTC
TCTCTTGGTCTGTTCGTTGCTCCGCCAGTTGGTTCACTCAGCCTCGTAACATCAGTATA
CCAGGCTAAGTCAGGACTTTGGCCCCCATACTGCTTCCCCTTTTTTTATAAAACTCAAT
CCTTCTGGAAAGGATTCTATTTCTCAATTCTCAGACTACTTAATACGTTCTTTGTTTTC
AAATTGTTTTGTTTCTGAAACTTGCCGGGCCCTATCCCCTCTTTTTTATAGTCCGCCTG
TCGACATCATATCCAGAGTGAGCCACCATGCAGCTCCTCCAGTCCCTCATTGTTGCCGT
TTGCTTCAGCTACGGCGTCCTCTCCTTACCCCATGGCCCGTCAAACCAGCACAAAGCAC
GTTCCTTCAAGGTTGAACGGGTCCGTCGTGGAACCGGTGCTCTGCATGGGCCCGCTGCT
CTCCGCAAAGCATACCGGAAGTACGGAATAGCTCCCAGCAGTTTCAACATCGATCTGGC
AGACTTTAAACCCATTACGACAACCCATGCTGCTGCTGGGAGCGAGATTGCAGAGCCTG
ATCAGACTGGCGCTGTCAGTGCTACTTCCGTCGAGAACGATGCCGAGTTCGTTTCGCCT
GTTCTTATTGGCGGCCAGAAGATCGTCATGACATTTGACACTGGTTCTTCTGACTTGTA
AGTCTTGGATGCAGCTGTTTACTCTTTGGTACAGTGATTAACGTCGATCTACAGTTGGG
TGTTCGATACGAATCTCAATGAAACCTTGACGGGACACACGGAGTACAACCCTTCGAAC
TCCTCGACCTTCAAGAAGATGGACGGATACACCTTCGATGTCTCGTATGGTGACGACTC
GTACGCCTCTGGCCCCGTCGGAACGGATACCGTCAACATTGGCGGCGCCATTGTCAAGG
AGCAAGCCTTCGGTGTCCCCGACCAGGTATCCCAGTCGTTCATCGAGGACACGAACTCC
AACGGCCTGGTCGGGTTGGGCTTTTCCTCCATCAACACCATCAAACCGGAGGCGCAAGA
CACGTTCTTCGCCAATGTCGCACCAAGTCTGGACGAGCCCGTCATGACCGCCTCGCTCA
AGGCTGACGGAGTGGGCGAGTACGAGTTCGGCACGATCGACAAAGACAAGTACCAGGGC
```

FIG. 17B

AACATTGCCAACATCAGCGTGGACTCATCGAACGGATACTGGCAGTTCTCCACTCCCAA
GTACTCCGTGGCAGACGGAGAGCTGAAGGACATTGGAAGCTTGAACACCTCGATCGCGG
ACACCGGTACCTCCCTTATGCTGCTGGATGAAGACGTGGTTACTGCCTACTATGCGCAA
GTTCCCAACTCGGTCTACGTGAGCAGTGCCGGTGGTTACATCTACCCCTGCAACACCAC
TCTTCCCAGCTTCTCGCTTGTCCTCGGCGAGTCGAGCCTGGCCACGATCCCCGGTAACC
TGATCAATTTCTCCAAGGTTGGCACCAACACCACCACCGGACAGGCCTGTAAGTTGCTC
CCCTTCTTTTGCATGATTGAACATGATTGACTGATTGTGCTGGTTAGTGTGCTTTGGCG
GCATTCAATCCAACGGAAACACCTCGCTGCAGATTCTGGGCGATATTTTCCTGAAGGCC
TTTTTCGTTGTCTTCGACATGCGCGGCCCCTCGCTTGGTGTTGCCTCTCCCAAGAACTA
GTTTCCTTTTCCTGTACTTTTCCCCGCGTGTAATAATATCGTCTGATTTTTTGGACTG
TCTCCTACGTGGGCAAGATGGATGGATAGTTTGCTCACGTGCATTGCTTTACCTTGGGT
CTGTGAGTCAAGGCAGGAGTGCGTGGCTGTATCTACAATTCAAGTTACAGTGCCGACCG
TTATTGCCTTCCACATCGAAAAACATAGACACTCTTTCTAACCCTAATCCATGATACAA
GTATATACTTCGAGTCCATATTATGGTGGTGTATCAAGGCGCCATGTTTATATCTAATG
AAACCAACGTAGGTCTCATCTTCATACGTTGTTTAAAAGGTGCCGAAGAATATACGAAG
ATAGATATAGTAGCACCCCGAAAGTCTAACGGCTAATCAGCGCCGGTAAACGGTAAACT
CCAGGCAAAGGAACACGAGGTAGGCAACTAAGAGAACTACACCTGCACTCCTCCCCAGT
CCCAAAAAGATAACAGCACAAAATGCCCCAGAGGACACCCACACGGCCACCAGCTCAAA
AAGCACAAAATTATCTGCCTCTTGTACCTGGTACCCCGCCACTGCAACGACACCAACAC
AGAGCGTCAGCAAGAAATGTTGCTTCCTGCAGTCGTCGCAGCCATAATGCCGCCGTGC
CGCG

FIG. 18

MQLLQSLIVAVCFSYGVLSLPHGPSNQHKARSFKVERVRRGTGALHGPAALRKAYRKYG

IAPSSFNIDLADFKPITTTHAAAGSEIAEPDQTGAVSATSVENDAEFVSPVLIGGQKIV

MTFDTGSSDFWVFDTNLNETLTGHTEYNPSNSSTFKKMDGYTFDVSYGDDSYASGPVGT

DTVNIGGAIVKEQAFGVPDQVSQSFIEDTNSNGLVGLGFSSINTIKPEAQDTFFANVAP

SLDEPVMTASLKADGVGEYEFGTIDKDKYQGNIANISVDSSNGYWQFSTPKYSVADGEL

KDIGSLNTSIADTGTSLMLLDEDVVTAYYAQVPNSVYVSSAGGYIYPCNTTLPSFSLVL

GESSLATIPGNLINFSKVGTNTTTGQACKLLPFFCMIEHD

FIG. 19A

CTTTCCCCGAAAAGTGCCACCTGACGTCTAAGAAACCATTATTATCATGACATTAACCT
ATAAAAATAGGCGTATCACGAGGCCCTTTCGTCTCGCGCGTTTCGGTGATGACGGTGAA
AACCTCTGACACATGCAGCTCCCGGAGACGGTCACAGCTTGTCTGTAAGCGGATGCCGG
GAGCAGACAAGCCCGTCAGGGCGCGTCAGCGGGTGTTGGCGGGTGTCGGGCTGGCTTA
ACTATGCGGCATCAGAGCAGATTGTACTGAGAGTGCACCATATGCGGTGTGAAATACCG
CACAGATGCGTAAGGAGAAAATACCGCATCAGGCGCCATTCGCCATTCAGGCTGCGCAA
CTGTTGGGAAGGGCGATCGGTGCGGGCCTCTTCGCTATTACGCCAGCTGGCGAAAGGGG
GATGTGCTGCAAGGCGATTAAGTTGGGTAACGCCAGGGTTTTCCCAGTCACGACGTTGT
AAAACGACGGCCAGTGAATTGTAATACGACTCACTATAGGGCGAATTCGAGTTCGTTTC
GATGAGCGGTCAGCTGGTTACTATTAAGGTTCTTGCACTATTAAGGTTCTTACCCCTCT
GCCCTCTCTTCAAATGTGTACTATAATGACTCTAGGATAGATTGGGTTATTCTAAATCC
ATTGATTGCATTCTTCTGAGCAGATAATGAGGTATAGCAGTAATTCCTATTATCGCATA
GTCAATATATCTATAAGGCCCTTATGAAGTATCATCGTTTCTGAACGTGGCAGAGTTAG
TACGTTGCGTACCGCACCGGAGAGATAGGACGTAAACTTCATGAGGTGATTCCAGTCAT
GGTTTGCGTGCAATTATGACTAGTTACATAGGCATCTTTGCATCGTAACCATATCACAG
CTATATCCCCTCATTGTCTGTCTTGTTGACATCATTGATTTAGATCAGTCTCATAGAGA
ATGCATTATAGGAGGAGATTGTTGTGAGGCATGAGGCATTTCTGAGGCCCGCTACTCCG
CATTCTGCAGCATATCGTCTCTGCGTAGGGGAGGTCGAAACCAGCTGTAGGACTCGGCT
TCGGTGTATCTGTACCGACTGACTAGAAATCGCTCAATCGTGTAGTATAGCTGTCTCTT
TGTTCCTCACAACATGTCTACGATATGCTATCAAAAAAGCAGAAGATGGAGTCAGAGC
CACCCGGTTAGGGCCGGGCCGCCCGGGAGGAGAACAAAATACGGGACAGAATCTCAGTG
ATGGGGGAGAAGAGAGAGTGGCGACCTGACAATTCACACACGACACGAATAATAGCCGA
AACTAACAAGATAAATCACATCACATCATGAAGAAGACCTGCGTAATGATGATAAGCAA
TCCCACCAATAATACAATGCCATTGATAGTGGCTGACCTGAAGCAATTCGGGGAGGAGA
CGCCAAGCTCGACGATCACCGGAGCTTGAAAGACCAACGAGACAAGATGACAGGCCCGT
CGCACCACGCCACTAACTGCCCTAACAGAAATCGGCCTGAATAGTGCGACGAGTGTCCC
GGTTCTGGGCCTCCACGATAAGATAAGTCATGGGCTTATCGCGTCATCGGCGCCGATCT
CGCGATCAGCTGAAACCAATCATTCAATCGATTTGCATCACCCGACTGGGGGCGAGATT

FIG. 19B

```
TCAGGGCCAGCTGAAAGGGTCGGCTGCCGAGATTGTCAGTGGATGATGAATGTTATGCT
GGAAGAGAGGGGGAGAATGACGTCTCAATTCTGGGTCACTTACTAGTTGACTAGCCACC
TAGTATTTAGCTGCTAGCTAGGGATTCGGTTTAAAAGCCTGGTGGTTTCTCTCTTCTTC
TCGTCATTTTCTCTTCATCTCATACCCATTCTTCAANACTCCTCCACTTTGATCAATTA
TCCTCCATCATGGCTACCAAAATCAAGCTCATCCCCAATCTCAACTACAAGCGCTCAGG
CACCAAGTCCTACGTGCACTTGATGCGCAAGTACCGCTTCCATCCACCAAGCCTGGTC
CCTACACTCTCAGCAGCTCCATCCAACAGACCGGTCGTCCGTACACTGAAAAGCCCATC
GGGGGTCGGGCCCATATCCGGCAGCTGGTGCGGAAGAAGAGCACCACCAGCGATGAGGT
TGGCGAGGTTCCGGCCGAAGATGTGCAGAACGACTCCATGTATCTGGCGACCGTGGGGA
TCGGAACCCCGGCGCAGAACCTGAAGTTGGACTTTGACACTGGTTCAGCTGATCTTTGG
GTACACCCCATTATGAAAGACCTAATATGGAAACGAGCGTCACTGACAGATGTAGGTC
TGGTCCAACAAACTCCCCTCAACCCTTCTATCCGAGAACAAGACCCATGCGATCTTCGA
CTCGTCCAAATCGAGCACCTTCAAGACCTTGGAAGGTGAATCCTGGCAAATCTCCTACG
GAGATGGATCCTCCGCATCAGGGAGTGTGGGCACCGACGACGTCAACATTGGCGGCGTA
GTCGTCAAGAACCAAGCCGTTGAGCTGGCAGAGAAGATGTCCAGCACATTCGCCCAAGG
CGAAGGGGACGGATTGCTCGGTCTAGCATTCAGCAACATCAACACGGTACAGCCAAAGT
CCGTGAAAACGCCCGTCGAGAACATGATCCTGCAGGATGACATTCCCAAGTCGGCTGAG
CTGTTCACGGCCAAGCTGGATACCTGGCGGGACACTGATGACGAGTCGTTTTACACCTT
TGGCTTCATTGACCAGGATCTGGTGAAGACGGCAGGTGAAGAGGTCTACTACACCCCTG
TCGATAACAGTCAAGGCTTCTGGCTATTCAACTCGACCTCCGCGACGGTAAATGGAAAG
ACCATTAACCGGTCGGGTAACACCGCCATTGCTGATACCGGTACGACGCTGGCCTTGGT
GGACGATGACACGTGTGAGGCCATTTATAGTGCAATTGACGGCGCCTATTATGATCAGG
AAGTACAGGGCTGGATCTATCCGACCGATACGGCGCAGGATAAGCTACCCACTGTGTCG
TTTGCCGTGGGTGAAAAGCAGTTCGTGGTGCAGAAGGAGGACCTGGCGTTTTCGGAGGC
GAAGACGGGCTATGTCTATGGAGGAATCCAGAGTCGTGGTGATATGACCATGGACATCT
TGGGAGACACATTTTTGAAGAGTATTTATGCTGTAAGTGCATTGCTGTTGGCGTTAAGG
GGTGATATCGAAGCTCACTAACTGGATTGCAGATCTTTGATGTCGGGAACCTGCGCTTT
```

FIG. 19C

GGAGCCGTCCAGCGCGAGGAGTTGCGCCAGAGCTCGAATTCGCCCTATAGTGAGTCGTA

TTACAATTCACTGGCCGTCGTTTTACAACGTCGTGACTGGGAAAACCCTGGCGTTACCC

AACTTAATCGCCTTGCAGCACATCCCCCTTTCGCCAGCTGGCGTAATAGCGAAGAGGCC

CGCACCGATCGCCCTTCCCAACAGTTGCGCAGCCTGAATGGCGAATGGCGCCTGATGCG

GTATTTTCTCCTTACGCATCTGTGCGGTATTTCACACCGCATATGGTGCACTCTCAGTA

CAATCTGCTCTGATGCCGCATAGTTAAGCCAGCCCCGACACCCGCCAACACCCGCTGAC

GCGCCCTGACGGGCTTGTCTGCTCCCGGCATCCGCTTACAGACAAGCTGTGACCGTCTC

CGGGAGCTGCATGTGTCAGAGGTTTTCACCGTCATCACCGAAACGCGCGAGACGAAAGG

GCCTCGTGATACGCCTATTTTTATAGGTTAATGTCATGATAATAATGGTTTCTTAGACG

TCAGGTGGCACTTTTCGGGGAAATGTGCGCGGAACCCCTATTTGTTTATTTTTCTAAAT

ACATTCAAATATGTATCCG

FIG. 20

MATKIKLIPNLNYKRSGTKSYVHLMRKYRFHPTKPGPYTLSSSIQQTGRPYTEKPIGGR
AHIRQLVRKKSTTSDEVGEVPAEDVQNDSMYLATVGIGTPAQNLKLDFDTGSADLWVWS
NKLPSTLLSENKTHAIFDSSKSSTFKTLEGESWQISYGDGSSASGSVGTDDVNIGGVVV
KNQAVELAEKMSSTFAQGEGDGLLGLAFSNINTVQPKSVKTPVENMILQDDIPKSAELF
TAKLDTWRDTDDESFYTFGFIDQDLVKTAGEEVYYTPVDNSQGFWLFNSTSATVNGKTI
NRSGNTAIADTGTTLALVDDDTCEAIYSAIDGAYYDQEVQGWIYPTDTAQDKLPTVSFA
VGEKQFVVQKEDLAFSEAKTGYVYGGIQSRGDMTMDILGDTFLKSIYAVSALLLALRGD
IEAH

FIG. 21A

```
TGTGGCTTGAATGCAATTATGATTATGAACTCGTAAGTAGGTAGGCTGTACTATATA
TGTACTGTTTTCTCCGCCAGGGTACCGGATATCTAATCTATCACTGCTAAAAACCTATA
GTAGGAGGGTGTGATACTAAGAATGGAAAATTGATGTCTCACGGACTCATTTCTGCCTG
TACGCTCTCATTTGTGCTCAGGGNGAAAAACATGACCGGTCGTGCCTGGGCTCCACCGC
CGCCAAAAAAGGCCTGTAGATCGAGGCCTGGATCATTGGCAGCAGCCAGTCGCAGGCGT
CCGTTGCGCCGCGAAACCTGCCGAGTGGGCCGTTTAGGCTTTGGGTCTCCCCACGATG
TAAGCATAATCATTCTGTGCCTGAGTGTGAATTCTCCTGTTGGAGGCTGCATCTTAATT
CTTAACTGCATGAAAAGCACTTGGGTGCTATTTTCTTTTTCCTTTCTTTCTTTTCCGTG
TTCATTTCCATTCCCTTGCTCTTCTTCTTTGTGTCGACATTTACAAATCACATTTTTCT
TATACTTTCTTTTCTTCACCTCGTTTCTTCCTATTCACTCTCTGTGTTCAGCATTCGTT
ATCAAACACTTTATTTTTTGCTCGTCTCTTTTATCTTCACTTGTTTGTGCCCTTTCCCA
CTAGCAATCTATCGTTTGATCTTTCTAGAGCATTGTCTTGATTGTGTCATTCTGTCATT
GACTCCGGCTATGAAATATTATTCTCAATCTGCCTAAAACCAAATTCTACTCTATCATT
ACACATTTGTATCACCTGATCTGGCTGAGATAGGAGAGTCCAGCATCTCATCGTCTGCA
TCAGACAATTGCGATAAATTCATTGCTTGCACCTGTTATTGATTCTTCCAAGTTATGCA
TCTCCCACAGCGTCTCGTTACAGCAGCGTGTCTTTGCGCCAGTGCCACGGCTTTCATCC
CATACACCATCAAACTCGATACGTCGGACGACATCTCAGCCCGTGATTCATTAGCTCGT
CGTTTCCTGCCAGTACCAAACCCAAGCGATGCTCTAGCAGACGATTCCACCTCATCTGC
CAGCGATGAGTCCCTGTCACTGAACATCAAAGGATTCCCGTTCGTCGTGACAATGATT
TCAAGATTGTGGTAGCGGAAACTCCCTCTTGGTCTAACACCGCCGCTCTCGATCAAGAT
GGTAGCGACATTTCATACATCTCTGTCGTCAACATTGGGTCTGATGAGAAATCTATGTA
CATGTTGCTCGACACAGGCGGCTCTGATACCTGGGTTTTCGGTTCCAACTGCACGTCCA
CACCCTGCACGATGCACAATACCTTCGGTTCGGACGATTCTTCGACCCTTGAAATGACA
TCGGAAGAGTGGAGTGTGGGCTATGGAACTGGGTCTGTCAGCGGCTTGCTAGGAAAAGA
CAAGCTCACGATTGCAAATGTCACTGTACGCATGACTTTCGGACTTGCTTCCAACGCAT
CGGATAACTTCGAGTCGTACCCAATGGACGGCATTCTCGGTCTCGGTCGAACCAACGAT
AGTTCCTACGACAACCCAACATTCATGGATGCCGTTGCAGAAGTAACGTTTTCAAGTC
GAATATCGTTGGCTTCGCCCTTTCACGTAGCCCCGCCAAGGATGGCACGGTCAGCTTTG
```

FIG. 21B

GCACTACTGACAAGGACAAGTACACCGGCGATATCACCTACACCGATACCGTCGGATCG
GACAGCTATTGGCGCATTCCCGTGGACGATGTCTATGTTGGCGGCACTTCATGCGATTT
CTCCAACAAATCAGCCATCATCGATACCGGAACTTCTTATGCTATGCTGCCTTCAAGCG
ACTCGAAGACGCTGCACAGTCTCATTCCCGGCGCCAAATCTTCGGGGAGCTACCACATT
ATTCCGTGCAACACAACTACTAAGCTACAAGTGGCATTCTCTGGTGTGAATTACACCAT
CTCGCCGAAGGACTACGTGGGAGCAACTTCAGGTTCTGGATGCGTTTCGAACATTATCA
GCTACGACTTATTTGGTGATGACATCTGGCTCCTGGGTGACACGTTTCTCAAAAATGTG
TATGCTGTGTTTGACTACGATGAGTTACGGGTCGGATTTGCAGAGCGTTCCTCGAACAC
CACCTCTGCGTCGAACTCTACGAGCTCTGGAACAAGCAGCACCTCGGGTTCCACTACAA
CGGGCAGCTCAACGACTACGACGAGCTCTGCTAGCTCTAGTAGTTCATCTGATGCTGAA
TCAGGAAGTAGCATGACCATTCCCGCTCCTCAGTATTTCTTCTGCTCTGGCGATTGC
TTCCTTCATGCTTTGGCTCTAGTTAACCGCATCTTACTCGACGCCTGAACCTCGGGAAA
CATATGCATTATTTACACATGCTGCTGATTTGTATTTGCATATATTCTTCG

FIG. 22

MHLPQRLVTAACLCASATAFIPYTIKLDTSDDISARDSLARRFLPVPNPSDALADDSTS
SASDESLSLNIKRIPVRRDNDFKIVVAETPSWSNTAALDQDGSDISYISVVNIGSDEKS
MYMLLDTGGSDTWVFGSNCTSTPCTMHNTFGSDDSSTLEMTSEEWSVGYGTGSVSGLLG
KDKLTIANVTVRMTFGLASNASDNFESYPMDGILGLGRTNDSSYDNPTFMDAVAESNVF
KSNIVGFALSRSPAKDGTVSFGTTDKDKYTGDITYTDTVGSDSYWRIPVDDVYVGGTSC
DFSNKSAIIDTGTSYAMLPSSDSKTLHSLIPGAKSSGSYHIIPCNTTTKLQVAFSGVNY
TISPKDYVGATSGSGCVSNIISYDLFGDDIWLLGDTFLKNVYAVFDYDELRVGFAERSS
NTTSASNSTSSGTSSTSGSTTTGSSTTTTSSASSSSSDAESGSSMTIPAPQYFFSALA
IASFMLWL

FIG. 23A

GTCGACTTGGTCGTTGTGCACCGACTAAACATACAGAAGCACGTGCCTGTTTCTCCCTC
TGACGGGAGCGGACAGTCATGGCAGCATTGAACTTGGCTTGGCGAAGCAAACTCCCTTT
TTCTTATTCTTACTACACAACGGCTTTCTAAAGAAGAATGGAGAACATCTCATTCTTAC
TGAGCTATATTTGAATAGCCGATTGAATGATCACCACGATGCTGATTGGTGCAGGCTGC
CGTCCCAAGAACGAACTATTATGATTTCCCGTCTAGATCTAAAGGGCCCTCTGCAGAAT
CCGGCCGGAGTATTTGCACACACTCGAGCTTAATGGGAAGGAATAAATGGACATAAA
AAGCATTTCAGTCTAAATGGCAACTGCATACTCGGTTTACCGGATAGCTGCGCGCTATC
TTTCTGCAGGACTGCAGTTCTGCACTCGGGCCCATTGCCGTTCGGACCCCGACGTACT
CCGCGAGACCTTGAGACATCGGCGGACCATCCATCGTATCACAGCCATCCAGCAAGGC
CGAGTGGAGGTGTTCAGGCTCCATTCATCACGATATCGGCTGATTAATGCCTCTTATCA
TTAGCGAATGCCGAAGCTTGACCTGATACGACTTCAAGGTATCGTCACCGACAATCGTT
ATCATCACGCTACAGGCCCGCAGTTTCCGCTTGAATTCCCGCATTAGGAAATGAGCATC
ACATTCCTCTTCCCACGAGGTCTCTTTCCGAGGGCAGCCGCTGCAACATCATTGGGATC
ATGCTTGGTTCTCCTCTCCCATAGCTGTCCGCGAGCTTCTCATTGGTACCTCTTCGCTA
CCTCGTTGCATCCTATTCGCGCATGGCCCCGCCAGAGATGTTTCTGCAAGGTCCCATCA
CCTTGCCGCGTTGCTATTCCCCGCCCTCGAGTTCCCGACAAGTTACTTTGTGTCAGTGG
CTGAGAAGCCTGGTTCTGAGAGTGTACTCAGACAATCATATGGTTCCCTCCATGTGCTA
CGTCGTCCTAGCGTCGCTGCACTACATCATCGTTAGGCAGCATGGAACTGGCACCCGCA
CATAAAGCCCCCGACACCCCATCGATAGGCTCGGTGTTCGTGCACGCCTGTCCACTGG
CCCCTCCCCCAAAGGCCCTTCATCAGTATGCTGTTTCGCAGTCTGTTGTCGACGGCTGT
CCTAGCCGTCTCGCTGTGCACGGATAATGCTTCAGCTGCTAAACATGGTCGATTTGGCC
AAAAAGCTCGCGACGCCATGAACATCGCGAAGCGTTCCGCTAACGCCGTGAAACACTCG
TTGAAGATCCCTGTCGAGGACTATCAGTTCTTGAACAACAAGACTAAGCGTATGTATCT
CAGTTCGATATTGAACGATGGCTGATTTGCTTCCGTCGGACAGCTTACCGCGTGGAAAG
CCTGCCTGATGTTCACTTCGATCTGGGCGAGATGTATTCCGGCTTGGTCCCTATTGAGA
AGGGCAACGTGTCACGGTCCCTTTTCTTTGTCTTCCAGCCCACTATTGGCGAGCCTGTG
GATGAGATCACCATCTGGCTGAATGGTGGCCCTGGTTGCAGTTCCCTTGAGGCCTTTCT
CCAGGAGAATGGTAGATTCGTGTGGCAGCCTGGAACCTACCAGCCTGTTGAGAACCCAT

FIG. 23B

```
ACTCGTGGGTGAATCTCACCAATGTTCTGTGGTAAGTGTGATATACTGGATCGCTAGTT
GAGTTTACATGGGCGGTATCGACCTAACCTATTTTTTGTAGGGTTGACCAACCTGTGGG
AACGGGATTCTCTCTGGGTGTCCCAACCGCTACGTCCGAGGAGGAGATTGCTGAAGACT
TTGTGAAGTTCTTCAAGAACTGGCAGCAGATCTTTGGGATCAAAAACTTCAAGATCTAT
GTTACTGGAGAAAGTTATGCGGGCCGTTATGTTCCTTACATATCCGCTGCTTTCCTAGA
TCAGAATGATACAGAACACTTCAACCTAAAAGGTGAGTTATACTTCACCAAGTAATCTT
TAACTAGGGCTTGTACTGATTGTACTATCTAGGTGCACTGGCATATGATCCCTGTATTG
GTCAGTTTGACTACGTGCAGGAGGAAGCACCTGTTGTTCCCTTTGTCCAGAAGAACAAT
GCCCTCTTCAATTTCAATGCAAGCTTTTTGGCGGAACTAGAGAGCATCCATGAGCAATG
TGGATACAAGGATTTCATCGACCAGTATCTAGTCTTCCCAGCATCCGGTGTCCAGCCGC
CAAAGGCTATGAACTGGAGCGATCCCACCTGTGATGTTTATGACATCGTTAATAACGCC
GTCCTGGATCCCAACCCGTGCTTCAACCCCTACGAAATCAACGAGATGTGCCCCATTCT
CTGGGACGTTCTTGGATTCCCCACCGAAGTCGACTATCTCCCTGCGGGCGCCAGCATCT
ACTTTGACCGCGCTGATGTTAAGCGTGCCATGCACGCTCCTAACATCACCTGGTCCGAG
TGCTCGGTGGAGAGCGTCTTTGTCGGGGGCGACGGCGGTCCCGAGCAGGAGGGCGACTA
CTCGGCCAACCCCATCGAGCATGTCTTGCCCCAGGTCATCGAAGGCACCAACCGAGTTC
TGATCGGTAACGGTGATTATGACATGGTCATCCTTACCAACGGCACCCTTCTCTCGATC
CAGAACATGACATGGAATGGAAAGCTTGGATTCGACACGGCCCCCAGCACCCCCATCAA
CATCGACATCCCTGACCTGATGTACAATGAAGTGTTCATTGAGAACGGCTATGACCCAC
AAGGTGGTCAGGGTGTCATGGGCATCCAGCACTATGAGCGTGGTCTTATGTGGGCTGAG
ACCTTCCAGAGCGGACACATGCAGCCCCAATTCCAACCCAGAGTGTCATACCGTCACCT
TGAGTGGCTGCTTGGCCGGCGTGATACCCTGTAAGGTCGGGTAGGCTACCACGGGGAC
GATGTCACGATGATAGTCATAAGTTATGATCTGTAGATACGTTGTATGCGAATGTACAT
GAATTGCTTTTACTGGCAGTCTCTAAAGCAAAATTCATAGTAGAGTACTGGCCTACTTA
CCCTCACTTCCCCTATCTTTTCAACCTGAAGACCGGAAGAATTGTAACTAACAAGCATA
ACGTAGCTGATTTGAAGCAGAGCATAACACACTCTACCCCTCGGCACTTCTACTTATGA
CGCTATTTGACTGCTAACTCGGGTTTAATCCTGAAGCTGCAGTCCAATCGTACATTAAA
```

FIG. 23C

CTCAATGTGCCTTGCCCAGGAAACGATATTTGACTTATATGATCTGAAAATGAACAATT

GTCCCCGAGAGAGAGAGAGAGCGAGCGGTAAATACTTAGCAAGTCAGTCACGCAGTA

TCTCCACTAATGCCGTAACACAGGAAATGGACACGAATGGAGCAAGCGAGTATATCAGA

TACACCTTTCCTAACAATGCATGTCTGTAAGCAATTGGCACTAAAGCTAGCTAGATAGA

GAATCTATTTACAATCAAGATAGTAAGGATGATGCCAACCAGAA

FIG. 24

MLFRSLLSTAVLAVSLCTDNASAAKHGRFGQKARDAMNIAKRSANAVKHSLKIPVEDYQ

FLNNKTKPYRVESLPDVHFDLGEMYSGLVPIEKGNVSRSLFFVFQPTIGEPVDEITIWL

NGGPGCSSLEAFLQENGRFVWQPGTYQPVENPYSWVNLTNVLWVDQPVGTGFSLGVPTA

TSEEEIAEDFVKFFKNWQQIFGIKNFKIYVTGESYAGRYVPYISAAFLDQNDTEHFNLK

GALAYDPCIGQFDYVQEEAPVVPFVQKNNALFNFNASFLAELESIHEQCGYKDFIDQYL

VFPASGVQPPKAMNWSDPTCDVYDIVNNAVLDPNPCFNPYEINEMCPILWDVLGFPTEV

DYLPAGASIYFDRADVKRAMHAPNITWSECSVESVFVGGDGGPEQEGDYSANPIEHVLP

QVIEGTNRVLIGNGDYDMVILTNGTLLSIQNMTWNGKLGFDTAPSTPINIDIPDLMYNE

VFIENGYDPQGGQGVMGIQHYERGLMWAETFQSGHMQPQFQPRVSYRHLEWLLGRRDTL

FIG. 25A

```
TGTTGTGCCTGCGCCGGTGCCGCTTCCCTCCCCTCCTCCCCTGCCTTTTCGGGCGACGCC
ATCCGCGCACTAACCCTCCACGTATTCCAATATACCAAATCTGCCCAAAGCGCCAGCCA
GCTTCCTCAAGCCTTGCGGTCAGATAAGGCCCTGTACCTAGCTAGTTGCCGCTGCTCCC
GGCGCTGGGCCAAGCCGTCGGACGTCCGTCCCCCCTCTTTCCCCCTCCTCTCCCCTCTC
CACTGGTGGAACGATGTCTGGCTGTTGCCATCGTTCTCAGAAGCAACGCCCCCTGGATC
GGGTGGCTGTCGTACTATTGCATGTTCGTCCGCGCTACTAGGAAAGTTTTTTTCCCACC
CGGAGTATCCGTGTTTAGTTCGCGGGCTGGCTGACCGGCTAGCTGGCCGTGCCAGTTGG
GTAAGGTTCCAAGGGAGGACCTTACTAGGTAGAAACGGGATCCAACAATGAGGGGAAAA
GGGCGGATATGGCTTGCCGGGGGTTCATTGCGGCCTGGACGAAGAAAGGGAGATGATCA
CTAATGCAACACAATCTTGGCTTGCAAGGAATTGCGCTCCAACCAGAATGTCTCTGCGT
AGGGATGCCAATTCGTGCGGGCCATGCTGGATGGATAGTACGCTGCTCCACTCTCGCTC
GACCTTTTGCAGTCCACAATCGTTTCCCCGTATCGTTGGGCGGGGCGTTTTCTGCAG
CTATGGTTGCTGCTGCCCCGACGGTGAACCTTTCTGCATCCCCGGTTTTAGTCGATTTT
AGTTGGCGGGCCTGGAGATTAAACTCCGTCGGACGAAGAGGAGCAGTGGTGTCATCGTC
GGCGGATTGCATGCTATCGGAAGAGCATGGAAGAGGGAAAACATCAACTTCATTTGCAA
AACGCTCGAGCATAAATAGAGGCCTGGATTCCGCCGTTCTGGTGTCTTTTCTTCTTCAT
CCAGCATCGCAAGTCTCTCAAGCATCGCCTGGTTCGTTCTTCTCACTCTTCCACCACCA
GCCTTGTCAATAAGTTAGCTCTTCATCTTTTCGAAGAAACCAATTCTCCAAACGTCAAA
ATGAAGTTCTCTACCATCCTTACCGGCTCCCTCTTCGCCACTGCCGCTCTGGCTGCTCC
TCTCACTGAGAAGCGCCGTGCTCGCAAGGAGGCCCGCGCCGCTGGCAAGCGCCACAGCA
ACCCTCCCTACATCCCCGGTTCCGACAAGGAGATCCTCAAGCTGAACGGCACCTCCAAC
GAGGAGTACAGCTCCAACTGGGCTGGTGCCGTCCTGATCGGCGACGGCTACACCAAGGT
CACTGGCGAGTTCACTGTCCCCAGTGTCTCTGCTGGATCTAGCAGCTCCAGTGGCTACG
GCGGTGGCTACGGCTACTGGAAGAACAAGAGACAATCCGAGGAGTACTGCGCCTCCGCT
TGGGTTGGTATCGACGGTGACACCTGCGAGACCGCTATTCTCCAGACTGGTGTCGACTT
CTGCTACGAGGATGGCCAGACTTCCTACGATGCCTGGTATGAGTGGTACCCCGACTACG
CCTACGACTTCAGCGACATCACCATCTCTGAGGGTGACAGCATCAAGGTCACTGTCGAG
TGCCACCAGCAAGAGCAGCGGTAGCGCCACCGTTGAGAACCTGACCACTGGCCAGTCCG
```

FIG. 25B

```
TCACCCACACCTTCAGCGGCAACGTTGAGGGTGATCTTTGCGAGACCAACGCTGAGTGG
ATCGTTGAGGACTTCGAGTCCGGTGACTCCCCTTGTTGCTTTCGCTGACTTCGGCTCCG
TTACCTTCACCAATGCTGAGGCCACCAGCGGCGGCTCCACTGTCGGCCCTCTGACGCT
ACCATTATGGACATTGAGCAGGATGGCACCGTCCTCACCGAGACCTCCGTCTCTGGCGA
CAGCGTCACTGTCACCTACGTCTAAATGCATCTCTATGCATGAGATATCGGTCGCTTCA
ATGTCTTCGTCTCGAAGACAAACCCTGGGGATGAATGAAAAAATGAGTGATGAGCTATC
CGGATTGATCTGATCTTGTTGAGTTGTTAATTCTGTTTCTGTTGATGTTTTTGAATGAT
TGTACCTACTTTTAAGTAGAAGAAATGGATGAGCGCGTGCATGCTGAAAATGGCTGTCC
CTGCTTATATTGTAGAAGATCTTCCAGAAAGCTGTGCTGCCGATCTGAAGATCTGAAGA
TCACTAGTGAGATCTCGCAGCTCGGCTGTGTAAGTGCTTTCGCTCTGTCGATCATAACT
TTGTAAAAGCTTGTATGCATAGCGGACATCTATCGATTATTTAGATGCCTCAAATTGAT
CTTTACTAGAATTCCCATCCGAATAGAGCTTCAGAGCGTCGGGTGGAAATGTCGGGCCG
TGGATGGTATCGGAGAAGTCTCACCACATGAACGAAAGACCCGCGGTATATGGCCAGTG
TAGGGAGGAAGCGCTGAAAAAGACTTTCCCTATAGTTCATAAGAGGCTTTGCAGTTAGT
CAGAGCTTCAGGAATAGAAATACTAGACGGGCTGGCTTACCGTTCCCCGATAATAGTCC
GCGAGCCATAGTGACATAGACATGGTCAAACAGGAATCGAGCACAGCAGATACCTATGT
AGAAGCCCTCTCCATCAGAATTTGTTCCAGAGAAGAGAGGGAGGTATTTCTCAGATTAT
TTTGAATGTACAGGGGCCATATGATGGTCGTAGCTCGGTTGCAGTGATGGATGTAGGCC
ATAAAGTCTCAAGCTGGGGGAGACATGACGTTGGGAAGGTACACGTGATCCGTATAGG
CAGCAGTAGCGCCATATCTACTTTTGTAGTATCAATGATAGCAGAGAATTTGGGCGCTG
CGTTTAAGGTTAGCAGAAGGAACAGCTTATCACCTTGGTAATCGTCGGTGTCTCTCTCT
CTATCAGGAACGCAGATGCTCTCAAGTCTTCAGCCAGGAGTAATGCGACATGTTACCCC
CGACAACTGGATCACTGCTTGAAGCGCATTGTGTACGAAGCTATAACGA
```

FIG. 26

MKFSTILTGSLFATAALAAPLTEKRRARKEARAAGKRHSNPPYIPGSDKEILKLNGTTN

EEYSSNWAGAVLIGDGYTKVTGEFTVPSVSAGSSGSSGYGGGYGYWKNKRQSEEYCASA

WVGIDGDTCETAILQTGVDFCYEDGQTSYDAWYEWYPDYAYDFSDITISEGDSIKVTVE

ATSKSSGSATVENLTTGQSVTHTFSGNVEGDLCETNAEWIVEDFESGDSLVAFADFGSV

TFTNAEATSGGSTVGPSDATVMDIEQDGSVLTETSVSGDSVTVTYV

FIG 27A

GGATCCATCCATTCACTCAGCTTTCCTTGTCGGTGGACTGTCGAGTCTACCCCAGGTCC
CAGTTTCTCCGACCGCGCTAATCGGGGGCTATCGACAACCAGTGATTCTGCTGTGTCAT
CCGGGCGTATGGCGTAAATTACCGTATGCCGGTTGCATCATCACCTGCTGCCCTTGCCT
CTTGCTGAATACCGTCCGCCATCCATCTGTCCTCCTCTCCCTCTCTCTTCATCTCCAAC
CTCCCCTTCCTCCTCCCTCCCTCCTTCTCTTCATCTTTATCTTGACCTATTTCCATCTT
TCTCATCTCTCAGTTGTTTCAATCTCTTGTACACGCCCTACTCACTCTCCTTTTCACCG
GGCTGCTGTGGGTTCCGTCTTAAGCTATCCATCATGAAGGGCATCCTCGGCCTTTCCCT
CCTCCCGTTGCTGACGGCTGCGTCGCCCGTCTTCGTTGACTCCATCCATAATGAAGCTG
CCCCCATCTTGTCTGCTACCAACGCGAAGGAGGTTCCCGACTCCTACATCGTCGTTTTC
AAGAAGCACGTCACTTCAGAGCTGGCTTCGGCTCACCACAGCTGGGTGCAGGACATCCA
TGACTCTCAGAGCGAGCGGACTGAGCTGAAGAAGCGGTCGCTCTTCGGCCTTGGGGACG
AGGTCTATCTGGGTCTCAAGAACACCTTTGACATTGCTGGTTCTCTGATCGGTTACTCT
GGTCACTTCCACGAGGATGTCATCGAGCAAGTCCGCAGACACCCCGATGTGAGTTACAC
CCCCTATCTAAGCATCCCTCGTTATCTCTAAGATAAGCTTCTAACATCGGTCAATGTAG
GTCGATTACATCGAGCGGGATTCCGAAGTTCACACCATGGAAGGGGCCACCGAAAAGAA
CGCCCCTTGGGGTCTGGCTCGTATCTCTCACCGTGATAGCCTGACCTTCGGTAACTTCA
ACAAGTACCTGTATGCCTCCGAGGGGGGTGAGGGCGTTGACGCCTACACCATTGACACG
GGTATCAACGTTGACCACGTTGACTTCGAGGGCCGTGCCACTTGGGGCAAGACAATCCC
TACCAACGATGAAGATCTCGATGGCAATGGTCACGGAACTCACTGCTCCGGAACCATGG
CTGGTAAGAAGTACGGTGTTGCCAAGAAGGCCAACCTCTATGCTGTCAAGGTCCTCCGG
TCGAGCGGCTCTGGCACCATGTCTGATGTCGTTTCTGGTGTCGAGTATGCCGTCCAGGC
TCATATCAAGAAGGCCAAGGATGCCAAGAACGGCAAGGTCAAGGGATTCAAGGGCAGCG
TTGCCAACATGAGTCTCGGTGGTGGCAAGTCTAAGACCCTCGAGGATGCTGTTAACGCT
GGTGTTGAGGCTGGTCTTCACTTCGCCGTTGCCGCCGGTAATGACAATGCTGATGCTTG
CAACTACTCCTGCTGCTGCCGAGAAGGCCATCACCGTTGGTGCCTCGACACTTGCTG
ACGAGCGTGCGTACTTCTCCAACTACGGAGAGTGCACTGACATCTTCGCTCCTGGTCTC
AACATCCTGTCCACCTGGATTGGCAGCAACTACGCCACCAACATCATCTCTGGCACTTC
CATGGCCTCTCCTCACATTGCTGGCCTGCTGGCCTACTTTGTCTCCCTCCAGCCCTCCT

FIG. 27B

```
CGGACTCTGCATTCGCTGTTGAGGAGCTTACTCCTGCTAAGCTGAAGAAGGACATCATC
GCCATCGCCACCGAGGGCGCTCTCACTGACATTCCCTCCAACACCCCCAGGATCCATCC
ATTCACTCAGCTTTCCTTGTCGGTGGACTGTCGAGTCTACCCCAGGTCCCAGTTTCTCC
GACCGCGCTAATCGGGGGCTATCGACAACCAGTGATTCTGCTGTGTCATCCGGGCGTAT
GGCGTAAATTACCGTATGCCGGTTGCATCATCACCTGCTGCCCTTGCCTCTTGCTGAAT
ACCGTCCGCCATCCATCTGTCCTCCTCTCCCTCTCTCTTCATCTCCAACCTCCCCTTCC
TCCTCCCTCCCTCCTTCTCTTCATCTTTATCTTGACCTATTTCCATCTTTCTCATCTCT
CAGTTGTTTCAATCTCTTGTACACGCCCTACTCACTCTCCTTTTCACCGGGCTGCTGTG
GGTTCCGTCTTAAGCTATCCATCATGAAGGGCATCCTCGGCCTTTCCCTCCTCCCGTTG
CTGACGGCTGCGTCGCCCGTCTTCGTTGACTCCATCCATAATGAAGCTGCCCCCATCTT
GTCTGCTACCAACGCGAAGGAGGTTCCCGACTCCTACATCGTCGTTTTCAAGAAGCACG
TCACTTCAGAGCTGGCTTCGGCTCACCACAGCTGGGTGCAGGACATCCATGACTCTCAG
AGCGAGCGGACTGAGCTGAAGAAGCGGTCGCTCTTCGGCCTTGGGGACGAGGTCTATCT
GGGTCTCAAGAACACCTTTGACATTGCTGGTTCTCTGATCGGTTACTCTGGTCACTTCC
ACGAGGATGTCATCGAGCAAGTCCGCAGACACCCCGATGTGAGTTACACCCCCTATCTA
AGCATCCCTCGTTATCTCTAAGATAAGCTTCTAACATCGGTCAATGTAGGTCGATTACA
TCGAGCGGGATTCCGAAGTTCACACCATGGAAGGGGCCACCGAAAAGAACGCCCCTTGG
GGTCTGGCTCGTATCTCTCACCGTGATAGCCTGACCTTCGGTAACTTCAACAAGTACCT
GTATGCCTCCGAGGGGGGTGAGGGCGTTGACGCCTACACCATTGACACGGGTATCAACG
TTGACCACGTTGACTTCGAGGGCCGTGCCACTTGGGGCAAGACAATCCCTACCAACGAT
GAAGATCTCGATGGCAATGGTCACGGAACTCACTGCTCCGGAACCATGGCTGGTAAGAA
GTACGGTGTTGCCAAGAAGGCCAACCTCTATGCTGTCAAGGTCCTCCGGTCGAGCGGCT
CTGGCACCATGTCTGATGTCGTTTCTGGTGTCGAGTATGCCGTCCAGGCTCATATCAAG
AAGGCCAAGGATGCCAAGAACGGCAAGGTCAAGGGATTCAAGGGCAGCGTTGCCAACAT
GAGTCTCGGTGGTGGCAAGTCTAAGACCCTCGAGGATGCTGTTAACGCTGGTGTTGAGG
CTGGTCTTCACTTCGCCGTTGCCGCCGGTAATGACAATGCTGATGCTTGCAACTACTCT
CCTGCTGCTGCCGAGAAGGCCATCACCGTTGGTGCCTCGACACTTGCTGACGAGCGTGC
```

FIG. 27C

GTACTTCTCCAACTACGGAGAGTGCACTGACATCTTCGCTCCTGGTCTCAACATCCTGT
CCACCTGGATTGGCAGCAACTACGCCACCAACATCATCTCTGGCACTTCCATGGCCTCT
CCTCACATTGCTGGCCTGCTGGCCTACTTTGTCTCCCTCCAGCCCTCCTCGGACTCTGC
ATTCGCTGTTGAGGAGCTTACTCCTGCTAAGCTGAAGAAGGACATCATCGCCATCGCCA
CCGAGGGCGCTCTCACTGACATTCCCTCCAACACCCCCAACGTAAGTCATGCCGCTGTT
GGTATTTATAAGAGAAACGAGCTAACTCAGAAATTCAGCTCCTTGCCTGGAACGGTGGT
GGTTCCGAGAACTACACCGACATCGTTGGCAGCGGTGGCTACAAGGTCTCCTCTGCCAA
GAACCGCATCGAGGACCGTATTGAGGGTCTCGTTCACAAGGCCGAAGAGCTGCTCACCG
AGGAGCTTGGTGCCATCTACAGCGAGATCCAGGATGCCGTCGTCGCATAGATCAGAACT
CGTGCTTTCCAGACGTAGATCGGAAGACTTGGTTTTTTTTGAGGTATGGGATGGTTGA
TCGGACATTTTGGCGCTGGTCTCTTTTATTGTGTTTGGTCTCGAAGACGCTGATGCAT
TGACTGTATCGGCTGTATCACTCCGCCCTGCTTATCTGTTTGGTTCATCTTTATGGTA
GTATACATGTCTGCAAAGAAGGTTTTGTTACCTCACTTAGAATGTTCTGGTTCTATAAC
AGACTGACAATCTCACTGGGTTATCTAAGAGATCTGACAAACGCTTGGTAGAAGAGAAA
GGTGAGGGAGTAGACATCATCAGTCTAAATCCACATTACGACATGCCGTAATAGATGAG
AGCACCGGATGCTAGCCTTTGTAGACTACAAAGGAGAAAACCCCTAGGAAAGGTAATTT
CTAAGTCATGCCCACCTATTCTCTATCTCTTACTGAGACAGTCAATCCCATGACGAA
CAACTAATGACATCATGGGTCACGCTACGGGGTCATGCCGAAACGAAGCCGAAGTACTA
CTCCTAAGTAAAGCCACAACTTTGCATACGTTCATTCAGGAAACGGAAACACAGGAGGA
AGAATATTGAAATATCTTGAGGGGCTTCATATAGAATAGACAGATATATAATAGTTGTC
AAAGTATACAAAAGACCTCATGCATGCTAACAGATAAAGCAAAGGATCTCATATTGAT
AGACTGTGCTGTATACCACCTCTTAATGCAGCGCCTGCGCTATGCCACGATGAAATATA
AAGGGGGAAAAAGTCATGTAAGTAGTAAGTAGAAACTCCAAGCGCCAAATATATAGATA
GTAATAGGGGTGGCGACATAATTTGGCTTTTATACTTGATAGGTTGAACAAATCAAGTG
GCCCTGTGCTCGTCTTCCTCCTCATCACTGCCGGAATCTTGGTCTTCGTCATCGTCATC
GACGTCAAGGTCCTCGTCGGAGTCGCTACCGCCGAAGACGTCGTCGTCCACATCGCTCT
CGGCCCAGAAGTCGGAGTCGTCCTTCTCCACAGGTTTGGAGACTGTCGTGGTGGATTCG

FIG. 27D

TGAGTCGGCATGACGAATCCCTCGGGAATATCGTTCTTCGAATCCTCCACGTGCTGTTT

CACGATCGATTTGTATTCGTCGGGGCTCTTGCGCAACATGACCGAGGCGTCAACGTTGG

CGGGGGAAGAGATCCGGGGAATTC

FIG. 28

MKGILGLSLLPLLTAASPVFVDSIHNEAAPILSATNAKEVPDSYIVVFKKHVTSELASA
HHSWVQDIHDSQSERTELKKRSLFGLGDEVYLGLKNTFDIAGSLIGYSGHFHEDVIEQV
RRHPDVDYIERDSEVHTMEGATEKNAPWGLARISHRDSLTFGNFNKYLYASEGGEGVDA
YTIDTGINVDHVDFEGRATWGKTIPTNDEDLDGNHGTHCSGTMAGKKYGVAKKANLYA
VKVLRSSGSGTMSDVVSGVEYAVQAHIKKAKDAKNGKVKGFKGSVANMSLGGGKSKTLE
DAVNAGVEAGLHFAVAAGNDNADACNYSPAAAEKAITVGASTLADERAYFSNYGECTDI
FAPGLNILSTWIGSNYATNIISGTSMASPHIAGLLAYFVSLQPSSDSAFAVEELTPAKL
KKDIIAIATEGALTDIPSNTPNVSHAAVGIYKRNELTQKFSSLPGTVVVPRTTPTSLAA
VATRSPLPRTASRTVLRVSFTRPKSCSPRSLVPSTARSRMPSSHRSELVLSRRRSEDLV
FF

FIG. 29A

AAGCTTCGTATATAATTCCCTTTTGACAATGTCAAAATCTTTTGGACCACTAATATAGC
TGCATGGACCGGTTAATCAGAGGTTATTTTTGTGCTCGAATGCCGTGTAACATTGGATA
ATAGTACACTCCTTTCACCCACCCTCAGATGCCCGCCCCCTACAGTAGGGTTGTCAATA
TCCCTCACCTTTCCAATTGCTGATGCAGAATGGACCTGATATAGAAGCCTCACAGCACC
AGAGACTACCGCCTGAAGATGCCAAGTATTGATGGGTTACATTGGCTGGCGAATAGACT
GTTCACCATCCCCGCCTGTACAAGGCTCATTGAGCGACCTTTATTTCTATGAAGGCTT
CTTGCAGTGTAGAGCCGCTGTTTAGAACTCGGAAATAGGCGTGCATAGTATGAACTCAA
TCAGCAGAGTCAATCGATTGACACTAACGCCTAGCAAGCAATCAGTGCTCAGAGGAAGC
TAACAGATGGCTGGTTAAGCTGCCCCAGAAACGAAATGTGTCCGCAATCCCATCCCTGC
ATGCTTATCTGTATTCTGTGCATGCATGATGCTTTCCTCACGGGGCATTACCCAGTAGT
CCGAAGACGCAATGTGACCATCTGACTGAGTTTTAAATATACTGTCCAAGTGCCTTCTG
ACCCGGTCCCCGCTTGATGACAATCAACAAAGGTGAATGTGACTGAAAGGCGTGGTCC
AGACAACAGGCCTTAGACTTTATTGTGAGACTATAAAAGGATCTAACTATTGCACTACT
GAAATTAAGCATTCTAGTCTACCATTGACATTTCTCCCCTTTCGGTGGGCCACTCGCTC
AACATGGCTTTCCTCAAACGCATTCTCCCGCTGCTGGCCCTCATCTTGCCTGCAGTTTT
CAGTGCCACAGAACAGGTCCCTCATCCGACCATCCAGACCATCCCGGGGAAGTACATTG
TTACTTTCAAGTCCGGCATTGACAATGCGAAAATTGAGTCTCATGCCGCATGGGTAACG
GAGCTCCACAGGCGCAGCTTAGAAGGCCGCAGTACAA
CCGAAGATGACCTTCCCGCCGGGATCGAGAGAACTTACAGAATTGCCAATTTTGCTGGG
TACGCGGGGTCTTTCGATGAGAAAACTATCGAGGAGATCCGCAAACATAACCATGTTTG
TGTCCACGTATCCCAGGCCGTATGGTTTCGACTAACTGCTGTACAGGTAGCCTATGTGG
AACAAGATCAGGTCTGGTACCTCGATACGCTAGTTACCGAAAGACGAGCTCCTTGGGGA
CTGGGGAGCATCTCTCACCGTGGTGCGTCTAGCACCGACTACATCTATGATGACAGCGC
TGGGGAGGGTACATACGCTTATGTAGTGGACACTGGCATCTTGGCTACGCATAATGAGT
TTGGTGGTCGTGCTAGCCTGGCATACAATGCTGCAGGGGGTGAGCACGTTGATGGTGTT
GGACATGGCACACATGTAGCAGGGACCATCGGTGGCAAAACATACGGGGTTTCGAAAAA
TGCTCACCTACTGTCCGTGAAGGTGTTTGTAGGTGAATCCAGCTCGACATCGGTCATTC
TGGATGGCTTCAATTGGGCTGCCAATGATATCGTGAGCAAGAACCGGACCAGTAAGGCG

FIG. 29B

GCGATTAACATGAGTCTTGGTATGTGCGCCCTCTCTGGGGATCTAATGCCGTTAACCGT
GATGCAGGTGGAGGCTACTCCTATGCGTTTAACAATGCAGTTGAGAATGCTTTTGACGA
GGGTGTGCTCTCTTGTGTTGCCGCTGGAAATGAGAATGTAAGCTCTGCTGAACTGTCCA
CCATTGAGCTAAATTTAGACTAATGTTTTGCAGAGAGATGCAGCACGGACTAGCCCGGC
TTCTGCACCCGACGCCATTACTGTTGCCGCTATCAACAGAAGCAATGCCCGTGCGTCAT
TCTCAAACTACGGCTCTGTGGTTGACATTTTGCCCCGGGAGAGCAAGTACTTTCTGCA
TGGACCGGCTCGAACTCGGCCACCAACACGATCTCCGGCACGTCCATGGCTACACCTCA
TGTGACAGGTTTGATCCTCTATTTGATGGGCTTGCGGGACCTTGCTACCCCAGCGGCTG
CAACGACCGAGCTCAAGAGGTTGGCTACGCGGAATGCTGTCACCAATGTGGCGGGTAGC
CCCAATCTTCTGGCCTACAATGGAAACAGCGGCGTGTCAAAGGGGGTAGCGATGATGG
AGATGAGGACTAGGTGCGTAACATGAGTGAATATGGCTTAGAATAGTGGGGATCGGAGA
GTAGACTAGTTTATATGCGAAATAAAGTGTGTATCAGCACCCTGGCCTGTTCATGTAAG
TCGGCATTTTCACTTTTGCCGACACCGCAAATATGCTGTGCTTGAGGCTGTTGCCTCCC
CAGCCAGCCTTCCCGAGACTGAAACTCACACATCCATTGGATGTATAAAGTTCTGCACA
TGCGAAATGCCGCTGCCGCTTACCTCCCGACGTGGTACCGGACCGAAGGCAGACACAGA
TCATGGACCGCTATACCGCACAGACAACTTGTGCTCCTTACTGAAAGTACCATTCCACA
GGTCATTGCAGCATGATGAGTGATGATGTACTTCTCCCCATCAAGAACCACTGACGGTG
GTTGGAATGAATCTAGATCAAAGAGATCAACCGCTTCCCCAGACAGATCAGGCCTATGC
CCATAATGAACCGGTGACTGTGTAACCCTGTTACAATCCGTTTGTTATTGGTCCTTTCT
GTTTGCTGGATGGCGTGTACTACCTCAGAGCTTGTGCTCCTAGGAGCTCATACTGGAGA
CAGGTTCTTGTATATAGTCATAGCCTAAGTCCGGTGTCTAGGAAACAGTATGCTCGAGG
TCTTTTCCGATTCTCACAATGAGAACTGTCGCCCGGGTCTTTACGGCCCTGTGGAAAG
CGAAAAGGAGACGCTTCTGGCGCTGCTTCCGCAATACGGGCTCAAACTAGCCCCGGACG
GGATCC

FIG. 30

MAFLKRILPLLALILPAVFSATEQVPHPTIQTIPGKYIVTFKSGIDNAKIESHAAWVTE
LHRRSLEGRSTTEDDLPAGIERTYRIANFAGYAGSFDEKTIEEIRKHNHVAYVEQDQVW
YLDTLVTERRAPWGLGSISHRGASSTDYIYDDSAGEGTYAYVVDTGILATHNEFGGRAS
LAYNAAGGEHVDGVHGTHVAGTIGGKTYGVSKNAHLLSVKVFVGESSSTSVILDGFNW
AANDIVSKNRTSKAAINMSLGGGYSYAFNNAVENAFDEGVLSCVAAGNENRDAARTSPA
SAPDAITVAAINRSNARASFSNYGSVVDIFAPGEQVLSAWTGSNSATNTISGTSMATPH
VTGLILYLMGLRDLATPAAATTELKRLATRNAVTNVAGSPNLLAYNGNSGVSKGGSDDG
DED

FIG. 31A

```
GCTACGGACCAACCCCACCACATCAACCTACATGACTCACGAAGCCGAGGACGAGCT
CCTCCGCTCCGCATTGCACAAGTTCACCAACGTGGATGGCACCAACGGCCGTACTGT
CCTGCCCTTCCCGCATGACATGTTCTATGTTCCTGAGTTCAGGAAGTATGATGAGAT
GTCATACTCGGAGCGGATTGATCAAATCCGGGATGAGTTGAGCCTTAATGAACGGAG
TTCTCTGGAAGCGTTTATATTGCTTTGCTCTGGCGGAACGCTGGAGAATAGCTCATT
TGGAGAATTCCTGCATTGGTGGGCGATGAGCGGATATACGTATCAGGGATGCATGGA
CTGCTTGATAAGTTATAAGTTCAAGGATGGGCAGTCTGCATTTGCGAGGAGGTTTTG
GGAGGAGGCGGCCGGGACGGGGAGGTTGGGGTATGTGTTTGGGTGTCCGGTTAGGAG
TGTTGTTAATGAGAGAGATGCGGTGAGAGTGACGGCGAGGGATGGGAGGGAGTTCGT
TGCGAAGCGGGTGGTTTGCACTATTCCCCTCAATGTCTTGTCCACGATCCAGTTCTC
ACCTGCGCTGTCGACGGAGAGGATCTCTGCTATGCAGGCAGGTCATGTGAATATGTG
CACGAAGGTGCATGCCGAAGTGGACAATAAGGATATGCGGTCGTGGACGGGCATTGC
GTACCCTTTCAATAAACTGTGCTATGCTATTGGTGATGGGACGACTCCCGCGGGAAA
CACGCATCTGGTGTGTTTCGGGACGGATGCGAATCATATCCAGCCGGATGAGGACGT
GCGGGAGACGTTGAAGGCGGTTGGGCAGTTAGCGCCTGGGACATTTGGAGTGAAGCG
GTTGGTGTTTCACAATTGGGTGAAGGATGAGTTTGCGAAGGGCGCGTGGTTCTTCTC
TAGGCCTGGGATGGTGAGTGAGTGTTTGCAGGGGTTGAGGGAGAAGCATGGGGGTGT
GGTGTTTGCGAATTCAGATTGGGCGTTGGGGTGGAGGAGCTTTATTGATGGGCGAT
TGAGGAGGGGACGAGAGCTGCTAGGGTGGTGTTGGAGGAATTGGGAACGAAGAGGGA
GGTGAAGGCTCGTTTGTGATTGATTAAAGCCATTAAGGGGTATTGATTGTGAACATG
AATTTCATACTACATTCAACATAACTATACATGTGAATAATGGGGACATATCCAGTC
TATATCTAGTAGGTGTCGTTGGAGGTGTAGTTCTCGCGAGCAGCGAATCTCAGCTCC
GTGGCGCCAATGTCGAACACAGTGACGACATTCTTCTGGAAGGTGTCGCCCAGAATG
TAGAGATCTTCGGAGGTGTCGCTACCACCGTCAACGATACCGGAAATGCAGATGGTG
TTGCCCTCGTCGTCGGTGCCAGCATCGAGGATCATGTCGAGGGGTTGATGTAGAAG
GTCTTTCCGCTGATGGTGATGCCGTGAGTGGGAGGGTGGCGTCGCAGTCTACAATG
TAGGCGCCCTCCTCGTCCGAGTAAGTCGCCGCAGGGGAGAAAGCGGCGTTGATCTCC
TCAGCGATGGAAGTTGGGTAGTAGTTCAGGGTGGTGCCCGAATCGACCTGCATCTGT
TAGACACCATCAGGTAAAGGGGTGCTGGAGTCAACGTACGATGTACTGGATGTCGTC
```

FIG. 31B

```
GCCACCAGCGCTGGTCAAGCTCTTGCCGTTCAGAGTGACAGCGTCAATGTTGATGGT
GTAGAAGTCGTAGGCCTTGGAGTAGCCTTCGATGTTGGTGACCAGGATTGAGGTTTT
GGTGAAGTCTTCCACGAAGTCCACAGGAGGCAGACCGCCGAGAGCCAGATAGCCAGC
GGCACCGGAAACATCGCGCTCAATGGCCAGACTAAACAGAGGTTCGATCAGGCCCTC
CTCCCACATGGTGGTAATGATATTGCTGTAGACAATCTGCTCGTCGGTGGTTGTGGA
GTAGGCGCTCGTACTGATACATGTTAGAAGCCTGACTATCAGTAATTGGGGCAGAAT
ACATACAGGGCAGGGTACGCAAGACCAGTCAGGCCAGAGGTGGTTCCGTCGCCCTCC
CAGGCGGCCTCAGTGACCACTCCGATGGTTTGATCCACAGTGATATCGGCAAGAGCG
ACGGTTTCGTTACCCATCACTCCGTAGAGGTACTCACCATCACCATACTCGATGGCG
AATTCTTCGCCCTCAATTTCCTTGAAAGAGCTCTCGACAGTCCAGGTGGAGCCAAAG
TCGCAGCTCGACTCGGAGGTTTCGCGGCCGGTGTCGAGGTCAATACATGTGAAGCCC
GTCTTAACGACCCAGGTATCACTGGAACCGGTGTCGACGATAACGTCAAAAGAATCA
CCACCGATGGTGATTGAGGTAGCGAACTCCTCGCCTTCGAAGAGGGAGATCAAGCTG
GAGCTGCCACTGCTGGTGGAGCGCTTCACGTAGGCAGCACTACGAGGGTTCACATTT
CCCTTGGACTTGGTCTTGCTCAGCTCGAGGTACTTGGAGGAGGCCTTGTTGTGACTG
GGAGCAGCGAAGGCGGCGGGCTTGTAGACGGTGTGGCTGCCGCTTCTGCGGACGATA
TTTCTTCCCTTGAGCGGGGAGGGAGTGGGTGCAGCCAGAGCAGCCCCGGCAAGGAGC
GAGGCAGTGGCAAGGGTACCGACGGGGATATACATGGCGGCAGCTGAGTGAGAAGTG
ATCTAAGTGATTGCTTGACTGACAGGAGAGAAGCCTCGTGCAGAAGAGGGGTGCGTT
CGGGAGATTATATAGTGTTGGGAAATTACATCCGGTAGTCGGACAAGACCACCAATC
TAGCTACAATTAAACATACAGGAATGAGAGACATTCGCTGGATTGCAGAATCTCGCT
GTTGTCGACTAGCATAGCTCGCAGCTTCCGAAGTGGCGGTTAGCAATGACGCGATGC
GAGTGGTTGAAAAGACAAGGCGGACCGGTATAGTGCTGCCTGATAGTGACGAGACAT
GGCCTCCCACTCGATGGCTAGGAACAATAGCGCCGTGTGGGCCCGGCACCGATATTG
CTGATAGGGAGCGTTGCGTCAGCGCTGGTCCTGGATTGGTGCGAAGCCAGGCCCACA
GAAGATAAGACGCAAGGTGCGCGTCGGAGTCCGCAGGGGAGGGGTCGAAGGTTGAAG
ACTGAACAGATGATAGATTGGAATATATTGGGGCAGCCAGAAATTGCTTCATGCGCT
CGATGTGATCATTGTTGCGCTTTTCCTTCCCTGTAATAGAGTAACCGAGCCTTGAAT
AATTGTATCGGGCACCATCTCGGGGATAACCCTGAAGGCATTAGCGCCCGGCGAAAT
```

FIG. 31C

```
GTCGACGAGTGCAGCACACGGAGACTGTCATCCGACAAGGCCATTGTGACGAATCTG
AGGCACACACAGTTCCCCTTCATTTGATAACGACCAATAATTGCCATCGTAAGAATG
GCAATAGAGCAATCCCTCGTTGAGACATGTATCAGCTGCTTTTCGTCCGAGACGCCC
CTCTGTTAGACGTTGACAAGCGTGCTATAACCTTGAAACCCACATCTGACTCCTGAC
AGGCCCATGACTGGGTCCAAGGTAGGCCAAGCATCGGAGACAACCGAGAGGGGAGA
TGGTTTCATGCTTGATGCTGTCAAGCTCAGATCGGCGGATTATCGGAGTAGCTGTCA
GATCACGTGGTGGGGCATAGATAGCAGCCCTGTGTTGCTGGTATGTGACATTTTAGT
AGCCCATCACTAAACAGGCACATACCGCAGACTTGTTAATTAACTCTGCGATAAGGG
ACGTCCTTCTTAGTCCCTGAAGTGTATAGTAACGACGGAGATGCCGTGAAGAAAGAA
CGCTGAGAGGCAAACACGTGCGGGAACCTCGGAAGAGAAAGACCCGCACCGCCCCG
GGCAGCCATCGGACATCCGCGGATTTCATTTCAGCGTCCTTGGAGTTTCCACAACAC
TCTTCATATCAGCCCACTATCGGATAGCGCCATCAGTAGCTAATATCCGCGCATACT
TGCATGGCTTTTATGCCTTGATGGTCGCCGAGCGGGTCCCCATGGGTCGCGACGGAC
TCCGGTAGTAATCCCCAGTCGCGAGGTATGCCCAGTTTTCGTCGCACACCCGCAGGT
CATGGCTAACGTCTTCTCGCGTCCCAGGATGCTTTCAATGCTCAAAACGCCGGATTG
TCTGCGACAGAGGGGAACCTACCTGCTTCAAGTGTCAGAAGAAAGGGATTGAATGCT
CGGGATCCGGTCGCTTTCGCTTCAGCCCCGGCCTAGCGAGTCGGGGAAAACTCAAAG
GCTGCACGATTCCGATACCTGATGTCGACCCGAGATCGGTATACAAAGAAGGCTTAG
ATGGCCCTCGTCCGATTCGGTGGAAGGATGACCTGAATAGAGTCAACAAAACCAGAA
GCCCAGACTTAGCGGGAAGGAGCGGGTAGTCCGGAATGGACTGGTCACAGAGAGGGG
TTCGGCCAGTGGAGGCAGAGCTTCGCANCCANATCGATATCTATCGCAAACCAGACG
TATCCTAGCTCAGACAATNGTTCCGCGA
```

FIG. 32

MYIPVGTLATASLLAGAALAAPTPSPLKGRNIVRRSGSHTVYKPAAFAAPSHNKASS
KYLELSKTKSKGNVNPRSAAYVKRSTSSGSSSLISLFEGEEFATSITIGGDSFDVIV
DTGSSDTWVVKTGFTCIDLDTGRETSESSCDFGSTWTVESSFKEIEGEEFAIEYGDG
EYLYGVMGNETVALADITVDQTIGVVTEAAWEGDGTTSGLTGLAYPALTSAYSTTTD
EQIVYSNIITTMWEEGLIEPLFSLAIERDVSGAAGYLALGGLPPVDFVEDFTKTSIL
VTNIEGYSKAYDFYTINIDAVTLNGKSLTSAGGDDIQYIMQVDSGTTLNYYPTSIAE
EINAAFSPAATYSDEEGAYIVDCDATPPTHGITISGKTFYINPLDMILDAGTDDEGN
TICISGIVDGGSDTSEDLYILGDTFQKNVVTVFDIGATELRFAARENYTSNDTY

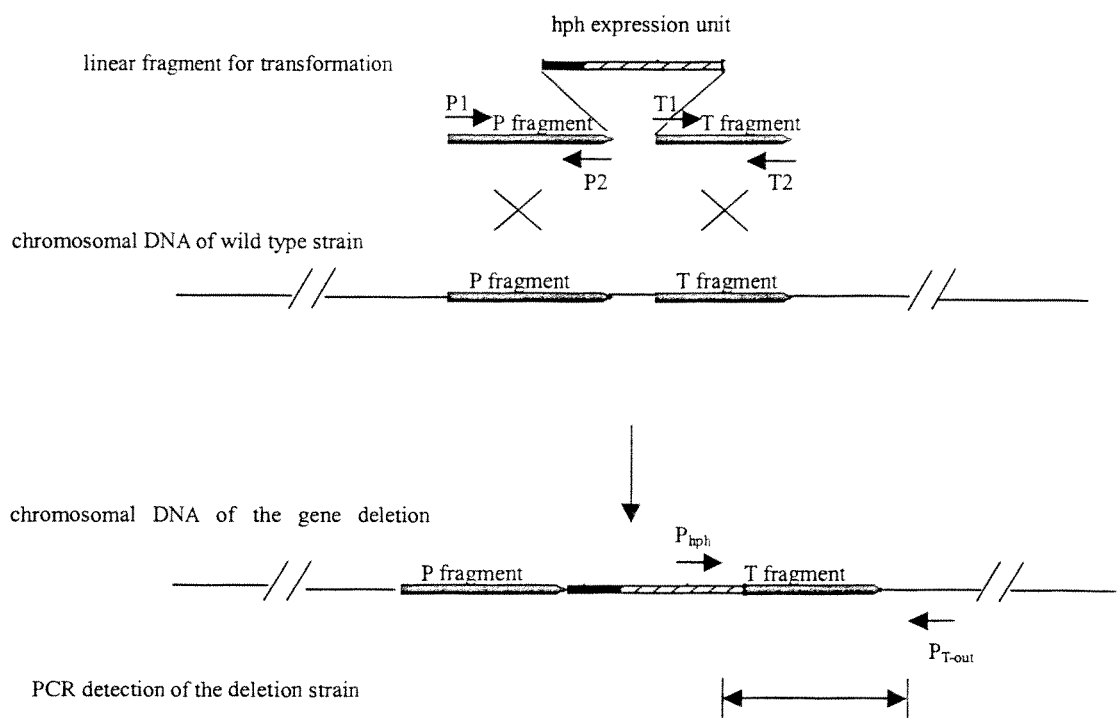
FIG. 33A: General cloning strategy for gene deletion in Aspergillus.

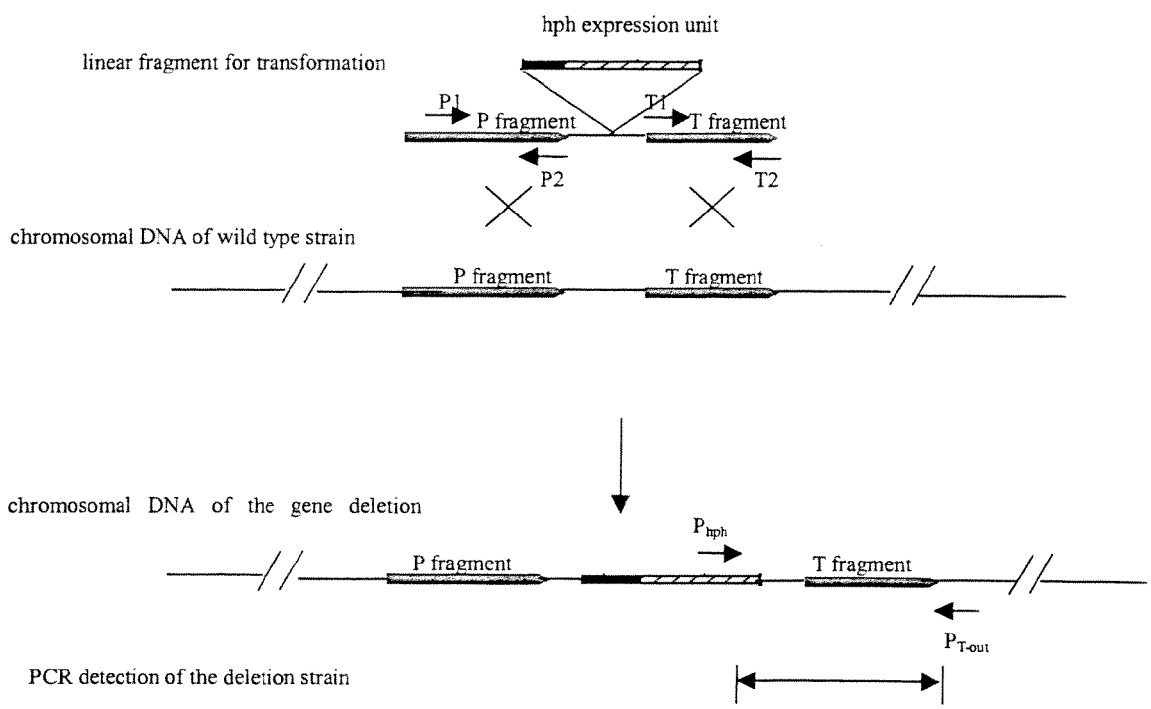
FIG. 33B: General cloning strategy for gene disruption in Aspergillus.

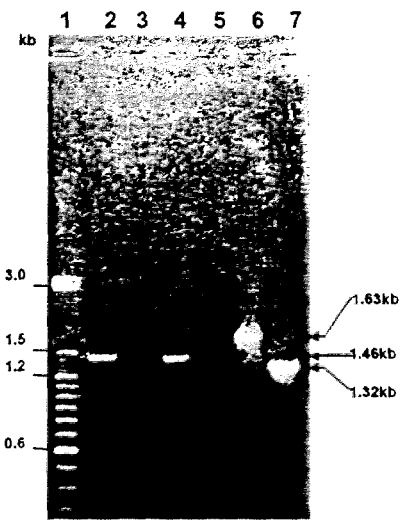
FIG. 34A: PCR analysis of the *mnn9* deletion strain
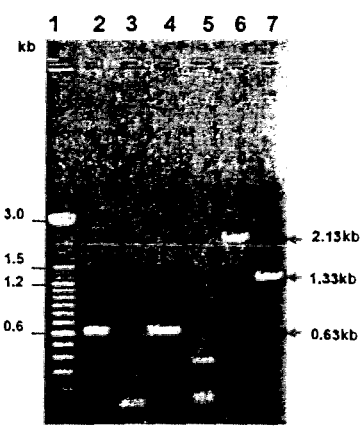
FIG. 34B: PCR analysis of *ochA* disruption strain

SEQUENCE LISTING

<160> NUMBER OF SEQ ID NOS: 97

<210> SEQ ID NO 1
<211> LENGTH: 2400
<212> TYPE: DNA
<213> ORGANISM: Aspergillus sp.

<400> SEQUENCE: 1

```
ccccgggcga gtcaatgacg ctttaggttt aaatggtgtg aggtggtgcg ccaactcgtc      60
gtctcctggc ggcctgaggc tttgaataaa ttgagctctg ggcgcgatcg actggcacag     120
tcgagaaata agctgcaagg cgaaaaccgc ggaggagcgt ttgtcaggga tgagattgca     180
tgcgagagag ggacccatcc gggaggccga acggactatg aagtgatgga atccccagcc     240
atccgaattc ttgtccggac gcgtgcgagg cgcgtctttg cggcgtcgaa gcgcgcggga     300
```

```
gcgacacgtg acatatgcgc cggggagtga caggtgacac ctgaggccaa aaggccagct    360
ggagctcggc gattacggcg gaactaaact ggcagttatt tagtggtgat tcggcatcat    420
ccccttatcg atcatactcg cccgtcttct ctcgagtcct taaacgccaa aagacgactg    480
tctgcatcct ctctatttcg cttaccgctt cgtcgcatcg tacccgccac ccgagcaacc    540
tcccccctaa gttaatccca acgttcgcaa ctctactacc catcaattat ggccgccatc    600
tggggtaacg gcgggcaggc tggccagttc ccgctggagc aatggttcta tgaaatgccc    660
cctgtaactc gatggtggac agcagccaca gttgccactt cagtcttggt ccaatgtcac    720
gtcctcaccc cattccagct gttttatagc ttccgcgcag tctatgttaa gtctcaggta    780
cgtcgcagct agtacttccg tccactgtat agggtagacg aatcacgcgg ctaaccatcg    840
catagtattg gcgtctgttc acaaccttcc tatacttcgg accactcaat ctcgacttac    900
tatttcatgt gttcttcttg cagcgatact cgcgcctctt ggaggaatca tcggggcgat    960
cgccggccca cttctcgtgg cttctgttct acgccatggc ctctctcctc gtcctctcgc   1020
catttctctc ccttccattc ctgggcacgg ctctctcttc cagtctggtc tacatctgga   1080
gtcgtcgcaa cccggaaact cgcctcagct tcctaggaat gctggtcttc accgcccccct  1140
atctcccctg ggttctgatg gcattcagcc tggtcgtcca tggcatcgtg cccaaggatg   1200
aaatctgcgg cgttgtcgtc ggccacgtct ggtacttctt caacgatgtt tacccttcgc   1260
ttcacggtgg tcaccgtcct ttcgatcctc ctatgtggtg ggtgcgtctg tttgagtcag   1320
ggcccgggga acgaggcacc gacgctgcca acgtcaacgg ggaattcgcc gctgctgctg   1380
cacccgaagt tcggtgagct atttgtgcac cccactgggg catttactgc atggcgatgc   1440
aaagaatcgt ccgcgtaatc gctctggaaa cgtcagcata tatgtgtgta ctgccaacta   1500
ctcgcgccga cacgcgcgaa gcatgagaag ttaatactgt caggatataa gcaaggatca   1560
cggcggcaga cttgatggga tttcttatcg tgtggcttgt cttgtccagg agagtcatt    1620
tgatctgccc ccacgccgcc gtggctgatt gcgctctggc ctcctattag aaatgccgca   1680
aggacaagac cgtcagagtc cccgagtatc aatatgcgag aggcagagca atcaacttat   1740
ttcgccaacc agtggaagga gttgggatca cttgtgggga agatgtgcaa gaaaggaaga   1800
gaggagtatc atcaaggcaa tagcgggcgc tctgtctgcg gggggttagta acaggtgtgt   1860
ctgtaagaga gacagactat catggcgatc aatcagctag tagttcaatg aaaataccca   1920
agtcatgttt ttagctgata atttacattt tgcgagaggg gaggaggggg gccgtgaacg   1980
catggacgca tgaggctgct ctcccatatg cagtaggaat atcgtagcat cccaattacc   2040
tgaacgggcg gccacgtgt cgatccaggg tgcaagctcg aagtttgggg taaattctcc    2100
gcaatgtcta tcccaatgtc gctttctact ttcttctttc ccacttttaa tcaatgccat   2160
acagacttgt atccaggatt tgcccctagt tcagtatcgt atggtttgat ccaatcgatc   2220
gatctggact tcctctcttt ccccgcgtta catagcacca ccggtatagt taccatgtag   2280
aacaaccatg acaatacttc tctgcctgag cgttgatcaa ccagtcagag acagacgctt   2340
tggccgatca aagacaagat agtcttaatt ctctcaccat gaagactagc tatctacaca   2400
```

<210> SEQ ID NO 2
<211> LENGTH: 246
<212> TYPE: PRT
<213> ORGANISM: Aspergillus sp.

<400> SEQUENCE: 2

Met Ala Ala Ile Trp Gly Asn Gly Gly Gln Ala Gly Gln Phe Pro Leu

```
                1               5               10              15
Glu Gln Trp Phe Tyr Glu Met Pro Pro Val Thr Arg Trp Trp Thr Ala
                20              25              30

Ala Thr Val Ala Thr Ser Val Leu Val Gln Cys His Val Leu Thr Pro
        35              40              45

Phe Gln Leu Phe Tyr Ser Phe Arg Ala Val Tyr Val Lys Ser Gln Tyr
    50              55              60

Trp Arg Leu Phe Thr Thr Phe Leu Tyr Phe Gly Pro Leu Asn Leu Asp
65              70              75              80

Leu Leu Phe His Val Phe Phe Leu Gln Arg Tyr Ser Arg Leu Leu Glu
                85              90              95

Glu Ser Ser Gly Arg Ser Pro Ala His Phe Ser Trp Leu Leu Phe Tyr
                100             105             110

Ala Met Ala Ser Leu Leu Val Leu Ser Pro Phe Leu Ser Leu Pro Phe
            115             120             125

Leu Gly Thr Ala Leu Ser Ser Leu Val Tyr Ile Trp Ser Arg Arg
        130             135             140

Asn Pro Glu Thr Arg Leu Ser Phe Leu Gly Met Leu Val Phe Thr Ala
145             150             155             160

Pro Tyr Leu Pro Trp Val Leu Met Ala Phe Ser Leu Val Val His Gly
                165             170             175

Ile Val Pro Lys Asp Glu Ile Cys Gly Val Val Val Gly His Val Trp
                180             185             190

Tyr Phe Phe Asn Asp Val Tyr Pro Ser Leu His Gly Gly His Arg Pro
                195             200             205

Phe Asp Pro Pro Met Trp Trp Val Arg Leu Phe Glu Ser Gly Pro Gly
            210             215             220

Glu Arg Gly Thr Asp Ala Ala Asn Val Asn Gly Glu Phe Ala Ala Ala
225             230             235             240

Ala Ala Pro Glu Val Arg
            245

<210> SEQ ID NO 3
<211> LENGTH: 2673
<212> TYPE: DNA
<213> ORGANISM: Aspergillus sp.

<400> SEQUENCE: 3
ggctcagcac aatgggctcc actacggcgg aaatacaacc tcttcacgta tcaccactcg      60
ccaaatccag cgacagagat gaaaacagag aagctaccgc ttaaccagat ggatttgtct     120
aataagcagc aaatgcagct ggtccaatca tctcagagtg ccaagaaac  gggcgaatat     180 caccaattcg cctacgtgga cgagcctttc ttgtcgtggg attttggtct acgctcggct     240
gacaaacagc tgatcggctc tgtgaatcgc aactttgccg ggtttgcccg ggaaatcttc     300
acggatacgg gtgtctatgc tctgcgaatg gactctgctt ctcccagcga agagttcctc     360
gacaagaacc gtgcggctac tgggatgaca ttcgaccagc gtgccgtgat gctggcaacc     420
gctgtgagca ttgactttga ctactttagt cgccatagca actcgggtgg atttggtttc     480
atgcctctct ggatccctgg atttggtggt gaggcagctg ctgggggtgc tgccgggggc     540
gcagcagccg gtgaagcagg tgccgtgggg aagcggccg  cggaactct  tggtcgggct     600 ggggcagccg gtggaatggc tgatggcgct gcagcaggtg cagcaggtgc gggcgcaatg     660
gctggctaca agccatgtc  ccgtgggatg ggaggcagcc agcctgctcc cgatcagcaa     720
gcggcacctg tagaccaaca gccaccgacg ccaggtcaaa cgggtccgta tggagatgtc     780
```

```
tgggggggaag agtccgagaa cccatgggga aggagcctg agaacacatg gggccaggaa      840
gaggatccgt gggcagatga agccgacgag ggcgagggag gcgatgattt cgattggttt      900
taagcggctg ataactacaa acaggcagta agatcaggat ggttgacatt gtgagacggt      960
cagacatata ctatcccccc attcatgcag ggataacgac gacagagctc atgtaatcgg     1020
gggcactgag aatcaccgta acggcttcaa tgacatggcc tgcggcatac tcgacatgat     1080
ctgaccgagt agacatcgac gtcattcata ctcggccctg cttgaagtgc aaagcggttt     1140
atgcagctga ctgacgatga ttagcccgat gtaccataac gacaataaaa tctccaaata     1200
actgtataat atcacgcgaa aaatgaaaca atgctagcca gaaataaact caagatcatt     1260
ctcctttcat actgatgaaa gcggcgataa gcatcattgc agcctcaggc acccaacaca     1320
tcccaccggc tcaaccatcg atgaatggaa cctcaatcac tcaatcattc attggctttc     1380
agagtggcaa accttgattt ctcctccaat tcaattccaa cccactcatc ttccccagta     1440
aaccgacctc taaaaagttt ttcttagtcc tatctcctca acgccacccc aggtacataa     1500
ccaccacccc tattaagtac ccccggtgtc ctcaccctct ccggtccgat ctccgcactc     1560
tcctctcccc tctttatcta atcgccagat agacagccag accgccacca ccaccagcac     1620
caaaaaccca ctacctgctt ccctcccacg acgccggaga aattaagcca ataattaaaa     1680
ccaatacttc aatagagaaa gaaaggcagt gatcaatcaa aatgtcctcc gtcgcccaga     1740
aacgcctctt tcacgataca aaaacctctc caccaacccc cccgagggca tcaccgccgg     1800
ccccgtcacc gaagatgaca tgttccactg ggaagcacta atccagggcc ctgaaggtac     1860
gcccttcgag ggcggcgtgt tcgcggccga gttgaagttc cctaaagatt atccgcttag     1920
tccgcctaca atgaagtttg tgggtggtgg ggtttggcat cctaatggta aataactcct     1980
tcttttcccc ttctttctct gtctggattt ttctttgtct tcaagtcttt tctggtgatg     2040
cttggttgag cttatgctaa cgtgtttgg acatacgtat agtataccc aacggaaccg     2100 tgtgcatttc catcctccac cccccggtg acgaccccaa ccattacgaa catgcttcgg     2160
agcggtggtc tcctatccag agcgtggaga agattctcat ctccgttatg agtatgttgg     2220
cggagccgaa tgatgagtct ccggcgaacg tggaggctgc gaagatgtgg agggagcgga     2280
ggggggagta tgagcggaag gtgagggatg aggttaggaa gggattgggg ctgtgaaacc     2340
ctctcttctt taatttgagt tgaatggtga aggggagggg cttggtcata tataagtgac     2400
cggttggtgc gctggttgct cactgtctgt ctatactctg tgtcgtggag gaaaatgtgg     2460
catagcttgg atggatgcat tggttgcttg ggttggcgtt gtggtgcgtt cgttctttct     2520
ctttctttca tctttatata tattctattt gatgcccact tctaggggta gatgcatggc     2580
caggaatgca tagatgcttt gttcagtata tatcggtatc tttcgtcgtg ataatggtac     2640
gaagtcatga atactcgaat tcgccctata gta                                  2673
```

<210> SEQ ID NO 4  
<211> LENGTH: 166  
<212> TYPE: PRT  
<213> ORGANISM: Aspergillus sp.  
<220> FEATURE:  
<221> NAME/KEY: misc_feature  
<222> LOCATION: (11)..(11)  
<223> OTHER INFORMATION: Xaa can be any naturally occurring amino acid  
<220> FEATURE:  
<221> NAME/KEY: misc_feature  
<222> LOCATION: (15)..(15)  
<223> OTHER INFORMATION: Xaa can be any naturally occurring amino acid  
<220> FEATURE:  
<221> NAME/KEY: misc_feature

```
<222> LOCATION: (17)..(17)
<223> OTHER INFORMATION: Xaa can be any naturally occurring amino acid

<400> SEQUENCE: 4
```

Met Ser Ser Val Ala Gln Lys Arg Leu Phe Xaa Ile Gln Lys Xaa Phe
1               5                   10                  15

Xaa Thr Asn Pro Pro Glu Gly Ile Thr Ala Gly Pro Val Thr Glu Asp
                20                  25                  30

Asp Met Phe His Trp Glu Ala Leu Ile Gln Gly Pro Gly Thr Pro
            35                  40                  45

Phe Glu Gly Gly Val Phe Ala Ala Glu Leu Lys Phe Pro Lys Asp Tyr
        50                  55                  60

Pro Leu Ser Pro Pro Thr Met Lys Phe Val Gly Gly Val Trp His
65                  70                  75                  80

Pro Asn Val Tyr Pro Asn Gly Thr Val Cys Ile Ser Ile Leu His Pro
                85                  90                  95

Pro Gly Asp Asp Pro Asn His Tyr Glu His Ala Ser Glu Arg Trp Ser
            100                 105                 110

Pro Ile Gln Ser Val Glu Lys Ile Leu Ile Ser Val Met Ser Met Leu
        115                 120                 125

Ala Glu Pro Asn Asp Glu Ser Pro Ala Asn Val Glu Ala Ala Lys Met
130                 135                 140

Trp Arg Glu Arg Arg Gly Glu Tyr Glu Arg Lys Val Arg Asp Glu Val
145                 150                 155                 160

Arg Lys Gly Leu Gly Leu
                165

```
<210> SEQ ID NO 5
<211> LENGTH: 7000
<212> TYPE: DNA
<213> ORGANISM: Aspergillus sp.

<400> SEQUENCE: 5
```

| | | | | | |
|---|---|---|---|---|---|
| gatataatag | tgaactgctt | gtcgcactct | ctccgtgctg | aaccgaatca | ccctccccta | 60 |
| accggctggc | ctggtgctcg | ccctgttcct | tcgcttttc | tacgcgttcg | tttcaaagcc | 120 |
| caatttctt | ctatctactc | tatcccgaga | cggatttacc | aatcctcttg | ctatctaatt | 180 |
| gcctttgggt | cgccatcgcc | cgtgtcctgt | gactccgcga | tcgggattcc | tgcgtctgat | 240 |
| gctgctctcc | cctgggcccc | cctcctacac | cccaggctcg | atcttcatta | tgaatgtata | 300 |
| gcgtccgaaa | tcataacgaa | tttcccagtt | cggccacaga | tatccgcctt | cgccagcaat | 360 |
| tatccgcttt | gcgtcgtaaa | ggtcctcatt | ccaggcggtt | tgcatccggt | tctgcgttcc | 420 |
| cgcgacgctt | atttgtgtgt | tgttcaacga | atgcggaagt | gggcagtaca | tatcgacgca | 480 |
| aaacatatca | tattcgcgat | tggagttacc | gctgtcgacg | cctataatat | taatcagtga | 540 |
| tctctgcgaa | acacttgaaa | gtcgcgccct | acgtctgtcc | agatgtcatt | gtacgattgc | 600 |
| tagtttgaat | tgacatggaa | tcggttcagc | tgtctcattc | gggatcgaca | acacattcca | 660 |
| gctcgatccc | cggcatgttc | tcgcccgatc | gctcttcgca | tgtcaatacc | agtgggtcaa | 720 |
| tcgcagatga | ccagcctcga | cgagctccca | atcgggagga | gcgattcaca | tcatgggtag | 780 |
| ccgaccatcg | tctcgacctg | aacagcgaa | tccttggtga | ccgcgctgag | cgtcgcgaat | 840 |
| cgcgtctacc | tggtcgacca | gcgccatcgc | atagttctct | tagagacgct | gctgcatctc | 900 |
| aatatgcgcc | aagagggccg | tatgtcccaa | ttgagttgca | gtccgcagca | gcaggaagct | 960 |
| ccggcgaagc | gcggtcgcat | gcgcgctcag | aacgagaatc | gcattcagca | cactccccgc | 1020 |

```
ctgaccctga agacctccga tgcaggcaat cgcaatcgtt cgtatcacgg ctgaaggaga      1080
agaggctacg gaggcgactg attacgctgg ttatatctgc atgttttctc atcctcgtta      1140
tcgccattta cctcgcattc gctgcttccc gtacgacatt gggccgagag ctccaaatac      1200
ttctcatctt catgatctta attcttggca ttgttttctg tcattctctc acgcgcttct      1260
tgatggcact attacgacgg cctgactctg atgtcgctac gaatcgcata cccagtaggg      1320
cagggccagc cggctatgcg caaccagcgc gtcccatcca cgttattcta gctgagatg       1380 aggacgttgg agccgcgagt ccgaatgccg tgcgcgaaaa ggtcacggcg cctcctccgg      1440
catacggtct ttggcgagaa agtgtggtaa gtacatgatt acaggaatgg cgttatttcc      1500
ttgatggtga ccagtcccgc taactttgtg cagaggatta accccgactt gttgtactgg      1560
cagcgcatcg aaataacaa tgcgcacgta cccaagggtg tttggcaggc atgggagcaa       1620
taaatcgcgg atcccacggc cgcctagcta cacctctgac aacggcgtcg actatgtgat      1680
agaagcgcaa ccccgatcat tcacccaatg gcggattcct gaagaatcag ggcatcagcc      1740
atgacccata catatctctc tctcttttct cgacatactg aagctggatt caccgacaca      1800
atgcatccaa caatcgtctc gttatccgca aaatcattta tatagcggta ctgtgatcac      1860
cttcatctgt atttcttttg ctcgagatat cccctgtgac ttggcttctt tcccttttt       1920 ttcacccttt tgcggcattc tcatcaccaa tcatgtgatg tttctttgtt ttcttttgta      1980
cctgaaaatt cttggatgaa gcgggagtta cattggcata cacactgatc ttcctggcga      2040
gcatttgttt gagcgctatt tcattaagct tggttttcta acttactgca aagtacatct      2100 taaccctttct aaatgttaaa gtatctggga aacgaggcct accgtaagca agccgattcg     2160
tcaaaaatcc tgtattaata atataaacat cccctaaaat tgaattaagg gatcctgtag      2220
tccgaaggga aggggagtg gagggagaat gtaaacggca tatctggccg caaattggtt       2280
cgccgcggat tgaatacgac ctcacgtgcg gcgccgctgc caccaccaac ttcccctcaa      2340
gcctcccccc tcaggaaccc ttctctggag gcagttcagt tcgccggtct gcggggtttt     2400
cacattgaac agttcatcaa cgcgctccca tgccattgat aactgtttcg ctactgcggt      2460
aatgcgctcg ggatgttggc actcgcagat gtccgccctc cgttcagcat ggatcatgac      2520
ctgggtcttg ctgctgtcgc tgtggctcgc catggcccag ggcatgcgga ccggtcaggt      2580
taacgaactc aggtaaatct caccagtcat tacctgattc ccggtttcgc tggtataggg      2640
gccgatcgac tgacaccctc gatatttagg aaggagacag agcatatgtt ctaccacgga     2700
ttcgaaaact atctcgaaca cgcctttcct gaagacgaac tccgtccttt aacatgccgt      2760
ccgctggttc gcgaccgaga gaatcccgcg catgcagagc tcaacgatgt cctgggtaat     2820
tattcattga ctctgatcga cagtctgtcc tccctggcaa tactttcgtc gagtcccgac     2880
cagggccaga aggcttggga ttacttccag aatggagtga aggattttgt tacactgtac      2940
ggcgatggat ccgatggccc cgcgggccag ggtcagaggg gacgaggatt cgatatggat     3000
agtaaagtgc aagtgttcga gacggtgatt cgagggttag gtaggcatcg gatcttgtgc     3060
atggggagta tgcatctcga ttaatggttt tctctaggtg gcctactcag cgctcatctt      3120
tttgctgtgg gcgatcttcc tatcaccgga tacaatccgc cggagaccga agccaacttc      3180
gccagagcct gggataagca ctccttccct gaaggcagtc gcggcatcga gtggaaggac      3240
ggattcgtct acgatggcca acttctacgg cttgctgtcg atcttgcaaa tcgaatttta      3300
cccgcgttct atacggacac tggactccct taccctcgag tgaacttgaa gtacggggtg     3360
caacggcagc cgtactacgc aaactcaccg tttaatgcag cccctacgtg tgataaagcc      3420
```

-continued

```
aatcctgaac agtgccaaaa gcctcgccgc tcctcgacct ttgagactac ggaaacctgc    3480
agcgctggcg ctggcagtct agtcctcgag tttacagttt tgagcagact acaggcgat    3540 ggacgatatg aggagcttgc caagcgagca ttctgggccg tttgggcaag gaggagtgat    3600
attggactga ttgggtccgg tattgatgcc gagtcaggta gatgggttca ttcctatacc    3660
ggggtgagtc aaatcaagca cgtgcatttg aatatggcta acactaccac gtcccagatc    3720
ggcgcaggaa ttgatagctt tttcgagtat gctttcaagt cctacgtact actctcgtca    3780
ggggaacggc ccccggccaa tactagcagc ccgtggcatg ccctggacga ctatttccta    3840
ccactttcag aatacgagca ctccgccgat gcctttctga aggtctggga gaagtctcat    3900
gcctcaataa aacgtcacct ataccgcgga gagggccatc agcacccgca tctgatccag    3960
ggagacatct tcaccggagc gactcgtgct ttttggatcg acagtcttag cgccttctac    4020
cccggacttc ttactttagc gggagaagtg gatgaagcca ttggcatcca tcttctgacg    4080
acggcagtct ggactcgatt ttccggtctt cctgagcgat ggaatgttgc caccggggac    4140
attgaacagg cctttcctg gtatggtggc cgccctgagt tcgtggaatc tacttactac    4200
ctctaccgag cgacaaagga cccctggtat ctgcatgtcg gagagatggt actgcgggat    4260
ttgaaacggc gatgctggac caagtgcggt tgggctggta ttcaggacgt tcggaatggc    4320
gagctcaatg accgcatgga gagcttcttc ctgggtgaaa ctgccaagta catgtttctg    4380
ctgtacgatt ttgatcatcc cctcaataag ctagaccagc cgttcgtctt ctccaccgag    4440
ggccaccctc taattatccc caagaacagc acggcacagc gcgctgagcg caagcaggta    4500
ccagtcgttg tggagagcga gggtttgaca tgcccaacag cacctcagcc tccaacgctg    4560
ggggtttcat ccactgcggc acggtccgat ctgttccacg ccgcgaacct ggcacgccta    4620
cacctcatgc cgagtagagg tctagcggaa ggccctcttc tggattacgc tcgggaccac    4680
ccgagcgtat cagtgtcgga cttgtcgtcg cccaccaact acacattctt cccatggaca    4740
ttgcctccag agcttgtgcc atttaacgca accagcgcgc cgatgacaat ccgtcctacg    4800
ctcgacattt cttccccgc gcttccggt atggtcgtgg gcctggatc actggaacga    4860 gtgcgggatg gcatctttat caaagccatc ggggcctac gactaagtat ggttcaggat    4920
gtccctgtgc aagggaatc cgggagcgca gagagtgatg aattccgggt ccaggttatc    4980
aacaacgtgc cactgggcaa agacgagaag gtatatcttc tacgggaaat cacatttgat    5040
gtcctcgacc ccaccgaccc gaatttcacg cgggttcgcg acaccgccat gattgacatc    5100
gtcattgacg ttatcccaga gattatccgt cgacgaaatg attcagatga tagtcatgaa    5160
ccagctgcgc ctcgacgtgc caacggagcc atcgtccatg gctccagctc cgtcgacagt    5220
aaagtcggca gcgtagatgc gtcgacctcc agcatgaaga ctgtgctctc ctcgctagtc    5280
aacactctat ctacactcct tcgggatgaa gtacagggcc agaccagcct gccgcagaag    5340
aaagccacct cgttacgtct cctgctcccg gccgccatct ccacgggct cggctcggcc    5400 ccgctccccg acgtggaaga cgccacgaca gtctccatca cgggcgaccc ttccaagcaa    5460
cgcctcacat ggaacagcat ctacttcgcg gacgagctct gcgacaaccg catcctacga    5520
gaagttgcac agaaccacca ggtcctcgta atcaagcgag gcggatgcaa cttttcgcag    5580
aagctgcgca acattgccgc gtatccgcct tctcggtacg ccctgaaact agtcatcgtg    5640
gtctcctacg acgatgaagt agtcgaggag gagcagcgcg aggaatcaga caccaccacg    5700
accccggggc tagctgcggt ccgcgcggaa ccttatctgg tgcggccccca tctgacgag    5760 acgcaaatga cagccgcggg cgtcccgcgg cgccagctgc tcagcgtagt catggtaggc    5820
```

```
ggagggcaag aaacatacga gctactgcga caagccacgg gggtgggcat taaacggcga  5880
tattcggtgc gatcgcaggg agttcccatc aacaatctgt atattttgtg agaaggatat  5940
gagtgaccct tagcacatgc cccattgcaa cgagtttacc tatatgatat agcatcatag  6000
catagctttt tcatcctagt cataacatat tagtagcatt cccagtacac gtcactcctc  6060
ccgcctccct ccaccttggg aatactgaca taccaaacac tatgcccatg acatacgtac  6120
atacatacat acatacatac catgaatgac atgatgacat accaaaaaca ccctgatctt  6180
cattttcaac cctcgccacc tccggacggg aaaccccgat cgatcggcaa tcgttcggtg  6240
gccctccccc tgccacaacc gagatccggc gtcacgtcaa atgtcgccat taagattaat  6300
ggttaagcaa agtattggct gtggctgcca cggggaacca gctgactcag ctgctcagcc  6360
ttcagatgtt ccgaatgttt gaaaggcttg aaggcttgaa gaagtggcgg tggggcaggt  6420
ttacttgccg attggttcaa tccccgtgg agcaacggat aagaaaaccc ctgccgatag  6480
aacgaaaagc aaaatgtaag gcgggatggc aaatgaaagc gaggaggttt aaggtttacg  6540
tggtttggaa tgtgtccctg atttggggg gggtgtgtgg cagtgggctg tgggaagggt  6600
tataaatacc tgcttccttt tctctttctt ttttaagggt agagagagag ggatctctag  6660
atctgaatca ataacgagga tttacttgtc tatttgatta tacatataca tatttggact  6720
ggttctggta ctatatatcc ggacactcat tgagtcctag tatttactca ttcacttctt  6780
tcctcgagta tatatctatt ataacagtcc tatccctctc aactactact attactacac  6840
aacccactac gaaccaaaat caaaatgcat ctccacacag acctcgacgt cgacaccacc  6900
ccctccaccc tcatcaacat caccacggcc acctccgcag ccaaacccac cacaaccgcc  6960
acaaccaccc tcaccgaact cacctccaca accccgtccc                         7000
```

<210> SEQ ID NO 6
<211> LENGTH: 1076
<212> TYPE: PRT
<213> ORGANISM: Aspergillus sp.

<400> SEQUENCE: 6

```
Arg Thr Gln Val Asn Leu Thr Ser His Tyr Leu Ile Pro Gly Phe Ala
1               5                   10                  15

Gly Ile Gly Ala Asp Arg Leu Thr Pro Ser Ile Phe Arg Lys Glu Thr
            20                  25                  30

Glu His Met Phe Tyr His Gly Phe Glu Asn Tyr Leu Glu His Ala Phe
        35                  40                  45

Pro Glu Asp Glu Leu Arg Pro Leu Thr Cys Arg Pro Leu Val Arg Asp
    50                  55                  60

Arg Glu Asn Pro Ala His Ala Glu Leu Asn Asp Val Leu Gly Asn Tyr
65                  70                  75                  80

Ser Leu Thr Leu Ile Asp Ser Leu Ser Ser Leu Ala Ile Leu Ser Ser
                85                  90                  95

Ser Pro Asp Gln Gly Gln Lys Ala Trp Asp Tyr Phe Gln Asn Gly Arg
            100                 105                 110

Gly Arg Gly Phe Asp Met Asp Ser Lys Val Gln Val Phe Glu Thr Val
        115                 120                 125

Ile Arg Gly Leu Gly Gly Leu Leu Ser Ala His Leu Phe Ala Val Gly
    130                 135                 140

Asp Leu Pro Ile Thr Gly Tyr Asn Pro Pro Glu Thr Glu Ala Asn Phe
145                 150                 155                 160

Ala Arg Ala Trp Asp Lys His Ser Phe Pro Glu Gly Ser Arg Gly Ile
                165                 170                 175
```

```
Glu Trp Lys Asp Gly Phe Val Tyr Asp Gly Gln Leu Leu Arg Leu Ala
            180                 185                 190

Val Asp Leu Ala Asn Arg Ile Leu Pro Ala Phe Tyr Thr Asp Thr Gly
            195                 200                 205

Leu Pro Tyr Pro Arg Val Asn Leu Lys Tyr Gly Val Gln Arg Gln Pro
            210                 215                 220

Tyr Tyr Ala Asn Ser Pro Phe Asn Ala Ala Pro Thr Cys Asp Lys Ala
225                 230                 235                 240

Asn Pro Glu Gln Cys Gln Lys Pro Arg Ser Ser Thr Phe Glu Thr
            245                 250                 255

Thr Glu Thr Cys Ser Ala Gly Ala Gly Ser Leu Val Leu Glu Phe Thr
            260                 265                 270

Val Leu Ser Arg Leu Thr Gly Asp Gly Arg Tyr Glu Glu Leu Ala Lys
            275                 280                 285

Arg Ala Phe Trp Ala Val Trp Ala Arg Arg Ser Asp Ile Gly Leu Ile
            290                 295                 300

Gly Ser Gly Ile Asp Ala Glu Ser Gly Arg Trp Val His Ser Tyr Thr
305                 310                 315                 320

Gly Val Ser Gln Ile Lys His Val His Leu Asn Met Ala Asn Thr Thr
            325                 330                 335

Thr Ser Gln Ile Gly Ala Gly Ile Asp Ser Phe Phe Glu Tyr Ala Phe
            340                 345                 350

Lys Ser Tyr Val Leu Leu Ser Ser Gly Glu Arg Pro Pro Ala Asn Thr
            355                 360                 365

Ser Ser Pro Trp His Ala Leu Asp Asp Tyr Phe Leu Pro Leu Ser Glu
            370                 375                 380

Tyr Glu His Ser Ala Asp Ala Phe Leu Lys Val Trp Glu Lys Ser His
385                 390                 395                 400

Ala Ser Ile Lys Arg His Leu Tyr Arg Gly Glu Gly His Gln His Pro
            405                 410                 415

His Leu Ile Gln Gly Asp Ile Phe Thr Gly Ala Thr Arg Ala Phe Trp
            420                 425                 430

Ile Asp Ser Leu Ser Ala Phe Tyr Pro Gly Leu Leu Thr Leu Ala Gly
            435                 440                 445

Glu Val Asp Glu Ala Ile Gly Ile His Leu Leu Thr Thr Ala Val Trp
            450                 455                 460

Thr Arg Phe Ser Gly Leu Pro Glu Arg Trp Asn Val Ala Thr Gly Asp
465                 470                 475                 480

Ile Glu Gln Gly Leu Ser Trp Tyr Gly Gly Arg Pro Glu Phe Val Glu
            485                 490                 495

Ser Thr Tyr Tyr Leu Tyr Arg Ala Thr Lys Asp Pro Trp Tyr Leu His
            500                 505                 510

Val Gly Glu Met Val Leu Arg Asp Leu Lys Arg Arg Cys Trp Thr Lys
            515                 520                 525

Cys Gly Trp Ala Gly Ile Gln Asp Val Arg Asn Gly Glu Leu Asn Asp
            530                 535                 540

Arg Met Glu Ser Phe Phe Leu Gly Glu Thr Ala Lys Tyr Met Phe Leu
545                 550                 555                 560

Leu Tyr Asp Phe Asp His Pro Leu Asn Lys Leu Asp Gln Pro Phe Val
            565                 570                 575

Phe Ser Thr Glu Gly His Pro Leu Ile Ile Pro Lys Asn Ser Thr Ala
            580                 585                 590

Gln Arg Ala Glu Arg Lys Gln Val Pro Val Val Val Glu Ser Glu Gly
```

```
                595                 600                 605
Leu Thr Cys Pro Thr Ala Pro Gln Pro Pro Leu Gly Val Ser Ser
610                 615                 620

Thr Ala Ala Arg Ser Asp Leu Phe His Ala Ala Asn Leu Ala Arg Leu
625                 630                 635                 640

His Leu Met Pro Ser Arg Gly Leu Ala Glu Gly Pro Leu Leu Asp Tyr
                645                 650                 655

Ala Arg Asp His Pro Ser Val Ser Val Ser Asp Leu Ser Pro Thr
                660                 665                 670

Asn Tyr Thr Phe Phe Pro Trp Thr Leu Pro Pro Glu Leu Val Pro Phe
                675                 680                 685

Asn Ala Thr Ser Ala Pro Met Thr Ile Arg Pro Thr Leu Asp Ile Ser
690                 695                 700

Phe Pro Ala Leu Pro Gly Met Val Val Gly Pro Gly Ser Leu Glu Arg
705                 710                 715                 720

Val Arg Asp Gly Ile Phe Ile Lys Ala Ile Gly Gly Leu Arg Leu Ser
                725                 730                 735

Met Val Gln Asp Val Pro Val Gln Gly Glu Ser Gly Ser Ala Glu Ser
                740                 745                 750

Asp Glu Phe Arg Val Gln Val Ile Asn Asn Val Pro Leu Gly Lys Asp
                755                 760                 765

Glu Lys Val Tyr Leu Leu Arg Glu Ile Thr Phe Asp Val Leu Asp Pro
770                 775                 780

Thr Asp Pro Asn Phe Thr Arg Val Arg Asp Thr Ala Met Ile Asp Ile
785                 790                 795                 800

Val Ile Asp Val Ile Pro Glu Ile Ile Arg Arg Asn Asp Ser Asp
                805                 810                 815

Asp Ser His Glu Pro Ala Ala Pro Arg Arg Ala Asn Gly Ala Ile Val
                820                 825                 830

His Gly Ser Ser Ser Val Asp Lys Val Gly Ser Val Asp Ala Ser
                835                 840                 845

Thr Ser Ser Met Lys Thr Val Leu Ser Ser Leu Val Asn Thr Leu Ser
850                 855                 860

Thr Leu Leu Arg Asp Glu Val Gln Gly Gln Thr Ser Leu Pro Gln Lys
865                 870                 875                 880

Lys Ala Thr Ser Leu Arg Leu Leu Leu Pro Ala Ala Ile Ser Thr Gly
                885                 890                 895

Leu Gly Ser Ala Pro Leu Pro Asp Val Glu Asp Ala Thr Thr Val Ser
                900                 905                 910

Ile Thr Gly Asp Pro Ser Lys Gln Arg Leu Thr Trp Asn Ser Ile Tyr
                915                 920                 925

Phe Ala Asp Glu Leu Cys Asp Asn Arg Ile Leu Arg Glu Val Ala Gln
                930                 935                 940

Asn His Gln Val Leu Val Ile Lys Arg Gly Gly Cys Asn Phe Ser Gln
945                 950                 955                 960

Lys Leu Arg Asn Ile Ala Ala Tyr Pro Pro Ser Arg Tyr Ala Leu Lys
                965                 970                 975

Leu Val Ile Val Val Ser Tyr Asp Asp Glu Val Val Glu Glu Glu Gln
                980                 985                 990

Arg Glu Glu Ser Asp Thr Thr Thr  Thr Pro Gly Leu Ala  Ala Val Arg
                995                 1000                1005

Ala Glu  Pro Tyr Leu Val Arg  Pro His Leu Asp Glu  Thr Gln Met
    1010                1015                1020
```

-continued

```
Thr Ala  Ala Gly Val Pro Arg Arg Gln Leu Leu Ser  Val Val Met
   1025          1030                1035

Val Gly  Gly Gly Gln Glu Thr  Tyr Glu Leu Leu Arg  Gln Ala Thr
   1040          1045                1050

Gly Val  Gly Ile Lys Arg Arg  Tyr Ser Val Arg Ser  Gln Gly Val
   1055          1060                1065

Pro Ile  Asn Asn Leu Tyr Ile  Leu
   1070              1075

<210> SEQ ID NO 7
<211> LENGTH: 4947
<212> TYPE: DNA
<213> ORGANISM: Aspergillus sp.
<220> FEATURE:
<221> NAME/KEY: misc_feature
<222> LOCATION: (3117)..(3117)
<223> OTHER INFORMATION: n is a, c, g, or t

<400> SEQUENCE: 7
atccggagta ccagagcaac attcttccgg gattatggcc aaggccgata caccaaagaa    60
cagcccgcca aagtcacaaa gctctaagca tgactataaa ggctttgtag cgggagtctt   120
ctcaggaatc gccaaactta gtggtatgtt ctggcccgcg gtgcgcatag tctgcgtgct   180
tttttgggag taaccatcgc taacagattc cgatgcatag ttggccatcc gtacgtgact   240
gcgcaccttc ttcctcttcc ccgccactta tactgcctct caatggacaa ctccatataa   300
tctcacaaat tgaccatggg tgattctcgc gcagattcga cacaatcaag gtacgcttac   360
agacgagcca tgatgggcat ttccggggcc cattggactg tctgctacaa acggtccgca   420
aagagggtgt tagtgggttg tataagggag ccactccgcc gctggtcggt tggatggtca   480
tggactctgt gtgagtaact ttgcccggcg gctggaaaac gccaaaaaga gaaagagag    540 agagagagag agagagagac ggaaggactg atcagtcaaa cacagcatgc tgggttcctt   600
aaccttatat cgccggctat tactggaaag cgtgttttcg aaaccagaga ttcgcgcaag   660
catgccgttc attggcaagc agacggatct tcacacgctc cctagcttcg gtcatggcat   720
tgcgggcatc atggctggaa cgactgtcag tttcattgcc gcaccggtgg agcacgtcaa   780
ggcgcgtctt cagattcagt actctgcaga taaatccaag cgcctgtata gtggacctat   840
agattgcgtt cgcaagatgg taagaaatac gggtctccta aaacgtccga ccttgttggc   900
tgacctatat acatagcttc gcacacacgg cattgccggg ttatatcgtg gactctgcgc   960
gaccatggta tttcggtcgt tctttttctt ctggtggggt tcctacgacg tccttactcg  1020
gttgatgaag gagaagacca gcctgtctgc tcctgccatc aacttctggg ccggggggat  1080
ttccgcgcaa gttttctgga tcacgtcgta tccgtccgat gtggtgaagc agcgcctcat  1140
gacggacccg atgggaggcg ccctgggcga cgggcagcgc aggttccagt ggtggaagga  1200
tgctgcagtg gcggtctatc gggaacgagg gtggaggggg tattggcgag ggtttgtgcc  1260
atgcttctta cgagcattcc cggcgaatgc catggctttg gttgcatttg agggtgtgat  1320
gcggtggctg ccgtgagatc gtggttcgcc gccgaggcag aaggcgacga tgaagctaca  1380
gaagcacaac acacggatct cgctagaccc gaacgattaa aatgaacggg actccaatag  1440
atcctgaaaa gaaggctatg taatgtgata gacgatagaa atagaattga attctccagc  1500
caacccatcc aacgggcccg atcgtggggc gcgtctcaca gcaggattc atcaatctgg   1560 ccgggtgcaa cggccgcatg cggcgatgcc tcgcccaatg cagccactgc tgcaccttcc  1620
actaccttgt gcaatccatg gaacaaatcc ttcggattct tgtctacgaa gaaatcaagt  1680
```

-continued

```
ttgactgacc caaatcggtg agaggagacg gcaggatgtt gtggtagaca gaagagacag    1740
agagtgagag agacaagtgt gtgcaggagg tgaatcggga gacagagaga gggttcgggc    1800
tccgcgtgta cttttccgg cctgcttcaa ccttgccata gttcgttcca tcccgtcatc    1860
tccaatctat cttcttccct cacttcctcc tcatctcctt gtccgtcttg aacttcttcg    1920
gctccctctc cttccctcc gcagtctctt ccgctatgtc cggggaccgg gatcatccgc    1980
cttctgattg ctggctaaag agctctctcg ccttctcgcc gggccagatc gattccgccg    2040
ccgccttatc caatcgcgca gtccaaccac aaccatcacc ttgactgcga acctccccc    2100 ttctcccctca atcagcaaac ggctacgatg ccgtcgcac gctcgatgcg tcgcacaagc    2160
cccattacgg tcttcctggc tgctctgcta gctttcggat tcctttgctt tctgctctcc    2220
ccttcctcgt ccgccgccgc ccgccgctcc tcctgtcacc gattcctcct cgcagctacg    2280
acgagaagat gccgccgaac atccccttc tcctccgacg aaaccttcc tcaaatctca    2340 agccgtccgc gaagatggcc tgaaagcacc ccgccagtg atgcactaca atctgaacga    2400
gctcagcagc accagcgaat ccattaagaa aggggaacgg gtgctgattc tgaccccatt    2460
ggcccgcttc taccaagaat tctgggacaa tgtagtgaaa ctgagctatc cacatgagct    2520
catctcgatt ggattcatcg tccctaacac caaggacggc catgccgcgg tcaccgcgct    2580
ggagcaggca atcagcgaga ctcagtctgg tccgattgac agccgctttc gccagcatca    2640
gcatccttcg ccaggacttc gacccgccca ttcaatcgca ggacgagaaa gagcgccaca    2700
aaatgtccaa ccagaaagca cgtcgtgagt ccatgagtcg cgcccgcaaa cagcctcctc    2760
ttcaccaccc tcggtcctag cacctcctgg gtactctggc tcgactccga cattgtcgag    2820
accccagcga cccttattca agatctgact gcccacaacc gacctgtgat tgtcccgaac    2880
tgcttccagc gctactataa caaggatgcc aagaagatgg atgtccgccc ttatgacttc    2940
aactcgtgga tcgacagttc gaccgccgaa cagcttgcgg agacaatggg gccggacgag    3000
atctcctcga gggaaaagct ggactgccca ccctccggca cccggaggc ccacaaggcc    3060 aaattccggg ggcgccccg tcctagccgc gaaatcgaac tcgacggcgt cggtggnaca    3120
gcactccttg tcaaagcgga tgtgcatcgt gacggcgcca tgttccccgc cttcccgttc    3180
tatcacctcg tcgagacgga gggtttcgcc aagatggcga agcgtctggg atattccgtc    3240
tacggcttgc ctgattactt tgtacgttcc cctacaattt cccatccgat tgaacccact    3300
aacgccatgg ccacaggtgt atcactataa cgagtgatgc gatagatttc aattacgaga    3360
tgagttcaca tgaagcgaac atccgacaat agaccggaac ggagaatgtt tttttttttt    3420
tttttcttgc tttgctttat tttgctttga ttagactatc ctagttggcg atttccacgt    3480
ccactacaag attcagactt cactttatcc atctacatct acttggggcg ttattatttt    3540
acgtccgcgc gctgggcgct tagtggttct ggtgttcggg ctgagtagct gtcttacaac    3600
tactactact atatatagtt aggatttatg tccatttgct atacactgca ctcgcctgtt    3660
caatgcgcaa acagtcaata agccgaggaa gcgtaggttt cgtccgtgca atatggacga    3720
gattactcct tagtggtaat atggcactag tacctcgaaa cttcggtatt gaaattgtct    3780
attctgtggc gaagtccaca ccattattta ctactaagat actgattcta tatccataag    3840
ccgtctctcc gttttcaat gtgcttcctt ctcataatcg tcagtcgagc tatcgcgttg    3900
ggcttgttgt ctaatcccaa gaaatgctac gatgaccgtt agcgatggag ataatcacga    3960
tgtgtcgtac caaggaagga gggatagaaa catacacaag cataatcccc gcccccaacc    4020
ataacggcca agaactgcac gattgtcttc ttgatctcca cgcgcttatc cttgcccgtt    4080
```

-continued

```
tccaataact ccgggataac ggaaactgtt cctacgtaga ggaatgtccc tgccgtgaag    4140
ggtaggagca tatcgcccca ggtgaggctt gttccgagga ggccggttgg caggctatta    4200
gtggatgtgg aggtggcagc agtggagcca ttcccgccca actcttggac ggcgattccg    4260
atgaaagtgc cgaggaaggc gccaatggct gtgacgaatt gcgcgcccat agctttgcgc    4320
tttgagaagc cggattggat gaggagtgcg aagtcgccaa cctcgtgggg gatttcgtgg    4380
aagaagacgg cgacagtggt ggttgcgccg atggtggggg aggcgtagaa ggacgaggac    4440
atggcgaggc cgtcggtaat gttgtgagtg aagtcggcaa tcaggttgag gtagccgccc    4500
aatttgacgc tgaggttgat atccttctcg tcgtccttgt cggcgggttg gggagcggtg    4560
ttgctgcttg cgggcttgcg ctgtttgaga tcggtggagg gttgcgggga ggcgccggtt    4620
gttgtgcctg tgggtttgtg gtcgtcgttg gcgctgtcag tgtgagcgtg ggcgtgggag    4680
tggtcgtgtc cagctcctcc ggtggcgata cgtagggttt tgtccattgc gacgaaggtg    4740
aagaagccca ccatgattcc caggcccagg aggaggttgc ggtttggctc aaccatcacg    4800
aagcgaacat ggtctgggga gtcttcgccg agaaagatct cggggagcaa gtggaagatg    4860
gtatcgccta ggaggccgcc tactgcgaac gcgaccatga cggacaggga ggagggatcg    4920
atgtttggag ggcataggcc aggagga                                       4947
```

<210> SEQ ID NO 8
<211> LENGTH: 369
<212> TYPE: PRT
<213> ORGANISM: Aspergillus sp.

<400> SEQUENCE: 8

```
Leu Ser Asp Ser Phe Ala Phe Cys Ser Pro Leu Pro Arg Pro Pro Pro
1               5                   10                  15

Pro Ala Ala Pro Pro Val Thr Asp Ser Ser Gln Leu Arg Arg Glu
            20                  25                  30

Asp Ala Ala Glu His Pro Leu Ser Pro Pro Thr Lys Pro Phe Leu Lys
        35                  40                  45

Ser Gln Ala Val Arg Glu Asp Gly Leu Lys Ala Pro Pro Pro Val Met
    50                  55                  60

His Tyr Asn Leu Asn Glu Leu Ser Ser Thr Ser Glu Ser Ile Lys Lys
65                  70                  75                  80

Gly Glu Arg Val Leu Ile Leu Thr Pro Leu Ala Arg Phe Tyr Gln Glu
                85                  90                  95

Phe Trp Asp Asn Val Val Lys Leu Ser Tyr Pro His Glu Leu Ile Ser
            100                 105                 110

Ile Gly Phe Ile Val Pro Asn Thr Lys Asp Gly His Ala Ala Val Thr
        115                 120                 125

Ala Leu Glu Gln Ala Ile Ser Glu Thr Gln Ser Gly Pro Ile Asp Ser
    130                 135                 140

Arg Phe Arg Gln His Gln His Pro Ser Pro Gly Leu Arg Pro Ala His
145                 150                 155                 160

Ser Ile Ala Gly Arg Glu Arg Ala Pro Gln Asn Val Gln Pro Glu Ser
                165                 170                 175

Thr Ser Leu Leu Phe Thr Thr Leu Gly Pro Ser Thr Ser Trp Val Leu
            180                 185                 190

Trp Leu Asp Ser Asp Ile Val Glu Thr Pro Ala Thr Leu Ile Gln Asp
        195                 200                 205

Leu Thr Ala His Asn Arg Pro Val Ile Val Pro Asn Cys Phe Gln Arg
    210                 215                 220
```

```
Tyr Tyr Asn Lys Asp Ala Lys Lys Met Asp Val Arg Pro Tyr Asp Phe
225                 230                 235                 240

Asn Ser Trp Ile Asp Ser Ser Thr Ala Glu Gln Leu Ala Glu Thr Met
            245                 250                 255

Gly Pro Asp Glu Ile Ser Ser Arg Glu Lys Leu Asp Cys Pro Pro Ser
        260                 265                 270

Gly Thr Pro Glu Ala His Lys Ala Lys Phe Arg Gly Arg Pro Arg Pro
    275                 280                 285

Ser Arg Glu Ile Glu Leu Asp Gly Val Gly Gly Thr Ala Leu Leu Val
290                 295                 300

Lys Ala Asp Val His Arg Asp Gly Ala Met Phe Pro Ala Phe Pro Phe
305                 310                 315                 320

Tyr His Leu Val Glu Thr Glu Gly Phe Ala Lys Met Ala Lys Arg Leu
                325                 330                 335

Gly Tyr Ser Val Tyr Gly Leu Pro Asp Tyr Phe Val Arg Ser Pro Thr
            340                 345                 350

Ile Ser His Pro Ile Glu Pro Thr Asn Ala Met Ala Thr Gly Val Ser
        355                 360                 365

Leu

<210> SEQ ID NO 9
<211> LENGTH: 4524
<212> TYPE: DNA
<213> ORGANISM: Aspergillus sp.

<400> SEQUENCE: 9
cgaaatgctg atatgttcgg cttttggcga ctggtgatcc agttttatt caacgacatg      60 tcatgctatt cctcttccgt cgtttcgagc tggtgactcc tgaaccgaag agtaatttta    120
ctttaatttc tagctctctt ttaattttct gggtcgatag cgatctgtta cttcactaac    180
gtatctccta cacctccgct ccaaaacctc gtcctttttt tccatcctgc tgcgctcctg    240
ttccccaagt tgcgggcgcc cgtttcaaag aaagacatct cccattgacc tcctccacag    300
cggccctctg ccgagcacga actcccaat  acgcccgcc tgtggctgct ccgcgggccg    360
ttgtgctcgc ccgccattgc ccttcctgcc ggcatccctg tcggttccga ctcccgctc    420 atgtccttgt cgcgatcgcc ctctccccac cccgcgggag caggatggtc tagtcctgga    480
ctcacttcgc ccagtggctc taccacgcct cacaatggct tcctgtcgcc aaatcccata    540
ggcgccagcg gcatctcctg gccgccgcc  aaagcgaaga gcgacgaggt acgaggctac    600
ccgtcctttt cgacgaagaa cagcggattc ttctcgcgct caagacgcca gctctccgcc    660
actttgccgc gctttcgtct gggctcgggg tctccgaatg ttatgtcga  taaggatgag    720 tttggccggg ggcggcctct ctccccagct acgggctggc gcttggggtt tggcaggtcg    780
gttctgcggc gcagacgatc gcgcttgctc gtggcgctga tctttctttt gctgggctat    840
atgttttttg gggcgtgtaa gtgaatcgca taccaatggg aagaaagcct gcaggtagct    900
gaccttgtta cagctcttct ccagaagtat cggcgctctc cgctaggcgg tgggcgcaaa    960
ttcgtgatca tactggaatc caacatagaa ggcggcgtga tggagtggaa gggagcgcgc   1020
gaatgggcga tcgagcgcaa cagcatatg  aacaagaaga attatgtgga acgatggggc   1080
tacgagttgg aaaccgtcaa catgttgcg  aagaagcggt attcacacga atggcgcgag   1140
agctgggaga aggtggacct tatccgggag acgatgcgaa agcatcccga tgctgaatgg   1200
tatgcttgcc gtatttgatt ccgtgagcgt cactgacatc ttgtgcaggt tttggtggct   1260
ggaccttagc acttggatca tggaatactc ctactcgtta caggaccata tattcgaccg   1320
```

```
cttggatgaa atcatttacc gggacatcaa tgtctataac ccattgaaca tcagccaccc    1380
gccggacgac gcttatctgg acgaggtgtc tcgttcgcca aacggagacg ggacccatc    1440
atcggtacat atgctattgt cgcaggactg tgggggcttc aacctcggct ctttcttcat    1500
ccggcgctcc ctctgggccg accgcctgct ggacgcgtgg tgggacccag tcatgtacga    1560
acagaaacat atggagtggg agcataaaga gcaggatgcg atggaatacc tctatgcgac    1620
gcagccgtgg gttcgcagcc acgttggctt cctccctcaa cgctatatca actcgtatcc    1680
ccagggggca tgtggggacg agaatgaccc gaatgtccac taccaggaag atgaaagaga    1740
cttcctggtc aacatggctg ggtgtcagta tggacgcgac tgctgggggcg agatgtacca    1800
gtaccgtgaa atcagcaagc agctgaacct gacatggtgg gagcggatga aggacaagtt    1860
gaacggcctt tacgagaagc ttttcccggg cgaggaacag caagttgaat gaaaaagtcc    1920
gttgctggga tacggcatgt tgcttcactt tgatgtttac tgcagatgat gattggtctg    1980
agacatgacc atgtaaaatg cggactaata acgacctggc tgacggcgta tgggatggat    2040
tctacgtgtt tggctgattt gctattttttg gcgaggcgtt tggtgttagc ggtagctatc    2100
tagacttcaa gtagctcatc tactacctct ttatctgtgc tctgcaataa tcaaaagact    2160
tacgaactaa gtattataca attgtagttg cacaactaac cactcataac ccgcttagta    2220
attatccaca gccccacgtg acacaatgaa cttagcacac ccgaccgccc acacccccca    2280
accaatcaaa ccaccgcaat tgcatctgct actctcgcga cctccggaat tgaacttgat    2340
acactgactg acctctctac gtacgtactc tccctccggt ccctcctcca acctacacac    2400
cgaacctcct cccccgaag gcaacaacca agggaacacc gaaaatgccg accccgaat    2460
ccgcctcctt cctggccaag aagcccaccg tgccgccgac ctacgacggc gtcgacttcg    2520
aagacaacgt cgctgtccac aacgcccgcg acgccattat ccgtgaacaa tgggtccgca    2580
gtatgatgtc tcgtctggtc ggggaggaat tgggaaagtg ttatgcgcgt gagggcgtta    2640
atcatttgga gaagtgtggg gttttgaggg gtgagtttat acctgttctt tctttctttc    2700
tatcccggga gccctttgg ggatggtgtg ggctagcgaa gatagagtga gaattatggc    2760
taatatgtgt ctctctttttc ggtgtgtaga gaagtacttc gagttgctgg gcgagcgcaa    2820
gatcaagggt tacttgttcc aggagaagaa ctactttgct ggggagggaa acaagtctgc    2880
ttagattttg ctcggtggat tgaatcgaaa ttgggtttgc agggtttctg tgttatgtta    2940
tgtgatatac aatatatgca ttgtggtttc ttttcctact tctttttctt tttcttctgg    3000
gtttggtttg tggggagtta gagggtgtgg atgctggttt tgaccagtcc cgggctgtga    3060
ttgtatgata tgcttcgaga tggggtggat ttggctctgc cgtggtttat atactgggtt    3120
gtgaggtgcg agtgaggggt cgagtgtctg tattgatact gcgtatgtgg agtaagcatt    3180
atgggatggt aatatgcttg tgctcagtga tacatgtata ggaagaagct cgaagctcga    3240
agctcgaagc tcgaagctga gatcaataat aggcactgtc gctccgctcc ggtactgtcc    3300
ccggcgtata cacacgcgcc acactggctg cctcctcgtc actgtcctcg acatcacttc    3360
ccggtccaaa gtcgtcctcc accggcggcg cacgcatgcg caccagctgc tcctcatcca    3420
gcgagggaat cttgtatggt gctggcgccg aatggatatc tcgaccggag ggcaagttgg    3480
caagcaaggt ccgtagaggg tgggatcagc tgggtattga tctgtgttcg tcagcaacat    3540
catcctaaac caatgacgtg aacatcacca accgtatcat tcatccgcac ccacttcgtc    3600
tccaacatct caatcactcg actctcctcc tcccgacctg cattatcccc cggtcctagc    3660
tcgcccttct ccgtccgatc ccgactgccc gcatctttct ccattcgtct ctcctcccgc    3720
```

```
cgctccatcc aaccctgctt caatctcgac agtccggtcc gactcttagt attcgtctcc    3780
tttgtttccg ctgcagctgt tccagctccc cggacccca atgccccctt cgctgctctc    3840
agccatgcaa tgccctcccc gatcttccca gacaattccg catccacccc gaagaaccgg    3900
caggctctcg cccgcgcaac ccgtcccagt acccgcgtat accctagcag atcatcatca    3960
attcccatcc gccctctga gcggacagat cccagccccg cagcagcttg ttccgcatac    4020
tccgcagccc ggatacataa tctagcgaag aggtgcgccc ggaccttggg gatctccggc    4080
gcgcggacca tccagtcctt gtcattggga ttgcgcgctt gaatacaggc cgcgacgtag    4140
gaatcgtcct tcaagacagc gaggagagtt gcttctgcga gggcgagaca ggacagggcc    4200
gcttgcgtgg cggggtcgag gtccgggagg gtagatgttc cattttttgtt attgcagatg    4260 gaatgggctg cagttgcgaa agacggcgag gaagcgagga gcgagtgtac ggcgctggct    4320
tggaggaggt gtttggtggc tgtttggatg gcggcggtgc gctgttccgg agtcggggtc    4380
gcggatgcgt aaagtgtgcg ggtgacgcca atgcgggcga gcgagttgag cacgtagctc    4440
agggtggaga ggacaaaggc tatctcgaag tcgaggccct gtcctggatg cgggtggtgg    4500
tgggccgctg ttgaggagag cgtg                                            4524
```

<210> SEQ ID NO 10
<211> LENGTH: 466
<212> TYPE: PRT
<213> ORGANISM: Aspergillus sp.

<400> SEQUENCE: 10

```
Met Ser Leu Ser Arg Ser Pro Ser Pro His Pro Ala Gly Ala Gly Trp
1               5                   10                  15

Ser Ser Pro Gly Leu Thr Ser Pro Ser Gly Ser Thr Thr Pro His Asn
            20                  25                  30

Gly Phe Leu Ser Pro Asn Pro Ile Gly Ala Ser Gly Ile Ser Trp Ala
        35                  40                  45

Ala Ala Lys Ala Lys Ser Asp Glu Val Arg Gly Tyr Pro Ser Phe Ser
    50                  55                  60

Thr Lys Asn Ser Gly Phe Phe Ser Arg Ser Arg Arg Gln Leu Ser Ala
65                  70                  75                  80

Thr Leu Pro Arg Phe Arg Leu Gly Ser Gly Ser Pro Asn Gly Tyr Val
                85                  90                  95

Asp Lys Asp Glu Phe Gly Arg Gly Arg Pro Leu Ser Pro Ala Thr Gly
            100                 105                 110

Trp Arg Leu Gly Phe Gly Arg Ser Val Leu Arg Arg Arg Ser Arg
        115                 120                 125

Leu Leu Val Ala Leu Ile Phe Leu Leu Leu Gly Tyr Met Phe Phe Gly
    130                 135                 140

Ala Ser Asp Leu Val Thr Ala Leu Leu Gln Lys Tyr Arg Arg Ser Pro
145                 150                 155                 160

Leu Gly Gly Gly Arg Lys Phe Val Ile Ile Leu Glu Ser Asn Ile Glu
                165                 170                 175

Gly Gly Val Met Glu Trp Lys Gly Ala Arg Glu Trp Ala Ile Glu Arg
            180                 185                 190

Asn Ser Ile Trp Asn Lys Asn Tyr Val Glu Arg Trp Gly Tyr Glu
        195                 200                 205

Leu Glu Thr Val Asn Met Leu Ala Lys Lys Arg Tyr Ser His Glu Trp
    210                 215                 220

Arg Glu Ser Trp Glu Lys Val Asp Leu Ile Arg Glu Thr Met Arg Lys
```

```
                225                 230                 235                 240
His Pro Asp Ala Glu Trp Phe Trp Trp Leu Asp Leu Ser Thr Trp Ile
                245                 250                 255

Met Glu Tyr Ser Tyr Ser Leu Gln Asp His Ile Phe Asp Arg Leu Asp
                260                 265                 270

Glu Ile Ile Tyr Arg Asp Ile Asn Val Tyr Asn Pro Leu Asn Ile Ser
                275                 280                 285

His Pro Pro Asp Asp Ala Tyr Leu Asp Glu Val Ser Arg Ser Pro Asn
            290                 295                 300

Gly Asp Gly Asp Pro Ser Ser Val His Met Leu Leu Ser Gln Asp Cys
305                 310                 315                 320

Gly Gly Phe Asn Leu Gly Ser Phe Phe Ile Arg Arg Ser Leu Trp Ala
                325                 330                 335

Asp Arg Leu Leu Asp Ala Trp Trp Asp Pro Val Met Tyr Glu Gln Lys
                340                 345                 350

His Met Glu Trp Glu His Lys Glu Gln Asp Ala Met Glu Tyr Leu Tyr
                355                 360                 365

Ala Thr Gln Pro Trp Val Arg Ser His Val Gly Phe Leu Pro Gln Arg
            370                 375                 380

Tyr Ile Asn Ser Tyr Pro Gln Gly Ala Cys Gly Asp Glu Asn Asp Pro
385                 390                 395                 400

Asn Val His Tyr Gln Glu Asp Glu Arg Asp Phe Leu Val Asn Met Ala
                405                 410                 415

Gly Cys Gln Tyr Gly Arg Asp Cys Trp Gly Glu Met Tyr Gln Tyr Arg
                420                 425                 430

Glu Ile Ser Lys Gln Leu Asn Leu Thr Trp Trp Glu Arg Met Lys Asp
                435                 440                 445

Lys Leu Asn Gly Leu Tyr Glu Lys Leu Phe Pro Gly Glu Glu Gln Gln
            450                 455                 460

Val Glu
465

<210> SEQ ID NO 11
<211> LENGTH: 6724
<212> TYPE: DNA
<213> ORGANISM: Aspergillus sp.

<400> SEQUENCE: 11
ctatatgctg cttacactga tctgcttttg atcgtcggcg gagcttagcg gcagagacgg      60
ctgcggttct acataacaca gctgtctgcc agctcattgc gcctgtgtga caatccacct     120
aattagcgat cttctcatat tcccacagag atgctcacct tccggaagtc gctactcgcg     180
gctgcgcttc tgattacctt tatcgtctac ctccgatcgt cgcataccgc ctcttccctt     240
ccgtctccgg ataccttctc cgccggacac ctctacaacc aggattacga tggtcatgca     300
gacaatgagc gaaaaggtgg aactagagac accgtacaac agctgccgct gaccccgcca     360
ccgagcgccc ccttgcgcga tcgcttgcgc taccactttc cgtacgatct ggaagccaag     420
ttcccggcgt tcatctggca gacgtggaaa tatgcgccgt catcgatgtt cttcagcgaa     480
agcctgcgtg atccggagtc cagctggtcc gagttacatc ccggattcgt ccacgaggtc     540
gttcccgatg atacccaacg ccatctgatc aaatacctgt acggcgctgt tcctgatgtg     600
ttcgaggctt acgatgctat gccgttgccc gtcttgaagg ccgacttctt ccgatacttg     660
atcttgctcg cgcggggtgg aatctacagc gatatcgata ccacggcgtt gaagccggcg     720
tctgactggc tgccagccga gttggatctg gccacagttg gagcggtggt gggcattgag     780
```

```
gcggatcctg accgccccga ctggcatgac tggtatgcgc gcagaatcca gttctgccaa    840
tggaccatcc aagccaaacc cggacacccc atcatgcgcg atattgtctc ctacattacg    900
gaggagacat tgcggatgaa gaaggcgggt attctaaaga ctggcaagat ggacaagacc    960
gtcatggagt acactgggcc aggcgcttgg acggatgcgg ttttccggta tttcaacgat   1020
ccagagtact tcaacattga acccggctcg acgttgaaca tcacctatga ggactttacg   1080
ggtcaggagg atataagaa ggtcggagat gtggtggtct tgcccatcac cagcttcagc   1140 ccggagtgc accaaatggg tgccggagat gttgatgatc ccatggcatt cgtgaagcat   1200
cactttgaag gtatgccgcc tcaattcctc ctattgcttg actcaaagct aacacgccaa   1260
ccaggaactt ggaaggatga ctcctctcta aagccgtca ttataaatcg ctttacatta   1320
caccttacac tacgatacgt gcgcgtggtt gaatcccact gcttcgtcga caggacttgc   1380
acaacgcacg tccttagaca gctggatatg accatatagc ataagtggca tatcatcaga   1440
tccttgcacc ttgtcggtcg acacgagca ggggcccttc atggccacct acacaacaac   1500
ctcgcagcat ccacccaaca ttttccgtcc tcaaactcaa tctaatgccc cttgctcacc   1560
caagctagcc atgtcccgta tacgaaaatg ctggctctcc ggcagagtga gctattgctt   1620
tgtgctcatg actcacggct ctcagcttag cttttccatcc atgacaagca tgtccgagct   1680
gtagctcgat cgctagcatg cttgtcaaat gggcccccgt ctgtttcttc tctgtgtcca   1740
tataacctac atatgttttt agtgtcttgc tccaaaatct ttagaatttg atacccgcag   1800
gctgggaaca cgaatgagaa cagcgatgca ctttgatctc ttgacatatg ttttacctaa   1860
tctagagtta cattgcattc cggaatgtgc ctttgcgcat actttaatag aaactcgtaa   1920
tttgcgctct tcctttcctt cataggtcga atgaaacggt aatgctttaa ttgtctacaa   1980
gaacgacaac atcttgctgt cttgaagcat tatgactcta cttcatagcg gaaatcactt   2040
cgtatccgct ctaccaaccg cagacaatcg cgtctcttct cagccgtgac caacatccag   2100
gcaataaaat ggacctcgct cgactttggt ccgaccaatc tgtccccttt cttcttgatt   2160
gtcgcgtaca gcggcacatg tggctccaat tcagggtact gatggagcag ctccgctgtg   2220
gcatcttcgg tcttcatgat cccggcaaca tcttcttgga ggacgagcac cgagagatta   2280
tagcgaggtc catttaagaa tggatggcac aaagccctgt atcgaagctc gtcattgact   2340
gcgaagagca tctgctgggc gaaataatcc actccgtaga ccaagttgac gccaacagtc   2400
tccagatacc ctgctgggcg ggcgtttatc tcgaggaggt acacacgcac actcttcttc   2460
ccatcattgg tcttaccttg tcgaggatac aaatcctcaa ccccgttctc cctgtctttt   2520
cggaactcat gactcgaata ctgtaaacgt gcttcacaat gaaaggtacc cgttagaaat   2580
ccttgacgaa gaatactctg gtgcagcgcg ttccggatgg ccttcagctc atgcggtgga   2640
agcgcagagg ggatatggac catagtctcc acgaagttat ggctttgttg tgcgtctagg   2700
gtccccaggg cttggaaagt cgtcactaat ctcgcaaaag atgacttcac catttagcag   2760
gacgaagttc gcgtcgactt ccggtccatc gatgtatggc tcaataacgg cgtcacttcg   2820
cttctgtgga ccaagtgcat ggcagtcaca ggcttttttcg actgcttgaa atagctcgtc   2880
ttccgtggac actttggtga cagcttgact tccccaccct aagcacggct tgacgatgag   2940
gggatatgac acttcggtgg accgaagaac cttatctaac tcgtccgtcc cgaagacccg   3000
aaatgccccg tgcgtgtctg gttccattag tcgagtttga tacttatctc cggcgaggat   3060
ataggctgaa gatggtgagg tagggtatcc gaggatctca cacgctcgag ccaccccgat   3120
catgcggcta tcgctcactg tcatcaagcc atcaatgggc ttatcgtagc tgcggacggc   3180
```

```
cgtgatgatc ctatcgacga atccctcatc cacgtcaata tttgcggcga caaatccttc   3240
tcggagatgg gcgtacgggc cgttgtcatt ctgcagccaa tgccccggct tgtcaatgat   3300
caccagagag atccctaggg ctgctgccgc ctcgtacatg cgtcgactcg tatccgcgtc   3360
tttgcgacct tctacccatg caaggcgttt tggcacaatt gatgtaggga ctacccatgg   3420
atatgaaatc cggttacaga gcgcctcttc gacgctctgg agggtgtcgt gaagatcaga   3480
gccagagcca gtgtcgagaa ggaccgcacc gacagacatc gacagaagtg tgctcagatc   3540
atgcgctgtt ccatctatct ggacttgagc ggtcgtgact tgttgtagtg gacgcgaaag   3600
agctaccacc ttggcaatgt gcttcacccc atctaagcgc tgctctaaga aatcggatcg   3660
agcgagatag ccgtctaccc tggataggat aaacttcatg ataaccgggc tcttattatc   3720 agccccttg ttgcgttcaa aaatagtcgt ggtaatgaaa cttgtgattt ctggggtcag    3780
ataccaaggg gtgcaggact ccttgtcatt atcattttgg taaccgtcga agcatactgc   3840
tgatgcagca tctttgttgt tataggtctt tgtaactatg gtattcgtag ggtagagtgt   3900
gagattgaca gattcatgtt tctggccaac aaagcccttg actgggatcg ccttgttcca   3960
ttcacatgta aaatggtctg atatgcaaat ccatgattag ataatgatca gtgaagcaag   4020
aaatggcttg ttggtggtgg tgtaccaatc tgatcctggg tagtgagagc taggaagcaa   4080
ctgtaggcca ttgtgggcgc tggcaagaca gagtctcgat gaaattgggt ttggggggg    4140 gggaaagatg agttagtaga tgagagcctt tcagcctgga gttttaatac ccgagtagca   4200
ggaacacctt cacctgtgtc atactctttc cttgaccaag cgaggcagtt tcagtattgg   4260
gagaagctcc aggctcggat tcggcgtacc gtactgactg gctacgtagt cagtcactac   4320
ttactccgca gtccggggtt tactccgatg ccgtccacca gtgagccctt attcgtgcaa   4380
attatgtggg tacctggaat tataggccac tttagcccctt atccgcatat gatacttctt   4440
gggttaattc tcaaacagaa gtgtcatttg ctgttgacac tcactccaag gcaagatact   4500
attgagtact tgcattggtt cgatgattac aattgctaga tctgcaccgc gtgtccagtc   4560
actggcctca ctgttccctg atttaaggac ttcaagtcaa attcacatca cccaattgcc   4620
cttcccggtt aggcattcat ctctggcaca tgtgcattaa tgtaggtcag cctttttgaa   4680
atgcgtgaca aagtggagta tgatcttttc ggccagcaac ctgcacagct cggtgtccca   4740
agattagcgg ccattggaaa ttattttagt aagtccagta cttgtcattc ttggggtcgg   4800
tcccttttgg gtaagaagta gtacaaatta gctaccactg tttcattagg agcctccacc   4860
ggttttctac cgtcaccaag tcagaaccgg aattaaccat ttggaccagg atggaccatc   4920
ttaaaacttg attcccagaa tctgtattta ttgccttcaa caaaccagaa ggtcccaaaa   4980
attgttcttt tggattgcat tgacaaataa gcattcttat caaagcatct ccttgcacgg   5040
gcccacaggc gggtattttg ccaatatttt cttcggacaa gtcctcacgg atagcttcga   5100
tgagatcagc gtcacaactt tcaaacacct ttactaaccg ttctgttact ggaacaggca   5160
agctatgcat aatacatatt tcgatcagag gcattaagcc actgtagtgt cttttaatcg   5220
agtcttgatc acgagcagat gaattccggg cactctgaaa gacttcctcc gatagatcga   5280
ctgctctagt atatcgaaca atgtggctcg cagctttata ctgaactgtt ggcagaatga   5340
aaggcttatg acaatttaaa tagtcacagt tgttcctttc aaacctccag atcgctctcc   5400
aaacgtcgtt gaagtctatt tcggcaggcc acttatggag gagccactgt agcccggaaa   5460
ggctggttgc ggcagcagca accatgactc tttcagtaag tggcagtgcc tggaagccat   5520
acctttcaat taaccaaggt aatgcagaca gttttgata agtggcaagc ataaccactt     5580
```

```
tctcagttag gaaaggaggc acatcgggtc caagtgcgtg gagaagaagt tgaaaagcgt     5640
ccaaggtgta cgaggctgcc aacagaactt tctcagttat tggtacttgt gggccacaat     5700
gagcgagaat ccgtcttata ttgttggtcg gtctttctgc tcctgccacg gctatcatga     5760
attcttccga gattggaata tcctctattc gctcatcgag cagaatgcac agtgctttct     5820
cgtgggatgc tgctgctgct cggatggcgg cttctctgt gatgcataca cacggtgctg       5880
tccgcagcag gagttccaaa gctggatgat tgtgcgcaaa tctttccaca attccttggt     5940
caacttcgaa gagctttctg tccaaaagga gttggattat ttctgtagca ctctgatgat     6000
taccgtactt ttcaatgttt attagcatct tcgagaccgg taattgtcca tgcggttgtt     6060
tcattagaag cgctagcatc gatgaatcgc aactgcatgc ttcaacaaac atattatcgc     6120
tcactttggc cattggtcgt acgcggaaaa ttgccttcac agtgttagtt gtgaagcgtc     6180
ttacagcatg cgacatgact ttttccgtga gaggaagggc ctctatttga gaccttgctt     6240
caagatctaa tagaaaacag atcaaggctt cactccttga attgagcaat atgtcttcgg     6300
ttattgagat cctcaagcct ccgttgttca tgagtatctc aaagatatct ttaccttgtg     6360
ggttagaggc tgcttggcat agaattgcat gagtgacggt gaatccagct tgctgcctgt     6420
gtaaaagcat gttgagaatc tcagctgcat atatccattt gttcacgatc ttcagcatga     6480 cttttcgct tattgaaaaa tccggaccac agtcatctag taggagttca agcatttcga       6540
gacaatgggg tgcgttcgta ttacacactg ccgtacagag tacatcctcg ctaacctgtg     6600
cccgattctg tcgtcgacga agaatttgac gcaagacatc gacatggagt ccattattag     6660
ccgctcctac gaacactttt cagccagcaa gaaatcgtca ttcatgtact agatctcga      6720 tcta                                                                  6724
```

<210> SEQ ID NO 12
<211> LENGTH: 380
<212> TYPE: PRT
<213> ORGANISM: Aspergillus sp.

<400> SEQUENCE: 12

```
Met Leu Thr Phe Arg Lys Ser Leu Leu Ala Ala Ala Leu Leu Ile Thr
1               5                   10                  15

Phe Ile Val Tyr Leu Arg Ser Ser His Thr Ala Ser Ser Leu Pro Ser
            20                  25                  30

Pro Asp Thr Ser Ser Ala Gly His Leu Tyr Asn Gln Asp Tyr Asp Gly
        35                  40                  45

His Ala Asp Asn Glu Arg Lys Gly Gly Thr Arg Asp Thr Val Gln Gln
    50                  55                  60

Leu Pro Leu Thr Pro Pro Ser Ala Pro Leu Arg Asp Arg Leu Arg
65                  70                  75                  80

Tyr His Phe Pro Tyr Asp Leu Glu Ala Lys Phe Pro Ala Phe Ile Trp
                85                  90                  95

Gln Thr Trp Lys Tyr Ala Pro Ser Ser Met Phe Phe Ser Glu Ser Leu
            100                 105                 110

Arg Asp Pro Glu Ser Ser Trp Ser Glu Leu His Pro Gly Phe Val His
        115                 120                 125

Glu Val Val Pro Asp Asp Thr Gln Arg His Leu Ile Lys Tyr Leu Tyr
    130                 135                 140

Gly Ala Val Pro Asp Val Phe Glu Ala Tyr Asp Ala Met Pro Leu Pro
145                 150                 155                 160

Val Leu Lys Ala Asp Phe Phe Arg Tyr Leu Ile Leu Leu Ala Arg Gly
```

```
                    165                 170                 175
Gly Ile Tyr Ser Asp Ile Asp Thr Thr Ala Leu Lys Pro Ala Ser Asp
                180                 185                 190

Trp Leu Pro Ala Glu Leu Asp Leu Ala Thr Val Gly Ala Val Val Gly
            195                 200                 205

Ile Glu Ala Asp Pro Asp Arg Pro Asp Trp His Asp Trp Tyr Ala Arg
        210                 215                 220

Arg Ile Gln Phe Cys Gln Trp Thr Ile Gln Ala Lys Pro Gly His Pro
225                 230                 235                 240

Ile Met Arg Asp Ile Val Ser Tyr Ile Thr Glu Glu Thr Leu Arg Met
                245                 250                 255

Lys Lys Ala Gly Ile Leu Lys Thr Gly Lys Met Asp Lys Thr Val Met
            260                 265                 270

Glu Tyr Thr Gly Pro Gly Ala Trp Thr Asp Ala Val Phe Arg Tyr Phe
        275                 280                 285

Asn Asp Pro Glu Tyr Phe Asn Ile Glu Pro Gly Ser Thr Leu Asn Ile
290                 295                 300

Thr Tyr Glu Asp Phe Thr Gly Gln Gly Tyr Lys Lys Val Gly Asp
305                 310                 315                 320

Val Val Val Leu Pro Ile Thr Ser Phe Ser Pro Gly Val His Gln Met
                325                 330                 335

Gly Ala Gly Asp Val Asp Pro Met Ala Phe Val Lys His His Phe
            340                 345                 350

Glu Gly Met Pro Pro Gln Phe Leu Leu Leu Leu Asp Ser Lys Leu Thr
        355                 360                 365

Arg Gln Pro Gly Thr Trp Lys Asp Asp Ser Ser Leu
370                 375                 380

<210> SEQ ID NO 13
<211> LENGTH: 3989
<212> TYPE: DNA
<213> ORGANISM: Aspergillus sp.

<400> SEQUENCE: 13
gtcgacgcca ccggccgact ccgagagcag gtggtcttgg gtgacggctg agggaagggg      60 gtttttattaa cttaactcat gttgtacgcg gtgcatgtac ctagaactat ggcaggtggg    120
aaggccgggc gggcggtggg aaaaggcctt cacaccgaga tggttatgag ccgtcttata    180
tatcatcaac taccctcaat acctacaatg aatcattcga ccacatttga cgatggtagt    240
agtagtagta gtagtagtag tagtatagat gttctgtaga agtatgtata agcctcaagc    300
ctaatgtcca tccccattgg ttgcatttcc aaccagtaat aataagattt tagtagtatg    360
ctgcagaaca tcccgaaaag gccgtcaata gaagcccggc ttgaataaca cagtggatgc    420
ctcaggcgac aaacaccccc gtagatctgc tgcgcctccc gtttcacttg ctgatctcct    480
ccaactctcc ggccgtcgtg tcggaaactc aaccttgaca tccctcttc tgctttgatt    540 ctcgagtcca tgactgcatt cgttctttaa gagcacgaac cggtgcacaa actgttcact    600 accttcgca ctcctcttcg accccatcac cgccgatccc cgagccgac gataacgatc    660 cctcggctct tatctaccgg agctgccagt gactcccttc caccgctacc ctcgtgatca    720
tatgtgacac ggagacactc tccagccttg cctcctttag gatcctctcc cagaatgggg    780
aaatacccaa gagggtgaca caacgaatt cctcccatga gcagtccacg gccgtccacg    840
tcctcaacat cctccgattc gggtctctcc gtcgatacca ccgcctaccc cgaagaatcc    900
aagtacactt caaccgcccc cggcgccggt ggactgtccg atgagaatag ataccgagat    960
```

```
gtagaagagg gagaagcagg ggcagacgag ccgttcctcc cttcggcaaa gaagcaagct   1020
gcctccggaa gccgcacgtc tcgtctgatt tggggcctgg tgatactctg cgtcgccggt   1080
tggctttggg gcctggtgtt gtttgtgact caaaatcgct cggcccagca gtcagtttcc   1140
gaagcgctgc aatcgcacga gtcgggtgcg atctccggga gttcgagttc tggaaaaccg   1200
gttacgctgg agcaggtgct tacgggacag tggcttcctc ggtcccatgc tgtttcttgg   1260
attgcaggac ctaatggcga ggatggtctt ttggtggagc aaggagagga tcagggcaag   1320
ggatatttgc gggtcgacga cattcggagt cgcaaaggcg atgcgactag ccaggaaagc   1380
agggtgctga tggaaaaggc aattgtgcaa gtggatggac ggacgatctt cccggtctca   1440
acatggccga gcccaaactt gaacaaggtg ctgcttttgt ccgagcgcga gaagaactgg   1500
agacactctt tcactgggaa atattggatc ttcgatgtgg ctacccaaac cgcacagccg   1560
cttgacccaa gtaaccctga tggacgcgtg cagctcgcaa tctggtcgcc aacctcagac   1620
atggttgcct tcgtgaggga caacaacttg tacttgcgta gattgtcctc gaaggaggtg   1680
gttcctatta caaagacgg cggtgcggat ctttttctacg gcattcccga ttgggtctat   1740
gaggaagagg tcttttcggg caatagtgta acatggtggt ctggagacgg gaaatacgtg   1800
gctttcctgc gaaccaacga gacggctgtc cctgaatttc ccgtccagta ctacctgtca   1860
cggccatctg gcaagcgacc tcccccgggg ctggaggatt acccagaagt cagggagatc   1920
aagtacccca aggctggcgc tcccaacccc gttgtcagtc tgcagttcta cgacgttgag   1980
aaacaagaag tcttctcgat cgaagcaccg gatgatttcg aggatgacga tcgcatcgtc   2040
attgagatcg tgtggggcac cgaagggaag atccttgtgc gcgcaaccaa ccgagaaagc   2100
gatgtcctga aggtgttctt gttcgacacg aaagccagaa ccagcaaact tgtacgtact   2160
gagaatgtcg ctgatatcga cggtggctgg gtagagccta cgcagtacac atggttcatc   2220
ccagcagatc ccagcaatgg ccgccctcat gatggatatc tcgatactgt gatccacgag   2280
ggttacgagc acctgggtta cttcacgccc ctggacaact cagaacccat tctcctcacc   2340
cagggtgagt gggaagtagt ggacgcgcca accgccgtgg acttgcgcaa aggcatcgtg   2400
tacttcatct ctacaaagga atcccccact gagcgacacc tctaccaggt gaatctagac   2460
ggatccaacc tcaagcctct aacagacacc tccaagcccg gctactacga cgtatccttc   2520
tcccacggaa ccggctacgc cctgctcagc taccgaggtc cttccattcc atggcaagcg   2580
atcgtcaaca ccgagaccga cgagctgaag tacgaggaga ccatcgaaga caacgccggt   2640
ctggcacgta tggttgactc atacgccctt cccactgaga tctaccagaa cgtgacgatc   2700
gacggcttca ccctacaagt cgtcgagcgc cgtcccccac acttcaaccc agccaagaag   2760
tacccggtcc tcttctacct ctacaacggc ccacgctccc aaaccgtcga ccgcaaattc   2820
agcatcgact ccaatcctta cgtcgcctcc agcctcggct acatcgtcgt gaccgtcgac   2880
ggccgcggca ccggtttctc tggccgcaaa accgctgca tcgtccgcgg caacctaggc   2940
tactacgaag cctacgacca aatcaccacg gcgaacctct ggggcgagaa gccttacgtc   3000
gatgaaaccc gcatgtccat ctggggctgg agttacggcg gattcatgac acttaagaca   3060
ttggaacaag atgccgggca gaccttccag tacggcatgg ccgtagcccc tgtgactgac   3120
tggcgacatt atggtaggcc cctccttaac cctctcctct tataaactca cactaaaact   3180
aataataaat agactcgatc tacaccgaac gctacatgca caccccagcc cacaacccca   3240
acggctacga caacacctcc ataaccgaca tgaccgctct ccaacaaacc gtgcgattcc   3300
tcgtcatcca cggcgcctcg gacgacaacg tccacattca aaacacgctc gtcctcgtgg   3360
```

```
ataaactgga cctggcgggc gtgcagaact acgatttgca tttctatcca gattcagatc    3420
atagtatcaa ctttcacaat gcgcatagga tggtttatga gcgtgagccc ccttcccctt    3480
ccccaatccc gtggatgtca agtacgggtg gtattgagac atgtactgat gatattgata    3540
ataggactat cgagctggct cgtcaacgct ttcaacgatg aatggcatcg catagcggat    3600
ccggtcccgg atgactcaat gtgggagaag gtgaagaggt cgttgccgat gttggtgaat    3660
tgaattgaat tgatttgttt gatactagtg catacatata tatcatggtt tcgggtcat    3720 atctagttcc tacatactac atagcatgat acgtatgtat ggacatgtca aaggcgtttt    3780
ctattcacta taggtactca tctatcacgg aaaagggaag tactttaatc gcattaaagc    3840
attacagtag tagtagtatt tttcatatca ccatgcaact gaaacaacaa tcaacaaaac    3900
atcccaacat ctctatgcta tgcaagtttc agctcaaaac caacatcaac atcaacacca    3960
acatctgtac aatgaaggca tatagcaag                                      3989
```

<210> SEQ ID NO 14
<211> LENGTH: 915
<212> TYPE: PRT
<213> ORGANISM: Aspergillus sp.

<400> SEQUENCE: 14

```
Met Gly Lys Tyr Gln Glu Asp Asp Asn Asn Glu Phe Leu Pro Met Ser
1               5                   10                  15

Ser Pro Arg Pro Ser Thr Ser Ser Thr Ser Ser Asp Ser Gly Leu Ser
            20                  25                  30

Val Asp Thr Thr Ala Tyr Pro Glu Glu Ser Lys Tyr Thr Ser Thr Ala
        35                  40                  45

Pro Gly Ala Gly Gly Leu Ser Asp Glu Asn Arg Tyr Arg Asp Val Glu
    50                  55                  60

Glu Gly Glu Ala Gly Ala Asp Glu Pro Phe Leu Pro Ser Ala Lys Lys
65                  70                  75                  80

Gln Ala Ala Ser Gly Ser Arg Thr Ser Arg Leu Ile Trp Gly Leu Val
                85                  90                  95

Ile Leu Cys Val Ala Gly Trp Leu Trp Gly Leu Val Leu Phe Val Thr
            100                 105                 110

Gln Asn Arg Ser Ala Gln Ser Val Ser Glu Ala Leu Gln Ser His
        115                 120                 125

Glu Ser Gly Ala Ile Ser Gly Ser Ser Ser Gly Lys Pro Val Thr
    130                 135                 140

Leu Glu Gln Val Leu Thr Gly Gln Trp Leu Pro Arg Ser His Ala Val
145                 150                 155                 160

Ser Trp Ile Ala Gly Pro Asn Gly Glu Asp Gly Leu Leu Val Glu Gln
                165                 170                 175

Gly Glu Asp Gln Gly Lys Gly Tyr Leu Arg Val Asp Asp Ile Arg Ser
            180                 185                 190

Arg Lys Gly Asp Ala Thr Ser Gln Glu Ser Arg Val Leu Met Glu Lys
        195                 200                 205

Ala Ile Val Gln Val Asp Gly Arg Thr Ile Phe Pro Val Ser Thr Trp
    210                 215                 220

Pro Ser Pro Asn Leu Asn Lys Val Leu Leu Ser Glu Arg Glu Lys
225                 230                 235                 240

Asn Trp Arg His Ser Phe Thr Gly Lys Tyr Trp Ile Phe Asp Val Ala
                245                 250                 255

Thr Gln Thr Ala Gln Pro Leu Asp Pro Ser Asn Pro Asp Gly Arg Val
```

```
                260             265             270
Gln Leu Ala Ile Trp Ser Pro Thr Ser Asp Met Val Ala Phe Val Arg
        275                 280                 285
Asp Asn Asn Leu Tyr Leu Arg Arg Leu Ser Ser Lys Glu Val Val Pro
        290                 295                 300
Ile Thr Lys Asp Gly Ala Asp Leu Phe Tyr Gly Ile Pro Asp Trp
305                 310                 315                 320
Val Tyr Glu Glu Val Phe Ser Gly Asn Ser Val Thr Trp Trp Ser
                325                 330                 335
Gly Asp Gly Lys Tyr Val Ala Phe Leu Arg Thr Asn Glu Thr Ala Val
        340                 345                 350
Pro Glu Phe Pro Val Gln Tyr Tyr Leu Ser Arg Pro Ser Gly Lys Arg
        355                 360                 365
Pro Pro Pro Gly Leu Glu Asp Tyr Pro Glu Val Arg Glu Ile Lys Tyr
        370                 375                 380
Pro Lys Ala Gly Ala Pro Asn Pro Val Val Ser Leu Gln Phe Tyr Asp
385                 390                 395                 400
Val Glu Lys Gln Glu Val Phe Ser Ile Glu Ala Pro Asp Asp Phe Glu
                405                 410                 415
Asp Asp Asp Arg Ile Val Ile Glu Ile Val Trp Gly Thr Glu Gly Lys
        420                 425                 430
Ile Leu Val Arg Ala Thr Asn Arg Glu Ser Asp Val Leu Lys Val Phe
        435                 440                 445
Leu Phe Asp Thr Lys Ala Arg Thr Ser Lys Leu Val Arg Thr Glu Asn
        450                 455                 460
Val Ala Asp Ile Asp Gly Gly Trp Val Glu Pro Thr Gln Tyr Thr Trp
465                 470                 475                 480
Phe Ile Pro Ala Asp Pro Ser Asn Gly Arg Pro His Asp Gly Tyr Leu
                485                 490                 495
Asp Thr Val Ile His Glu Gly Tyr Glu His Leu Gly Tyr Phe Thr Pro
        500                 505                 510
Leu Asp Asn Ser Glu Pro Ile Leu Leu Thr Gln Gly Glu Trp Glu Val
        515                 520                 525
Val Asp Ala Pro Thr Ala Val Asp Leu Arg Lys Gly Ile Val Tyr Phe
        530                 535                 540
Ile Ser Thr Lys Glu Ser Pro Thr Glu Arg His Leu Tyr Gln Val Asn
545                 550                 555                 560
Leu Asp Gly Ser Asn Leu Lys Pro Leu Thr Asp Thr Ser Lys Pro Gly
                565                 570                 575
Tyr Tyr Asp Val Ser Phe Ser His Gly Thr Gly Tyr Ala Leu Leu Ser
        580                 585                 590
Tyr Arg Gly Pro Ser Ile Pro Trp Gln Ala Ile Val Asn Thr Glu Thr
        595                 600                 605
Asp Glu Leu Lys Tyr Glu Glu Thr Ile Glu Asp Asn Ala Gly Leu Ala
        610                 615                 620
Arg Met Val Asp Ser Tyr Ala Leu Pro Thr Glu Ile Tyr Gln Asn Val
625                 630                 635                 640
Thr Ile Asp Gly Phe Thr Leu Gln Val Val Glu Arg Arg Pro Pro His
                645                 650                 655
Phe Asn Pro Ala Lys Lys Tyr Pro Val Leu Phe Tyr Leu Tyr Asn Gly
        660                 665                 670
Pro Arg Ser Gln Thr Val Asp Arg Lys Phe Ser Ile Asp Phe Gln Ser
        675                 680                 685
```

```
Tyr Val Ala Ser Ser Leu Gly Tyr Ile Val Val Thr Val Asp Gly Arg
    690                 695                 700
Gly Thr Gly Phe Ser Gly Arg Lys Thr Arg Cys Ile Val Arg Gly Asn
705                 710                 715                 720
Leu Gly Tyr Tyr Glu Ala Tyr Asp Gln Ile Thr Thr Ala Lys Leu Trp
                725                 730                 735
Gly Glu Lys Pro Tyr Val Asp Glu Thr Arg Met Ser Ile Trp Gly Trp
                740                 745                 750
Ser Tyr Gly Gly Phe Met Thr Leu Lys Thr Leu Glu Gln Asp Ala Gly
            755                 760                 765
Gln Thr Phe Gln Tyr Gly Met Ala Val Ala Pro Val Thr Asp Trp Arg
770                 775                 780
His Tyr Asp Ser Ile Tyr Thr Glu Arg Tyr Met His Thr Pro Ala His
785                 790                 795                 800
Asn Pro Asn Gly Tyr Asp Asn Thr Ser Ile Thr Asp Met Thr Ala Leu
                805                 810                 815
Gln Gln Thr Val Arg Phe Leu Val Ile His Gly Ala Ser Asp Asp Asn
            820                 825                 830
Val His Ile Gln Asn Thr Leu Val Leu Val Asp Lys Leu Asp Leu Ala
835                 840                 845
Gly Val Gln Asn Tyr Asp Leu His Phe Tyr Pro Asp Ser Asp His Ser
850                 855                 860
Ile Asn Phe His Asn Ala His Arg Met Val Tyr Glu Arg Leu Ser Ser
865                 870                 875                 880
Trp Leu Val Asn Ala Phe Asn Asp Glu Trp His Arg Ile Ala Asp Pro
                885                 890                 895
Val Pro Asp Asp Ser Met Trp Glu Lys Val Lys Arg Ser Leu Pro Met
                900                 905                 910
Leu Val Asn
        915

<210> SEQ ID NO 15
<211> LENGTH: 2647
<212> TYPE: DNA
<213> ORGANISM: Aspergillus sp.

<400> SEQUENCE: 15
atgggagctc ttcagtggct gtccatcacg gctgctgcgg cctccgcagt gtcagccttg      60
accccggagt aagtatctcc aatcatctcg aattgaccca tatcgtgcat agctaaccag     120
cttacctgca taggcagatg atcggtgccc cacggagaac cgaagttata ccaaacccct     180
ccggtgtatg cccattgcca ggtccagcct tacaaagaag cgtcgtctgc tgacacgaga     240
aggacaccgg tctattctcg acctcccaat ggtcgtttga cactcattct gagagcacct     300
ggtggagctt gatcgacctc gaatcgggcg agaccaccac tctcaccgat gatagcgata     360
tcgaggagat catctggctg ggttccgaca gttccacgct cctctacatc aacagcacca     420
acgcgcaggt tcccggtggt gtggagctgt ggattgcaga ctcttctgac tttgctaatg     480
cgttggttca gacctttaac catgcctctg cagactagtg ctaatcctac ctgctgcagt     540
tacaaggcag cctctctctc cgccggtttc ctcggcatca aatcaaccgt gacagattcc     600
ggcgacgtgc atttcatcct tcgtggaaag tcctatccca acggaacggc atacaatgat     660
cagctcgcag agacctatcc agtacagcc cgcatctacg acagcatctt tgtgcggcac     720
tgggacactt acctgaccac cgcctcccac gctgtattct ccggtactct gcaaagctcg     780
accagcgacg acggcaatgt tcaatatacc tcttcagggg gattgacgaa cctggttaac     840
```

```
ccagtcaagg gtgccgaaag cccattccct cctttggag gcaacgacga ctatgacctc    900
tcgcctgacg gcaaatgggt taccttcaag agcaaagcgc cagagctgcc tcttgctaac    960
aacacggctg cctatgtcta tctcgtccca cacgacggct ctgcgactgc ctttgctgtc   1020
aacggccctg atagtcctgc aaccccggag ggagttgaag gagaatccaa taatcccgtg   1080
ttctcccctg atagcgacaa aatagcgtac ttccaaatgg caactaatac atacgagtcg   1140
gaccgcaacg tgctatacgt atactccatc gccgatgaca ctatcacccc ccttgcaaag   1200
gactgggacc gatccctag ctccgtgaca tgggtcgatg gagacaacct cgtcgtggca   1260
agccaagatc taggacgaac cagacttttc gccatcccag gcgatgcagg gacgacttca   1320
agcccacgaa cttcaccgac ggcgggtccg tgtcggctca atacgtccta tccaactcta   1380
ccctccttgt cacgtccagc gccttctgga caagctggac cgtctacacc gccagccctg   1440
acgagggcgt gatcaacaca ctggcctcag ccaacgagat cgaccccgag cttagcggcc   1500
ttagttcctc cgactttgaa gagttctact ttgacggcaa ctggactacc gtaagtctat   1560
ccctccttcc ctccaccacc acatcacaaa catactaaac tcaccgcagc tccaaggatg   1620
gatcacctac cccaagact tcgactcatc caagaaatac cccctcgcct tcctcattca   1680
cggcggcccc gaagacgcct gggcggatga gtggaacctg aaatggcact ccaaggtctt   1740
cgccgaccag ggatacgtcg tcgtccagcc aaacccaca ggaagcaccg ggttcggcca   1800
gcagctcaca gacgctatcc aacttaactg gagtacgcca ttccctatcc ccaaactccc   1860
ctcttaaaca tacagctaac aaatgaaata acagccggcg ccgcctacga cgacctaacc   1920
aaagcctggc aatacgtgca cgatacctac gacttcatcg acacagacaa cggcgtcgcc   1980
gcgggtccca gcttcggcgc gttcatgatc acctggatcc agggcgatga ctttggacgc   2040
aagttcaagg cgctggttag ccatgatggt ccgttcattg gcgatgcgtg ggtcgagacg   2100
gatgagttat ggtttgttga gcatgaggtg agtggaccaa accaaccccc cttttcttc    2160 ccttacacca ttagccctat acaaatatga tgattctgac cgtgtatagt tcaacggcac   2220
cttctggcaa gcgcgcgacg cattccacaa cacggaccca tccggcccca gccgcgtcct   2280
cgcatacagc acccccagc tcgtcatcca cagtgacaag gattatcgca tacctgtggc   2340
gaatgggatt ggactgttta atacgctgca ggagaggggc gtgcccagtc ggtttttgaa   2400
tttcccggat gaggatcatt ggtatgttca taccttttc ttccccctt tttctcccat    2460 gattatgggt gttgtggatg ctgatgtagc tatgtgtgtg tttagggtca ccgggcaaga   2520
aaacagcctc gtctggtatc agcaggtgct gggatggatc aatcggtatt ctggggtggg   2580
agggtcgaat cctgatgcga ttgctttgga ggatacggtg aatccggtgg tggatttgaa   2640
tccttga                                                              2647
```

<210> SEQ ID NO 16
<211> LENGTH: 726
<212> TYPE: PRT
<213> ORGANISM: Aspergillus sp.
<220> FEATURE:
<221> NAME/KEY: misc_feature
<222> LOCATION: (378)..(378)
<223> OTHER INFORMATION: Xaa can be any naturally occurring amino acid

<400> SEQUENCE: 16

Met Gly Ala Leu Gln Trp Leu Ser Ile Thr Ala Ala Ala Ser Ala
1               5                   10                  15

Val Ser Ala Leu Thr Pro Glu Gln Met Ile Gly Ala Pro Arg Arg Thr
            20                  25                  30

```
Glu Val Ile Pro Asn Pro Ser Gly Asp Thr Gly Leu Phe Ser Thr Ser
         35                  40                  45

Gln Trp Ser Phe Asp Thr His Ser Glu Ser Thr Trp Trp Ser Leu Ile
 50                      55                  60

Asp Leu Glu Ser Gly Glu Thr Thr Thr Leu Thr Asp Asp Ser Asp Ile
 65                  70                  75                  80

Glu Glu Ile Ile Trp Leu Gly Ser Asp Ser Thr Leu Leu Tyr Ile
                 85                  90                  95

Asn Ser Thr Asn Ala Gln Val Pro Gly Gly Val Glu Leu Trp Ile Ala
             100                 105                 110

Asp Ser Ser Asp Phe Ala Asn Ala Tyr Lys Ala Ala Ser Leu Ser Ala
             115                 120                 125

Gly Phe Leu Gly Ile Lys Ser Thr Val Thr Asp Ser Gly Asp Val His
         130                 135                 140

Phe Ile Leu Arg Gly Lys Ser Tyr Pro Asn Gly Thr Ala Tyr Asn Asp
145                 150                 155                 160

Gln Leu Ala Glu Thr Tyr Pro Ser Thr Ala Arg Ile Tyr Asp Ser Ile
                 165                 170                 175

Phe Val Arg His Trp Asp Thr Tyr Leu Thr Thr Ala Ser His Ala Val
             180                 185                 190

Phe Ser Gly Thr Leu Gln Ser Ser Thr Ser Asp Asp Gly Asn Val Gln
         195                 200                 205

Tyr Thr Ser Ser Gly Gly Leu Thr Asn Leu Val Asn Pro Val Lys Gly
         210                 215                 220

Ala Glu Ser Pro Phe Pro Pro Phe Gly Gly Asn Asp Asp Tyr Asp Leu
225                 230                 235                 240

Ser Pro Asp Gly Lys Trp Val Thr Phe Lys Ser Lys Ala Pro Glu Leu
                 245                 250                 255

Pro Leu Ala Asn Asn Thr Ala Ala Tyr Val Tyr Leu Val Pro His Asp
             260                 265                 270

Gly Ser Ala Thr Ala Phe Ala Val Asn Gly Pro Asp Ser Pro Ala Thr
         275                 280                 285

Pro Glu Gly Val Glu Gly Glu Ser Asn Asn Pro Val Phe Ser Pro Asp
         290                 295                 300

Ser Asp Lys Ile Ala Tyr Phe Gln Met Ala Thr Asn Thr Tyr Glu Ser
305                 310                 315                 320

Asp Arg Asn Val Leu Tyr Val Tyr Ser Ile Ala Asp Asp Thr Ile Thr
                 325                 330                 335

Pro Leu Ala Lys Asp Trp Asp Arg Ser Pro Ser Ser Val Thr Trp Val
             340                 345                 350

Asp Gly Asp Asn Leu Val Val Ala Ser Gln Asp Leu Gly Arg Thr Arg
         355                 360                 365

Leu Phe Ala Ile Pro Gly Asp Ala Gly Xaa Asp Phe Lys Pro Thr Asn
370                 375                 380

Phe Thr Asp Gly Gly Ser Val Ser Ala Gln Tyr Val Leu Ser Asn Ser
385                 390                 395                 400

Thr Leu Leu Val Thr Ser Ser Ala Phe Trp Thr Ser Trp Ser Val Tyr
                 405                 410                 415

Thr Ala Ser Pro Asp Glu Gly Val Ile Asn Thr Leu Ala Ser Ala Asn
             420                 425                 430

Glu Ile Asp Pro Glu Leu Ser Gly Leu Ser Ser Ser Asp Phe Glu Glu
         435                 440                 445

Phe Tyr Phe Asp Gly Asn Trp Thr Thr Leu Gln Gly Trp Ile Thr Tyr
```

|   |   |   | 450 |   |   |   | 455 |   |   |   | 460 |   |
|---|---|---|---|---|---|---|---|---|---|---|---|---|
| Pro | Gln | Asp | Phe | Asp | Ser | Ser | Lys | Lys | Tyr | Pro | Leu | Ala | Phe | Leu | Ile |
| 465 |   |   |   |   | 470 |   |   |   |   | 475 |   |   |   |   | 480 |
| His | Gly | Gly | Pro | Glu | Asp | Ala | Trp | Ala | Asp | Glu | Trp | Asn | Leu | Lys | Trp |
|   |   |   |   | 485 |   |   |   |   | 490 |   |   |   |   | 495 |   |
| His | Ser | Lys | Val | Phe | Ala | Asp | Gln | Gly | Tyr | Val | Val | Gln | Pro | Asn |
|   |   |   |   | 500 |   |   |   |   | 505 |   |   |   |   | 510 |
| Pro | Thr | Gly | Ser | Thr | Gly | Phe | Gly | Gln | Gln | Leu | Thr | Asp | Ala | Ile | Gln |
|   |   |   |   | 515 |   |   |   |   | 520 |   |   |   |   | 525 |   |
| Leu | Asn | Trp | Thr | Gly | Ala | Ala | Tyr | Asp | Asp | Leu | Thr | Lys | Ala | Trp | Gln |
|   |   |   | 530 |   |   |   |   | 535 |   |   |   |   | 540 |   |   |
| Tyr | Val | His | Asp | Thr | Tyr | Asp | Phe | Ile | Asp | Thr | Asp | Asn | Gly | Val | Ala |
| 545 |   |   |   |   | 550 |   |   |   |   | 555 |   |   |   |   | 560 |
| Ala | Gly | Pro | Ser | Phe | Gly | Ala | Phe | Met | Ile | Thr | Trp | Ile | Gln | Gly | Asp |
|   |   |   |   | 565 |   |   |   |   | 570 |   |   |   |   | 575 |   |
| Asp | Phe | Gly | Arg | Lys | Phe | Lys | Ala | Leu | Val | Ser | His | Asp | Gly | Pro | Phe |
|   |   |   | 580 |   |   |   |   | 585 |   |   |   |   | 590 |   |   |
| Ile | Gly | Asp | Ala | Trp | Val | Glu | Thr | Asp | Glu | Leu | Trp | Phe | Val | Glu | His |
|   |   |   |   | 595 |   |   |   |   | 600 |   |   |   |   | 605 |   |
| Glu | Phe | Asn | Gly | Thr | Phe | Trp | Gln | Ala | Arg | Asp | Ala | Phe | His | Asn | Thr |
|   |   |   | 610 |   |   |   |   | 615 |   |   |   |   | 620 |   |   |
| Asp | Pro | Ser | Gly | Pro | Ser | Arg | Val | Leu | Ala | Tyr | Ser | Thr | Pro | Gln | Leu |
| 625 |   |   |   |   | 630 |   |   |   |   | 635 |   |   |   |   | 640 |
| Val | Ile | His | Ser | Asp | Lys | Asp | Tyr | Arg | Ile | Pro | Val | Ala | Asn | Gly | Ile |
|   |   |   |   | 645 |   |   |   |   | 650 |   |   |   |   | 655 |   |
| Gly | Leu | Phe | Asn | Thr | Leu | Gln | Glu | Arg | Gly | Val | Pro | Ser | Arg | Phe | Leu |
|   |   |   | 660 |   |   |   |   | 665 |   |   |   |   | 670 |   |   |
| Asn | Phe | Pro | Asp | Glu | Asp | His | Trp | Val | Thr | Gly | Gln | Glu | Asn | Ser | Leu |
|   |   |   | 675 |   |   |   |   | 680 |   |   |   |   | 685 |   |   |
| Val | Trp | Tyr | Gln | Gln | Val | Leu | Gly | Trp | Ile | Asn | Arg | Tyr | Ser | Gly | Val |
|   |   |   | 690 |   |   |   |   | 695 |   |   |   |   | 700 |   |   |
| Gly | Gly | Ser | Asn | Pro | Asp | Ala | Ile | Ala | Leu | Glu | Asp | Thr | Val | Asn | Pro |
| 705 |   |   |   |   | 710 |   |   |   |   | 715 |   |   |   |   | 720 |
| Val | Val | Asp | Leu | Asn | Pro |
|   |   |   |   | 725 |   |

<210> SEQ ID NO 17
<211> LENGTH: 2777
<212> TYPE: DNA
<213> ORGANISM: Aspergillus sp.

<400> SEQUENCE: 17

```
ctatggacac tttcttctct tccctcccct cccatcccccg ccggtgtcag gcaaatgaag    60
atgggtttcc cctgggtttc tcccgtgagt ccaggctaac tgggcctgga tcatccagga   120
ttggttgatg attccaccgc tgggcttttg ggaccagact ggtccagcta gttgaacaa    180
tgccacccct ccagcctccg tgctgggtgg atcgatgtag agtgcgaaag tcttggtgtc   240
tggggcgaat caactatagt aggcctgcta aaagtcgctc gacggtgaat aatgcctcgc   300
cgaacttttt cctgttcgac ttgctgccct ttatagact gcacttcttt ccccttttg    360
tttacatttc tcttctagtt tgttaacctt agtgttcttt catttctcgt tcccgctgtc   420
actttctttc tcatctgccg ggctttgttg ggctgagcgc tacttctttc tctctcttgg   480
tctgttcgtt gctccgccag ttggttcact cagcctcgta acatcagtat accaggctaa   540
gtcaggactt tggcccccat actgcttccc ctttttttat aaaactcaat ccttctggaa   600
```

```
aggattctat tctcaattc tcagactact taatacgttc tttgttttca aattgttttg    660
tttctgaaac ttgccgggcc ctatcccctc ttttttatag tccgcctgtc gacatcatat    720
ccagagtgag ccaccatgca gctcctccag tccctcattg ttgccgtttg cttcagctac    780
ggcgtcctct ccttacccca tggcccgtca accagcaca aagcacgttc cttcaaggtt     840
gaacgggtcc gtcgtggaac cggtgctctg catgggcccg ctgctctccg caaagcatac    900
cggaagtacg gaatagctcc cagcagtttc aacatcgatc tggcagactt taaacccatt    960
acgacaaccc atgctgctgc tgggagcgag attgcagagc ctgatcagac tggcgctgtc   1020
agtgctactt ccgtcgagaa cgatgccgag ttcgtttcgc ctgttcttat tggcggccag   1080
aagatcgtca tgacatttga cactggttct tctgacttgt aagtcttgga tgcagctgtt   1140
tactctttgg tacagtgatt aacgtcgatc tacagttggg tgttcgatac gaatctcaat   1200
gaaaccttga cggacacac ggagtacaac ccttcgaact cctcgacctt caagaagatg    1260
gacggataca ccttcgatgt ctcgtatggt gacgactcgt acgcctctgg ccccgtcgga   1320
acggataccg tcaacattgg cggcgccatt gtcaaggagc aagccttcgg tgtccccgac   1380
caggtatccc agtcgttcat cgaggacacg aactccaacg gcctggtcgg gttgggctttt  1440 tcctccatca acaccatcaa accggaggcg caagacacgt tcttcgccaa tgtcgcacca   1500
agtctggacg agcccgtcat gaccgcctcg ctcaaggctg acggagtggg cgagtacgag   1560
ttcggcacga tcgacaaaga caagtaccag ggcaacattg ccaacatcag cgtggactca   1620
tcgaacggat actggcagtt ctccactccc aagtactccg tggcagacgg agagctgaag   1680
gacattggaa gcttgaacac ctcgatcgcg gacaccggta cctcccttat gctgctggat   1740
gaagacgtgt ttactgccta ctatgcgcaa gttcccaact cggtctacgt gagcagtgcc   1800
ggtggttaca tctacccctg caacaccact cttcccagct tctcgcttgt cctcggcgag   1860
tcgagcctgg ccacgatccc cggtaacctg atcaatttct ccaaggttgg caccaacacc   1920
accaccggac aggcctgtaa gttgctcccc ttctttttgca tgattgaaca tgattgactg    1980
attgtgctgg ttagtgtgct ttggcggcat tcaatccaac ggaaacacct cgctgcagat   2040
tctgggcgat atttttcctga aggccttttt cgttgtcttc gacatgcgcg ccccctcgct    2100
tggtgttgcc tctcccaaga actagtttcc ttttcctgta cttttccccc gcgtgtaata    2160
atatcgtctg atttttttgga ctgtctccta cgtgggcaag atggatggat agtttgctca    2220
cgtgcattgc tttaccttgg gtctgtgagt caaggcagga gtgcgtggct gtatctacaa    2280
ttcaagttac agtgccgacc gttattgcct tccacatcga aaaacataga cactctttct    2340
aaccctaatc catgatacaa gtatatactt cgagtccata ttatggtggt gtatcaaggc    2400
gccatgttta tatctaatga aaccaacgta ggtctcatct tcatacgttg tttaaaaggt    2460
gccgaagaat atacgaagat agatatagta gcaccccgaa agtctaacgg ctaatcagcg    2520
ccggtaaacg gtaaactcca ggcaaaggaa cacgaggtag gcaactaaga gaactacacc    2580
tgcactcctc cccagtccca aaagataac agcacaaaat gccccagagg acacccacac     2640
ggccaccagc tcaaaaagca caaattatc tgcctcttgt acctggtacc ccgccactgc      2700
aacgacacca acacagagcg tcagcaagaa aatgttgctt cctgcagtcg tcgcagccat    2760
aatgccgccg tgccgcg                                                     2777
```

<210> SEQ ID NO 18
<211> LENGTH: 394
<212> TYPE: PRT
<213> ORGANISM: Aspergillus sp.

<400> SEQUENCE: 18

```
Met Gln Leu Leu Gln Ser Leu Ile Val Ala Val Cys Phe Ser Tyr Gly
1               5                   10                  15

Val Leu Ser Leu Pro His Gly Pro Ser Asn Gln His Lys Ala Arg Ser
            20                  25                  30

Phe Lys Val Glu Arg Val Arg Arg Gly Thr Gly Ala Leu His Gly Pro
        35                  40                  45

Ala Ala Leu Arg Lys Ala Tyr Arg Lys Tyr Gly Ile Ala Pro Ser Ser
    50                  55                  60

Phe Asn Ile Asp Leu Ala Asp Phe Lys Pro Ile Thr Thr Thr His Ala
65                  70                  75                  80

Ala Ala Gly Ser Glu Ile Ala Glu Pro Asp Gln Thr Gly Ala Val Ser
                85                  90                  95

Ala Thr Ser Val Glu Asn Asp Ala Glu Phe Val Ser Pro Val Leu Ile
            100                 105                 110

Gly Gly Gln Lys Ile Val Met Thr Phe Asp Thr Gly Ser Ser Asp Phe
        115                 120                 125

Trp Val Phe Asp Thr Asn Leu Asn Glu Thr Leu Thr Gly His Thr Glu
130                 135                 140

Tyr Asn Pro Ser Asn Ser Ser Thr Phe Lys Lys Met Asp Gly Tyr Thr
145                 150                 155                 160

Phe Asp Val Ser Tyr Gly Asp Ser Tyr Ala Ser Gly Pro Val Gly
                165                 170                 175

Thr Asp Thr Val Asn Ile Gly Gly Ala Ile Val Lys Glu Gln Ala Phe
            180                 185                 190

Gly Val Pro Asp Gln Val Ser Gln Ser Phe Ile Glu Asp Thr Asn Ser
        195                 200                 205

Asn Gly Leu Val Gly Leu Gly Phe Ser Ser Ile Asn Thr Ile Lys Pro
    210                 215                 220

Glu Ala Gln Asp Thr Phe Phe Ala Asn Val Ala Pro Ser Leu Asp Glu
225                 230                 235                 240

Pro Val Met Thr Ala Ser Leu Lys Ala Asp Gly Val Gly Glu Tyr Glu
                245                 250                 255

Phe Gly Thr Ile Asp Lys Asp Lys Tyr Gln Gly Asn Ile Ala Asn Ile
            260                 265                 270

Ser Val Asp Ser Ser Asn Gly Tyr Trp Gln Phe Ser Thr Pro Lys Tyr
        275                 280                 285

Ser Val Ala Asp Gly Glu Leu Lys Asp Ile Gly Ser Leu Asn Thr Ser
    290                 295                 300

Ile Ala Asp Thr Gly Thr Ser Leu Met Leu Leu Asp Glu Asp Val Val
305                 310                 315                 320

Thr Ala Tyr Tyr Ala Gln Val Pro Asn Ser Val Tyr Val Ser Ser Ala
                325                 330                 335

Gly Gly Tyr Ile Tyr Pro Cys Asn Thr Thr Leu Pro Ser Phe Ser Leu
            340                 345                 350

Val Leu Gly Glu Ser Ser Leu Ala Thr Ile Pro Gly Asn Leu Ile Asn
        355                 360                 365

Phe Ser Lys Val Gly Thr Asn Thr Thr Gly Gln Ala Cys Lys Leu
    370                 375                 380

Leu Pro Phe Phe Cys Met Ile Glu His Asp
385                 390
```

<210> SEQ ID NO 19

<211> LENGTH: 3854
<212> TYPE: DNA
<213> ORGANISM: Aspergillus sp.
<220> FEATURE:
<221> NAME/KEY: misc_feature
<222> LOCATION: (1866)..(1866)
<223> OTHER INFORMATION: n is a, c, g, or t

<400> SEQUENCE: 19

| | | | | | |
|---|---|---|---|---|---|
| ctttccccga | aaagtgccac | ctgacgtcta | agaaaccatt | attatcatga | cattaaccta | 60 |
| taaaaatagg | cgtatcacga | ggcccttcg | tctcgcgcgt | ttcggtgatg | acggtgaaaa | 120 |
| cctctgacac | atgcagctcc | cggagacggt | cacagcttgt | ctgtaagcgg | atgccgggag | 180 |
| cagacaagcc | cgtcagggcg | cgtcagcggg | tgttggcggg | tgtcggggct | ggcttaacta | 240 |
| tgcggcatca | gagcagattg | tactgagagt | gcaccatatg | cggtgtgaaa | taccgcacag | 300 |
| atgcgtaagg | agaaaatacc | gcatcaggcg | ccattcgcca | ttcaggctgc | gcaactgttg | 360 |
| ggaagggcga | tcggtgcggg | cctcttcgct | attacgccag | ctggcgaaag | ggggatgtgc | 420 |
| tgcaaggcga | ttaagttggg | taacgccagg | gttttcccag | tcacgacgtt | gtaaaacgac | 480 |
| ggccagtgaa | ttgtaatacg | actcactata | gggcgaattc | gagttcgttt | cgatgagcgg | 540 |
| tcagctggtt | actattaagg | ttcttgcact | attaaggttc | ttacccctct | gccctctctt | 600 |
| caaatgtgta | ctataatgac | tctaggatag | attgggttat | tctaaatcca | ttgattgcat | 660 |
| tcttctgagc | agataatgag | gtatagcagt | aattcctatt | atcgcatagt | caatatatct | 720 |
| ataaggccct | tatgaagtat | catcgtttct | gaacgtggca | gagttagtac | gttgcgtacc | 780 |
| gcaccggaga | gataggacgt | aaacttcatg | aggtgattcc | agtcatggtt | tgcgtgcaat | 840 |
| tatgactagt | tacataggca | tctttgcatc | gtaaccatat | cacagctata | tccctcatt | 900 |
| gtctgtcttg | ttgacatcat | tgatttagat | cagtctcata | gagaatgcat | tataggagga | 960 |
| gattgttgtg | aggcatgagg | catttctgag | gcccgctact | ccgcattctg | cagcatatcg | 1020 |
| tctctgcgta | ggggaggtcg | aaaccagctg | taggactcgg | cttcggtgta | tctgtaccga | 1080 |
| ctgactagaa | atcgctcaat | cgtgtagtat | agctgtctct | tgttcctca | caacatgtct | 1140 |
| acgatatgct | atcaaaaaaa | gcagaagatg | gagtcagagc | cacccggtta | gggccgggcc | 1200 |
| gcccgggagg | agaacaaaat | acgggacaga | atctcagtga | tgggggagaa | gagagagtgg | 1260 |
| cgacctgaca | attcacacac | gacacgaata | atagccgaaa | ctaacaagat | aaatcacatc | 1320 |
| acatcatgaa | gaagacctgc | gtaatgatga | taagcaatcc | caccaataat | acaatgccat | 1380 |
| tgatagtggc | tgacctgaag | caattcgggg | aggagacgcc | aagctcgacg | atcaccggag | 1440 |
| cttgaaagac | caacgagaca | agatgacagg | cccgtcgcac | cacgccacta | actgccctaa | 1500 |
| cagaaatcgg | cctgaatagt | gcgacgagtg | tcccggttct | gggcctccac | gataagataa | 1560 |
| gtcatgggct | tatcgcgtca | tcggcgccga | tctcgcgatc | agctgaaacc | aatcattcaa | 1620 |
| tcgatttgca | tcacccgact | ggggggcgaga | tttcagggcc | agctgaaagg | gtcggctgcc | 1680 |
| gagattgtca | gtggatgatg | aatgttatgc | tggaagagag | ggggagaatg | acgtctcaat | 1740 |
| tctgggtcac | ttactagttg | actagccacc | tagtatttag | ctgctagcta | gggattcggt | 1800 |
| ttaaaagcct | ggtggtttct | ctcttcttct | cgtcattttc | tcttcatctc | atacccattc | 1860 |
| ttcaanactc | ctccactttg | atcaattatc | ctccatcatg | gctaccaaaa | tcaagctcat | 1920 |
| ccccaatctc | aactacaagc | gctcaggcac | caagtcctac | gtgcacttga | tgcgcaagta | 1980 |
| ccgcttccat | cccaccaagc | ctggtcccta | cactctcagc | agctccatcc | aacagaccgg | 2040 |
| tcgtccgtac | actgaaaagc | ccatcggggg | tcgggcccat | atccggcagc | tggtgcggaa | 2100 |

```
gaagagcacc accagcgatg aggttggcga ggttccggcc gaagatgtgc agaacgactc    2160
catgtatctg cgaccgtggg ggatcggaac cccggcgcag aacctgaagt tggactttga    2220
cactggttca gctgatcttt gggtacaccc ccattatgaa agacctaata tggaaacgag    2280
cgtcactgac agatgtaggt ctggtccaac aaactcccct caaccttcct atccgagaac    2340
aagacccatg cgatcttcga ctcgtccaaa tcgagcacct tcaagacctt ggaaggtgaa    2400
tcctggcaaa tctcctacgg agatggatcc tccgcatcag ggagtgtggg caccgacgac    2460
gtcaacattg gcggcgtagt cgtcaagaac caagccgttg agctggcaga agatgtcc     2520 agcacattcg cccaaggcga aggggacgga ttgctcggtc tagcattcag caacatcaac    2580
acggtacagc caaagtccgt gaaaacgccc gtcgagaaca tgatcctgca ggatgacatt    2640
cccaagtcgg ctgagctgtt cacggccaag ctggatacct gcgggacac tgatgacgag    2700 tcgtttttaca ccttttggctt cattgaccag gatctggtga agacggcagg tgaagaggtc    2760
tactacaccc ctgtcgataa cagtcaaggc ttctggctat tcaactcgac ctccgcgacg    2820
gtaaatggaa agaccattaa ccggtcgggt aacaccgcca ttgctgatac cggtacgacg    2880
ctggccttgg tggacgatga cacgtgtgag gccatttata gtgcaattga cggcgcctat    2940
tatgatcagg aagtacaggg ctggatctat ccgaccgata cggcgcagga taagctaccc    3000
actgtgtcgt ttgccgtggg tgaaaagcag ttcgtggtgc agaaggagga cctggcgttt    3060
tcggaggcga agacgggcta tgtctatgga ggaatccaga gtcgtggtga tatgaccatg    3120
gacatcttgg gagacacatt tttgaagagt atttatgctg taagtgcatt gctgttggcg    3180
ttaaggggtg atatcgaagc tcactaactg gattgcagat ctttgatgtc gggaacctgc    3240
gctttggagc cgtccagcgc gaggagttgc gccagagctc gaattcgccc tatagtgagt    3300
cgtattacaa ttcactggcc gtcgttttac aacgtcgtga ctgggaaaac cctggcgtta    3360
cccaacttaa tcgccttgca gcacatcccc ctttcgccag ctggcgtaat agcgaagagg    3420
cccgcaccga tcgcccttcc caacagttgc gcagcctgaa tggcgaatgg cgcctgatgc    3480
ggtattttct ccttacgcat ctgtgcggta tttcacaccg catatggtgc actctcagta    3540
caatctgctc tgatgccgca tagttaagcc agccccgaca cccgccaaca cccgctgacg    3600
cgccctgacg ggcttgtctg ctcccggcat ccgcttacag acaagctgtg accgtctccg    3660
ggagctgcat gtgtcagagg ttttcaccgt catcaccgaa acgcgcgaga cgaaagggcc    3720
tcgtgatacg cctatttttta taggttaatg tcatgataat aatggtttct tagacgtcag    3780
gtggcacttt tcggggaaat gtgcgcggaa cccctatttg tttatttttc taaatacatt    3840
caaatatgta tccg                                                     3854
```

<210> SEQ ID NO 20
<211> LENGTH: 417
<212> TYPE: PRT
<213> ORGANISM: Aspergillus sp.

<400> SEQUENCE: 20

Met Ala Thr Lys Ile Lys Leu Ile Pro Asn Leu Asn Tyr Lys Arg Ser
1               5                   10                  15

Gly Thr Lys Ser Tyr Val His Leu Met Arg Lys Tyr Arg Phe His Pro
            20                  25                  30

Thr Lys Pro Gly Pro Tyr Thr Leu Ser Ser Ser Ile Gln Gln Thr Gly
        35                  40                  45

Arg Pro Tyr Thr Glu Lys Pro Ile Gly Gly Arg Ala His Ile Arg Gln
    50                  55                  60

Leu Val Arg Lys Lys Ser Thr Thr Ser Asp Glu Val Gly Glu Val Pro
65                  70                  75                  80

Ala Glu Asp Val Gln Asn Asp Ser Met Tyr Leu Ala Thr Val Gly Ile
                85                  90                  95

Gly Thr Pro Ala Gln Asn Leu Lys Leu Asp Phe Asp Thr Gly Ser Ala
            100                 105                 110

Asp Leu Trp Val Trp Ser Asn Lys Leu Pro Ser Thr Leu Leu Ser Glu
        115                 120                 125

Asn Lys Thr His Ala Ile Phe Asp Ser Ser Lys Ser Ser Thr Phe Lys
130                 135                 140

Thr Leu Glu Gly Glu Ser Trp Gln Ile Ser Tyr Gly Asp Gly Ser Ser
145                 150                 155                 160

Ala Ser Gly Ser Val Gly Thr Asp Asp Val Asn Ile Gly Gly Val Val
                165                 170                 175

Val Lys Asn Gln Ala Val Glu Leu Ala Glu Lys Met Ser Ser Thr Phe
            180                 185                 190

Ala Gln Gly Glu Gly Asp Gly Leu Leu Gly Leu Ala Phe Ser Asn Ile
        195                 200                 205

Asn Thr Val Gln Pro Lys Ser Val Lys Thr Pro Val Glu Asn Met Ile
210                 215                 220

Leu Gln Asp Asp Ile Pro Lys Ser Ala Glu Leu Phe Thr Ala Lys Leu
225                 230                 235                 240

Asp Thr Trp Arg Asp Thr Asp Glu Ser Phe Tyr Thr Phe Gly Phe
                245                 250                 255

Ile Asp Gln Asp Leu Val Lys Thr Ala Gly Glu Glu Val Tyr Tyr Thr
        260                 265                 270

Pro Val Asp Asn Ser Gln Gly Phe Trp Leu Phe Asn Ser Thr Ser Ala
            275                 280                 285

Thr Val Asn Gly Lys Thr Ile Asn Arg Ser Gly Asn Thr Ala Ile Ala
290                 295                 300

Asp Thr Gly Thr Thr Leu Ala Leu Val Asp Asp Thr Cys Glu Ala
305                 310                 315                 320

Ile Tyr Ser Ala Ile Asp Gly Ala Tyr Tyr Asp Gln Glu Val Gln Gly
        325                 330                 335

Trp Ile Tyr Pro Thr Asp Thr Ala Gln Asp Lys Leu Pro Thr Val Ser
            340                 345                 350

Phe Ala Val Gly Glu Lys Gln Phe Val Val Gln Lys Glu Asp Leu Ala
        355                 360                 365

Phe Ser Glu Ala Lys Thr Gly Tyr Val Tyr Gly Ile Gln Ser Arg
    370                 375                 380

Gly Asp Met Thr Met Asp Ile Leu Gly Asp Thr Phe Leu Lys Ser Ile
385                 390                 395                 400

Tyr Ala Val Ser Ala Leu Leu Leu Ala Leu Arg Gly Asp Ile Glu Ala
                405                 410                 415

His

<210> SEQ ID NO 21
<211> LENGTH: 2411
<212> TYPE: DNA
<213> ORGANISM: Aspergillus sp.
<220> FEATURE:
<221> NAME/KEY: misc_feature
<222> LOCATION: (201)..(201)
<223> OTHER INFORMATION: n is a, c, g, or t

<400> SEQUENCE: 21

```
tgtggcttga atgcaattat gattatgaac tcgtaagtag gtaggctgta ctatatatat    60
gtactgtttt ctccgccagg gtaccggata tctaatctat cactgctaaa aacctatagt   120
aggagggtgt gatactaaga atggaaaatt gatgtctcac ggactcattt ctgcctgtac   180
gctctcattt gtgctcaggg ngaaaaacat gaccggtcgt gcctgggctc caccgccgcc   240
aaaaaaggcc tgtagatcga ggcctggatc attggcagca gccagtcgca ggcgtccgtt   300
gcgccgcgaa aacctgccga gtgggccgtt taggctttgg gtctccccac gatgtaagca   360
taatcattct gtgcctgagt gtgaattctc ctgttggagg ctgcatctta attcttaact   420
gcatgaaaag cacttgggtg ctatttttctt tttcctttct ttcttttccg tgttcatttc   480
cattcccttg ctcttcttct ttgtgtcgac atttacaaat cacattttcc ttatactttc   540
ttttcttcac ctcgtttctt cctattcact ctctgtgttc agcattcgtt atcaaacact   600
ttattttttg ctcgtctctt ttatcttcac ttgtttgtgc ccttcccac tagcaatcta   660
tcgtttgatc tttctagagc attgtcttga ttgtgtcatt ctgtcattga ctccggctat   720
gaaatattat tctcaatctg cctaaaacca aattctactc tatcattaca catttgtatc   780
acctgatctg gctgagatag gagagtccag catctcatcg tctgcatcag acaattgcga   840
taaattcatt gcttgcacct gttattgatt cttccaagtt atgcatctcc cacagcgtct   900
cgttacagca gcgtgtcttt gcgccagtgc cacggctttc atcccataca ccatcaaact   960
cgatacgtcg gacgacatct cagcccgtga ttcattagct cgtcgtttcc tgccagtacc  1020
aaacccaagc gatgctctag cagacgattc cacctcatct gccagcgatg agtccctgtc  1080
actgaacatc aaaaggattc ccgttcgtcg tgacaatgat ttcaagattg tggtagcgga  1140
aactccctct tggtctaaca ccgccgctct cgatcaagat ggtagcgaca tttcatacat  1200
ctctgtcgtc aacattgggt ctgatgagaa atctatgtac atgttgctcg acacaggcgg  1260
ctctgatacc tgggttttcg gttccaactg cacgtccaca ccctgcacga tgcacaatac  1320
cttcggttcg gacgattctt cgacccttga aatgacatcg gaagagtgga gtgtgggcta  1380
tggaactggg tctgtcagcg gcttgctagg aaaagacaag ctcacgattg caaatgtcac  1440
tgtacgcatg actttcggac ttgcttccaa cgcatcggat aacttcgagt cgtacccaat  1500
ggacggcatt ctcggtctcg gtcgaaccaa cgatagttcc tacgacaacc caacattcat  1560
ggatgccgtt gcagaaagta acgttttcaa gtcgaatatc gttggcttcg ccctttcacg  1620
tagcccccgcc aaggatggca cggtcagctt tggcactact gacaaggaca agtacaccgg  1680
cgatatcacc tacaccgata ccgtcggatc ggacagctat ggcgcattc ccgtggacga  1740
tgtctatgtt ggcggcactt catgcgattt ctccaacaaa tcagccatca tcgataccgg  1800
aacttcttat gctatgctgc cttcaagcga ctcgaagacg ctgcacagtc tcattcccgg  1860
cgccaaatct tcggggagct accacattat tccgtgcaac acaactacta agctacaagt  1920
ggcattctct ggtgtgaatt acaccatctc gccgaaggac tacgtgggag caacttcagg  1980
ttctggatgc gtttcgaaca ttatcagcta cgacttattt ggtgatgaca tctggctcct  2040
gggtgacacg tttctcaaaa atgtgtatgc tgtgtttgac tacgatgagt tacgggtcgg  2100
atttgcagag cgttcctcga acaccacctc tgcgtcgaac tctacgagct ctggaacaag  2160
cagcacctcg ggttccacta caacgggcag ctcaacgact acgacgagct ctgctagctc  2220
tagtagttca tctgatgctg aatcaggaag tagcatgacc attcccgctc ctcagtatttt  2280
cttctctgct ctggcgattg cttccttcat gctttggctc tagttaaccg catcttactc  2340
gacgcctgaa cctcgggaaa catatgcatt atttacacat gctgctgatt tgtatttgca  2400
```
tatattcttc g                                                                                          2411

<210> SEQ ID NO 22
<211> LENGTH: 480
<212> TYPE: PRT
<213> ORGANISM: Aspergillus sp.

<400> SEQUENCE: 22

```
Met His Leu Pro Gln Arg Leu Val Thr Ala Ala Cys Leu Cys Ala Ser
1               5                   10                  15

Ala Thr Ala Phe Ile Pro Tyr Thr Ile Lys Leu Asp Thr Ser Asp Asp
            20                  25                  30

Ile Ser Ala Arg Asp Ser Leu Ala Arg Arg Phe Leu Pro Val Pro Asn
        35                  40                  45

Pro Ser Asp Ala Leu Ala Asp Asp Ser Thr Ser Ala Ser Asp Glu
    50                  55                  60

Ser Leu Ser Leu Asn Ile Lys Arg Ile Pro Val Arg Arg Asp Asn Asp
65                  70                  75                  80

Phe Lys Ile Val Val Ala Glu Thr Pro Ser Trp Ser Asn Thr Ala Ala
                85                  90                  95

Leu Asp Gln Asp Gly Ser Asp Ile Ser Tyr Ile Ser Val Val Asn Ile
            100                 105                 110

Gly Ser Asp Glu Lys Ser Met Tyr Met Leu Leu Asp Thr Gly Gly Ser
        115                 120                 125

Asp Thr Trp Val Phe Gly Ser Asn Cys Thr Ser Thr Pro Cys Thr Met
    130                 135                 140

His Asn Thr Phe Gly Ser Asp Asp Ser Ser Thr Leu Glu Met Thr Ser
145                 150                 155                 160

Glu Glu Trp Ser Val Gly Tyr Gly Thr Gly Ser Val Ser Gly Leu Leu
                165                 170                 175

Gly Lys Asp Lys Leu Thr Ile Ala Asn Val Thr Val Arg Met Thr Phe
            180                 185                 190

Gly Leu Ala Ser Asn Ala Ser Asp Asn Phe Glu Ser Tyr Pro Met Asp
        195                 200                 205

Gly Ile Leu Gly Leu Gly Arg Thr Asn Asp Ser Ser Tyr Asp Asn Pro
    210                 215                 220

Thr Phe Met Asp Ala Val Ala Glu Ser Asn Val Phe Lys Ser Asn Ile
225                 230                 235                 240

Val Gly Phe Ala Leu Ser Arg Ser Pro Ala Lys Asp Gly Thr Val Ser
                245                 250                 255

Phe Gly Thr Thr Asp Lys Asp Lys Tyr Thr Gly Asp Ile Thr Tyr Thr
            260                 265                 270

Asp Thr Val Gly Ser Asp Ser Tyr Trp Arg Ile Pro Val Asp Asp Val
        275                 280                 285

Tyr Val Gly Gly Thr Ser Cys Asp Phe Ser Asn Lys Ser Ala Ile Ile
    290                 295                 300

Asp Thr Gly Thr Ser Tyr Ala Met Leu Pro Ser Ser Asp Ser Lys Thr
305                 310                 315                 320

Leu His Ser Leu Ile Pro Gly Ala Lys Ser Ser Gly Ser Tyr His Ile
                325                 330                 335

Ile Pro Cys Asn Thr Thr Thr Lys Leu Gln Val Ala Phe Ser Gly Val
            340                 345                 350

Asn Tyr Thr Ile Ser Pro Lys Asp Tyr Val Gly Ala Thr Ser Gly Ser
        355                 360                 365

Gly Cys Val Ser Asn Ile Ile Ser Tyr Asp Leu Phe Gly Asp Asp Ile
```

```
                    370               375                 380
Trp Leu Leu Gly Asp Thr Phe Leu Lys Asn Val Tyr Ala Val Phe Asp
385                 390                 395                 400

Tyr Asp Glu Leu Arg Val Gly Phe Ala Glu Arg Ser Ser Asn Thr Thr
                405                 410                 415

Ser Ala Ser Asn Ser Thr Ser Ser Gly Thr Ser Thr Ser Thr Gly Ser
                420                 425                 430

Thr Thr Thr Gly Ser Ser Thr Ser Thr Thr Ser Ala Ser Ser Ser
            435                 440                 445

Ser Ser Ser Asp Ala Glu Ser Gly Ser Ser Met Thr Ile Pro Ala Pro
            450                 455                 460

Gln Tyr Phe Phe Ser Ala Leu Ala Ile Ala Ser Phe Met Leu Trp Leu
465                 470                 475                 480

<210> SEQ ID NO 23
<211> LENGTH: 3525
<212> TYPE: DNA
<213> ORGANISM: Aspergillus sp.

<400> SEQUENCE: 23
gtcgacttgg tcgttgtgca ccgactaaac atacagaagc acgtgcctgt ttctccctct      60
gacgggagcg acagtcatg gcagcattga acttggcttg gcgaagcaaa ctcccttttt    120
cttattctta ctacacaacg gctttctaaa gaagaatgga gaacatctca ttcttactga    180
gctatatttg aatagccgat tgaatgatca ccacgatgct gattggtgca ggctgccgtc    240
ccaagaacga actattatga tttcccgtct agatctaaag ggccctctgc agaatccggc    300
cggagtattt gcacacacac tcgagcttaa tgggaaggaa taaatggaca taaaaagcat    360
ttcagtctaa atggcaactg catactcggt ttaccggata gctgcgcgct atctttctgc    420
aggactgcag ttctgcactc gggcccattg ccgttcggac ccccgacgta ctccgcgaga    480
ccttgagaca tcggcgggac catccatcgt atcacagcca tccagcaagg ccgagtggag    540
gtgttcaggc tccattcatc acgatatcgg ctgattaatg cctcttatca ttagcgaatg    600
ccgaagcttg acctgatacg acttcaaggt atcgtcaccg acaatcgtta tcatcacgct    660
acaggcccgc agtttccgct tgaattcccg cattaggaaa tgagcatcac attcctcttc    720
ccacgaggtc tctttccgag ggcagccgct gcaacatcat tgggatcatg cttggttctc    780
ctctcccata gctgtccgcg agcttctcat tggtacctct tcgctacctc gttgcatcct    840
attcgcgcat ggccccgcca gagatgtttc tgcaaggtcc catcaccttg ccgcgttgct    900
attccccgcc ctcgagttcc cgacaagtta ctttgtgtca gtggctgaga agcctggttc    960
tgagagtgta ctcagacaat catatggttc cctccatgtg ctacgtcgtc ctagcgtcgc   1020
tgcactacat catcgttagg cagcatggaa ctggcacccg cacataaagc ccccgacacc   1080
cccatcgata ggctcggtgt tcgtgcacgc ctgtccactg gcccctcccc caaaggccct   1140
tcatcagtat gctgtttcgc agtctgttgt cgacggctgt cctagccgtc tcgctgtgca   1200
cggataatgc ttcagctgct aaacatggtc gatttggcca aaaagctcgc gacgccatga   1260
acatcgcgaa gcgttccgct aacgccgtga acactcgtt gaagatccct gtcgaggact   1320
atcagttctt gaacaacaag actaagcgta tgtatctcag ttcgatattg aacgatggct   1380
gatttgcttc cgtcggacag cttaccgcgt ggaaagcctg cctgatgttc acttcgatct   1440
gggcgagatg tattccggct tggtcccctat tgagaagggc aacgtgtcac ggtccctttt   1500 cttttgtcttc cagcccacta ttggcgagcc tgtggatgag atcaccatct ggctgaatgg   1560
```

```
tggccctggt tgcagttccc ttgaggcctt tctccaggag aatggtagat cgtgtggca    1620
gcctggaacc taccagcctg ttgagaaccc atactcgtgg gtgaatctca ccaatgttct    1680
gtggtaagtg tgatatactg gatcgctagt tgagtttaca tgggcggtat cgacctaacc    1740
tattttttgt agggttgacc aacctgtggg aacgggattc tctctgggtg tcccaaccgc    1800
tacgtccgag gaggagattg ctgaagactt tgtgaagttc ttcaagaact ggcagcagat    1860
ctttgggatc aaaaacttca agatctatgt tactggagaa agttatgcgg ccgttatgt     1920
tccttacata tccgctgctt tcctagatca gaatgataca gaacacttca acctaaaagg    1980
tgagttatac ttcaccaagt aatctttaac tagggcttgt actgattgta ctatctaggt    2040
gcactggcat atgatccctg tattggtcag tttgactacg tgcaggagga agcacctgtt    2100
gttcccttg tccagaagaa caatgccctc ttcaatttca atgcaagctt tttggcggaa     2160
ctagagagca tccatgagca atgtggatac aaggatttca tcgaccagta tctagtcttc    2220
ccagcatccg gtgtccagcc gccaaaggct atgaactgga gcgatcccac ctgtgatgtt    2280
tatgacatcg ttaataacgc cgtcctggat cccaacccgt gcttcaaccc ctacgaaatc    2340
aacgagatgt gccccattct ctgggacgtt cttggattcc ccaccgaagt cgactatctc    2400
cctgcgggcg ccagcatcta ctttgaccgc gctgatgtta agcgtgccat gcacgctcct    2460
aacatcacct ggtccgagtg ctcggtggag agcgtctttg tcggggcga cggcggtccc     2520
gagcaggagg gcgactactc ggccaacccc atcgagcatg tcttgcccca ggtcatcgaa    2580
ggcaccaacc gagttctgat cggtaacggt gattatgaca tggtcatcct taccaacggc    2640
acccttctct cgatccagaa catgacatgg aatggaaagc ttggattcga cacggccccc    2700
agcaccccca tcaacatcga catccctgac ctgatgtaca atgaagtgtt cattgagaac    2760
ggctatgacc acaaggtgg tcagggtgtc atgggcatcc agcactatga gcgtggtctt     2820
atgtgggctg agaccttcca gagcggacac atgcagcccc aattccaacc cagagtgtca    2880
taccgtcacc ttgagtggct gcttggccgg cgtgataccc tgtaaggtcg ggtaggctac    2940
cacgggggac gatgtcacga tgatagtcat aagttatgat ctgtagatac gttgtatgcg    3000
aatgtacatg aattgctttt actggcagtc tctaaagcaa aattcatagt agagtactgg    3060
cctacttacc ctcacttccc ctatcttttc aacctgaaga ccggaagaat tgtaactaac    3120
aagcataacg tagctgattt gaagcagagc ataacacact ctaccctcg gcacttctac     3180
ttatgacgct atttgactgc taactcgggt ttaatcctga agctgcagtc caatcgtaca    3240
ttaaactcaa tgtgccttgc ccaggaaacg atatttgact tatatgatct gaaaatgaac    3300
aattgtcccc gagagagaga gagagagcga gcggtaaata cttagcaagt cagtcacgca    3360
gtatctccac taatgccgta acacaggaaa tggacacgaa tggagcaagc gagtatatca    3420
gatacacctt tcctaacaat gcatgtctgt aagcaattgg cactaaagct agctagatag    3480
agaatctatt tacaatcaag atagtaagga tgatgccaac cagaa                    3525
```

<210> SEQ ID NO 24
<211> LENGTH: 531
<212> TYPE: PRT
<213> ORGANISM: Aspergillus sp.

<400> SEQUENCE: 24

Met Leu Phe Arg Ser Leu Leu Ser Thr Ala Val Leu Ala Val Ser Leu
1               5                   10                  15

Cys Thr Asp Asn Ala Ser Ala Ala Lys His Gly Arg Phe Gly Gln Lys
            20                  25                  30

-continued

```
Ala Arg Asp Ala Met Asn Ile Ala Lys Arg Ser Ala Asn Ala Val Lys
         35                  40                  45

His Ser Leu Lys Ile Pro Val Glu Asp Tyr Gln Phe Leu Asn Asn Lys
 50                  55                  60

Thr Lys Pro Tyr Arg Val Glu Ser Leu Pro Asp Val His Phe Asp Leu
 65                  70                  75                  80

Gly Glu Met Tyr Ser Gly Leu Val Pro Ile Glu Lys Gly Asn Val Ser
                 85                  90                  95

Arg Ser Leu Phe Phe Val Phe Gln Pro Thr Ile Gly Glu Pro Val Asp
                100                 105                 110

Glu Ile Thr Ile Trp Leu Asn Gly Gly Pro Gly Cys Ser Ser Leu Glu
        115                 120                 125

Ala Phe Leu Gln Glu Asn Gly Arg Phe Val Trp Gln Pro Gly Thr Tyr
    130                 135                 140

Gln Pro Val Glu Asn Pro Tyr Ser Trp Val Asn Leu Thr Asn Val Leu
145                 150                 155                 160

Trp Val Asp Gln Pro Val Gly Thr Gly Phe Ser Leu Gly Val Pro Thr
                165                 170                 175

Ala Thr Ser Glu Glu Glu Ile Ala Glu Asp Phe Val Lys Phe Phe Lys
            180                 185                 190

Asn Trp Gln Gln Ile Phe Gly Ile Lys Asn Phe Lys Ile Tyr Val Thr
    195                 200                 205

Gly Glu Ser Tyr Ala Gly Arg Tyr Val Pro Tyr Ile Ser Ala Ala Phe
210                 215                 220

Leu Asp Gln Asn Asp Thr Glu His Phe Asn Leu Lys Gly Ala Leu Ala
225                 230                 235                 240

Tyr Asp Pro Cys Ile Gly Gln Phe Asp Tyr Val Gln Glu Glu Ala Pro
                245                 250                 255

Val Val Pro Phe Val Gln Lys Asn Asn Ala Leu Phe Asn Phe Asn Ala
            260                 265                 270

Ser Phe Leu Ala Glu Leu Glu Ser Ile His Glu Gln Cys Gly Tyr Lys
    275                 280                 285

Asp Phe Ile Asp Gln Tyr Leu Val Phe Pro Ala Ser Gly Val Gln Pro
290                 295                 300

Pro Lys Ala Met Asn Trp Ser Asp Pro Thr Cys Asp Val Tyr Asp Ile
305                 310                 315                 320

Val Asn Asn Ala Val Leu Asp Pro Asn Pro Cys Phe Asn Pro Tyr Glu
                325                 330                 335

Ile Asn Glu Met Cys Pro Ile Leu Trp Asp Val Leu Gly Phe Pro Thr
            340                 345                 350

Glu Val Asp Tyr Leu Pro Ala Gly Ala Ser Ile Tyr Phe Asp Arg Ala
    355                 360                 365

Asp Val Lys Arg Ala Met His Ala Pro Asn Ile Thr Trp Ser Glu Cys
370                 375                 380

Ser Val Glu Ser Val Phe Val Gly Gly Asp Gly Pro Glu Gln Glu
385                 390                 395                 400

Gly Asp Tyr Ser Ala Asn Pro Ile Glu His Val Leu Pro Gln Val Ile
                405                 410                 415

Glu Gly Thr Asn Arg Val Leu Ile Gly Asn Gly Asp Tyr Asp Met Val
            420                 425                 430

Ile Leu Thr Asn Gly Thr Leu Leu Ser Ile Gln Asn Met Thr Trp Asn
    435                 440                 445

Gly Lys Leu Gly Phe Asp Thr Ala Pro Ser Thr Pro Ile Asn Ile Asp
450                 455                 460
```

```
Ile Pro Asp Leu Met Tyr Asn Glu Val Phe Ile Glu Asn Gly Tyr Asp
465                 470                 475                 480

Pro Gln Gly Gly Gln Gly Val Met Gly Ile Gln His Tyr Glu Arg Gly
            485                 490                 495

Leu Met Trp Ala Glu Thr Phe Gln Ser Gly His Met Gln Pro Gln Phe
        500                 505                 510

Gln Pro Arg Val Ser Tyr Arg His Leu Glu Trp Leu Leu Gly Arg Arg
    515                 520                 525

Asp Thr Leu
    530

<210> SEQ ID NO 25
<211> LENGTH: 3000
<212> TYPE: DNA
<213> ORGANISM: Aspergillus sp.

<400> SEQUENCE: 25
tgttgtgcct gcgccggtgc cgcttccctc ccctcctccc ctgccttttc gggcgacgcc      60
atccgcgcac taaccctcca cgtattccaa tataccaaat ctgcccaaag cgccagccag     120
cttcctcaag ccttgcggtc agataaggcc ctgtacctag ctagttgccg ctgctcccgg     180
cgctgggcca agccgtcgga cgtccgtccc cctctttttcc cctcctctc ccctctccac     240
tggtggaacg atgtctggct gttgccatcg ttctcagaag caacgcccc tggatcgggt     300
ggctgtcgta ctattgcatg ttcgtccgcg ctactaggaa agttttttttc ccacccggag     360
tatccgtgtt tagttcgcgg gctggctgac cggctagctg gccgtgccag ttgggtaagg     420
ttccaaggga ggaccttact aggtagaaac gggatccaac aatgagggga aaagggcgga     480
tatggcttgc cgggggttca ttgcggcctg acgaagaaa gggagatgat cactaatgca     540
acacaatctt ggcttgcaag gaattgcgct ccaaccagaa tgtctctgcg tagggatgcc     600
aattcgtgcg ggccatgctg gatggatagt acgctgctcc actctcgctc gaccttttgc     660
agtccacaat cgtttccccg tatcgttggg cgggggcgtt tttctgcagc tatggttgct     720
gctgccccga cggtgaacct ttctgcatcc ccggttttag tcgattttag ttggcgggcc     780
tggagattaa actccgtcgg acgaagagga gcagtggtgt catcgtcggc ggattgcatg     840
ctatcggaag agcatggaag agggaaaaca tcaacttcat ttgcaaaacg ctcgagcata     900
aatagaggcc tggattccgc cgttctggtg tcttttcttc ttcatccagc atcgcaagtc     960
tctcaagcat cgcctggttc gttcttctca ctcttccacc accagccttg tcaataagtt    1020
agctcttcat cttttcgaag aaaccaattc tccaaacgtc aaaatgaagt tctctaccat    1080
ccttaccggc tccctcttcg ccactgccgc tctggctgct cctctcactg agaagcgccg    1140
tgctcgcaag gaggcccgcg ccgctggcaa gcgccacagc aaccctccct acatccccgg    1200
ttccgacaag gagatcctca agctgaacgg cacctccaac gaggagtaca gctccaactg    1260
ggctggtgcc gtcctgatcg gcgacggcta caccaaggtc actggcgagt tcactgtccc    1320
cagtgtctct gctggatcta gcagctccag tggctacggc ggtggctacg gctactggaa    1380
gaacaagaga caatccgagg agtactgcgc ctccgcttgg gttggtatcg acggtgacac    1440
ctgcgagacc gctattctcc agactggtgt cgacttctgc tacgaggatg ccagacttc    1500
ctacgatgcc tggtatgagt ggtaccccga ctacgcctac gacttcagcg acatcaccat    1560
ctctgagggt gacagcatca aggtcactgt cgagtgccac cagcaagagc agcggtagcg    1620
ccaccgttga gaacctgacc actggccagt ccgtcaccca caccttcagc ggcaacgttg    1680
```

-continued

```
agggtgatct tgcgagacc aacgctgagt ggatcgttga ggacttcgag tccggtgact  1740
cccttgttg ctttcgctga cttcggctcc gttaccttca ccaatgctga ggccaccagc  1800
ggcggctcca ctgtcggccc tctgacgct accattatgg acattgagca ggatggcacc  1860
gtcctcaccg agacctccgt tctggcgac agcgtcactg tcacctacgt ctaaatgcat  1920
ctctatgcat gagatatcgg tcgcttcaat gtcttcgtct cgaagacaaa ccctggggat  1980
gaatgaaaaa atgagtgatg agctatccgg attgatctga tcttgttgag ttgttaattc  2040
tgtttctgtt gatgttttg aatgattgta cctacttta agtagaagaa atggatgagc  2100
gcgtgcatgc tgaaaatggc tgtccctgct tatattgtag aagatcttcc agaaagctgt  2160
gctgccgatc tgaagatctg aagatcacta gtgagatctc gcagctcggc tgtgtaagtg  2220
ctttcgctct gtcgatcata actttgtaaa agcttgtatg catagcggac atctatcgat  2280
tatttagatg cctcaaattg atctttacta gaattcccat ccgaatagag cttcagagcg  2340
tcgggtggaa atgtcgggcc gtggatggta tcggagaagt ctcaccacat gaacgaaaga  2400
cccgcggtat atggccagtg tagggaggaa gcgctgaaaa agactttccc tatagttcat  2460
aagaggcttt gcagttagtc agagcttcag gaatagaaat actagacggg ctggcttacc  2520
gttccccgat aatagtccgc gagccatagt gacatagaca tggtcaaaca ggaatcgagc  2580
acagcagata cctatgtaga agccctctcc atcagaattt gttccagaga agagaggag  2640
gtatttctca gattatttg aatgtacagg ggccatatga tggtcgtagc tcggttgcag  2700
tgatggatgt aggccataaa gtctcaagct gggggagac atgacgttgg aaggtacac   2760
gtgatccgta taggcagcag tagcgccata tctacttttg tagtatcaat gatagcagag  2820
aatttgggcg ctgcgtttaa ggttagcaga aggaacagct tatcaccttg gtaatcgtcg  2880
gtgtctctct ctctatcagg aacgcagatg ctctcaagtc ttcagccagg agtaatgcga  2940
catgttaccc ccgacaactg gatcactgct tgaagcgcat tgtgtacgaa gctataacga  3000
```

<210> SEQ ID NO 26
<211> LENGTH: 282
<212> TYPE: PRT
<213> ORGANISM: Aspergillus sp.

<400> SEQUENCE: 26

```
Met Lys Phe Ser Thr Ile Leu Thr Gly Ser Leu Phe Ala Thr Ala Ala
1               5                   10                  15

Leu Ala Ala Pro Leu Thr Glu Lys Arg Arg Ala Arg Lys Glu Ala Arg
            20                  25                  30

Ala Ala Gly Lys Arg His Ser Asn Pro Pro Tyr Ile Pro Gly Ser Asp
        35                  40                  45

Lys Glu Ile Leu Lys Leu Asn Gly Thr Thr Asn Glu Glu Tyr Ser Ser
    50                  55                  60

Asn Trp Ala Gly Ala Val Leu Ile Gly Asp Gly Tyr Thr Lys Val Thr
65                  70                  75                  80

Gly Glu Phe Thr Val Pro Ser Val Ser Ala Gly Ser Ser Gly Ser Ser
                85                  90                  95

Gly Tyr Gly Gly Gly Tyr Gly Tyr Trp Lys Asn Lys Arg Gln Ser Glu
            100                 105                 110

Glu Tyr Cys Ala Ser Ala Trp Val Gly Ile Asp Gly Asp Thr Cys Glu
        115                 120                 125

Thr Ala Ile Leu Gln Thr Gly Val Asp Phe Cys Tyr Glu Asp Gly Gln
    130                 135                 140

Thr Ser Tyr Asp Ala Trp Tyr Glu Trp Tyr Pro Asp Tyr Ala Tyr Asp
```

```
            145                 150                 155                 160
Phe Ser Asp Ile Thr Ile Ser Glu Gly Asp Ser Ile Lys Val Thr Val
                165                 170                 175

Glu Ala Thr Ser Lys Ser Ser Gly Ser Ala Thr Val Glu Asn Leu Thr
            180                 185                 190

Thr Gly Gln Ser Val Thr His Thr Phe Ser Gly Asn Val Glu Gly Asp
        195                 200                 205

Leu Cys Glu Thr Asn Ala Glu Trp Ile Val Glu Asp Phe Glu Ser Gly
    210                 215                 220

Asp Ser Leu Val Ala Phe Ala Asp Phe Gly Ser Val Thr Phe Thr Asn
225                 230                 235                 240

Ala Glu Ala Thr Ser Gly Gly Ser Thr Val Gly Pro Ser Asp Ala Thr
                245                 250                 255

Val Met Asp Ile Glu Gln Asp Gly Ser Val Leu Thr Glu Thr Ser Val
            260                 265                 270

Ser Gly Asp Ser Val Thr Val Thr Tyr Val
        275                 280

<210> SEQ ID NO 27
<211> LENGTH: 4980
<212> TYPE: DNA
<213> ORGANISM: Aspergillus sp.

<400> SEQUENCE: 27
ggatccatcc attcactcag ctttccttgt cggtggactg tcgagtctac cccaggtccc      60
agtttctccg accgcgctaa tcgggggcta tcgacaacca gtgattctgc tgtgtcatcc     120
gggcgtatgg cgtaaattac cgtatgccgg ttgcatcatc acctgctgcc cttgcctctt     180
gctgaatacc gtccgccatc catctgtcct cctctccctc tctcttcatc tccaacctcc     240
ccttcctcct ccctccctcc ttctcttcat ctttatcttg acctatttcc atctttctca     300
tctctcagtt gtttcaatct cttgtacacg ccctactcac tctccttttc accgggctgc     360
tgtgggttcc gtcttaagct atccatcatg aagggcatcc tcggcctttc cctcctcccg     420
ttgctgacgg ctgcgtcgcc cgtcttcgtt gactccatcc ataatgaagc tgccccccatc    480 ttgtctgcta ccaacgcgaa ggaggttccc gactcctaca tcgtcgtttt caagaagcac     540
gtcacttcag agctggcttc ggctcaccac agctgggtgc aggacatcca tgactctcag     600
agcgagcgga ctgagctgaa gaagcggtcg ctcttcggcc ttggggacga ggtctatctg     660
ggtctcaaga acacctttga cattgctggt tctctgatcg ttactctggt cacttccac     720 gaggatgtca tcgagcaagt ccgcagacac cccgatgtga gttacacccc ctatctaagc     780
atccctcgtt atctctaaga taagcttcta acatcggtca atgtaggtcg attacatcga     840
gcgggattcc gaagttcaca ccatggaagg ggccaccgaa agaacgcccc ttggggtctc    900
ggctcgtatc tctcaccgtg atagcctgac cttcggtaac ttcaacaagt acctgtatgc    960
ctccgagggg ggtgagggcg ttgacgccta caccattgac acgggtatca cgttgacca    1020 cgttgacttc gagggccgtg ccacttgggg caagacaatc cctaccaacg atgaagatct    1080
cgatggcaat ggtcacggaa ctcactgctc cggaaccatg gctggtaaga gtacggtgt    1140 tgccaagaag gccaacctct atgctgtcaa ggtcctccgg tcgagcggct ctggcaccat    1200
gtctgatgtc gtttctggtg tcgagtatgc cgtccaggct catatcaaga aggccaagga    1260
tgccaagaac ggcaaggtca agggattcaa gggcagcgtt gccaacatga gtctcggtgg    1320
tggcaagtct aagaccctcg aggatgctgt taacgctggt gttgaggctg gtcttcactt    1380
```

```
cgccgttgcc gccggtaatg acaatgctga tgcttgcaac tactctcctg ctgctgccga    1440
gaaggccatc accgttggtg cctcgacact tgctgacgag cgtgcgtact tctccaacta    1500
cggagagtgc actgacatct tcgctcctgg tctcaacatc ctgtccacct ggattggcag    1560
caactacgcc accaacatca tctctggcac ttccatggcc tctcctcaca ttgctggcct    1620
gctggcctac tttgtctccc tccagccctc ctcggactct gcattcgctg ttgaggagct    1680
tactcctgct aagctgaaga aggacatcat cgccatcgcc accgagggcg ctctcactga    1740
cattccctcc aacacccca ggatccatcc attcactcag ctttccttgt cggtggactg     1800
tcgagtctac cccaggtccc agtttctccg accgcgctaa tcgggggcta tcgacaacca    1860
gtgattctgc tgtgtcatcc gggcgtatgg cgtaaattac cgtatgccgg ttgcatcatc    1920
acctgctgcc cttgcctctt gctgaatacc gtccgccatc catctgtcct cctctccctc    1980
tctcttcatc tccaacctcc ccttcctcct ccctccctcc ttctcttcat ctttatcttg    2040
acctatttcc atctttctca tctctcagtt gtttcaatct cttgtacacg ccctactcac    2100
tctccttttc accgggctgc tgtgggttcc gtcttaagct atccatcatg aagggcatcc    2160
tcggcctttc cctcctcccg ttgctgacgg ctgcgtcgcc cgtcttcgtt gactccatcc    2220
ataatgaagc tgccccccatc ttgtctgcta ccaacgcgaa ggaggttccc gactcctaca   2280
tcgtcgtttt caagaagcac gtcacttcag agctggcttc ggctcaccac agctgggtgc    2340
aggacatcca tgactctcag agcgagcgga ctgagctgaa gaagcggtcg ctcttcggcc    2400
ttggggacga ggtctatctg ggtctcaaga acacctttga cattgctggt tctctgatcg    2460
gttactctgg tcacttccac gaggatgtca tcgagcaagt ccgcagacac cccgatgtga    2520
gttacacccc ctatctaagc atccctcgtt atctctaaga taagcttcta acatcggtca    2580
atgtaggtcg attacatcga gcgggattcc gaagttcaca ccatggaagg ggccaccgaa    2640
aagaacgccc cttggggtct ggctcgtatc tctcaccgtg atagcctgac cttcggtaac    2700
ttcaacaagt acctgtatgc ctccgagggg ggtgagggcc ttgacgccta caccattgac    2760
acgggtatca acgttgacca cgttgacttc gagggccgtg ccacttgggg caagacaatc    2820
cctaccaacg atgaagatct cgatggcaat ggtcacggaa ctcactgctc cggaaccatg    2880
gctggtaaga agtacggtgt tgccaagaag gccaacctct atgctgtcaa ggtcctccgg    2940
tcgagcggct ctggcaccat gtctgatgtc gtttctggtg tcgagtatgc cgtccaggct    3000
catatcaaga aggccaagga tgccaagaac ggcaaggtca agggattcaa gggcagcgtt    3060
gccaacatga gtctcggtgg tggcaagtct aagaccctcg aggatgctgt taacgctggt    3120
gttgaggctg gtcttcactt cgccgttgcc gccggtaatg acaatgctga tgcttgcaac    3180
tactctcctg ctgctgccga gaaggccatc accgttggtg cctcgacact tgctgacgag    3240
cgtgcgtact tctccaacta cggagagtgc actgacatct tcgctcctgg tctcaacatc    3300
ctgtccacct ggattggcag caactacgcc accaacatca tctctggcac ttccatggcc    3360
tctcctcaca ttgctggcct gctggcctac tttgtctccc tccagccctc ctcggactct    3420
gcattcgctg ttgaggagct tactcctgct aagctgaaga aggacatcat cgccatcgcc    3480
accgagggcg ctctcactga cattccctcc aacacccca acgtaagtca tgccgctgtt     3540
ggtatttata agagaaacga gctaactcag aaattcagct ccttgcctgg aacggtggtg    3600
gttccgagaa ctacaccgac atcgttggca gcggtggcta caaggtctcc tctgccaaga    3660
accgcatcga ggaccgtatt gagggtctcg ttcacaaggc cgaagagctg ctcaccgagg    3720
agcttggtgc catctacagc gagatccagg atgccgtcgt cgcatagatc agaactcgtg    3780
```

-continued

```
ctttccagac gtagatcgga agacttggtt ttttttgag gtatgggatg gttgatcgga     3840
cattttggcg ctggtctctt tttattgtgt ttggtctcga agacgctgat gcattgactg     3900
tatcggctgt atcactccgc ccctgcttat ctgtttggtt catctttatg gtagtataca     3960
tgtctgcaaa gaaggttttg ttacctcact tagaatgttc tggttctata acagactgac     4020
aatctcactg ggttatctaa gagatctgac aaacgcttgg tagaagagaa aggtgaggga     4080
gtagacatca tcagtctaaa tccacattac gacatgccgt aatagatgag agcaccggat     4140
gctagccttt gtagactaca aaggagaaaa ccctaggaa aggtaatttc taagtcatgc      4200
ccacctattc tctctatctc ttactgagac agtcaatccc atgacgaaca actaatgaca     4260
tcatgggtca cgctacgggg tcatgccgaa acgaagccga agtactactc ctaagtaaag     4320
ccacaacttt gcatacgttc attcaggaaa cggaaacaca ggaggaagaa tattgaaata     4380
tcttgagggg cttcatatag aatagacaga tatataatag ttgtcaaagt atacaaaaag     4440
acctcatgca tgctaacaga taaagcaaag gatctctatat tgatagactg tgctgtatac     4500
cacctcttaa tgcagcgcct gcgctatgcc acgatgaaat ataaggggg aaaaagtcat      4560
gtaagtagta agtagaaact ccaagcgcca aatatataga tagtaatagg ggtggcgaca     4620
taatttggct tttatacttg ataggttgaa caaatcaagt ggccctgtgc tcgtcttcct     4680
cctcatcact gccggaatct tggtcttcgt catcgtcatc gacgtcaagg tcctcgtcgg     4740
agtcgctacc gccgaagacg tcgtcgtcca catcgctctc ggcccagaag tcggagtcgt     4800
ccttctccac aggtttggag actgtcgtgg tggattcgtg agtcggcatg acgaatccct     4860
cgggaatatc gttcttcgaa tcctccacgt gctgtttcac gatcgatttg tattcgtcgg     4920
ggctcttgcg caacatgacc gaggcgtcaa cgttggcggg ggaagagatc cggggaattc    4980
```

<210> SEQ ID NO 28
<211> LENGTH: 533
<212> TYPE: PRT
<213> ORGANISM: Aspergillus sp.

<400> SEQUENCE: 28

```
Met Lys Gly Ile Leu Gly Leu Ser Leu Leu Pro Leu Leu Thr Ala Ala
1               5                   10                  15

Ser Pro Val Phe Val Asp Ser Ile His Asn Glu Ala Ala Pro Ile Leu
            20                  25                  30

Ser Ala Thr Asn Ala Lys Glu Val Pro Asp Ser Tyr Ile Val Val Phe
        35                  40                  45

Lys Lys His Val Thr Ser Glu Leu Ala Ser Ala His His Ser Trp Val
    50                  55                  60

Gln Asp Ile His Asp Ser Gln Ser Glu Arg Thr Glu Leu Lys Lys Arg
65                  70                  75                  80

Ser Leu Phe Gly Leu Gly Asp Glu Val Tyr Leu Gly Leu Lys Asn Thr
                85                  90                  95

Phe Asp Ile Ala Gly Ser Leu Ile Gly Tyr Ser Gly His Phe His Glu
            100                 105                 110

Asp Val Ile Glu Gln Val Arg Arg His Pro Asp Val Asp Tyr Ile Glu
        115                 120                 125

Arg Asp Ser Glu Val His Thr Met Glu Gly Ala Thr Glu Lys Asn Ala
    130                 135                 140

Pro Trp Gly Leu Ala Arg Ile Ser His Arg Asp Ser Leu Thr Phe Gly
145                 150                 155                 160

Asn Phe Asn Lys Tyr Leu Tyr Ala Ser Glu Gly Gly Glu Gly Val Asp
                165                 170                 175
```

Ala Tyr Thr Ile Asp Thr Gly Ile Asn Val Asp His Val Asp Phe Glu
            180                 185                 190

Gly Arg Ala Thr Trp Gly Lys Thr Ile Pro Thr Asn Asp Glu Asp Leu
        195                 200                 205

Asp Gly Asn Gly His Gly Thr His Cys Ser Gly Thr Met Ala Gly Lys
    210                 215                 220

Lys Tyr Gly Val Ala Lys Ala Asn Leu Tyr Ala Val Lys Val Leu
225                 230                 235                 240

Arg Ser Ser Gly Ser Gly Thr Met Ser Asp Val Val Ser Gly Val Glu
                245                 250                 255

Tyr Ala Val Gln Ala His Ile Lys Lys Ala Lys Asp Ala Lys Asn Gly
            260                 265                 270

Lys Val Lys Gly Phe Lys Gly Ser Val Ala Asn Met Ser Leu Gly Gly
        275                 280                 285

Gly Lys Ser Lys Thr Leu Glu Asp Ala Val Asn Ala Gly Val Glu Ala
    290                 295                 300

Gly Leu His Phe Ala Val Ala Ala Gly Asn Asp Asn Ala Asp Ala Cys
305                 310                 315                 320

Asn Tyr Ser Pro Ala Ala Ala Glu Lys Ala Ile Thr Val Gly Ala Ser
                325                 330                 335

Thr Leu Ala Asp Glu Arg Ala Tyr Phe Ser Asn Tyr Gly Glu Cys Thr
            340                 345                 350

Asp Ile Phe Ala Pro Gly Leu Asn Ile Leu Ser Thr Trp Ile Gly Ser
        355                 360                 365

Asn Tyr Ala Thr Asn Ile Ile Ser Gly Thr Ser Met Ala Ser Pro His
    370                 375                 380

Ile Ala Gly Leu Leu Ala Tyr Phe Val Ser Leu Gln Pro Ser Ser Asp
385                 390                 395                 400

Ser Ala Phe Ala Val Glu Glu Leu Thr Pro Ala Lys Leu Lys Lys Asp
                405                 410                 415

Ile Ile Ala Ile Ala Thr Glu Gly Ala Leu Thr Asp Ile Pro Ser Asn
            420                 425                 430

Thr Pro Asn Val Ser His Ala Ala Val Gly Ile Tyr Lys Arg Asn Glu
        435                 440                 445

Leu Thr Gln Lys Phe Ser Ser Leu Pro Gly Thr Val Val Pro Arg
    450                 455                 460

Thr Thr Pro Thr Ser Leu Ala Ala Val Ala Thr Arg Ser Pro Leu Pro
465                 470                 475                 480

Arg Thr Ala Ser Arg Thr Val Leu Arg Val Ser Phe Thr Arg Pro Lys
                485                 490                 495

Ser Cys Ser Pro Arg Ser Leu Val Pro Ser Thr Ala Arg Ser Arg Met
            500                 505                 510

Pro Ser Ser His Arg Ser Glu Leu Val Leu Ser Arg Arg Arg Ser Glu
        515                 520                 525

Asp Leu Val Phe Phe
    530

<210> SEQ ID NO 29
<211> LENGTH: 2993
<212> TYPE: DNA
<213> ORGANISM: Aspergillus sp.

<400> SEQUENCE: 29
aagcttcgta tataattccc ttttgacaat gtcaaaatct tttggaccac taatatagct        60

```
gcatggaccg gttaatcaga ggttatttt gtgctcgaat gccgtgtaac attggataat    120
agtacactcc tttcacccac cctcagatgc ccgcccccta cagtagggtt gtcaatatcc    180
ctcacctttc caattgctga tgcagaatgg acctgatata gaagcctcac agcaccagag    240
actaccgcct gaagatgcca agtattgatg ggttacattg ctggcgaat agactgttca     300 ccatcccccg cctgtacaag gctcattgag cgacctttat ttctatgaag gcttcttgca    360
gtgtagagcc gctgtttaga actcggaaat aggcgtgcat agtatgaact caatcagcag    420
agtcaatcga ttgacactaa cgcctagcaa gcaatcagtg ctcagaggaa gctaacagat    480
ggctggttaa gctgccccag aaacgaaatg tgtccgcaat cccatccctg catgcttatc    540
tgtattctgt gcatgcatga tgcttcctc acggggcatt acccagtagt ccgaagacgc     600
aatgtgacca tctgactgag ttttaaatat actgtccaag tgccttctga cccggtcccc    660
gcttgatgac aatcaacaaa aggtgaatgt gactgaaagg cgtggtccag acaacaggcc    720
ttagacttta ttgtgagact ataaaaggat ctaactattg cactactgaa attaagcatt    780
ctagtctacc attgacattt ctccccttc ggtgggccac tcgctcaaca tggctttcct    840
caaacgcatt ctcccgctgc tggccctcat cttgcctgca gttttcagtg ccacagaaca    900
ggtccctcat ccgaccatcc agaccatccc ggggaagtac attgttactt tcaagtccgg    960
cattgacaat gcgaaaattg agtctcatgc cgcatgggta acggagctcc acaggcgcag    1020
cttagaaggc cgcagtacaa ccgaagatga ccttcccgcc gggatcgaga gaacttacag    1080
aattgccaat tttgctgggt acgcggggtc tttcgatgag aaaactatcg aggagatccg    1140
caaacataac catgtttgtg tccacgtatc ccaggccgta tggtttcgac taactgctgt    1200
acaggtagcc tatgtggaac aagatcaggt ctggtacctc gatacgctag ttaccgaaag    1260
acgagctcct tggggactgg ggagcatctc tcaccgtggt gcgtctagca ccgactacat    1320
ctatgatgac agcgctgggg agggtacata cgcttatgta gtggacactg gcatcttggc    1380
tacgcataat gagtttggtg gtcgtgctag cctggcatac aatgctgcag ggggtgagca    1440
cgttgatggt gttggacatg gcacacatgt agcagggacc atcggtggca aaacatacgg    1500
ggtttcgaaa aatgctcacc tactgtccgt gaaggtgttt gtaggtgaat ccagctcgac    1560
atcggtcatt ctggatggct tcaattgggc tgccaatgat atcgtgagca agaaccggac    1620
cagtaaggcg gcgattaaca tgagtcttgg tatgtgcgcc ctctctgggg atctaatgcc    1680
gttaaccgtg atgcaggtgg aggctactcc tatgcgttta acaatgcagt tgagaatgct    1740
tttgacgagg gtgtgctctc ttgtgttgcc gctggaaatg agaatgtaag ctctgctgaa    1800
ctgtccacca ttgagctaaa tttagactaa tgttttgcag agagatgcag cacggactag    1860
cccggcttct gcaccgacg ccattactgt tgccgctatc aacagaagca atgcccgtgc     1920
gtcattctca aactacggct ctgtggttga cattttgcc ccgggagagc aagtactttc     1980
tgcatggacc ggctcgaact cggccaccaa cacgatctcc ggcacgtcca tggctacacc    2040
tcatgtgaca ggtttgatcc tctatttgat gggcttgcgg gaccttgcta ccccagcggc    2100
tgcaacgacc gagctcaaga ggttggctac gcggaatgct gtcaccaatg tggcgggtag    2160
ccccaatctt ctggcctaca atggaaacag cggcgtgtca aaaggggta gcgatgatgg     2220 agatgaggac taggtgcgta acatgagtga atatggctta gaatagtggg gatcggagag    2280
tagactagtt tatatgcgaa ataaagtgtg tatcagcacc ctggcctgtt catgtaagtc    2340
ggcattttca cttttgccga caccgcaaat atgctgtgct tgaggctgtt gcctccccag    2400
ccagccttcc cgagactgaa actcacacat ccattggatg tataaagttc tgcacatgcg    2460
```

```
aaatgccgct gccgcttacc tcccgacgtg gtaccggacc gaaggcagac acagatcatg    2520
gaccgctata ccgcacagac aacttgtgct ccttactgaa agtaccattc cacaggtcat    2580
tgcagcatga tgagtgatga tgtacttctc cccatcaaga accactgacg gtggttggaa    2640
tgaatctaga tcaaagagat caaccgcttc cccagacaga tcaggcctat gcccataatg    2700
aaccggtgac tgtgtaaccc tgttacaatc cgtttgttat tggtcctttc tgtttgctgg    2760
atggcgtgta ctacctcaga gcttgtgctc ctaggagctc atactggaga caggttcttg    2820
tatatagtca tagcctaagt ccggtgtcta ggaaacagta tgctcgaggt ctttccgat     2880 tctcacaatg agaactgtcg cccgggtctt tacggcccct gtggaaagcg aaaaggagac    2940
gcttctggcg ctgcttccgc aatacgggct caaactagcc ccggacggga tcc           2993
```

<210> SEQ ID NO 30
<211> LENGTH: 416
<212> TYPE: PRT
<213> ORGANISM: Aspergillus sp.

<400> SEQUENCE: 30

```
Met Ala Phe Leu Lys Arg Ile Leu Pro Leu Leu Ala Leu Ile Leu Pro
1               5                   10                  15

Ala Val Phe Ser Ala Thr Glu Gln Val Pro His Pro Thr Ile Gln Thr
            20                  25                  30

Ile Pro Gly Lys Tyr Ile Val Thr Phe Lys Ser Gly Ile Asp Asn Ala
        35                  40                  45

Lys Ile Glu Ser His Ala Ala Trp Val Thr Glu Leu His Arg Arg Ser
    50                  55                  60

Leu Glu Gly Arg Ser Thr Thr Glu Asp Asp Leu Pro Ala Gly Ile Glu
65                  70                  75                  80

Arg Thr Tyr Arg Ile Ala Asn Phe Ala Gly Tyr Ala Gly Ser Phe Asp
                85                  90                  95

Glu Lys Thr Ile Glu Glu Ile Arg Lys His Asn His Val Ala Tyr Val
            100                 105                 110

Glu Gln Asp Gln Val Trp Tyr Leu Asp Thr Leu Val Thr Glu Arg Arg
        115                 120                 125

Ala Pro Trp Gly Leu Gly Ser Ile Ser His Arg Gly Ala Ser Ser Thr
    130                 135                 140

Asp Tyr Ile Tyr Asp Asp Ser Ala Gly Glu Gly Thr Tyr Ala Tyr Val
145                 150                 155                 160

Val Asp Thr Gly Ile Leu Ala Thr His Asn Glu Phe Gly Gly Arg Ala
                165                 170                 175

Ser Leu Ala Tyr Asn Ala Ala Gly Gly Glu His Val Asp Gly Val Gly
            180                 185                 190

His Gly Thr His Val Ala Gly Thr Ile Gly Gly Lys Thr Tyr Gly Val
        195                 200                 205

Ser Lys Asn Ala His Leu Leu Ser Val Lys Val Phe Val Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Asn Arg Thr Ser Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Cys Val Ala Ala Gly Asn Glu Asn Arg Asp
        275                 280                 285
```

```
Ala Ala Arg Thr Ser Pro Ala Ser Ala Pro Asp Ala Ile Thr Val Ala
    290                 295                 300

Ala Ile Asn Arg Ser Asn Ala Arg Ala Ser Phe Ser Asn Tyr Gly Ser
305                 310                 315                 320

Val Val Asp Ile Phe Ala Pro Gly Glu Gln Val Leu Ser Ala Trp Thr
                325                 330                 335

Gly Ser Asn Ser Ala Thr Asn Thr Ile Ser Gly Thr Ser Met Ala Thr
                340                 345                 350

Pro His Val Thr Gly Leu Ile Leu Tyr Leu Met Gly Leu Arg Asp Leu
        355                 360                 365

Ala Thr Pro Ala Ala Ala Thr Thr Glu Leu Lys Arg Leu Ala Thr Arg
    370                 375                 380

Asn Ala Val Thr Asn Val Ala Gly Ser Pro Asn Leu Leu Ala Tyr Asn
385                 390                 395                 400

Gly Asn Ser Gly Val Ser Lys Gly Gly Ser Asp Asp Gly Asp Glu Asp
                405                 410                 415

<210> SEQ ID NO 31
<211> LENGTH: 4531
<212> TYPE: DNA
<213> ORGANISM: Aspergillus sp.
<220> FEATURE:
<221> NAME/KEY: misc_feature
<222> LOCATION: (4474)..(4474)
<223> OTHER INFORMATION: n is a, c, g, or t
<220> FEATURE:
<221> NAME/KEY: misc_feature
<222> LOCATION: (4478)..(4478)
<223> OTHER INFORMATION: n is a, c, g, or t
<220> FEATURE:
<221> NAME/KEY: misc_feature
<222> LOCATION: (4522)..(4522)
<223> OTHER INFORMATION: n is a, c, g, or t

<400> SEQUENCE: 31
gctacggacc aaccccacca catcaaccta catgactcac gaagccgagg acgagctcct      60
ccgctccgca ttgcacaagt tcaccaacgt ggatggcacc aacggccgta ctgtcctgcc     120
cttcccgcat gacatgttct atgttcctga gttcaggaag tatgatgaga tgtcatactc     180
ggagcggatt gatcaaatcc gggatgagtt gagccttaat gaacggagtt ctctggaagc     240
gtttatattg ctttgctctg gcggaacgct ggagaatagc tcatttggag aattcctgca     300
ttggtgggcg atgagcggat atacgtatca gggatgcatg gactgcttga taagttataa     360
gttcaaggat gggcagtctg catttgcgag gaggttttgg gaggaggcgg ccgggacggg     420
gaggttgggg tatgtgtttg ggtgtccggt taggagtgtt gttaatgaga gagatgcggt     480
gagagtgacg gcgagggatg ggaggagtt cgttgcgaag cgggtggttt gcactattcc     540
cctcaatgtc ttgtccacga tccagttctc acctgcgctg tcgacggaga ggatctctgc     600
tatgcaggca ggtcatgtga atatgtgcac gaaggtgcat gccgaagtgg acaataagga     660
tatgcggtcg tggacgggca ttgcgtaccc tttcaataaa ctgtgctatg ctattggtga     720
tgggacgact cccgcgggaa acacgcatct ggtgtgtttc gggacggatg cgaatcatat     780
ccagccggat gaggacgtgc gggagacgtt gaaggcggtt gggcagttag cgcctgggac     840
atttggagtg aagcggttgg tgtttcacaa ttgggtgaag gatgagtttg cgaagggcgc     900
gtggttcttc tctaggcctg ggatggtgag tgagtgtttg caggggttga gggagaagca     960
tgggggtgtg gtgtttgcga attcagattg ggcgttgggg tggaggagct ttattgatgg    1020
ggcgattgag gaggggacga gagctgctag ggtggtgttg gaggaattgg gaacgaagag    1080
```

```
ggaggtgaag gctcgtttgt gattgattaa agccattaag gggtattgat tgtgaacatg    1140
aatttcatac tacattcaac ataactatac atgtgaataa tggggacata tccagtctat    1200
atctagtagg tgtcgttgga ggtgtagttc tcgcgagcag cgaatctcag ctccgtggcg    1260
ccaatgtcga acacagtgac gacattcttc tggaaggtgt cgcccagaat gtagagatct    1320
tcggaggtgt cgctaccacc gtcaacgata ccggaaatgc agatggtgtt gccctcgtcg    1380
tcggtgccag catcgaggat catgtcgagg gggttgatgt agaaggtctt tccgctgatg    1440
gtgatgccgt gagtgggagg ggtggcgtcg cagtctacaa tgtaggcgcc ctcctcgtcc    1500
gagtaagtcg ccgcagggga gaaagcggcg ttgatctcct cagcgatgga agttgggtag    1560
tagttcaggg tggtgcccga atcgacctgc atctgttaga caccatcagg taaaggggtg    1620
ctggagtcaa cgtacgatgt actggatgtc gtcgccacca cgctggtca agctcttgcc    1680 gttcagagtg acagcgtcaa tgttgatggt gtagaagtcg taggccttgg agtagccttc    1740
gatgttggtg accaggattg aggttttggt gaagtcttcc acgaagtcca caggaggcag    1800
accgccgaga gccagatagc cagcggcacc ggaaacatcg cgctcaatgg ccagactaaa    1860
cagaggttcg atcaggccct cctcccacat ggtggtaatg atattgctgt agacaatctg    1920
ctcgtcggtg gttgtggagt aggcgctcgt actgatacat gttagaagcc tgactatcag    1980 taattgggc agaatacata cagggcaggg tacgcaagac cagtcaggcc agaggtggtt    2040
ccgtcgccct cccaggcggc ctcagtgacc actccgatgg tttgatccac agtgatatcg    2100
gcaagagcga cggtttcgtt acccatcact ccgtagaggt actcaccatc accatactcg    2160
atggcgaatt cttcgccctc aatttccttg aaagagctct cgacagtcca ggtggagcca    2220
aagtcgcagc tcgactcgga ggtttcgcgg ccggtgtcga ggtcaataca tgtgaagccc    2280
gtcttaacga cccaggtatc actggaaccg gtgtcgacga taacgtcaaa gaatcacca    2340 ccgatggtga ttgaggtagc gaactcctcg ccttcgaaga gggagatcaa gctggagctg    2400
ccactgctgg tggagcgctt cacgtaggca gcactacgag ggttcacatt tcccttggac    2460
ttggtcttgc tcagctcgag gtacttggag gaggccttgt tgtgactggg agcagcgaag    2520
gcggcgggct tgtagacggt gtggctgccg cttctgcgga cgatatttct tcccttgagc    2580
ggggagggag tgggtgcagc cagagcagcc ccggcaagga gcgaggcagt ggcaagggta    2640
ccgacgggga tatacatggc ggcagctgag tgagaagtga tctaagtgat tgcttgactg    2700
acaggagaga agcctcgtgc agaagagggg tgcgttcggg agattatata gtgttgggaa    2760
attacatccg gtagtcggac aagaccacca atctagctac aattaaacat acaggaatga    2820
gagacattcg ctggattgca gaatctcgct gttgtcgact agcatagctc gcagcttccg    2880
aagtggcggt tagcaatgac gcgatgcgag tggttgaaaa gacaaggcgg accggtatag    2940
tgctgcctga tagtgacgag acatggcctc ccactcgatg gctaggaaca atagcgccgt    3000
gtgggcccgg caccgatatt gctgataggg agcgttgcgt cagcgctggt cctggattgg    3060
tgcgaagcca ggcccacaga agataagacg caaggtgcgc gtcggagtcc gcaggggagg    3120
ggtcgaaggt tgaagactga acagatgata gattggaata tattgggca gccagaaatt    3180 gcttcatgcg ctcgatgtga tcattgttgc gcttttcctt ccctgtaata gagtaaccga    3240
gccttgaata attgtatcgg gcaccatctc ggggataacc ctgaaggcat tagcgcccgg    3300
cgaaatgtcg acgagtgcag cacacggaga ctgtcatccg acaaggccat tgtgacgaat    3360
ctgaggcaca cacagttccc cttcatttga taacgaccaa taattgccat cgtaagaatg    3420
gcaatagagc aatccctcgt tgagacatgt atcagctgct tttcgtccga gacgcccctc    3480
```

```
tgttagacgt tgacaagcgt gctataacct tgaaacccac atctgactcc tgacaggccc    3540
atgactgggt ccaaggtagg ccaagcatcg gagacaaccg agaggggag atggtttcat      3600 gcttgatgct gtcaagctca gatcggcgga ttatcggagt agctgtcaga tcacgtggtg    3660
gggcatagat agcagccctg tgttgctggt atgtgacatt ttagtagccc atcactaaac    3720
aggcacatac cgcagacttg ttaattaact ctgcgataag ggacgtcctt cttagtccct    3780
gaagtgtata gtaacgacgg agatgccgtg aagaaagaac gctgagaggc aaacacgtgc    3840
ggggaacctc ggaagagaaa gacccgcacc gccccgggca gccatcggac atccgcggat    3900
ttcatttcag cgtccttgga gtttccacaa cactcttcat atcagcccac tatcggatag    3960
cgccatcagt agctaatatc cgcgcatact tgcatggctt ttatgccttg atggtcgccg    4020
agcgggtccc catgggtcgc gacggactcc ggtagtaatc cccagtcgcg aggtatgccc    4080
agttttcgtc gcacacccgc aggtcatggc taacgtcttc tcgcgtccca ggatgctttc    4140
aatgctcaaa cgccggatt gtctgcgaca gaggggaacc tacctgcttc aagtgtcaga    4200
agaaagggat tgaatgctcg ggatccggtc gctttcgctt cagccccggc ctagcgagtc    4260
ggggaaaact caaaggctgc acgattccga tacctgatgt cgacccgaga tcggtataca    4320
aagaaggctt agatggccct cgtccgattc ggtggaagga tgacctgaat agagtcaaca    4380
aaaccagaag cccagactta gcgggaagga gcgggtagtc cggaatggac tggtcacaga    4440
gaggggttcg gccagtggag gcagagcttc gcanccanat cgatatctat cgcaaaccag    4500
acgtatccta gctcagacaa tngttccgcg a                                  4531
```

<210> SEQ ID NO 32
<211> LENGTH: 453
<212> TYPE: PRT
<213> ORGANISM: Aspergillus sp.

<400> SEQUENCE: 32

```
Met Tyr Ile Pro Val Gly Thr Leu Ala Thr Ala Ser Leu Leu Ala Gly
1               5                   10                  15

Ala Ala Leu Ala Ala Pro Thr Pro Ser Pro Leu Lys Gly Arg Asn Ile
                20                  25                  30

Val Arg Arg Ser Gly Ser His Thr Val Tyr Lys Pro Ala Ala Phe Ala
            35                  40                  45

Ala Pro Ser His Asn Lys Ala Ser Ser Lys Tyr Leu Glu Leu Ser Lys
        50                  55                  60

Thr Lys Ser Lys Gly Asn Val Asn Pro Arg Ser Ala Ala Tyr Val Lys
65                  70                  75                  80

Arg Ser Thr Ser Ser Gly Ser Ser Ser Leu Ile Ser Leu Phe Glu Gly
                85                  90                  95

Glu Glu Phe Ala Thr Ser Ile Thr Ile Gly Gly Asp Ser Phe Asp Val
                100                 105                 110

Ile Val Asp Thr Gly Ser Ser Asp Thr Trp Val Lys Thr Gly Phe
            115                 120                 125

Thr Cys Ile Asp Leu Asp Thr Gly Arg Glu Thr Ser Glu Ser Ser Cys
        130                 135                 140

Asp Phe Gly Ser Thr Trp Thr Val Glu Ser Ser Phe Lys Glu Ile Glu
145                 150                 155                 160

Gly Glu Glu Phe Ala Ile Glu Tyr Gly Asp Gly Glu Tyr Leu Tyr Gly
                165                 170                 175

Val Met Gly Asn Glu Thr Val Ala Leu Ala Asp Ile Thr Val Asp Gln
                180                 185                 190
```

```
Thr Ile Gly Val Val Thr Glu Ala Ala Trp Glu Gly Asp Gly Thr Thr
        195                 200                 205
Ser Gly Leu Thr Gly Leu Ala Tyr Pro Ala Leu Thr Ser Ala Tyr Ser
    210                 215                 220
Thr Thr Thr Asp Glu Gln Ile Val Tyr Ser Asn Ile Ile Thr Met
225                 230                 235                 240
Trp Glu Glu Gly Leu Ile Glu Pro Leu Phe Ser Leu Ala Ile Glu Arg
                245                 250                 255
Asp Val Ser Gly Ala Ala Gly Tyr Leu Ala Leu Gly Gly Leu Pro Pro
            260                 265                 270
Val Asp Phe Val Glu Asp Phe Thr Lys Thr Ser Ile Leu Val Thr Asn
        275                 280                 285
Ile Glu Gly Tyr Ser Lys Ala Tyr Asp Phe Tyr Thr Ile Asn Ile Asp
    290                 295                 300
Ala Val Thr Leu Asn Gly Lys Ser Leu Thr Ser Ala Gly Gly Asp Asp
305                 310                 315                 320
Ile Gln Tyr Ile Met Gln Val Asp Ser Gly Thr Thr Leu Asn Tyr Tyr
                325                 330                 335
Pro Thr Ser Ile Ala Glu Glu Ile Asn Ala Ala Phe Ser Pro Ala Ala
            340                 345                 350
Thr Tyr Ser Asp Glu Glu Gly Ala Tyr Ile Val Asp Cys Asp Ala Thr
        355                 360                 365
Pro Pro Thr His Gly Ile Thr Ile Ser Gly Lys Thr Phe Tyr Ile Asn
    370                 375                 380
Pro Leu Asp Met Ile Leu Asp Ala Gly Thr Asp Glu Gly Asn Thr
385                 390                 395                 400
Ile Cys Ile Ser Gly Ile Val Asp Gly Gly Ser Asp Thr Ser Glu Asp
                405                 410                 415
Leu Tyr Ile Leu Gly Asp Thr Phe Gln Lys Asn Val Val Thr Val Phe
            420                 425                 430
Asp Ile Gly Ala Thr Glu Leu Arg Phe Ala Ala Arg Glu Asn Tyr Thr
        435                 440                 445
Ser Asn Asp Thr Tyr
    450
```

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
tagttaactc gtcgtctcct ggcggc                26

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
aggtcgacga agtataggaa ggttgtgaac ag          32

<210> SEQ ID NO 35
<211> LENGTH: 29
<212> TYPE: DNA
<213> ORGANISM: Artificial Sequence

```
<220> FEATURE:
<223> OTHER INFORMATION: primer

<400> SEQUENCE: 35
agggatccac gtctggtact tcttcaacg                              29

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
tctcgcgatt ggatcaaacc atacgatac                              29

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
gagggcaaag gaatagagta g                                      21

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
ctcaggcaga gaagtattgt c                                      21

<210> SEQ ID NO 39
<211> LENGTH: 32
<212> TYPE: DNA
<213> ORGANISM: Artificial Sequence
<220> FEATURE:
<223> OTHER INFORMATION: primer

<400> SEQUENCE: 39
cggttaacca gatggatttg tctaataagc ag                          32

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
agggatccct aaagattatc cgcttagtcc                             30

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
agggatccct aaagattatc cgcttagtcc                             30
```

```
<210> SEQ ID NO 42
<211> LENGTH: 35
<212> TYPE: DNA
<213> ORGANISM: Artificial Sequence
<220> FEATURE:
<223> OTHER INFORMATION: primer

<400> SEQUENCE: 42
aagatatcca tccaagctat gccacatttt cctcc                             35

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
tagaagtggg catcaaatag                                              20

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
cggttaacat atcatattcg cgattggagt tac                               33

<210> SEQ ID NO 45
<211> LENGTH: 29
<212> TYPE: DNA
<213> ORGANISM: Artificial Sequence
<220> FEATURE:
<223> OTHER INFORMATION: primer

<400> SEQUENCE: 45
tatctcgagc aaaagaaata cagatgaag                                    29

<210> SEQ ID NO 46
<211> LENGTH: 33
<212> TYPE: DNA
<213> ORGANISM: Artificial Sequence
<220> FEATURE:
<223> OTHER INFORMATION: primer

<400> SEQUENCE: 46
atggatccta aagtgcaagt gttcgagacg gtg                               33

<210> SEQ ID NO 47
<211> LENGTH: 27
<212> TYPE: DNA
<213> ORGANISM: Artificial Sequence
<220> FEATURE:
<223> OTHER INFORMATION: primer

<400> SEQUENCE: 47
aatgatatcc cgcagtacca tctctcc                                      27

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
```

```
tcttggggat aattagaggg tg                                          22
```

<210> SEQ ID NO 49
<211> LENGTH: 28
<212> TYPE: DNA
<213> ORGANISM: Artificial Sequence
<220> FEATURE:
<223> OTHER INFORMATION: primer

<400> SEQUENCE: 49

```
tagttaacag cccgccaaag tcacaaag                                    28
```

<210> SEQ ID NO 50
<211> LENGTH: 26
<212> TYPE: DNA
<213> ORGANISM: Artificial Sequence
<220> FEATURE:
<223> OTHER INFORMATION: primer

<400> SEQUENCE: 50

```
aggtcgacaa ggagatgagg aggaag                                      26
```

<210> SEQ ID NO 51
<211> LENGTH: 29
<212> TYPE: DNA
<213> ORGANISM: Artificial Sequence
<220> FEATURE:
<223> OTHER INFORMATION: primer

<400> SEQUENCE: 51

```
ttggatccgt ctacggcttg cctgattac                                   29
```

<210> SEQ ID NO 52
<211> LENGTH: 28
<212> TYPE: DNA
<213> ORGANISM: Artificial Sequence
<220> FEATURE:
<223> OTHER INFORMATION: primer

<400> SEQUENCE: 52

```
acctcgcgac ttcactcaca acattacc                                    28
```

<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53

```
ccgacaagga cgacgagaag g                                           21
```

<210> SEQ ID NO 54
<211> LENGTH: 21
<212> TYPE: DNA
<213> ORGANISM: Artificial Sequence
<220> FEATURE:
<223> OTHER INFORMATION: primer

<400> SEQUENCE: 54

```
tcatgctatt cctcttccgt c                                           21
```

<210> SEQ ID NO 55
<211> LENGTH: 22
<212> TYPE: DNA
<213> ORGANISM: Artificial Sequence

```
<220> FEATURE:
<223> OTHER INFORMATION: primer

<400> SEQUENCE: 55
aggcatgcac aagatgtcag tg                                        22

<210> SEQ ID NO 56
<211> LENGTH: 24
<212> TYPE: DNA
<213> ORGANISM: Artificial Sequence
<220> FEATURE:
<223> OTHER INFORMATION: primer

<400> SEQUENCE: 56
agggatccgg aattgaactt gata                                      24

<210> SEQ ID NO 57
<211> LENGTH: 23
<212> TYPE: DNA
<213> ORGANISM: Artificial Sequence
<220> FEATURE:
<223> OTHER INFORMATION: primer

<400> SEQUENCE: 57
tggtttagga tgatgttgct gac                                       23

<210> SEQ ID NO 58
<211> LENGTH: 24
<212> TYPE: DNA
<213> ORGANISM: Artificial Sequence
<220> FEATURE:
<223> OTHER INFORMATION: primer

<400> SEQUENCE: 58
tgaatgatac ggttggtgat gttc                                      24

<210> SEQ ID NO 59
<211> LENGTH: 23
<212> TYPE: DNA
<213> ORGANISM: Artificial Sequence
<220> FEATURE:
<223> OTHER INFORMATION: primer

<400> SEQUENCE: 59
tagttaacac agctgtctgc cag                                       23

<210> SEQ ID NO 60
<211> LENGTH: 30
<212> TYPE: DNA
<213> ORGANISM: Artificial Sequence
<220> FEATURE:
<223> OTHER INFORMATION: primer

<400> SEQUENCE: 60
aggttaacat atgtcaagag atcaaagtgc                                30

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
acagcaagat gttgtcgttc                                           20
```

```
<210> SEQ ID NO 62
<211> LENGTH: 27
<212> TYPE: DNA
<213> ORGANISM: Artificial Sequence
<220> FEATURE:
<223> OTHER INFORMATION: primer

<400> SEQUENCE: 62
agtcgcgaga tgtagaagag ggagaag                                        27

<210> SEQ ID NO 63
<211> LENGTH: 24
<212> TYPE: DNA
<213> ORGANISM: Artificial Sequence
<220> FEATURE:
<223> OTHER INFORMATION: primer

<400> SEQUENCE: 63
agtcgcgagc gtgttttgaa tgtg                                           24

<210> SEQ ID NO 64
<211> LENGTH: 24
<212> TYPE: DNA
<213> ORGANISM: Artificial Sequence
<220> FEATURE:
<223> OTHER INFORMATION: primer

<400> SEQUENCE: 64
tctggataga aatgcaaatc gtag                                           24

<210> SEQ ID NO 65
<211> LENGTH: 25
<212> TYPE: DNA
<213> ORGANISM: Artificial Sequence
<220> FEATURE:
<223> OTHER INFORMATION: primer

<400> SEQUENCE: 65
tgccaggtcc agccttacaa agaag                                          25

<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66
acgatatcag catccacaac acccataatc                                     30

<210> SEQ ID NO 67
<211> LENGTH: 23
<212> TYPE: DNA
<213> ORGANISM: Artificial Sequence
<220> FEATURE:
<223> OTHER INFORMATION: primer

<400> SEQUENCE: 67
tcgttatagc ttcgtacaca atg                                            23

<210> SEQ ID NO 68
<211> LENGTH: 25
<212> TYPE: DNA
<213> ORGANISM: Artificial Sequence
<220> FEATURE:
<223> OTHER INFORMATION: primer

<400> SEQUENCE: 68
```

```
gcacttcttt cccctttttg tttac                                      25

<210> SEQ ID NO 69
<211> LENGTH: 29
<212> TYPE: DNA
<213> ORGANISM: Artificial Sequence
<220> FEATURE:
<223> OTHER INFORMATION: primer

<400> SEQUENCE: 69
aggttaactt gaattgtaga tacagccac                                  29

<210> SEQ ID NO 70
<211> LENGTH: 25
<212> TYPE: DNA
<213> ORGANISM: Artificial Sequence
<220> FEATURE:
<223> OTHER INFORMATION: primer

<400> SEQUENCE: 70
tcatggatta gggttagaaa gagtg                                      25

<210> SEQ ID NO 71
<211> LENGTH: 28
<212> TYPE: DNA
<213> ORGANISM: Artificial Sequence
<220> FEATURE:
<223> OTHER INFORMATION: primer

<400> SEQUENCE: 71
acgttaacca tatcacagct atatcccc                                   28

<210> SEQ ID NO 72
<211> LENGTH: 26
<212> TYPE: DNA
<213> ORGANISM: Artificial Sequence
<220> FEATURE:
<223> OTHER INFORMATION: primer

<400> SEQUENCE: 72
acgttaacgc caggtcctcc ttctgc                                     26

<210> SEQ ID NO 73
<211> LENGTH: 25
<212> TYPE: DNA
<213> ORGANISM: Artificial Sequence
<220> FEATURE:
<223> OTHER INFORMATION: primer

<400> SEQUENCE: 73
ggagagatag gacgtaaact tcatg                                      25

<210> SEQ ID NO 74
<211> LENGTH: 29
<212> TYPE: DNA
<213> ORGANISM: Artificial Sequence
<220> FEATURE:
<223> OTHER INFORMATION: primer

<400> SEQUENCE: 74
tggttaactc gtaagtaggt aggctgtac                                  29

<210> SEQ ID NO 75
<211> LENGTH: 23
<212> TYPE: DNA
<213> ORGANISM: Artificial Sequence
```

```
<220> FEATURE:
<223> OTHER INFORMATION: primer

<400> SEQUENCE: 75
atgttaaccc gaggtgctgc ttg                                        23

<210> SEQ ID NO 76
<211> LENGTH: 25
<212> TYPE: DNA
<213> ORGANISM: Artificial Sequence
<220> FEATURE:
<223> OTHER INFORMATION: primer

<400> SEQUENCE: 76
agagcagaga agaaatactg aggag                                      25

<210> SEQ ID NO 77
<211> LENGTH: 29
<212> TYPE: DNA
<213> ORGANISM: Artificial Sequence
<220> FEATURE:
<223> OTHER INFORMATION: primer

<400> SEQUENCE: 77
aggttaactt ggcttggcga agcaaactc                                  29

<210> SEQ ID NO 78
<211> LENGTH: 27
<212> TYPE: DNA
<213> ORGANISM: Artificial Sequence
<220> FEATURE:
<223> OTHER INFORMATION: primer

<400> SEQUENCE: 78
aggttaacat cagcgcggtc aaagtag                                    27

<210> SEQ ID NO 79
<211> LENGTH: 23
<212> TYPE: DNA
<213> ORGANISM: Artificial Sequence
<220> FEATURE:
<223> OTHER INFORMATION: primer

<400> SEQUENCE: 79
tctgacggga gcggacagtc atg                                        23

<210> SEQ ID NO 80
<211> LENGTH: 30
<212> TYPE: DNA
<213> ORGANISM: Artificial Sequence
<220> FEATURE:
<223> OTHER INFORMATION: primer

<400> SEQUENCE: 80
ccgttaaccc tccacgtatt ccaatatacc                                 30

<210> SEQ ID NO 81
<211> LENGTH: 28
<212> TYPE: DNA
<213> ORGANISM: Artificial Sequence
<220> FEATURE:
<223> OTHER INFORMATION: primer

<400> SEQUENCE: 81
aagtcgacac cagtctggag aatagcgg                                   28
```

-continued

```
<210> SEQ ID NO 82
<211> LENGTH: 34
<212> TYPE: DNA
<213> ORGANISM: Artificial Sequence
<220> FEATURE:
<223> OTHER INFORMATION: primer

<400> SEQUENCE: 82
cgggatcctt gagggtgatc tttgcgagac caac                              34

<210> SEQ ID NO 83
<211> LENGTH: 32
<212> TYPE: DNA
<213> ORGANISM: Artificial Sequence
<220> FEATURE:
<223> OTHER INFORMATION: primer

<400> SEQUENCE: 83
gggttaacat gtcgcattac tcctggctga ag                                32

<210> SEQ ID NO 84
<211> LENGTH: 23
<212> TYPE: DNA
<213> ORGANISM: Artificial Sequence
<220> FEATURE:
<223> OTHER INFORMATION: primer

<400> SEQUENCE: 84
tcgttatagc ttcgtacaca atg                                          23

<210> SEQ ID NO 85
<211> LENGTH: 28
<212> TYPE: DNA
<213> ORGANISM: Artificial Sequence
<220> FEATURE:
<223> OTHER INFORMATION: primer

<400> SEQUENCE: 85
aagttaaccg tttccgtagc attgcccg                                     28

<210> SEQ ID NO 86
<211> LENGTH: 30
<212> TYPE: DNA
<213> ORGANISM: Artificial Sequence
<220> FEATURE:
<223> OTHER INFORMATION: primer

<400> SEQUENCE: 86
tcgtcgacag tgagttccgt gaccattgcc                                   30

<210> SEQ ID NO 87
<211> LENGTH: 30
<212> TYPE: DNA
<213> ORGANISM: Artificial Sequence
<220> FEATURE:
<223> OTHER INFORMATION: primer

<400> SEQUENCE: 87
ctggatccaa gctgaagaag aacatcatcg                                   30

<210> SEQ ID NO 88
<211> LENGTH: 32
<212> TYPE: DNA
<213> ORGANISM: Artificial Sequence
<220> FEATURE:
<223> OTHER INFORMATION: primer

<400> SEQUENCE: 88
```

```
tagatatctg tctattctat atgaagcccc tc                                  32

<210> SEQ ID NO 89
<211> LENGTH: 25
<212> TYPE: DNA
<213> ORGANISM: Artificial Sequence
<220> FEATURE:
<223> OTHER INFORMATION: primer

<400> SEQUENCE: 89
atacagcaca gtctatcaat atgag                                          25

<210> SEQ ID NO 90
<211> LENGTH: 23
<212> TYPE: DNA
<213> ORGANISM: Artificial Sequence
<220> FEATURE:
<223> OTHER INFORMATION: primer

<400> SEQUENCE: 90
taaggcctag caagcaatca gtg                                            23

<210> SEQ ID NO 91
<211> LENGTH: 25
<212> TYPE: DNA
<213> ORGANISM: Artificial Sequence
<220> FEATURE:
<223> OTHER INFORMATION: primer

<400> SEQUENCE: 91
aacagaaagg accaataaca aacgg                                          25

<210> SEQ ID NO 92
<211> LENGTH: 24
<212> TYPE: DNA
<213> ORGANISM: Artificial Sequence
<220> FEATURE:
<223> OTHER INFORMATION: primer

<400> SEQUENCE: 92
acaagaacct gtctccagta tgag                                           24

<210> SEQ ID NO 93
<211> LENGTH: 25
<212> TYPE: DNA
<213> ORGANISM: Artificial Sequence
<220> FEATURE:
<223> OTHER INFORMATION: primer

<400> SEQUENCE: 93
tggttaacga gggattgctc tattg                                          25

<210> SEQ ID NO 94
<211> LENGTH: 26
<212> TYPE: DNA
<213> ORGANISM: Artificial Sequence
<220> FEATURE:
<223> OTHER INFORMATION: primer

<400> SEQUENCE: 94
tggttaactg tgctatgcta ttggtg                                         26

<210> SEQ ID NO 95
<211> LENGTH: 20
<212> TYPE: DNA
<213> ORGANISM: Artificial Sequence
```

```
<220> FEATURE:
<223> OTHER INFORMATION: primer

<400> SEQUENCE: 95
tctgctcgtc ggtggttgtg                                              20

<210> SEQ ID NO 96
<211> LENGTH: 26
<212> TYPE: DNA
<213> ORGANISM: Artificial Sequence
<220> FEATURE:
<223> OTHER INFORMATION: primer

<400> SEQUENCE: 96
tttccagtct agacacgtat aacggc                                       26

<210> SEQ ID NO 97
<211> LENGTH: 26
<212> TYPE: DNA
<213> ORGANISM: Artificial Sequence
<220> FEATURE:
<223> OTHER INFORMATION: primer

<400> SEQUENCE: 97
tttccagtct agacacgtat aacggc                                       26
```

GENE INACTIVATED MUTANTS WITH ALTERED PROTEIN PRODUCTION

The present application claims priority to U.S. Provisional Patent Application Ser. No. 60/670,415 entitled Gene Inactivated Mutants with Altered Protein Production, filed Apr. 12, 2005, contents of which are incorporated by reference.

FIELD OF THE INVENTION

The present invention provides cells that have been genetically manipulated to have an altered capacity to produce expressed proteins. In particular, the present invention relates to filamentous fungal microorganisms, such as *Aspergillus* species wherein one or more chromosomal genes have been inactivated, and preferably, wherein one or more chromosomal genes have been deleted from the *Aspergillus* chromosome.

SEQUENCE LISTING

The sequence listing submitted on Dec. 4, 2010, via EFS-Web, in compliance with 37 C.F.R. 1.52(e)(2), is incorporated herein by reference. The sequence listing text file submitted via EFS-Web contains the file "30869-C1-US-seqlist.txt", created on Nov. 29, 2010, which is 158,031 bytes in size.

BACKGROUND OF THE INVENTION

Genetic engineering has allowed the improvement of microorganisms used as industrial bioreactors, cell factories and in food fermentations. In particular, filamentous fungi (e.g. *Aspergillus* and *Trichoderma* species) and certain bacteria (e.g., *Bacillus* species) produce and secrete a large number of useful proteins and metabolites (Bio/Technol. 5: 369-376, 713-719 and 1301-1304 [1987] and Zukowski, "Production of commercially valuable products," In: Doi and McGlouglin (eds.) Biology of Bacilli: Applications to Industry, Butterworth-Heinemann, Stoneham. Mass pp 311-337 [1992]). Important production enzymes include glucoamylases, α-amylases, cellulases, neutral proteases, and alkaline (or serine) proteases, and important production proteins include hormones and antibodies. However, the occurrence of protein degradation and modification in some of these host cells provides a major hurdle for protein production, and in spite of advances in the understanding of production of proteins in filamentous fungal host cells, there remains a need for methods to increase expression of important proteins.

Accordingly, an object of the present invention is to provide an *Aspergillus* strain defective in protein degrading genes and protein modification genes, which can be used for more efficient production of heterologous or homologous proteins of interest.

SUMMARY OF THE INVENTION

The present invention is concerned with the inactivation of genes, which may be involved in protein degradation and modification (e.g., protease genes, endoplasmic reticulum (ER) degradation pathway genes and glycosylation genes). In some embodiments, the gene inactivation is a non-revertable inactivation that results in a genetically engineered microbial cell referred to as an inactivated mutant. In some embodiments, the inactivated mutant has an altered capacity to produce an expressed protein of interest.

In one aspect, the invention relates to an *Aspergillus* inactivated mutant comprising one or more non-revertable inactivated chromosomal genes selected from the group consisting of derA, derB, htmA, mnn9, mnn10, ochA, dpp4, dpp5, pepAa, pepAb, pepAc, pepAd, and pepF combinations thereof and homologous sequences thereto. In some embodiments, the inactivated mutant will further include a non-revertable inactivated chromosomal gene selected from the group consisting of pepB, pepC, pepD, combinations thereof and homologous sequences thereto. In other embodiments, the *Aspergillus* inactivated mutant is an *A. niger* inactivated mutant. In further embodiments, the inactivated mutant further comprises a polynucleotide encoding a heterologous protein of interest. In additional embodiments, the protein of interest is an enzyme, a protease inhibitor or an antibody or fragment thereof. In yet other embodiments, the *Aspergillus* inactivated mutant has an enhanced level of expression of the protein of interest compared to a corresponding parent *Aspergillus* strain when said inactivated mutant and parent strain are cultured under essentially the same growth conditions. In yet further embodiments, the one or more inactivated chromosomal genes have been deleted or the one or more inactivated chromosomal genes have been disrupted in the protein-coding region.

In a second aspect, the invention relates to a method for producing a protein of interest in an *Aspergillus* inactivated mutant comprising a) obtaining an *Aspergillus* inactivated mutant capable of producing a protein of interest, wherein said *Aspergillus* inactivated mutant has at least one non-revertable inactivated chromosomal gene selected from the group consisting of consisting of derA, derB, htmA, mnn9, mnn10, ochA, dpp4, dpp5, pepAa, pepAb, pepAc, pepAd, and pepF gene fragments thereof, and homologous sequences thereto; b) growing said *Aspergillus* inactivated mutant under conditions such that said protein of interest is expressed; and c) recovering the protein of interest. In some embodiments, the expression of said protein of interest in the inactivated mutant is enhanced compared to the expression of said protein of interest in a corresponding parent *Aspergillus*. In some embodiments, two chromosomal genes are inactivated. In other embodiments, the *Aspergillus* inactivated mutant further comprises inactivated chromosomal genes selected from the group consisting of pepB, pepC, pepD and combinations thereof and homologous sequences thereto. In additional embodiments, the protein of interest is an enzyme, a protease inhibitor or an antibody or fragments thereof. In some preferred embodiments, the protein of interest is a heterologous protein and in other embodiments the protein of interest is a homologous protein.

In a third aspect, the invention relates to a DNA sequence encoding the protein sequences of DERA, DERB, HTMA, MNN9, MNN10, OCHA, DPP4, Dpp5, PEPAa, PEPAb, PEPAc and PEPAd and functionally homologous sequence thereto.

In a fourth aspect, the invention relates to the DNA sequences comprising the genes of derA, derB, htmA, mnn9, mnn10, ochA, dpp4, dpp5, pepAa, pepAb, pepAc and pepAd.

In a fifth aspect, the invention relates to a method of making a recombinant filamentous fungal cell comprising introducing into a filamentous fungal cell a DNA construct that recombines with a chromosomal gene selected from the group of derA, derB, htmA, mnn9, mnn10, ochA, dpp4, dpp5, pepAa, pepAb, pepAc, pepAd, pepF or functionally homologous sequences thereto wherein the chromosomal gene is inactivated. In one embodiment, the inactivated gene is deleted and in another embodiment, the inactivated gene is disrupted.

BRIEF DESCRIPTION OF THE DRAWINGS

FIGS. 1A-B set forth a genomic *Aspergillus* derA DNA sequence (SEQ ID NO: 1).

FIG. 2 sets forth the putative protein sequence of DERA (SEQ ID NO: 2).

FIGS. 3A-B set forth a genomic *Aspergillus* derB DNA sequence (SEQ ID NO: 3).

FIG. 4 sets forth the putative protein sequence of DERB (SEQ ID NO: 4).

FIGS. 5A-E set forth a genomic *Aspergillus* htmA DNA sequence (SEQ ID NO: 5).

FIG. 6 sets forth the putative protein sequence of HTMA (SEQ ID NO: 6).

FIGS. 7A-D set forth a genomic *Aspergillus* mnn9 DNA sequence (SEQ ID NO: 7).

FIG. 8 sets forth the putative protein sequence of MNN9 (SEQ ID NO: 8).

FIGS. 9A-C set forth a genomic *Aspergillus* mnn10 DNA sequence (SEQ ID NO: 9).

FIG. 10 sets forth the putative protein sequence of MNN10 (SEQ ID NO: 10).

FIGS. 11A-E set forth a genomic *Aspergillus* ochA DNA sequence (SEQ ID NO: 11).

FIG. 12 sets forth the putative protein sequence of OCHA (SEQ ID NO: 12).

FIGS. 13A-C set forth a genomic *Aspergillus* dpp4 DNA sequence (SEQ ID NO: 13).

FIG. 14 sets forth the putative protein sequence of DPP4 (SEQ ID NO: 14).

FIGS. 15A-B set forth a genomic *Aspergillus* dpp5 DNA sequence (SEQ ID NO: 15).

FIG. 16 sets forth the putative protein sequence of DPP5 (SEQ ID NO: 16).

FIGS. 17A-B set forth a genomic *Aspergillus* pepAa DNA sequence (SEQ ID NO: 17).

FIG. 18 sets forth the putative protein sequence of PEPAa (SEQ ID NO: 18).

FIGS. 19A-C set forth a genomic *Aspergillus* pepAb DNA sequence (SEQ ID NO: 19).

FIG. 20 sets forth the putative protein sequence of PEPAb (SEQ ID NO: 20).

FIGS. 21A-B set forth a genomic *Aspergillus* pepAd DNA sequence (SEQ ID NO: 21).

FIG. 22 sets forth the putative protein sequence of PEPAd (SEQ ID NO: 22).

FIGS. 23A-C set forth a genomic *Aspergillus* pepF DNA sequence (SEQ ID NO: 23).

FIG. 24 sets forth the putative protein sequence of PEPF (SEQ ID NO: 24).

FIGS. 25A-B set forth a genomic *Aspergillus* pepB DNA sequence (SEQ ID NO: 25).

FIG. 26 sets forth the putative protein sequence of PEPB (SEQ ID NO: 26).

FIGS. 27A-D set forth a genomic *Aspergillus* pepC DNA sequence (SEQ ID NO: 27).

FIG. 28 sets forth the putative protein sequence of PEPC (SEQ ID NO: 28).

FIGS. 29A-B set forth a genomic *Aspergillus* pepD DNA sequence (SEQ ID NO: 29).

FIG. 30 sets forth the putative protein sequence of PEPD (SEQ ID NO: 30).

FIGS. 31A-C set forth a genomic *Aspergillus* pepAc DNA sequence (SEQ ID NO: 31).

FIG. 32 sets forth the putative protein sequence of PEPAc (SEQ ID NO: 32).

FIG. 33 illustrates the general cloning strategy used for making inactivated mutants according to the invention. FIG. 33A illustrates the strategy for making a gene deletion using the vector pMW1-ΔderA to make a deletion of the derA gene. Further details are outlined in example 1a. FIG. 33B illustrates the strategy for making a disruption in the protein coding region of the gene using the vector pBS-disruption (ochA) as detailed for ochA in example 1f.

FIG. 34 depicts the analysis of the PCR fragment generated from total cellular DNA extracted from inactivated mutants of *Aspergillus niger* by fractionation on agarose gel. The gene mnn9 is representative of an inactivation by deletion (FIG. 34A), wherein lane 1 represents the DNA molecular weight marker, lane 3 represents a parent control which includes the mnn9 gene and lane 7 represents an inactivated strain with a mnn9 gene deletion. The gene ochA is representative of an inactivation by disruption (FIG. 34B), wherein lane 1 represents the DNA molecular weight marker, lane 3 represents a parent control, which includes an ochA gene and lane 7 represents an inactivated strain with an ochA gene deletion. The genomic DNA was extracted from strains harboring either a gene deletion or a gene disruption. For gene deletions or disruptions two primers were designed; one primer was located on the coding region of a hydromycin gene ($P_{hph}$, SEQ ID NO: 37) and one specific primer from each gene was used (See SEQ ID NOs: 38, 43, 48, 53, 58, 61, 67, 70, 73, 76, 79, 84, 89, 92 and 95). A specific PCR product was detected if the gene was deleted or disrupted. When DNA from the parent control strain was used as template PCR a band was not detected.

DETAILED DESCRIPTION OF THE INVENTION

The present invention provides recombinant fungal cells having one or more inactivated genes. In some embodiments, the fungal cells have been genetically manipulated to have an altered capacity to produce expressed proteins. In particular, the present invention relates to filamentous fungal cells, such as *Aspergillus* cells having enhanced expression of a protein of interest, wherein one or more chromosomal genes have been inactivated. In some preferred embodiments, the one or more chromosomal genes have been deleted from an *Aspergillus* chromosome and in other embodiments the one or more chromosome genes have been disrupted in the protein-coding region.

Definitions

All patents and publications, including all sequences disclosed within such patents and publications, referred to herein are expressly incorporated by reference. Unless defined otherwise herein, all technical and scientific terms used herein have the same meaning as commonly understood by one of ordinary skill in the art to which this invention belongs (See e.g., Singleton et al., DICTIONARY OF MICROBIOLOGY AND MOLECULAR BIOLOGY, 2D ED., John Wiley and Sons, New York [1994]; and Hale and Marham, THE HARPER COLLINS DICTIONARY OF BIOLOGY, Harper Perennial, NY [1991], both of which provide one of skill with a general dictionary of many of the terms used herein). Although any methods and materials similar or equivalent to those described herein can be used in the practice or testing of the present invention, the preferred methods and materials are described. Numeric ranges are inclusive of the numbers defining the range. As used herein, the singular "a", "an" and "the" includes the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxyl orientation, respectively. The headings provided herein are not limitations of the various aspects or embodiments of the invention that can be had by reference to the specification as a whole. Accordingly, the terms defined immediately below are more fully defined by reference to the Specification as a whole.

As used herein, "inactivated mutant" or "inactivated strain" (e.g., an *Aspergillus* inactivated mutant) refers to genetically engineered recombinant host cells having one or more inactivated genes as encompassed by the invention. The term encompasses progeny thereof. In some embodiments, inactivation is the result of gene deletions and these inactivated mutants are sometimes referred to as deletion mutants. In other embodiments, inactivation is the result of disruption to the protein coding sequence and these inactivated mutants are sometimes referred to as disruption mutants. In some embodiments, the inactivation is non-revertable. In some embodiments, non-revertable refers to a strain, which will naturally revert back to the parental strain with a frequency of less than $10^{-7}$. In some embodiments, inactivation will result in a cell having no detectable activity for the gene or gene product corresponding to the inactivated gene.

A "corresponding parent strain" refers to the host strain (e.g., the originating and/or wild-type strain) from which an inactivated mutant is derived.

The term "inactivation" includes any method that prevents the functional expression of one or more of the derA, derB, htmA, mnn9, mnn10, ochA, dpp4, dpp5, pepAa, pepAb, pepAc, pepAd, pepF, pepB, pepC, pepD genes, fragments or homologues thereof, wherein the gene or gene product is unable to exert its known function. Means of gene inactivation include deletions, disruptions of the protein-coding sequence, insertions, additions, mutations, gene silencing (e.g. RNAi genes antisense) and the like.

As used herein "protein-coding region" refers to the region of a gene that encodes the amino acid sequence of a protein.

As used herein "amino acid" refers to peptide or protein sequences or portions thereof. The terms "protein", "peptide" and "polypeptide" are used interchangeably.

As used herein, the term "heterologous protein" refers to a protein or polypeptide that does not naturally occur in the host cell.

As used herein, "homologous protein" or "endogenous protein" refers to a protein or polypeptide native or naturally occurring in a cell.

As used herein, "host cell" or "host strain" refers to a cell that has the capacity to act as a host or expression vehicle for a newly introduced DNA sequence. In preferred embodiments of the present invention, the host cells are *Aspergillus* sp.

As used herein, "the genus *Aspergillus*" includes all species within the genus "*Aspergillus*," as known to those of skill in the art, including but not limited to *A. niger*, *A. oryzae*, *A. awamori*, *A. kawachi* and *A. nidulans*.

As used herein, "nucleic acid" refers to a nucleotide or polynucleotide sequence, and fragments or portions thereof, as well as to DNA, cDNA, and RNA of genomic or synthetic origin which may be double-stranded or single-stranded, whether representing the sense or antisense strand. It will be understood that as a result of the degeneracy of the genetic code, a multitude of nucleotide sequences may encode a given protein.

As used herein the term "gene" means a chromosomal segment of DNA involved in producing a polypeptide chain that may or may not include regions preceding and following the coding regions (e.g. promoter, terminator, 5' untranslated (5' UTR) or leader sequences and 3' untranslated (3' UTR) or trailer sequences, as well as intervening sequence (introns) between individual coding segments (exons)).

As used herein, the term "vector" refers to any nucleic acid that can be replicated in cells and can carry new genes or DNA segments into cells. Thus, the term refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the terms "DNA construct," "expression cassette," and "expression vector," refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed, a promoter and a terminator. In some embodiments, DNA constructs also include a series of specified nucleic acid elements that permit transcription of a particular nucleic acid in a target cell. In some embodiments, a DNA construct of the invention comprises a selective marker.

As used herein, "transforming DNA," "transforming sequence," and "DNA construct" refer to DNA that is used to introduce sequences into a host cell or organism. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stutter sequences or flanks). The ends can be closed such that the transforming DNA forms a closed circle, such as, for example, insertion into a vector.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

As used herein, the terms "isolated" and "purified" refer to a nucleic acid or amino acid (or other component) that is removed from at least one component with which it is naturally associated.

As used herein, the term "enhanced expression" is broadly construed to include enhanced production of a protein of interest. Enhanced expression is that expression above the normal level of expression in the corresponding parent strain that has not been altered according to the teachings herein but has been grown under essentially the same growth conditions.

As used herein the term "expression" refers to a process by which a polypeptide is produced based on the nucleic acid sequence of a gene. The process includes both transcription and translation. In preferred embodiments, the process also includes secretion.

As used herein in the context of introducing a nucleic acid sequence into a cell, the term "introduced" refers to any method suitable for transferring the nucleic acid sequence into the cell.

As used herein, the terms "transformed" and "stably transformed" refers to a cell that has a non-native (heterologous) polynucleotide sequence integrated into its genome or as an episomal plasmid that is maintained for at least two generations.

As used herein "an incoming sequence" refers to a DNA sequence that is introduced into the host cell chromosome. In some embodiments, the incoming sequence is part of a DNA construct. In some embodiments, the incoming sequence encodes one or more proteins of interest. In other embodiments, the incoming sequence comprises a sequence that may or may not already be present in the genome of the cell to be transformed it may be either a homologous or heterologous sequence). In some embodiments, the incoming sequence includes a functional or non-functional gene and/or a mutated or modified gene. In a preferred embodiment, the incoming sequence comprises a gene selected from the group consisting of derA, derB, htmA, mnn9, mnn10, ochA, dpp4, dpp5, pepAa, pepAb, pepAc, pepAd, pepF, pepB, pepC, pepD, fragments and homologous sequences thereof. In yet another embodiment, the incoming sequence includes a selective marker. In a further embodiment the incoming sequence includes two homology boxes. In some embodiments, the incoming sequence encodes at least one heterologous protein of interest.

As used herein, "homology box" refers to a nucleic acid sequence, which is homologous to a sequence in the *Aspergillus* chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be inactivated according to the invention. These sequences direct where in the chromosome a DNA construct or incoming sequence is integrated and directs what part of the chromosome is replaced by the DNA construct or incoming sequence. While not meant to limit the invention, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

As used herein, the terms "selectable marker" and "selective marker" refer to a nucleic acid (e.g., a gene) capable of expression in host cell, which allows for ease of selection of those hosts containing the marker. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, preferably the marker is an antimicrobial resistant marker (e.g., $amp^R$; $phleo^R$; $spec^R$; $kan^R$; $ery^R$; $tet^R$; $cmp^R$; $hygro^R$ and $neo^R$; See e.g., Guerot-Fleury, Gene, 167:335-337 [1995]; Palmeros et al., Gene 247:255-264 [2000]; and Trieu-Cuot et al., *Gene*, 23:331-341 [1983]). Other markers useful in accordance with the invention include, but are not limited to auxotrophic markers, such as tryptophan, pyrG and amdS; and detection markers, such as β-galactosidase.

As used herein, the term "promoter" refers to a nucleic acid sequence that functions to direct transcription of a downstream gene. In preferred embodiments, the promoter is appropriate to the host cell in which a desired gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes). In preferred embodiments the homologous genes are functionally related.

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

"Homologous sequences" as used herein means a nucleic acid or polypeptide sequence having at least 100%, at least 99%, at least 98%, at least 97%, at least 96%, at least 95%, at least 94%, at least 93%, at least 92%, at least 91%, at least 90%, at least 88%, at least 85%, at least 80%, at least 75%, at least 70% or at least 60% sequence identity to a subject nucleic acid or polypeptide sequence when optimally aligned for comparison. In some embodiments, homologous sequences have between 80% and 100% sequence identity, while in other embodiments between 90% and 100% sequence identity, and in more preferred embodiments, between 95% and 100% sequence identity. A functionally homologous sequence means the corresponding gene or protein functions in the same manner as the subject gene or protein.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, underexpressed, overexpressed or not expressed at all as a result of deliberate human intervention. "Recombination, "recombining," or generating a "recombined" nucleic acid is generally the assembly of two or more nucleic acid fragments wherein the assembly gives rise to a chimeric gene.

In an alternative embodiment, the transforming DNA sequence comprises homology boxes without the presence of an incoming sequence. In this embodiment, it is desired to delete the endogenous DNA sequence between the two homology boxes. Furthermore, in some embodiments, the transforming sequences are wild-type, while in other embodiments, they are mutant or modified sequences. In addition, in some embodiments, the transforming sequences are homologous, while in other embodiments, they are heterologous.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a preferred embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Aspergillus* chromosome. These sequences direct where in the *Aspergillus* chromosome the new construct gets integrated and what part of the *Aspergillus* chromosome will be replaced by the incoming sequence. In some embodiments these sequences direct where in the *Aspergillus* chromosome the new construct gets integrated without any part of the chromosome being replaced by the incoming sequence. In a preferred embodiment, the 5' and 3' ends of a selective marker are flanked by a polynucleotide sequence comprising a section of the inactivating chromosomal segment. In some embodiments, a flanking sequence is present on only a single side (either 3' or 5'), while in preferred embodiments, it is present on each side of the sequence being flanked.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification. Preferably, the primer is an oligodeoxyribonucleotide.

As used herein, the term "polymerase chain reaction" ("PCR") refers to the methods of U.S. Pat. Nos. 4,683,195 4,683,202, and 4,965,188, hereby incorporated by reference.

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

As used herein, "strain viability" refers to reproductive viability. In preferred embodiments, the inactivation of a chromosomal gene does not deleteriously affect division and survival of the inactivated mutant under laboratory conditions.

As used herein, the term "chromosomal integration" refers to the process whereby an incoming sequence is introduced into the chromosome of a host cell (e.g., *Aspergillus*). The homologous regions of the introduced (transforming) DNA align with homologous regions of the chromosome. Subsequently, the sequence between the homology boxes is replaced by the incoming sequence in a double crossover (i.e., homologous recombination).

"Homologous recombination" means the exchange of DNA fragments between two DNA molecules or paired chromosomes at the site of identical or nearly identical nucleotide sequences. In a preferred embodiment, chromosomal integration is by homologous recombination.

Preferred Embodiments

The present invention provides inactivated mutants (e.g., deletion mutants and disruption mutants) that are capable of producing a protein of interest. In particular, the present invention relates to recombinant filamentous fungal microorganisms, such as *Aspergillus* species having altered expression of a protein of interest, wherein one or more chromosomal genes have been inactivated, and preferably wherein one or more chromosomal genes have been deleted from the *Aspergillus* chromosome or wherein the protein-coding region of one or more chromosomal genes has been disrupted. Indeed, the present invention provides means for deletion of single or multiple genes. In preferred embodiments, such deletions provide advantages such as improved production of a protein of interest.

Inactivated Genes

As indicated above, the present invention includes embodiments that involve single or multiple gene inactivations. In some embodiments, the gene inactivations are gene deletions or gene disruptions. In some embodiments the inactivations are non-revertable.

Genes to be inactivated according to the invention include but are not limited to those involved in protein degradation or protein modification, such as proteins in the ER degradation pathway, proteases genes, such as secreted serine and aspartic protease genes, glycosylation genes and glycoprotein degradation genes. In some embodiments, the chromosomal gene to be inactivated includes one or more of the following genes derA, derB, htmA, mnn9, mnn10, ochA, dpp4, dpp5, pepF, pepAa, pepAb, pepAc and pepAd, or functionally homologous sequences thereto having at least 99%, at least 98%, at least 97%, at least 96%, at least 95%, at least 94%, at least 93%, at least 92%, at least 91%, at least 90%, at least 88%, at least 85%, at least 80%, at least 70% or at least 60% sequence identity therewith.

With respect to the genes to be inactivated according to the invention derA and derB genes are believed to function in the ER degradation pathway. ER degradation pathway enzymes include ER resident proteins such as those involved in the translocation of misfolded protein from the ER to the cytosol, and non ER resident proteins such as ubiquitin conjugating enzymes which target the misfolded protein for proteasomal degradation (Bonifacino and Weissman [1998] *Ann. Rev. Cell. Biol.* 14:19-57). The htmA, mnn9, mnn10 and ochA genes are believed to function in glycoprotein modification. Glycoprotein modifying enzymes are enzymes that modify oligosaccharide molecules, which have been added to amino acid residues on a protein. The dpp4, dpp5, pepF, pepAa, pepAb, pepAc, pepAd, pepB, pepC and pepD genes are believed to be proteinases. Proteinases are protein-degrading enzymes, which catalyze the hydrolytic cleavage of proteins. More specifically, proteases are enzymes that cleave peptide bonds. In some embodiments, the protease genes are aspartic proteinases (e.g. pepAa, pepAb, pepAc, pepAd and pepB). Enzymatically active aspartic proteinases are those enzymes or fragments thereof that contain aspartic acid residues at their active site. (Kosta, V (Ed) ASPARTIC PROTEINASES AND THEIR INHIBITORS, Walter de Gruyter, NY pp 27-40; 151-161 and 163-177). In other embodiments, the protease genes are dipeptidyl peptidases (e.g. dpp4 and dpp5). In other embodiments, the protease genes are serine carboxylpeptidase (e.g., pepF), and in further embodiments, the protease genes are serine proteases (e.g. pepC and pepD).

In some embodiments, inactivated genes will include two or more (e.g. two, three or four) inactivated genes according to the invention. In other embodiments, the inactivated genes will include at least one of the above-enumerated genes and a gene selected from the group consisting of pepB, pepC, pepD, combinations thereof and functionally homologous sequences thereto having at least 99%, at least 98%, at least 97%, at least 96%, at least 95%, at least 94% at least 93%, at least 92%, at least 91%, at least 90%, at least 88%, at least 85%, at least 80%, at least 70% or at least 60% sequence identity therewith.

In other embodiments, inactivated genes will include any one of the above-enumerated genes and an inactivated pepA gene or homologous sequence thereto, such as the aspergillopesins disclosed in Berka et al., [1990] Gene 86:153-162, U.S. Pat. No. 5,840,570 and U.S. Pat. No. 6,509,171.

While not meant to limit the invention in any manner, genes to be inactivated include the following combinations and functionally homologous genes thereto: (a) mnn9 and mnn10; (b) mnn9 and ochA; (c) mnn9, mnn10 and ochA; (d) dpp4 and dpp5; (e) dpp4, dpp5 and pepA; (f) pepAa and pepAb; (g) pepAa, pepAb and pepAc; (h) pepAa and pepAc; (i) pepAa, pepAb, pepAc and pepB; (j) pepAa, pepAb, pepAc and pepC; (k) pepAa, pepAb, pepAc and pepD; (l) pepB, pepC, pepD and pepF; (m) pepAa, pepAb, and pepAc; and n) dpp4, dpp5 and mnn9. Further embodiments include any one of the above-mentioned combinations (a-n) and an inactivated pepA gene or homologous gene thereto.

In some embodiments, the DNA coding sequences of these genes from *Aspergillus* are provided in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 31. As indicated above, it is contemplated that functionally homologous genes found in filamentous fungal cells will find use in the present invention. In some embodiments, the functionally homologous genes will have at least 80% sequence identity to any one of the above enumerated sequences.

Methods for determining homologous sequences from host cells are known in the art and include using a nucleic acid sequence disclosed herein to construct an oligonucleotide probe, said probe corresponding to about 6 to 20 amino acids of the encoded protein. The probe may then be used to clone the homologous protein degradation gene. The filamentous fungal host genomic DNA is isolated and digested with appropriate restriction enzymes. The fragments are separated and probed with the oligonucleotide probe prepared from the protein degradation sequences by standard methods. A fragment corresponding to the DNA segment identified by hybridization to the oligonucleotide probe is isolated, ligated to an appropriate vector and then transformed into a host to produce DNA clones.

In other embodiments, the DNA encodes the protein sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24; SEQ ID NO: 26; SEQ ID NO: 28; SEQ ID NO: 30 and SEQ ID NO: 32 and functionally homologous sequence thereto. In some embodiments, a functionally homologous sequence will be a protein found in a filamentous fungal cell (i.e. *Aspergillus*) and have at least 95% sequence identity to any one of the above enumerated sequences. In some embodiments, the functionally homologous sequence will be found in an *Aspergillus niger* or *Aspergillus oryzae* and will have at least 90% or also at least 95% sequence identity to and one of the above enumerated sequences. In other embodiments, a protein sequence will differ from any one of the above enumerated protein sequences by one or more conservative amino acid replacements, such as but not limited to the groups of glycine and alanine; valine, isoleucine and leucine; aspartic acid and glutamic acid; asparagine and glutamine; serine and threonine; tryptophan, tyrosine and phenylalanine; and lysine and arginine.

Methods of Inactivation and General Construction of DNA Constructs to be Used to Inactivate Chromosomal Genes In some embodiments, the present invention includes a DNA construct comprising an incoming sequence. The DNA construct is assembled in vitro, followed by direct cloning of the construct into a competent host (e.g. an *Aspergillus* host), such that the DNA construct becomes integrated into the host chromosome. For example, PCR fusion and/or ligation can be employed to assemble a DNA construct in vitro. In some embodiments, the DNA construct is a non-plasmid construct, while in other embodiments it is incorporated into a vector (e.g., a plasmid). In some embodiments, circular plasmids are used. In preferred embodiments, circular plasmids are designed to use an appropriate restriction enzyme (i.e., one that does not disrupt the DNA construct). Thus, linear plasmids find use in the present invention.

In some embodiments, the incoming sequence comprises a derA, derB, htmA, mnn9, mnn10, ochA, dpp4, dpp5, pepAa, pepAb, pepAc, pepAd, pepF pepC, pepB, pepD gene, gene fragments thereof, homologous sequences thereto; or immediate chromosomal coding region flanking sequences. A homologous sequence is a nucleic acid sequence having functional similarity to one of the above enumerated sequences and having at least 99%, 98%, 97%, 96%, 95%, 94% 93%, 92%, 91%, 90%, 88%, 85%, 80%, 70% or 60% sequence identity to a derA, derB, htmA, mnn9, mnn10, ochA, dpp4, dpp5, pepAa, pepAb, pepAc, pepAd, pepF, pepB, pepC or pepD gene or gene fragment thereof.

In some embodiments, wherein the genomic DNA is already known the 5' flanking fragment and the 3' flanking fragment of the gene to be deleted is cloned by two PCR reactions, and in embodiments wherein the gene is disrupted, the DNA fragment is cloned by one PCR reaction.

In some embodiments, the coding region flanking sequences include a range of about 1 bp to 2500 bp; about 1 bp to 1500 bp, about 1 bp to 1000 bp, about 1 bp to 500 bp, and 1 bp to 250 bp. The number of nucleic acid sequences comprising the coding region flanking sequence may be different on each end of the gene coding sequence. For example, in some embodiments, the 5' end of the coding sequence includes less than 25 bp and the 3' end of the coding sequence includes more than 100 bp.

In some embodiments, the incoming sequence comprises a selective marker flanked on the 5' and 3' ends with a fragment of the gene sequence. In other embodiments, when the DNA construct comprising the selective marker and gene, gene fragment or homologous sequence thereto is transformed into a host cell, the location of the selective marker renders the gene non-functional for its intended purpose. In some embodiments, the incoming sequence comprises the selective marker located in the promoter region of the gene. In other embodiments, the incoming sequence comprises the selective marker located after the promoter region of gene. In yet other embodiments, the incoming sequence comprises the selective marker located in the coding region of the gene. In further embodiments, the incoming sequence comprises a selective marker flanked by a homology box on both ends. In still further embodiments, the incoming sequence includes a sequence that interrupts the transcription and/or translation of the coding sequence. In yet additional embodiments, the DNA construct includes restriction sites engineered at the upstream and downstream ends of the construct.

Whether the DNA construct is incorporated into a vector or used without the presence of plasmid DNA, it is used to transform a microorganism, which results in an inactivated mutant, preferably having a stable and non-reverting inactivation of the chromosomal gene. Methods used to ligate the DNA construct and to insert them into a suitable vector are well known in the art. Linking is generally accomplished by ligation at convenient restriction sites. If such sites do not exist, the synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology). Examples of suitable expression and/or integration vectors that may be used in the practice of the invention are provided in Sambrook et al., (1989) supra, Ausubel (1987) supra, van den Hondel et al. (1991) in Bennett and Lasure (Eds.) MORE GENE MANIPULATIONS IN FUNGI, Academic Press pp. 396-428 and U.S. Pat. No. 5,874,276. Particularly useful vectors include pFB6, pBR322, pUC18, pUC100 and pENTR/D.

In some embodiments, at least one copy of a DNA construct is integrated into the host chromosome. In some embodiments, one or more DNA constructs of the invention are used to transform host cells. For example, one DNA construct may be used to inactivate a derA gene and another construct may be used to inactivate a derB gene. Of course, additional combinations are contemplated and provided by the present invention.

Inactivation occurs via any suitable means, including deletions, substitutions (e.g., mutations), interruptions, and/or insertions in the nucleic acid gene sequence and gene silencing mechanisms, such as RNA interference (RNAi). In one embodiment, the expression product of an inactivated gene is a truncated protein with a corresponding change in the biological activity of the protein. In preferred embodiments, the inactivation results in a loss of biological activity of the gene. In some embodiments, the biological activity of the inactivated gene in a recombinant fungal cell will be less than 25% (e.g. 20%, 15%, 10%, 5% and 2%) compared to the biological activity of the same or functionally homologous gene in a corresponding parent strain.

In some preferred embodiments, inactivation is achieved by deletion and in other preferred embodiments inactivation is achieved by disruption of the protein-coding region of the gene. In some embodiments, the gene is inactivated by homologous recombination. As used herein, "deletion" of a gene refers to deletion of the entire coding sequence, deletion of part of the coding sequence, or deletion of the coding sequence including flanking regions. The deletion may be partial as long as the sequences left in the chromosome render the gene functionally inactive. In preferred embodiments, a deletion mutant comprises deletion of one or more genes that results in a stable and non-reverting deletion. Flanking regions of the coding sequence may include from about 1 bp to about 500 bp at the 5' and 3' ends. The flanking region may be larger than 500 bp but will preferably not include other genes in the region which may be inactivated or deleted according to the invention. The end result is that the deleted gene is effectively non-functional. In simple terms, a "deletion" is defined as a change in either nucleotide or amino acid sequence in which one or more nucleotides or amino acid residues, respectively, have been removed (i.e., are absent). While not meant to limit the methods used for inactivation in some embodiments, derA, derB, htmA, mnn9, mnn10, pepC, pepB and functionally homologous genes may be inactivated by deletion.

A "disruption" is a change in a nucleotide or amino acid sequence, which has resulted in the addition of one or more nucleotides or amino acid residues, respectively, as compared to the parent or naturally occurring sequence. In some embodiments, the disruption may be by insertion of a marker gene into the protein-coding region in vitro through a restriction enzyme site. Flanking regions of the coding sequence may include about 1 bp to about 500 bp at the 5' and 3' ends. The flanking region may be larger than 500 bp, but will preferably not include other genes in the region. The DNA construct aligns with the homologous sequence of the host chromosome and in a double crossover event the translation or transcription of the gene is disrupted. For example, ochA chromosomal gene is aligned with a plasmid comprising the gene or part of the gene coding sequence and a selective marker. In some embodiments, the selective marker is located within the gene coding sequence or on a part of the plasmid separate from the gene. The vector is integrated into the host chromosome, and the gene is inactivated by the insertion of the marker in the coding sequence. While not meant to limit the methods used for inactivation, in some embodiments ochA, dpp4, dpp5, pepAa, pepAb, pepAc, pepAd, pepF, pepD and functionally homologous sequences may be inactivated by this method.

An "insertion" or "addition" is a change in a nucleic acid or amino acid sequence in which one or more nucleotides or amino acid residues have been added as compared to the endogenous chromosomal sequence or protein product. In some embodiments inactivation is by insertion in a single crossover event with a plasmid as the vector. For example, the vector is integrated into the host cell chromosome and the gene is inactivated by the insertion of the vector in the protein-coding sequence of the gene or in the regulatory region of the gene.

In alternative embodiments, inactivation results due to mutation of the gene. Methods of mutating genes are well known in the art and include but are not limited to site-directed mutation, generation of random mutations, and gapped-duplex approaches (See e.g., U.S. Pat. No. 4,760,025; Moring et al., Biotech. 2:646 [1984]; and Kramer et al., Nucleic Acids Res., 12:9441 [1984]).

Host Cells

In the present invention, the host cell is preferably a filamentous fungal cell (See, Alexopoulos, C. J. (1962), INTRODUCTORY MYCOLOGY, Wiley, N.Y.) preferred filamentous fungal cells include *Aspergillus* sp., (e.g., *A. oryzae, A. niger, A. awamori, A. nidulans, A. sojae, A. japonicus, A. kawachi* and *A. aculeatus*); *Rhizopus* sp., *Trichoderma* sp. (e.g., *Trichoderma reesei* (previously classified as *T. longibrachiatum* and currently also known as *Hypocrea jecorina*), *Trichoderma viride, Trichoderma koningii*, and *Trichoderma harzianums*)) and *Mucor* sp. (e.g., *M. miehei* and *M. pusillus*). Most preferred host cells are *Aspergillus niger* cells. In some embodiments, particular strains of *Aspergillus niger* include ATCC 22342 (NRRL 3112), ATCC 44733, and ATCC 14331 and strains derived there from. In some embodiments, the host cell is one that is capable of expressing a heterologous gene. The host cell may be a recombinant cell, which includes a heterologous protein. In other embodiments, the host is one that overexpresses a protein that has been introduced into the cell. In some embodiments, the host strain is a mutant strain deficient in one or more genes such as genes corresponding to protease genes other than the protease genes disclosed herein. For example a preferred host is an *Aspergillus niger* in which a gene encoding the major secreted aspartyl protease, such as aspergillopepsin has been deleted (U.S. Pat. Nos. 5,840,570 and 6,509,171).

Methods of Determining Gene Inactivations

One skilled in the art may use various methods to determine if a gene has been inactivated. While not meant to limit the invention one method which can be used is the phenol/chloroform method described in Zhu (Zhu et al., *Acat Mycologica Sinica* 13:34-40 [1994]). Briefly, in this method the genomic DNA is used as a template for PCR reactions. Primers are designed so that one primer anneals to a selectable marker gene (e.g., a hygromycin resistant marker gene, hph) and a second primer anneals to a sequence further 3' from the DNA homologous fragment at the 3' end of the gene. An inactivated mutant will produce a specific PCR product when its genomic DNA is used as a PCR reaction template as opposed to the corresponding parent strain (having an non-inactivated gene) which will not generate PCR fragments when its genomic DNA is used as a template. In addition the PCR fragment from the inactivated mutant may be subjected to DNA sequencing to confirm the identity if the inactivated gene. Other useful methods include Southern analysis and reference is made to Sambrook (1989) supra.

Proteins of Interest

In some embodiments an inactivated mutant encompassed by the invention will overexpress a homologous protein of interest and in other embodiments an inactivated mutant encompassed by the invention will express a heterologous protein of interest.

In some embodiments, the protein of interest is intracellular while in other embodiments, the protein of interest is a secreted polypeptide. In addition the protein of interest may be a fusion or hybrid protein. Preferred polypeptides include enzymes, including, but not limited to those selected from amylolytic enzymes, proteolytic enzymes, cellulytic enzymes, oxidoreductase enzymes and plant cell-wall degrading enzymes. More particularly, these enzyme include, but are not limited to amylases, glucoamylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases. Particularly preferred enzymes include but are not limited to amylases, glucoamylases, proteases, phenol oxidases, cellulases, hemicellulases, glucose oxidases and phytases. In some particularly preferred embodiments of the present invention, the polypeptide of interest is a protease, cellulase, glucoamylase or amylase. These enzymes are well known in the art.

In some embodiments, the protein of interest is a secreted polypeptide, which is fused to a signal peptide (i.e., an amino-terminal extension on a protein to be secreted). Nearly all secreted proteins use an amino-terminal protein extension, which plays a crucial role in the targeting to and translocation of precursor proteins across the membrane. This extension is proteolytically removed by a signal peptidase during or immediately following membrane transfer.

In some embodiments of the present invention, the polypeptide of interest is a protein such as a protease inhibitor, which inhibits the action of proteases. Protease inhibitors are known in the art, for example the protease inhibitors belonging to the family of serine proteases inhibitors which are known to inhibit trysin, cathepsinG, thrombin and tissue kallikrein. Particularly preferred protease inhibitors include Bowman-Birk inhibitors and soybean trypsin inhibitors (See, Birk, *Int. J. Pept. Protein Res.* 25:113-131 [1985]; Kennedy, *Am. J. Clin. Neutr.* 68:1406S-1412S [1998] and Billings et al., *Proc. Natl. Acad. Sci.* 89:3120-3124 [1992]).

In some embodiments of the present invention, the polypeptide of interest is selected from hormones, antibodies, growth factors, receptors, cytokines, etc. Hormones encompassed by the present invention include but are not limited to, follicle-stimulating hormone, luteinizing hormone, corticotropin-releasing factor, somatostatin, gonadotropin hormone, vasopressin, oxytocin, erythropoietin, insulin and the like. Growth factors include, but are not limited to platelet-derived growth factor, insulin-like growth factors, epidermal growth factor, nerve growth factor, fibroblast growth factor, transforming growth factors, cytokines, such as interleukins (e.g., IL-1 through IL-13), interferons, colony stimulating factors, and the like. Antibodies include but are not limited to immunoglobulins obtained directly from any species from which it is desirable to produce antibodies. In addition, the present invention encompasses modified antibodies. Polyclonal and monoclonal antibodies are also encompassed by the present invention. In particularly preferred embodiments, the antibodies or fragments thereof are humanized antibodies, such as anti-p185$^{Her2}$ and HuID10-.

In a further embodiment, the nucleic acid encoding the protein of interest will be operably linked to a suitable promoter, which shows transcriptional activity in a fungal host cell. The promoter may be derived from genes encoding proteins either homologous or heterologous to the host cell. The promoter may be a truncated or hybrid promoter. Further the promoter may be an inducible promoter. Preferably, the promoter is useful in a *Trichoderma* host or an *Aspergillus* host. Suitable nonlimiting examples of promoters include cbh1, cbh2, egl1, egf2, xyn1 and amy. In one embodiment, the promoter is one that is native to the host cell. Other examples of useful promoters include promoters from the genes of *A. awamori* and *A. niger* glucoamylase genes (glaA) (Nunberg et al., (1984) *Mol. Cell Biol.* 4:2306-2315 and Boel et al., (1984) *EMBO J.* 3:1581-1585); *Aspergillus oryzae* TAKA amylase; *Rhizomucor miehei* aspartic proteinase; *Aspergillus niger* neutral alpha-amylase; *Aspergillus niger* acid stable alpha-amylase; *Trichoderma reesei* xln1 and the cellobiohydrolase 1 gene promoter (EPA 137280A1) and mutant, truncated and hybrid promoters thereof.

In some preferred embodiments, the polypeptide coding sequence is operably linked to a signal sequence which directs the encoded polypeptide into the cell's secretory pathway. The 5' end of the coding sequence may naturally contain a signal sequence naturally linked in translation reading frame with the segment of the coding region which encodes the secreted polypeptide. The DNA encoding the signal sequence is preferably that which is naturally associated with the polypeptide to be expressed. Preferably, the signal sequence is encoded by an *Aspergillus niger* alpha-amylase, *Aspergillus niger* neutral amylase or *Aspergillus niger* glucoamylase. In some embodiments, the signal sequence is the *Trichoderma* cdh1 signal sequence which is operably linked to a cdh1 promoter.

Transformation of Fungal Cells

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; agrobacterium mediated transformation and protoplast fusion. General transformation techniques are known in the art (See, e.g., Ausubel et al., (1987), supra, chapter 9; and Sambrook (1989) supra, Campbell et al., (1989) *Curr. Genet.* 16:53-56 and THE BIOTECHNOLOGY OF FILAMENTOUS FUNGI, Chap. 6. Eds. Finkelstein and Ball (1992) Butterworth and Heinenmann). The expression of heterologous protein in *Trichoderma* is described in U.S. Pat. No. 6,022,725; U.S. Pat. No. 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to Cao et al., (2000) *Sci.* 9:991-1001 and U.S. Pat. No. 6,509,171 for transformation of *Aspergillus* strains. Transformants are then purified by known techniques.

Cell Culture

The fungal cells may be grown in conventional culture medium. The culture media for transformed cells may be modified as appropriate for activating promoters and selecting transformants. The specific culture conditions, such as temperature, pH and the like will be apparent to those skilled in the art. Preferred culture conditions may be found in the scientific literature such as Sambrook, (1982) supra, and from the American Type Culture Collection. Additionally, fermentation procedures for production of heterologous proteins are known per se in the art. For example, proteins can be produced either by solid or submerged culture, including batch, fed-batch and continuous-flow processes. Fermentation temperature can vary somewhat, but for filamentous fungi such as *Aspergillus niger* the temperature generally will be within the range of about 20° C. to 40° C., generally preferably in the range of about 28° C. to 37° C., depending on the strain of microorganism chosen. The pH range in the aqueous microbial ferment (fermentation admixture) should be in the exemplary range of about 2.0 to 8.0. With filamentous fungi, the pH normally is within the range of about 2.5 to 8.0; with *Aspergillus niger* the pH normally is within the range of about 4.0 to 6.0, and preferably in the range of about 4.5 to 5.5. While the average retention time of the fermentation admixture in the fermentor can vary considerably, depending in part on the fermentation temperature and culture employed, generally it will be within the range of about 24 to 500 hours, preferably presently about 24 to 400 hours. The type of fermentor employed is not critical, though presently preferred is operation under 15 L Biolafitte (Saint-Germain-en-Laye, France).

Methods for Determining Expressed Protein Activity

Various assays are known to those of ordinary skill in the art for detecting and measuring activity of intracellularly and extracellularly expressed polypeptides. Means for determining the levels of secretion of a protein of interest in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS). However, other methods are known to those in the art and find use in assessing the protein of interest (See e.g., Hampton et al., SEROLOGICAL METHODS, A LABORATORY MANUAL, APS Press, St. Paul, Minn. [1990]; and Maddox et al., J. Exp. Med., 158:1211 [1983]). In some preferred embodiments, the expression and/or secretion of a protein of interest are enhanced in an inactivated mutant. In some embodiments the production of the protein of interest is at least 100%, at least 95%, at least 90%, at least 80%, at least 70%, at least 60%, at least 50%, at least 40%, at least 30%, at least 20%, at least 15%, at least 10%, at least 5% and at least 2% greater in the inactivated mutant as compared to the corresponding parent strain.

Protein Recovery

Once the desired protein is expressed and, optionally, secreted the protein of interest may be recovered and further purified. The recovery and purification of the protein of interest from a fermentation broth can be done by procedures known per se in the art. The fermentation broth will generally contain cellular debris, including cells, various suspended solids and other biomass contaminants, as well as the desired protein product.

Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate prior to crystallization using techniques such as ultrafiltration, evaporation or precipitation.

Precipitating the proteinaceous components of the supernatant or filtrate may be accomplished by means of a salt, followed by purification by a variety of chromatographic procedures, e.g., ion exchange chromatography, affinity chromatography or similar art recognized procedures. When the expressed desired polypeptide is secreted the polypeptide may be purified from the growth media. Preferably the expression host cells are removed from the media before purification of the polypeptide (e.g. by centrifugation).

When the expressed recombinant desired polypeptide is not secreted from the host cell, the host cell is preferably disrupted and the polypeptide released into an aqueous "extract" which is the first stage of purification. Preferably the expression host cells are collected from the media before the cell disruption (e.g. by centrifugation).

The manner and method of carrying out the present invention may be more fully understood by those of skill in the art by reference to the following examples, which examples are not intended in any manner to limit the scope of the present invention or of the claims directed thereto.

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); $H_2O$ (water); $dH_2O$ (deionized water); (HCl (hydrochloric acid); aa (amino acid); bp (base pair); kb (kilobase pair); kD (kilodaltons); gm (grams); μg (micrograms); mg (milligrams); μl (microliters); ml (milliliters); mm (millimeters); μm (micrometer); M (molar); mM (millimolar); μM (micromolar); MW (molecular weight); sec (seconds); min(s) (minute/minutes); hr(s) (hour/hours); NaCl (sodium chloride); PBS (phosphate buffered saline [150 mM NaCl, 10 mM sodium phosphate buffer, pH 7.2]); PCR (polymerase chain reaction); SDS (sodium dodecyl sulfate); w/v (weight to volume); v/v (volume to volume); ATCC (American Type Culture Collection, Rockville, Md.); BD BioSciences (Previously CLONTECH Laboratories, Palo Alto, Calif.); Invitrogen (Invitrogen Corp., San Diego, Calif.); and Sigma (Sigma Chemical Co., St. Louis, Mo.).

Table 1 below illustrates the primers (and their sequence identification) used in the examples to make the corresponding gene inactivations.

TABLE 1

| Gene | | Primer Sequence (5' to 3') | SEQ ID NO: |
|------|---|---------------------------|------------|
| derA | P1a | TAGTTAACTCGTCGTCTCCTGGCGGC | 33 |
|      | P2a | AGGTCGACGAAGTATAGGAAGGTTGTGAACAG | 34 |
|      | T1a | AGGGATCCACGTCTGGTACTTCTTCAACG | 35 |
|      | T2a | TCTCGCGATTGGATCAAACCATACGATAC | 36 |
|      | $P_{hph}$ | GAGGGCAAAGGAATAGAGTAG | 37 |
|      | $P_{T-OUT}$a | CTCAGGCAGAGAAGTATTGTC | 38 |
| derB | P1b | CGGTTAACCAGATGGATTTGTCTAATAAGCAG | 39 |
|      | P2b | TGGTCGACGGAGGACATTTTGATTG | 40 |
|      | T1b | AGGGATCCCTAAAGATTATCCGCTTAGTCC | 41 |
|      | T2b | AAGATATCCATCCAAGCTATGCCACATTTTCCTCC | 42 |
|      | $P_{T-OUT}$b | TAGAAGTGGGCATCAAATAG | 43 |
| htmA | P1c | CGGTTAACATATCATATTCGCGATTGGAGTTAC | 44 |
|      | P2c | TATCTCGAGCAAAAGAAATACAGATGAAG | 45 |
|      | T1c | ATGGATCCTAAAGTGCAAGTGTTCGAGACGGTG | 46 |
|      | T2c | AATGATATCCCGCAGTACCATCTCTCC | 47 |
|      | $P_{T-OUT}$c | TCTTGGGGATAATTAGAGGGTG | 48 |

TABLE 1-continued

| Gene | | Primer Sequence (5' to 3') | SEQ ID NO: |
|---|---|---|---|
| mnn9 | P1d | TAGTTAACAGCCCGCCAAAGTCACAAAG | 49 |
| | P2d | AGGTCGACAAGGAGATGAGGAGGAAG | 50 |
| | T1d | TTGGATCCGTCTACGGCTTGCCTGATTAC | 51 |
| | T2d | ACCTCGCGACTTCACTCACAACATTACC | 52 |
| | $P_{T-OUT}$d | CCGACAAGGACGACGAGAAGG | 53 |
| mnn10 | P1e | TCATGCTATTCCTCTTCCGTC | 54 |
| | P2e | AGGCATGCACAAGATGTCAGTG | 55 |
| | T1e | AGGGATCCGGAATTGAACTTGATA | 56 |
| | T2e | TGGTTTAGGATGATGTTGCTGAC | 57 |
| | $P_{T-OUT}$e | TGAATGATACGGTTGGTGATGTTC | 58 |
| ochA | Pf | TAGTTAACACAGCTGTCTGCCAG | 59 |
| | Tf | AGGTTAACATATGTCAAGAGATCAAAGTGC | 60 |
| | $P_{T-OUT}$f | ACAGCAAGATGTTGTCGTTC | 61 |
| dpp4 | Pg | AGTCGCGAGATGTAGAAGAGGGAGAAG | 62 |
| | Tg | AGTCGCGAGCGTGTTTTGAATGTG | 63 |
| | $P_{T-OUT}$g | TCTGGATAGAAATGCAAATCGTAG | 64 |
| dpp5 | Ph | TGCCAGGTCCAGCCTTACAAAGAAG | 65 |
| | Th | ACGATATCAGCATCCACAACACCCATAATC | 66 |
| | $P_{T-OUT}$h | TCGTTATAGCTTCGTACACAATG | 67 |
| pepAa | Pi | GCACTTCTTTCCCCTTTTTGTTTAC | 68 |
| | Ti | AGGTTAACTTGAATTGTAGATACAGCCAC | 69 |
| | $P_{T-OUT}$i | TCATGGATTAGGGTTAGAAAGAGTG | 70 |
| pepAb | Pj | ACGTTAACCATATCACAGCTATATCCCC | 71 |
| | Tj | ACGTTAACGCCAGGTCCTCCTTCTGC | 72 |
| | $P_{T-OUT}$j | GGAGAGATAGGACGTAAACTTCATG | 73 |
| pepAd | Pk | TGGTTAACTCGTAAGTAGGTAGGCTGTAC | 74 |
| | Tk | ATGTTAACCCGAGGTGCTGCTTG | 75 |
| | $P_{T-OUT}$k | AGAGCAGAGAAGAAATACTGAGGAG | 76 |
| pepF | Pl | AGGTTAACTTGGCTTGGCGAAGCAAACTC | 77 |
| | Tl | AGGTTAACATCAGCGCGGTCAAAGTAG | 78 |
| | $P_{T-OUT}$l | TCTGACGGGAGCGGACAGTCATG | 79 |
| pepB | P1m | CCGTTAACCCTCCACGTATTCCAATATACC | 80 |
| | P2m | AAGTCGACACCAGTCTGGAGAATAGCGG | 81 |
| | T1m | CGGGATCCTTGAGGGTGATCTTTGCGAGACCAAC | 82 |
| | T2m | GGGTTAACATGTCGCATTACTCCTGGCTGAAG | 83 |
| | $P_{T-OUT}$m | TCGTTATAGCTTCGTACACAATG | 84 |
| pepC | P1n | AAGTTAACCGTTTCCGTAGCATTGCCCG | 85 |
| | P2n | TCGTCGACAGTGAGTTCCGTGACCATTGCC | 86 |
| | T1n | CTGGATCCAAGCTGAAGAAGAACATCATCG | 87 |
| | T2n | TAGATATCTGTCTATTCTATATGAAGCCCCTC | 88 |
| | $P_{T-OUT}$n | ATACAGCACAGTCTATCAATATGAG | 89 |
| pepD | Po | TAAGGCCTAGCAAGCAATCAGTG | 90 |
| | To | AACAGAAAGGACCAATAACAAACGG | 91 |
| | $P_{T-OUT}$o | ACAAGAACCTGTCTCCAGTATGAG | 92 |
| pepAc | Pp | TGGTTAACGAGGGATTGCTCTATTG | 93 |
| | Tp | TGGTTAACTGTGCTATGCTATTGGTG | 94 |
| | $P_{T-OUT}$p | TCTGCTCGTCGGTGGTTGTG | 95 |

Example 1

Creation of *Aspergillus* Deletion Constructs and Strains

Yeast genes known to be involved in endoplasmic reticulum (ER) degradation [Der1 gene (M. Knop et al, [1996] *EMBO J.* 15:753-763), Der2 gene (Hiller et al, [1996] *Science* 273:1725-1728) and Htm1 gene (C. Jakob et al, [2001] *EMBO report* 21:423-430)] and glycosylation [(Mnn9 gene (Yip et al., [1994] *Proc. Natl Acad. Sci.* 91:2723-2727, Mnn10 (Dean et al., [1996] *Glycobiol.* 6:73-81 and Och1 (Nakayama et al. [1992] *EMBO J* 11:2511-2519)] were used to search an *Aspergillus* genomic sequence database to find homologous genes. The ddp4 and dpp5 genes were from the *Aspergillus* genomics database based on the annotation of the genes. *Aspergillus niger* pepA gene (Berka et al. [1990] *Gene* 86:153-162) was used to search the *Aspergillus* genomic sequence database to find homologous genes (pepAa, pepAb, pepAc and pepAd). *A. niger* pepB (Inoue et al. [1991] *J. Biol. Chem* 266:19484-19489); pepC (Frederick et al., [1993] *Gene* 125:57-64); pepD (Jarai et al., [1994] *Gene* 139:51-57) and pepF (van den Hombergh et al., [1994] *Gene* 151:73-79) can be found in public databases.

a. Deletion of the derA Gene.

FIG. 1 (SEQ ID NO: 1) sets forth the 2400 bp genomic DNA sequence of the *Aspergillus* derA gene and FIG. 2 (SEQ ID NO: 2) sets forth the 246 amino acids sequence translated from the derA genomic DNA of FIG. 1.

To construct the deletion plasmid, two pairs of PCR primers were designed. The first pair of PCR primers amplify the promoter region of the gene and they are indicated in Table 1 as SEQ ID NO: 33 (P1a) and SEQ ID NO: 34 (P2a). The second pair of PCR primers amplifies the terminator region of gene and they are indicated in Table 1 as SEQ ID NO: 35 (T1a) and SEQ ID NO: 36 (T2a). The terminator fragment DNA sequence (T1) was amplified in PCR using the following conditions: the PCR tube was heated at 94° C. for 3 minutes to denature template DNA. Then, the PCR reaction was run at 94° C. for 1 minute, 57° C. for 1 minute and 72° C. for 1 minute 30 seconds and this cycle was repeated 30 times. Finally, PCR reaction was extended at 72 C for 10 minutes before the tube was incubated at 4° C. The ends of the T1 fragment were then filled in with T4 DNA polymerase and then cut with restriction enzyme (BamH1). This modified PCR fragment was then cloned to pMW1 (Ulrich Kuck et al., [1989] *Appl. Micorbiol. Biotechnol.* 31:358-365) to construct plasmid pMW1-T1(derA).

The promoter DNA sequence, (the P1 fragment), was amplified in PCR reaction using the same condition as the T1 fragment with two primers (SEQ ID NO: 33 and SEQ ID NO: 34). The ends of the P1 fragment were then filled in with T4 DNA polymerase and cut with restriction enzyme SalI. This modified PCR fragment was cloned to pMW1-T1(derA) to generate pMW1-ΔderA. The plasmid was analyzed by restriction enzyme digestion to confirm its identity. The plasmid was linearized by two restriction enzymes digestion (HapI and NruI).

The digested DNA fragment was used to transform a derivative of an AP-4 *Aspergillus niger* strain (Ward et al. [1993] Appli. Microbiol. Biotechnol 39:738-743) comprising an expression plasmid expressing *Tramete versicolor* laccase under the glucoamylase promoter and terminator control.

FIG. 33A illustrates the general strategy used to make the deletion plasmids used in the examples provided and as described in detail herein.

The transformation protocol utilized was a modification of the Campbell method (Campbell et at. 1989. *Curr. Genet.* 16:53-56) wherein the beta-D-glucinase G (InterSpex Products, Inc. San Mateo, Calif.) was used to produce protoplasts and pH was adjusted to 5.5. All solutions and media were either autoclaved or filter sterilized through a 0.2 micron filter. The DNA was extracted from transformants using a phenol/chloroform method (Zhu et al. 1993. *Nucleic Acid Res.* 21:5279-80). The deletion strain was detected by PCR using two primers SEQ ID NO: 37 ($P_{hph}$) and SEQ ID NO: 38 ($P_{t-out}$a), which gave a specific PCR product of 1064 bp when the DNA from the deletion strain was used as template for PCR amplification while no band was seen when the DNA was from the parent strain (FIG. 34).

b. Deletion of the derB Gene.

FIG. 3 (SEQ ID NO: 3) sets forth the 2673 bp genomic DNA sequence of the *Aspergillus* derB gene and FIG. 4 (SEQ ID NO: 4) sets forth the 166 amino acid sequence translated from the derA genomic DNA of FIG. 3. The deletion plasmids were constructed as described above for Example 1a with the following differences.

The first pair of PCR primers used to amplify the promoter region are designated in Table 1 as SEQ ID NO: 39 (P1b) and SEQ ID NO: 40 (P2b). The second pair of primers used to amplify the terminator region are designated in Table 1 as SEQ ID NO: 41 (T1b) and SEQ ID NO: 42 (T2b). In this example, the ends of the T2 fragment were filled in with T4 DNA polymerase and then cut with restriction enzyme (BamHI). The modified PCR fragment was then cloned to pMW1 to construct plasmid pMW1-T2(derB). The P2 fragment was amplified in PCR reaction using the same conditions as the P1 fragment. The ends of the P2 fragment were then filled in with T4 DNA polymerase and cut with restriction enzyme SalI.

This modified PCR fragment was cloned to pMW1-T2 (derB) to generate pMW1-ΔderB. The plasmid was analyzed by restriction enzyme as described above in Example 1a. The plasmid was linearized by two restriction enzymes digestion (HpaI and EcoRV).

The digested DNA fragment was used to transform *Aspergillus niger* and DNA was extracted from the transformants as described above for example 1A. The deletion strain was detected by PCR using two primers SEQ ID NO: 37 and SEQ ID NO: 43 ($P_{t-out}$b), which gave a specific PCR product of 694 bp when the DNA from the deletion strain was used as template for PCR amplification while no band was seen when the DNA was from the parent strain. However, the wild type band was also identified from the deletion strain.

c. Deletion of the htmA Gene.

FIG. 5 (SEQ ID NO: 5) sets forth the 7000 bp genomic DNA sequence of the *Aspergillus* htmA gene and FIG. 6 (SEQ ID NO: 6) sets forth the 1076 amino acid sequence translated from the htmA genomic DNA of FIG. 5. The deletion plasmids were constructed as described above for Example 1a with the following differences.

The first pair of PCR primers used to amplify the promoter region are designated in Table 1 as SEQ ID NO: 44 (P1c) and SEQ ID NO: 45 (P2c). The second pair of primers used to amplify the terminator region are designated in Table 1 as SEQ ID NO: 46 (T1c) and SEQ ID NO: 47 (T2c). In this example, the P3 and T3 fragments were amplified in PCR reactions using the same conditions as the P1 and T1 fragments. The ends of the T3 fragment were filled in with T4 DNA polymerase and then cut with restriction enzyme (BamHI). The modified PCR fragment was then cloned to pMW1 to construct plasmid pMW1-T3(htmA). The ends of the P3 fragment were then filled in with T4 DNA polymerase and cut with restriction enzyme XhoI. This modified PCR fragment was cloned to pMW1-T3(htmA) to generate pMW1-ΔhtmA. The plasmid was analyzed by restriction enzyme as described above in Example 1a. The plasmid was linearized by two restriction enzymes digestion (HpaI and EcoRV).

The digested DNA fragment was used to transform *Aspergillus niger* GAP3-4 (Ward et al. [1993] Appl. Microbiol. Biotechnol. 39:738-743) and DNA was extracted from the transformants as described above for example 1A. The deletion strain was detected by PCR using two primers SEQ ID NO: 37 and SEQ ID NO: 48 ($P_{t-out}$c), which gave a specific PCR product of 1497 bp when the DNA from the deletion strain was used as template for PCR amplification while no band was seen when the DNA was from the parent strain.

d. Deletion of the mnn9 Gene.

FIG. 7 (SEQ ID NO: 7) sets forth the 4947 bp genomic DNA sequence of the *Aspergillus* mnn9 gene and FIG. 8 (SEQ ID NO: 8) sets forth the 369 amino acid sequence translated from the mnn9 genomic DNA of FIG. 7. The deletion plasmids were constructed as described above for Example 1a with the following differences.

The first pair of PCR primers used to amplify the promoter region are designated in Table 1 as SEQ ID NO: 49 (P1d) and SEQ ID NO: 50 (P2d). The second pair of primers used to amplify the terminator region are designated in Table 1 as SEQ ID NO: 51 (T1d) and SEQ ID NO: 52 (T2d).

In this example, the ends of the P4 fragment were filled with T4 DNA polymerase and then cut with restriction enzyme (SalI). The modified PCR fragment was cloned to pMW1 to construct plasmid pMW1-P4 (mnn9). The ends of the T4 fragment were filled in with T4 DNA polymerase and then cut with restriction enzyme (BamHI). The modified PCR fragment was then cloned to pMW1-P (mnn9) to generate plasmid pMW1-Δmnn9. The plasmid was analyzed by restriction enzyme as described above in Example 1a. The plasmid was linearized by two restriction enzymes (HpaI and NruI).

The digested DNA fragment was used to transform *Aspergillus niger* and DNA was extracted from the transformants as described above for example 1a. The deletion strain was detected by PCR using two primers SEQ ID NO: 37 and SEQ ID NO: 53 ($P_{t-out}$d), which gave a specific PCR product of 1330 bp when the DNA from the deletion strain was used as template for PCR amplification (FIG. 34A, lane 7). No band was seen when the DNA was from the parent strain (FIG. 34A, lane 3).

e. Deletion of the mnn10 Gene.

FIG. 9 (SEQ ID NO: 9) sets forth the 4524 bp genomic DNA sequence of the *Aspergillus* mnn10 gene and FIG. 10 (SEQ ID NO: 10) sets forth the 466 amino acid sequence translated from the mnn10 genomic DNA of FIG. 9. The deletion plasmids were constructed as described above for Example 1a with the following differences.

The first pair of PCR primers used to amplify the promoter region are designated in Table 1 as SEQ ID NO: 54 (P1e) and SEQ ID NO: 55 (P2e). The second pair of primers used to amplify the terminator region are designated in Table 1 as SEQ ID NO: 56 (T1e) and SEQ ID NO: 57 (T2e).

In this example, the ends of the P5 fragment were filled in with T4 DNA polymerase and then cut with restriction enzyme (SphI). The modified PCR fragment was then cloned to pMW1 to construct plasmid pMW1-P5 (mnn10). The ends of the T5 fragment were filled in with T4 DNA polymerase and then cut with restriction enzyme (BamHI). The modified PCR fragment was cloned to pMW1-P5 (mnn10) to generate plasmid pMW1-Δmnn10. The plasmid was analyzed by restriction enzyme as described above in Example 1a. The plasmid was linearized by two restriction enzymes (NruI and EcoRV).

The digested DNA fragment was used to transform *Aspergillus niger* and DNA was extracted from the transformants as described above for example 1a. The deletion strain was detected by PCR using two primers SEQ ID NO: 37 and SEQ ID NO: 53 ($P_{t-out}e$), which gave a specific PCR product of 1295 bp when the DNA from the deletion strain was used as template for PCR amplification while no band was seen when the DNA was from the parent strain.

f. Disruption of the ochA Gene.

FIG. 11 (SEQ ID NO: 11) sets forth the 6724 bp genomic DNA sequence of the *Aspergillus* ochA gene and FIG. 12 (SEQ ID NO: 12) sets forth the 380 amino acid sequence translated from the ochA genomic DNA of FIG. 11. The disruption plasmids were constructed as described above for Example 1a with the following differences.

The PCR primer used to amplify the promoter region is designated in Table 1 as SEQ ID NO: 59 (Pf) and the primer used to amplify the terminator region is designated in Table 1 as SEQ ID NO: 60 (Tf). Using these primers, the coding region of the ochA gene including the promoter region of 80 bp and terminator region of 624 bp was amplified. The DNA sequence, named the W6 fragment, was amplified in a PCR reaction using the following conditions: The PCR tube was heated at 94° C. for 4 min to denature template DNA, the PCR reaction was then run at 94° C. for 1 min, 55° C. for 2 min, and 72° C. for 1 min 30 sec and this cycle was repeated 30 times. The PCR reaction was extended at 72° C. for 10 min before the tube was incubated at 4° C. The produced 1787 bp PCR fragment W6 was cloned to pBS-T, a TA vector derived from pBlue-script (Tian Wei Biotech. Co. Ltd) to construct plasmid pBS-W6 (ochA). The DNA fragment containing the hygromycin resistant gene was inserted into the coding region of the ochA gene at the EcoRV site to generate pBS-disruption ochA. The plasmid was linearized by restriction enzyme (HpaI) digestion.

FIG. 33B illustrates the general strategy used to make the disruption plasmids used in the examples provided and as described in detail herein.

The digested DNA fragment was used to transform *Aspergillus niger* and DNA was extracted from the transformants as described above for example 1a. The deletion strain was detected by PCR using two primers SEQ ID NO: 37 and SEQ ID NO: 61 ($P_{t-out}f$), which gave a specific PCR product of 1336 bp when the DNA from the disruption strain was used as template for PCR amplification (FIG. 34B, lane 7), while no band was seen when the DNA was from the parent strain (FIG. 34B, lane 3).

g. Disruption of the dpp4 Gene.

FIG. 13 (SEQ ID NO: 13) sets forth the 3989 bp genomic DNA sequence of the *Aspergillus* ddp4 gene and FIG. 14 (SEQ ID NO: 14) sets forth the 915 amino acid sequence translated from the dpp4 genomic DNA of FIG. 13. The disruption plasmids were constructed as described above for Example 1f with the following differences.

The PCR primer used to amplify the promoter region is designated in Table 1 as SEQ ID NO: 62 (Pg) and the primer used to amplify the terminator region is designated in Table 1 as SEQ ID NO: 63 (Tg). Using these primers, the 950-3356 by region of the coding region (817-3663) of the ddp4 gene was amplified.

The produced 2407 bp PCR fragment W7 was cloned to pBS-T to construct plasmid pBS-W7 (ddp4). The DNA fragment containing the hygromycin resistant gene was inserted into the coding region of the dpp4 gene at the EcoRI-EcoRI (2175-2257 bp) site to generate pBS-disruption dpp4. The plasmid was linearized by restriction enzyme digestion (NruI).

The digested DNA fragment was used to transform *Aspergillus niger* and DNA was extracted from the transformants as described above for example 1a. The deletion strain was detected by PCR using two primers SEQ ID NO: 37 and SEQ ID NO: 64 ($P_{t-out}g$), which gave a specific PCR product of 1191 bp when the DNA from the disruption strain was used as template for PCR amplification while no band was seen when the DNA was from the parent strain.

h. Disruption of the dpp5 Gene.

FIG. 15 (SEQ ID NO: 15) sets forth the 2647 bp genomic DNA sequence of the *Aspergillus* dpp5 gene and FIG. 16 (SEQ ID NO: 16) sets forth the 726 amino acid sequence translated from the dpp5 genomic DNA of FIG. 15. The disruption plasmids were constructed as described above for Example 1f with the following differences.

The PCR primer used to amplify the promoter region is designated in Table 1 as SEQ ID NO: 65 (Ph) and the primer used to amplify the terminator region is designated in Table 1 as SEQ ID NO: 66 (Th).

Using these primers, the 195-2490 bp region of the coding region (1-2647 bp) of the dpp5 gene was amplified. The produced 2295 bp PCR fragment W8 was cloned to pBS-T to construct plasmid pBS-W8 (dpp5). The DNA fragment containing the hygromycin resistant gene was inserted into the coding region of the dpp5 gene at the BglII site to generate pBS-disruption dpp5. The plasmid was linearized by restriction enzyme (EcoRV) digestion.

The digested DNA fragment was used to transform *Aspergillus niger* and DNA was extracted from the transformants as described above for example 1a. The deletion strain was detected by PCR using two primers SEQ ID NO: 37 and SEQ ID NO: 67 ($P_{t-out}h$), which gave a specific PCR product of 1282 bp when the DNA from the disruption strain was used as template for PCR amplification while no band was seen when the DNA was from the parent strain.

i. Disruption of the pepAa Gene.

FIG. 17 (SEQ ID NO: 17) sets forth the 2777 bp genomic DNA sequence of the *Aspergillus* pepAa gene and FIG. 18 (SEQ ID NO: 18) sets forth the 394 amino acid sequence translated from the pepAa genomic DNA of FIG. 17.

The PCR primer used to amplify the promoter region is designated in Table 1 as SEQ ID NO: 68 (Pi) and the primer used to amplify the terminator region is designated in Table 1 as SEQ ID NO: 69 (Ti).

Using these primers, the coding region of the pepAa gene and some promoter region (355 bp) and terminator region (326 bp) was amplified. The DNA sequence, named as the W9 fragment was amplified in a PCR reaction as described above for Example 1f with the following differences.

The produced 1920 bp PCR fragment W9 was cloned to pBS-T to construct plasmid pBS-W9 (pepAa). The DNA fragment containing the hygromycin resistant gene was inserted into the coding region of the pepAa gene at the BstBI site to generate pBS-disruption pepAa. The plasmid was linearized by restriction enzyme (HpaI) digestion.

The digested DNA fragment was used to transform *Aspergillus niger* and DNA was extracted from the transformants as described above for example 1a. The deletion strain was detected by PCR using two primers SEQ ID NO: 37 and SEQ ID NO: 70 ($P_{t-out}$i), which gave a specific PCR product of 1140 bp when the DNA from the disruption strain was used as template for PCR amplification while no band was seen when the DNA was from the parent strain.

i. Disruption of the pepAb Gene.

FIG. 19 (SEQ ID NO: 19) sets forth the 3854 bp genomic DNA sequence of the *Aspergillus* pepAb gene and FIG. 20 (SEQ ID NO: 20) sets forth the 417 amino acid sequence translated from the pepAb genomic DNA of FIG. 19.

The PCR primer used to amplify the promoter region is designated in Table 1 as SEQ ID NO: 71 (Pj) and the primer used to amplify the terminator region is designated in Table 1 as SEQ ID NO: 72 (Tj).

Using these primers, the coding region of the pepAb gene and some promoter region (1025 bp) was amplified. The DNA sequence, named as the W10 fragment was amplified in a PCR reaction as described above for Example 1f with the following differences.

The produced 2170 bp PCR fragment W10 was cloned to pBS-T to construct plasmid pBS-W10 (pepAb). The DNA fragment containing the hygromycin resistant gene was inserted into the coding region of the pepAb gene at the Eco47III site to generate pBS-disruption pepAb. The plasmid was linearized by restriction enzyme (HpaI) digestion.

The digested DNA fragment was used to transform *Aspergillus niger* and DNA was extracted from the transformants as described above for example 1a. The deletion strain was detected by PCR using two primers SEQ ID NO: 37 and SEQ ID NO: 73 ($P_{t-out}$j), which gave a specific PCR product of 1191 bp when the DNA from the disruption strain was used as template for PCR amplification while no band was seen when the DNA was from the parent strain.

k. Disruption of the pepAd Gene.

FIG. 21 (SEQ ID NO: 21) sets forth the 2411 bp genomic DNA sequence of the *Aspergillus* pepAd gene and FIG. 22 (SEQ ID NO: 22) sets forth the 480 amino acid sequence translated from the pepAd genomic DNA of FIG. 21.

The PCR primer used to amplify the promoter region is designated in Table 1 as SEQ ID NO: 74 (Pk) and the primer used to amplify the terminator region is designated in Table 1 as SEQ ID NO: 75 (Tk).

Using these primers, the 1201 bp coding region of the 1443 bp pepAd gene and some promoter region (858 bp) was amplified. The DNA sequence, named as the W11 fragment was amplified in a PCR reaction as described above for Example 1f with the following differences.

The produced 2059 bp (23-2081 bp) PCR fragment W11 was cloned to pBS-T to construct plasmid pBS-W11 (pe-pAd). The DNA fragment containing the hygromycin resistant gene was inserted into the coding region of the pepAd gene at the AauI site to generate pBS-disruption pepAd. The plasmid was linearized by restriction enzyme (HpaI) digestion.

The digested DNA fragment was used to transform *Aspergillus niger* and DNA was extracted from the transformants as described above for example 1a. The deletion strain was detected by PCR using two primers SEQ ID NO: 37 and SEQ ID NO: 76 ($P_{t-out}$h), which gave a specific PCR product of 1086 bp when the DNA from the disruption strain was used as template for PCR amplification while no band was seen when the DNA was from the parent strain.

l. Disruption of the pepF Gene.

FIG. 23 (SEQ ID NO: 23) sets forth the 3525 bp genomic DNA sequence of the *Aspergillus* pepF gene and FIG. 24 (SEQ ID NO: 24) sets forth the 531 amino acid sequence translated from the pepF genomic DNA of FIG. 23. The disruption plasmids were constructed as described above for Example 1f with the following differences.

The PCR primer used to amplify the promoter region is designated in Table 1 as SEQ ID NO: 77 (PI) and the primer used to amplify the terminator region is designated in Table 1 as SEQ ID NO: 78 (TI).

Using these primers, the coding region of the pepF gene and some promoter region (1058 bp) was amplified. The DNA sequence, named as the W12 fragment was amplified in a PCR reaction as described above for Example 1f.

The produced 2350 bp PCR fragment W12 was cloned to pBS-T to construct plasmid pBS-W12 (pepF). The DNA fragment containing the hygromycin resistant gene was inserted into the coding region of the pepF gene at the NruI site to generate pBS-disruption pepF. The plasmid was linearized by restriction enzyme (HpaI) digestion.

The digested DNA fragment was used to transform *Aspergillus niger* and DNA was extracted from the transformants as described above for example 1a. The deletion strain was detected by PCR using two primers SEQ ID NO: 37 and SEQ ID NO: 79 ($P_{t-out}$l), which gave a specific PCR product of 1231 bp when the DNA from the disruption strain was used as template for PCR amplification while no band was seen when the DNA was from the parent strain.

m. Deletion of the pepB Gene.

FIG. 25 (SEQ ID NO: 25) sets forth the 3000 bp genomic DNA sequence of the *Aspergillus* pepB gene and FIG. 26 (SEQ ID NO: 26) sets forth the 282 amino acid sequence translated from the pepB genomic DNA of FIG. 25. The deletion plasmids were constructed as described above for Example 1a with the following differences.

The first pair of PCR primers used to amplify the promoter region are designated in Table 1 as SEQ ID NO: 80 (P1m) and SEQ ID NO: 81 (P2m). The second pair of primers used to amplify the terminator region are designated in Table 1 as SEQ ID NO: 82 (T1m) and SEQ ID NO: 83 (T2m).

In this example, the ends of the P13 fragment were filled in with T4 DNA polymerase and then cut with restriction enzyme (SalI). The modified PCR fragment was then cloned to pMW1 to construct plasmid pMW1-P13 (pepB). The ends of the T13 fragment were filled in with T4 DNA polymerase. The modified PCR fragment was then cloned to pMW1-P13 (pepB) to generate plasmid pMW1-ΔpepB. The plasmid was analyzed by restriction enzyme as described above in Example 1a. The plasmid was linearized by restriction enzyme (HpaI) digestion.

The digested DNA fragment was used to transform *Aspergillus niger* and DNA was extracted from the transformants as described above for example 1a. The deletion strain was detected by PCR using two primers SEQ ID NO: 37 and SEQ ID NO: 84 ($P_{t-out}$m), which gave a specific PCR product of 1357 bp when the DNA from the deletion strain was used as template for PCR amplification while no band was seen when the DNA was from the parent strain.

n. Deletion of the pepC Gene.

FIG. 27 (SEQ ID NO: 27) sets forth the 3220 bp genomic DNA sequence of the *Aspergillus* pepC gene and FIG. 28 (SEQ ID NO: 28) sets forth the 533 amino acid sequence translated from the pepC genomic DNA of FIG. 27. The deletion plasmids were constructed as described above for Example 1a with the following differences.

The first pair of PCR primers used to amplify the promoter region are designated in Table 1 as SEQ ID NO: 85 (P1n) and SEQ ID NO: 86 (P2n). The second pair of primers used to amplify the terminator region are designated in Table 1 as SEQ ID NO: 87 (T1n) and SEQ ID NO: 88 (T2n).

In this example, the ends of the T14 fragment were filled in with T4 DNA polymerase and then cut with restriction enzyme (BamHI). The modified PCR fragment was then cloned to pMW1 to construct plasmid pMW1-T14 (pepC). The ends of the P14 fragment were filled in with T4 DNA polymerase and cut with restriction (SalI). The modified PCR fragment was then cloned to pMW1-P14 (pepC) to generate plasmid pMW1-ΔpepC. The plasmid was analyzed by restriction enzyme as described above in Example 1a. The plasmid was linearized by two restriction enzymes (HpaI and EcoRV) digestion.

The digested DNA fragment was used to transform *Aspergillus niger* strain GAP3-4 (Ward et al. [1993] Appl. Microbiol. Biotechnol. 39:738-743) and DNA was extracted from the transformants as described above for example 1a. The deletion strain was detected by PCR using two primers SEQ ID NO: 37 and SEQ ID NO: 89 ($P_{t-out}$n), which gave a specific PCR product of 1054 bp when the DNA from the deletion strain was used as template for PCR amplification while no band was seen when the DNA was from the parent strain.

o. Disruption of the pepD Gene.

FIG. 29 (SEQ ID NO: 29) sets forth the 2993 bp genomic DNA sequence of the *Aspergillus* pepD gene and FIG. 30 (SEQ ID NO: 30) sets forth the 416 amino acid sequence translated from the pepD genomic DNA of FIG. 29. The disruption plasmids were constructed as described above for Example 1f with the following differences.

The PCR primer used to amplify the promoter region is designated in Table 1 as SEQ ID NO: 90 (Po) and the primer used to amplify the terminator region is designated in Table 1 as SEQ ID NO: 91 (To).

Using these primers, the coding region of the pepD gene and some promoter region (392 bp) and terminator region (521 bp) were amplified. The DNA sequence, named as the W15 fragment was amplified in a PCR reaction as described above for Example 1f. The produced 2317 bp PCR fragment W15 was cloned to pBS-T to construct plasmid pBS-W15 (pepD). The DNA fragment containing the hygromycin resistant gene was inserted into the coding region of the pepD gene at the BstBI site to generate pBS-disruption pepD. The plasmid was linearized by restriction enzyme digestion (StuI).

The digested DNA fragment was used to transform *Aspergillus niger* and DNA was extracted from the transformants as described above for example 1f. The disruption strain was detected by PCR using two primers SEQ ID NO: 37 and SEQ ID NO: 92 ($P_{t-out}$o), which gave a specific PCR product of 1344 bp when the DNA from the disruption strain was used as template for PCR amplification while no band was seen when the DNA was from the parent strain.

p. Disruption of the pepAc Gene.

FIG. 31 (SEQ ID NO: 31) sets forth the 4531 bp genomic DNA sequence of the *Aspergillus* pepAc gene and FIG. 32 (SEQ ID NO: 32) sets forth the 453 amino acid sequence translated from the pepAc genomic DNA of FIG. 31. The disruption plasmids were constructed as described above for Example 1f with the following differences.

The PCR primer used to amplify the promoter region is designated in Table 1 as SEQ ID NO: 93 (Pp) and the primer used to amplify the terminator region is designated in Table 1 as SEQ ID NO: 94 (Tp).

Using these primers, the coding region of the pepAc gene, some promoter region (789 bp) and some terminator region (509) were amplified. The DNA sequence, named the W16 fragment was amplified in a PCR reaction.

The produced 2753 bp PCR fragment W16 was cloned to pBS-T to construct plasmid pBS-W16 (pepAc). The DNA fragment containing the hygromycin resistant gene was inserted into the coding region of the pepAc gene at the EcoRV site to generate pBS-disruption pepAc. The plasmid was linearized by restriction enzyme (HpaI) digestion.

The digested DNA fragment was used to transform *Aspergillus niger* and DNA was extracted from the transformants as described above for example 1f. The disruption strain was detected by PCR using two primers SEQ ID NO: 37 and SEQ ID NO: 95 ($P_{t-out}$p), which would give a specific PCR product of 1520 bp when the DNA from the disruption strain was used as template for PCR amplification while no band was seen when the DNA was from the parent strain.

Example 2

Inactivated Double Deletion Mutants a. Disruption of dpp4 and dpp5.

To construct the dpp4 (amdS) deletion plasmid, the 2.7 kb DNA fragment containing the amdS gene was inserted into the coding region (position 950 to 3356) of the dpp4 gene at the EcoRV-EcoRV site (position 2175 to 2256) in plasmid pBS-W7 (dpp4) to generate plasmid pBS-disruption ddp4 (amdS). The plasmid was analyzed by restriction enzyme digestion to confirm its identity. The plasmid was linearized by restriction enzyme digestion (NruI). The digested DNA fragment was used to transform *A. niger* strain (Δdpp5-19) which expresses a Tramete laccase under the glucoamylase promoter and terminator control and carrying the disrupted dpp5 gene (as described in Example 1h). The double deletion strain was detected by PCR using two pairs of primers. The two primers of the first pair each respectively annealing to the amdS gene and 3' downstream the W7 fragment on the chromosomal DNA which gave a specific PCR product of 1224 bp when the DNA from dpp4 deletion strain was used as a template for PCR amplification while no band was seen when the DNA was from the recipient strain.

Primers:

SEQ ID NO: 64
$P_{out (dpp4)}$   5'-TCTGGATAGAAATGCAAATCGTAG-3'

SEQ ID NO: 96
$P_{amdS}$   5'-TTTCCAGTCTAGACACGTATAACGGC-3'

The second pair of primers was the same as the originally used primers for detection of the single dpp5 deletion strain (SEQ ID NOs: 37 and 67). The double deletion strain and its control strains were used for production of laccase and total protein production.

b. Disruption of mnn9 and ochA.

To construct the mnn9 (amdS) deletion plasmid, the 2.7 kb DNA fragment containing the amdS gene was inserted into the pMW1-Δmnn9 (the amdS fragment directly replacing the hph fragment) to generate plasmid pMW1-disruption mnn9 (amdS). The plasmid was analyzed by restriction enzyme digestion to confirm its identity. The plasmid was linearized by restriction enzyme digestion (AsuII-NruI). The digested DNA fragment was used to transform *A. niger* strain (ΔochA-23) which expresses a Tramete laccase under the glucoamylase promoter and terminator control and carrying the disrupted ochA gene as described in Example 1f. The double deletion strain was detected by PCR using two pairs of primers. The two primers of the first pair each respectively annealing to the amdS gene and 3' downstream the T4 fragment on the chromosomal DNA which gave a specific PCR product of 1380 bp when the DNA from mnn9 deletion strain was used as a template for PCR amplification while no band was seen when the DNA was from the recipient strain.

Primers:

```
                                            SEQ ID NO: 53
P_out(mnn9)   5'-GATATCAACCTCAGCGTCAAATTGG-3'

SEQ ID NO: 97
P_amdS        5'-TTTCC AGTCT AGACA CGTAT AACGGC-3'
```

The second pair of primers was the same as the originally used primers for detection of the single ochA deletion strain (SEQ ID NOs: 37 and 61). The double deletion strain and its control strains were then used for production of the laccase and total protein production.

Example 3

Use of Inactivated Mutants for the Production of a Heterologous Protein

To illustrate the advantages of using the inactivated mutant according to the invention, production of laccase in the parent (wild-type) was compared to the production of laccase in inactivated mutants as described above in examples 1 and 2.

Assays were performed in shake flask cultures using 250 ml baffled flasks containing 50 mL of growth media (Promosoy) suitable for laccase production as known in the art. The strains were grown in shake flasks for 120 hrs. Laccase activity was measured following a standard assay procedure based on the oxidation of ABTS; 2,2'-azino-bis(3-ethylbenzothiazoline-6-sulfonate by oxygen in sodium acetate buffer (pH 4.6). The culture broths were incubated with ABTS in sodium acetate buffer (SIGMA) at 37° C. for 30 min and color formation was measured at an optical density of OD 420 nM. The level of laccase produced by the inactivated strain was measured relative to the corresponding parent strain. Results are illustrated in Table 2A and 2B. Total extracellular protein was measured using the Folin phenol method as described in Lowry, et al., [1951] *J. Biol. Chem.* 193:265-275 and results are illustrated in Table 2A.

TABLE 2A

Single Inactivations

| Inactivated Mutant Strain (Δ) | Production of Laccase (% increase in OD420) | Total Protein % (compared to Parent (Wild-Type)) |
|---|---|---|
| ΔderA | −80 | 106.4 |
| ΔderB | 15.7 | 104.3 |
| ΔhtmA |  | 101.1 |
| Δmnn9 | 14.6 | 99.6 |
| Δmnn10 | 12.7 | 102.6 |
| ΔochA | 7.2 | 102.3 |
| Δdpp4 | 6.0 | 102.7 |
| Δdpp5 | 15.4 | 99.4 |
| ΔpepB | 8.6 | 99.3 |
| ΔpepC |  | 100.0 |
| ΔpepD | 4.8 | 102 |
| ΔpepF | 5.3 | 99.8 |
| ΔpepAa | 0.5 | 100.5 |
| ΔpepAb | 13.4 | 96.5 |
| ΔpepAd | 2.7 | 96.5 |

TABLE 2B

Multiple Inactivations

| Inactivated Mutant strain (Δ) | Production of Laccase (% Increase in OD 420) |
|---|---|
| Δdpp4 | 11.8 |
| Δdpp5 | 15.3 |
| Δdpp4/Δdpp5 | 26.6 |
| Δmnn9 | 13.0 |
| ΔochA | 8.5 |
| Δmnn9/ΔochA | 16.8 |

It is claimed:

1. A recombinant filamentous fungal cell comprising one or more inactivated chromosomal gene selected from mnn9 (SEQ ID NO:7), mnn10 (SEQ ID NO:9), ochA (SEQ ID NO:11), dpp4 (SEQ ID NO:13), pepAa (SEQ ID NO:17), pepAb (SEQ ID NO:19), pepAc (SEQ ID NO:31), pepAd (SEQ ID NO:21), pepF (SEQ ID NO:23), or functionally homologous sequences thereto, wherein the functionally homologous sequences have at least 95% sequence identity thereto, and combination thereof.

2. The recombinant filamentous fungal cell of claim 1 comprising two inactivated chromosomal genes.

3. The recombinant filamentous fungal cell of claim 2, wherein the two inactivated chromosomal genes are mnn9 (SEQ ID NO:7) and ochA (SEQ ID NO:11), or functionally homologous sequences thereto having at least 95% sequence identity thereto.

4. The recombinant filamentous fungal cell of claim 1, wherein the inactivated chromosomal gene is mnn9 (SEQ ID NO:7) and homologous sequences thereof having at least 95% sequence identity thereto.

5. The recombinant filamentous fungal cell of claim 4 further comprising a second inactivated chromosomal gene.

6. The recombinant filamentous fungal cell of claim 1, wherein the one or more inactivated chromosomal genes selected from derA (SEQ ID NO:1), derB (SEQ ID NO:3), htmA (SEQ ID NO:5), mnn9 (SEQ ID NO:7), mnn10 (SEQ ID NO:9), ochA (SEQ ID NO:11), dpp4 (SEQ ID NO:13), and functionally homologous sequences thereof having at least 95% sequence identity thereto.

7. The recombinant filamentous fungal cell of claim 6, further comprising an inactivated chromosomal gene selected from pepAa (SEQ ID NO:17), pepAb (SEQ ID NO:19), pepAc (SEQ ID NO:31), pepAd (SEQ ID NO:21), pepF (SEQ ID NO:23); and functionally homologous sequences thereto having at least 95% sequence identity.

8. The recombinant filamentous fungal cell of claim 1, wherein said filamentous fungal cell is an *Aspergillus* cell.

9. The recombinant filamentous fungal cell of claim 1, further comprising an inactivated pepA.

10. The recombinant filamentous fungal cell of claim 1, wherein the inactivated gene has been deleted.

11. The recombinant fungal cell of claim 1, wherein the inactivated gene has been disrupted.

12. The recombinant filamentous fungal cell of claim 1, further comprising an inactivated gene selected from pepB (SEQ ID NO:25), pepC (SEQ ID NO:27), pepD (SEQ ID NO:29) and sequences having at least 95% sequence identity thereto, and combinations thereof.

13. The recombinant filamentous fungal cell of claim 1 further comprising an introduced nucleic acid which encodes a protein of interest.

14. The recombinant filamentous fungal cell of claim 13, wherein the protein of interest is an enzyme.

15. The recombinant filamentous fungal cell of claim 13, wherein the protein of interest is a protease inhibitor.

16. The recombinant filamentous fungal cell of claim 13, wherein the protein of interest is an antibody of fragment thereof.

17. An isolated nucleic acid encoding a protein having an amino acid sequence selected from the group of SEQ ID NO:2, SEQ ID NO:4, SEQ ID NO:6, SEQ ID NO:8, SEQ ID NO:10, SEQ ID NO:12 and functionally homologous sequences having at least 95% sequence identity thereto.

18. The isolated nucleic acid sequence of claim 17, wherein the nucleic acid sequence is selected from the group of sequences corresponding to SEQ ID NO:1, SEQ ID NO:3, SEQ ID NO:5, SEQ ID NO:7, SEQ ID NO:9 and SEQ ID NO:11.

* * * * *

UNITED STATES PATENT AND TRADEMARK OFFICE
CERTIFICATE OF CORRECTION

| | | |
|---|---|---|
| PATENT NO. | : 8,716,004 B2 | Page 1 of 1 |
| APPLICATION NO. | : 12/639956 | |
| DATED | : May 6, 2014 | |
| INVENTOR(S) | : Huaming Wang | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this
Eighteenth Day of August, 2015

Michelle K. Lee
*Director of the United States Patent and Trademark Office*